US012049626B2

(12) United States Patent
Abeliovich et al.

(10) Patent No.: US 12,049,626 B2
(45) Date of Patent: Jul. 30, 2024

(54) GENE THERAPY FOR NEURODEGENERATIVE DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 659 days.

(21) Appl. No.: 16/838,993

(22) Filed: Apr. 2, 2020

(65) Prior Publication Data

US 2020/0318115 A1 Oct. 8, 2020

Related U.S. Application Data

(63) Continuation of application No. PCT/US2018/054223, filed on Oct. 3, 2018.

(60) Provisional application No. 62/567,305, filed on Oct. 3, 2017, provisional application No. 62/567,303, filed on Oct. 3, 2017.

(51) Int. Cl.

| | |
|---|---|
| ***C12N 15/113*** | (2010.01) |
| ***A61K 9/00*** | (2006.01) |
| ***A61K 48/00*** | (2006.01) |
| ***A61P 25/02*** | (2006.01) |
| ***A61P 25/16*** | (2006.01) |
| ***A61P 25/28*** | (2006.01) |
| ***C07K 14/005*** | (2006.01) |
| ***C12N 7/00*** | (2006.01) |
| ***C12N 9/24*** | (2006.01) |
| ***C12N 15/86*** | (2006.01) |

(52) U.S. Cl.

CPC .......... *C12N 15/113* (2013.01); *A61K 9/0019* (2013.01); *A61K 9/0085* (2013.01); *A61K 48/0075* (2013.01); *A61P 25/02* (2018.01); *A61P 25/16* (2018.01); *A61P 25/28* (2018.01); *C07K 14/005* (2013.01); *C12N 7/00* (2013.01); *C12N 9/2402* (2013.01); *C12N 15/86* (2013.01); *C12Y 302/01045* (2013.01); *A61K 48/00* (2013.01); *C12N 2310/141* (2013.01); *C12N 2310/531* (2013.01); *C12N 2710/14043* (2013.01); *C12N 2750/14133* (2013.01); *C12N 2750/14143* (2013.01); *C12N 2770/32022* (2013.01)

(58) Field of Classification Search

CPC ........ C12N 15/113; C12N 7/00; C12N 15/86; C12N 2310/141; C12N 2310/531; C12N 2710/14043; C12N 2750/14133; C12N 2750/14143; C12N 2770/32022; C12N 2310/14; C12N 2330/51; C12N 15/111; C12N 15/1138; C12N 9/24; C12N 2750/14121; C12N 2750/14152; C12N 2800/107; C12N 2830/001; C12N 2830/48; C07K 14/005; C07K 14/47; A61K 48/00; A61K 48/005

See application file for complete search history.

(56) References Cited

U.S. PATENT DOCUMENTS

| | | | |
|---|---|---|---|
| 5,879,680 A | 3/1999 | Ginns et al. | |
| 6,521,225 B1 | 2/2003 | Srivasta et al. | |
| 6,696,272 B1 | 2/2004 | Mahuran et al. | |
| 7,172,893 B2 | 2/2007 | Rabinowitz | |
| 7,452,716 B2 | 11/2008 | Yew | |
| 8,389,487 B2 | 3/2013 | Bohn et al. | |
| 8,454,954 B2 | 6/2013 | Schlossmacher et al. | |
| 8,486,635 B2 | 7/2013 | Hutton et al. | |
| 8,962,273 B2 | 2/2015 | Reczek | |
| 9,034,836 B2 | 5/2015 | Dodge et al. | |
| 9,290,759 B2 | 3/2016 | Abeliovich et al. | |
| 9,347,107 B2 | 5/2016 | Lai et al. | |
| 9,427,438 B2 * | 8/2016 | Alam | A61P 43/00 |
| 9,486,541 B2 | 11/2016 | Hutton et al. | |
| 10,213,494 B2 | 2/2019 | Schlossmacher et al. | |
| 10,689,625 B2 | 6/2020 | Abeliovich et al. | |
| 10,837,028 B2 | 11/2020 | Abeliovich et al. | |
| 11,060,113 B2 | 7/2021 | Abeliovich et al. | |
| 11,661,585 B2 | 5/2023 | Abeliovich et al. | |
| 2002/0107213 A1 | 8/2002 | Verlinden et al. | |

(Continued)

FOREIGN PATENT DOCUMENTS

| | | |
|---|---|---|
| CN | 104902923 A | 9/2015 |
| CN | 105377039 A | 3/2016 |

(Continued)

OTHER PUBLICATIONS

Siman "A Rapid Gene DeliveryYBased Mouse Model for Early-Stage Alzheimer DiseaseYType Tauopathy" JNEN 72(11):1-10 (Year: 2013).*

Genbank AA476718 "zw92f11.s1 Soares_total_fetus_Nb2HF8_9w *Homo sapiens* cDNA clone IMAGE:784461 3'similar to GB: X14474 Microtubule-Associated Protein Tau (Human), mRNAsequence" accessed from ncbi.nlm.nih.gov on Nov. 5, 2022 (Year: 1997).*

Vincent "Comparison of the efficacy of five adeno-associated virus vectors for transducing dorsal raphe nucleus cells in the mouse" JNM Sep. 30:L189-192 (Year: 2014).*

Alzforum "Tau (MAPT)" excerpt only; accessed from alzforum.org on Nov. 5, 2022 (Year: 2022).*

(Continued)

*Primary Examiner* — Kimberly Ballard
*Assistant Examiner* — Stacey N MacFarlane
(74) *Attorney, Agent, or Firm* — Wolf, Greenfield & Sacks, P.C.

(57) ABSTRACT

This Application is a continuation of international patent application serial number PCT/US2018/054223, filed Oct. 3, 2018, which claims the benefit under 35 U.S.C. § 119(e) of U.S. Provisional Application Ser. No. 62/567,303, filed Oct. 3, 2017, entitled "GENE THERAPIES FOR LYSOSOMAL DISORDERS", and 62/567,305, filed Oct. 3, 2017, entitled "GENE THERAPIES FOR LYSOSOMAL DISORDERS", the entire contents of each of which are incorporated herein by reference.

18 Claims, 23 Drawing Sheets

Specification includes a Sequence Listing.

(56) References Cited

U.S. PATENT DOCUMENTS

2003/0100115 A1 5/2003 Raj et al.
2003/0133924 A1 7/2003 Canfield
2006/0142200 A1 6/2006 Zannis et al.
2006/0287358 A1 12/2006 Wustman
2006/0292117 A1 12/2006 Loiler et al.
2008/0003204 A1 1/2008 Flotte et al.
2009/0176729 A1 7/2009 Tan
2013/0287736 A1 10/2013 Passini et al.
2015/0183850 A1 7/2015 Davidson et al.
2015/0284472 A1 10/2015 Sardi et al.
2016/0060656 A1 3/2016 Rebar
2016/0068821 A1* 3/2016 Yan ........................ A61K 39/00 435/235.1
2016/0120960 A1 5/2016 McIvor et al.
2016/0237414 A1 8/2016 Grabowski et al.
2016/0264965 A1 9/2016 Mouradian et al.
2017/0035860 A1 2/2017 Flynn
2017/0246263 A1 8/2017 Concino et al.
2018/0071373 A1 3/2018 Melvor et al.
2018/0147300 A1 5/2018 Park et al.
2018/0311290 A1 11/2018 Sena-Esteves et al.
2019/0038773 A1 2/2019 Esteves et al.
2019/0055578 A1 2/2019 Sah et al.
2019/0282662 A1 9/2019 Kay et al.
2019/0328906 A1 10/2019 Chen Plotkin et al.
2019/0388507 A1 12/2019 Kay
2020/0071680 A1 3/2020 Abeliovich et al.
2020/0071726 A1 3/2020 Abeliovich et al.
2020/0231954 A1 7/2020 Abeliovich et al.
2020/0231970 A1 7/2020 Abeliovich et al.
2020/0276335 A1 9/2020 Abeliovich et al.
2020/0282080 A1 9/2020 Abeliovich et al.
2020/0283800 A1 9/2020 Abeliovich et al.
2020/0332265 A1 10/2020 Abeliovich et al.
2020/0338148 A1 10/2020 Abeliovich et al.
2021/0010032 A1 1/2021 Abeliovich et al.
2021/0332385 A1 10/2021 Abeliovich et al.
2022/0211871 A1 7/2022 Abeliovich et al.

FOREIGN PATENT DOCUMENTS

EP 2687223 A1 1/2014
EP 3091087 A1 9/2016
EP 3701030 A1 9/2020
JP 2002-524468 A 8/2002
JP 2004-514407 A 5/2004
JP 2009-530257 A 8/2009
JP 2010-525303 A 7/2010
JP 2013-531471 A 8/2013
JP 2015-516143 A 6/2015
JP 2016-523980 A 8/2016
WO WO 2000/014113 A2 3/2000
WO WO 2001/083692 A2 11/2001
WO WO 2002/24932 A2 3/2002
WO WO 2004/098648 A1 11/2004
WO WO 2003/029403 A3 8/2007
WO WO 2007/107789 A2 9/2007
WO WO 2007/146046 A2 12/2007
WO WO 2008/019187 A2 2/2008
WO WO 2008/124066 A1 10/2008
WO WO 2009/079399 A2 6/2009
WO WO 2009/089635 A9 9/2009
WO WO 2009/120978 A2 10/2009
WO WO 2011/133890 A1 10/2011
WO WO 2012/027558 A2 3/2012
WO WO 2012/027713 A2 3/2012
WO WO 2012/057363 A1 5/2012
WO WO 2012/065248 A1 5/2012
WO WO 2013/172964 A1 11/2013
WO WO 2014/071282 A1 5/2014
WO WO 2014/186579 A1 11/2014
WO WO 2015/006705 A2 1/2015
WO WO 2016/081927 A2 3/2016
WO WO 2016/151523 A1 9/2016
WO WO 2016/179497 A1 11/2016
WO WO 2017/077451 A1 5/2017
WO WO 2017/136202 A1 8/2017
WO WO 2017/147509 A1 8/2017
WO WO 2017/151884 A1 9/2017
WO WO 2019/028306 A2 2/2019
WO WO 2019/070891 A1 4/2019
WO WO 2019/070893 A1 4/2019
WO WO 2019/070894 A1 4/2019
WO WO 2019/084068 A1 5/2019
WO WO 2020/112802 A1 6/2020
WO WO 2020/210615 A1 10/2020
WO WO 2013/151665 A2 10/2023

OTHER PUBLICATIONS

Crouch "Data on Transition Phrases in Patent Cases" accessed from patentlyo.com on Nov. 5, 2022 (excerpt) (Year: 2021).*

Extended European Search Report mailed Jun. 10, 2021 in connection with Application No. 18864256.5.

Invitation to Pay Additional Fees mailed Dec. 17, 2018 in connection with Application No. PCT/US2018/054223.

[No Author Listed] G0345 pFBAAVCAGmcsBgHpA Viral Vector Core updated Feb. 22, 2017 [retrieved from the internet on Jun. 10, 2022] https://medicine.uiowa.edu/vectorcore/sites/medicine.uiowa.edu.vectorcore/files/wysiwyg_uploads/Manual_G0345_pFBAAVCAGmcsBgHpA_0.pdf, University of Iowa, Viral Vextor Core, 7 pages.

Anderson et al., Human pathology in NCL. Biochim Biophys Acta. Nov. 2013;1832(11):1807-26. doi: 10.1016/j.bbadis.2012.11.014. Epub Nov. 29, 2012.

Bond et al., Use of model organisms for the study of neuronal ceroid lipofuscinosis. Biochim Biophys Acta. Nov. 2013;1832(11):1842-65. doi: 10.1016/j.bbadis.2013.01.009. Epub Jan. 18, 2013.

Calcutt et al., Prosaposin gene expression and the efficacy of a prosaposin-derived peptide in preventing structural and functional disorders of peripheral nerve in diabetic rats. J Neuropathol Exp Neurol. Jun. 1999;58(6):628-36. doi: 10.1097/00005072-199906000-00007.

Chen-Plotkin et al., TMEM106B, the risk gene for frontotemporal dementia, is regulated by the microRNA-132/212 cluster and affects progranulin pathways. J Neurosci. Aug. 15, 2012;32(33):11213-27. doi: 10.1523/JNEUROSCI.0521-12.2012.

Choi et al., Optimization of AAV expression cassettes to improve packaging capacity and transgene expression in neurons. Mol Brain. Mar. 11, 2014;7:17. doi: 10.1186/1756-6606-7-17.

Daya et al., Gene therapy using adeno-associated virus vectors. Clin Microbiol Rev. Oct. 2008;21(4):583-93. doi: 10.1128/CMR.00008-08.

Franco et al., Glucocerebrosidase Mutations and Synucleinopathies. Potential Role of Sterylglucosides and Relevance of Studying Both GBA1 and GBA2 Genes. Front Neuroanat. Jun. 28, 2018;12:52. doi: 10.3389/fnana.2018.00052.

Francois et al., The cellular TATA binding protein is required for rep-dependent replication of a minimal adeno-associated virus type 2 p5 element. J Virol. Sep. 2005;79(17):11082-94. doi: 10.1128/JVI.79.17.11082-11094.2005.

Fumoto et al., Targeted Gene Delivery: Importance of Administration Routes. In: Novel Gene Therapy Approaches. 2013. Wei et al., Eds. Chapter 1:3-31.

Garcia-Gomez et al., Modelling gaucher disease through interference RNA technology. Human Gene Therapy, Sep. 1, 2015;26(9):A22-A23.

Ge et al., Optimization of eGFP expression using a modified baculovirus expression system. J Biotechnol. Mar. 10, 2014;173:41-6. doi: 10.1016/j.jbiotec.2014.01.003. Epub Jan. 18, 2014.

GenBank Accession No. AAA60303.1 "Prosaposin [*Homo sapiens*]" Jan. 9, 1995 [online].

GenBank Accession No. AAC37547.1 "cathepsin B [*Homo sapiens*]" Apr. 7, 1994 [online].

GenBank Accession No. AAF69824. 1 "triggering receptor expressed on myeloid cells 2 [*Homo sapiens*]" May 23, 2000 [online].

GenBank Accession No. AAH01503.1 "Prosaposin [*Homo sapiens*]" Aug. 4, 2008 [online].

(56) References Cited

OTHER PUBLICATIONS

GenBank Accession No. AAH02585.1 "RAB7, member RAS oncogene family-like 1 [*Homo sapiens*]" Jul. 15, 2006 [online].
GenBank Accession No. AAH04275.1 "Prosaposin [*Homo sapiens*]" Aug. 4, 2008 [online].
GenBank Accession No. AAH07612.1 "Prosaposin [*Homo sapiens*]" Aug. 4, 2008 [online].
GenBank Accession No. AAH10240.1 "Cathepsin B [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAH95408.1 "Cathepsin B [*Homo sapiens*]" Jul. 17, 2006 [online].
GenBank Accession No. AAP36904. 1 "*Homo sapiens* glucosidase, beta; acid (includes glucosylceramidase), partial [synthetic construct]" Jul. 25, 2016 [online].
GenBank Accession No. BT008212.1 "Synthetic construct *Homo sapiens* glucosidase, beta; acid (includes glucosylceramidase) mRNA, partial eds" Jul. 25, 2016 [online].
GenBank Accession No. EAW68726. 1 "sphingomyelin phosphodiesterase 1, acid lysosomal (acid sphingomyelinase), isoform CRA a [*Homo sapiens*]" Mar. 23, 2015 [online].
GenBank Accession No. EAW68727.1 "sphingomyelin phosphodiesterase 1, acid lysosomal (acid sphingomyelinase), isoform CRA b [*Homo sapiens*]" Mar. 23, 2015 [online].
GenBank Accession No. EAW68728. 1 "sphingomyelin phosphodiesterase 1, acid lysosomal (acid sphingomyelinase), isoform CRA c [*Homo sapiens*]" Mar. 23, 2015 [online].
GenBank Accession No. EAW68729.1 "sphingomyelin phosphodiesterase 1, acid lysosomal (acid sphingomyelinase), isoform CRA d [*Homo sapiens*]" Mar. 23, 2015 [online].
GenBank Accession No. EAW81359.1 "galactosylceramidase, isoformCRA_a [*Homo sapiens*]" Mar. 23, 2015 [online].
GenBank Accession No. EAW81360.1 "galactosylceramidase, isoformCRA_b [*Homo sapiens*]" Mar. 23, 2015 [online].
GenBank Accession No. EAW81362.1 "galactosylceramidase, isoformCRA_c [*Homo sapiens*]" Mar. 23, 2015 [online].
GenBank Accession No. NP_000144.2 "galactocerebrosidase isoform a precursor [*Homo sapiens*]" Sep. 26, 2019 [online].
GenBank Accession No. NP_000148.2 "lysosomal acid glucosylceramidase isoform 1 precursor [*Homo sapiens*]" Jan. 8, 2020 [online].
GenBank Accession No. NP_000152.1 "GTP cyclohydrolase 1 isoform 1 [*Homo sapiens*]" Dec. 30, 2019 [online].
GenBank Accession No. NP_000534.3 "sphingomyelin phosphodiesterase isoform 1 precursor [*Homo sapiens*]" Jan. 13, 2020 [online].
GenBank Accession No. NP_001005742.1 "lysosomal acid glucosylceramidase isoform 1 precursor [*Homo sapiens*]" Nov. 11, 2019 [online].
GenBank Accession No. NP_001165282.1 "lysosomal acid glucosylceramidase isoform 2 [*Homo sapiens*]" Nov. 11, 2019 [online].
GenBank Accession No. NP_001165283.1 "lysosomal acid glucosylceramidase isoform 3 [*Homo sapiens*]" Nov. 11, 2019 [online].
GenBank Accession No. NP_001191184.1 "lysosome membrane protein 2 isoform 2 precursor [*Homo sapiens*]" Jan. 4, 2020 [online].
GenBank Accession No. NP_001317589.1 "non-lysosomal glucosylceramidase isoform 2 [*Homo sapiens*]" Aug. 7, 2019 [online].
GenBank Accession No. NP_001899.1 "cathepsinB isoform 1 preproprotein [*Homo sapiens*]" Jan. 27, 2020 [online].
GenBank Accession No. NP_002078.1 "progranulin precursor [*Homo sapiens*]" Jan. 21, 2020 [online].
GenBank Accession No. NP_002087.1 "general transcription factor IIF, polypeptide 1, 74kDa [*Homo sapiens*]" Jun. 3, 2007 [online].
GenBank Accession No. NP_002769.1 "prosaposin isoform a preproprotein [*Homo sapiens*]" Sep. 27, 2019 [online].
GenBank Accession No. NP_003920.1 "ras-related protein Rab-7L1 isoform 1 [*Homo sapiens*]" Dec. 31, 2019 [online].
GenBank Accession No. NP_005497.1 "lysosome membrane protein 2 isoform 1 precursor [*Homo sapiens*]" Jan. 1, 2020 [online].
GenBank Accession No. NP_060676.2 "vacuolar protein sorting-associated protein 35 [*Homo sapiens*]" Oct. 11, 2019 [online].
GenBank Accession No. NP_060844.2 "transmembrane protein 106B [*Homo sapiens*]" Jul. 28, 2019 [online].
GenBank Accession No. NP_061838.1 "triggering receptor expressed on myeloid cells 2 precursor isoform 1 precursor [*Homo sapiens*]" Feb. 2, 2020 [online].
GenBank Accession No. NP_065995.1 "non-lysosomal glucosylceramidase isoform 1 [*Homo sapiens*]" Aug. 22, 2019 [online].
GenBank Accession No. NP_689669.2 "interleukin-34 isoform 1 precursor [*Homo sapiens*]" Dec. 25, 2019 [online].
Geneseq Accession No. BDA66566. "Adeno-associated virus—2 (AAV2) IRE S-sequence, Seq Id 3." Jul. 14, 2016 [online].
Gotz et al., Animal models for Alzheimer's disease and frontotemporal dementia: a perspective. ASN Neuro. Nov. 9, 2009;1(4):e00019. doi: 10.1042/AN20090042.
Ham, Prosaposin precursor protein: Functions and medical applications. Scripta Medica (BRNO). Jun. 2004;77(3):127-34.
Huang et al., Targeting Visceral Fat by Intraperitoneal Delivery of Novel AAV Serotype Vector Restricting Off-Target Transduction in Liver. Mol Ther Methods Clin Dev. Jun. 19, 2017;6:68-78. doi: 10.1016/j.omtm.2017.06.002.
Hudry et al., Therapeutic AAV Gene Transfer to the Nervous System: A Clinical Reality. Neuron. Mar. 6, 2019;101(5):839-862. doi: 10.1016/j.neuron.2019.02.017. Erratum in: Neuron. Apr. 3, 2019;102(1):263.
Jian et al., Association Between Progranulin and Gaucher Disease. EBioMedicine. Sep. 2016;11:127-137. doi: 10.1016/j.ebiom.2016.08.004. Epub Aug. 4, 2016.
Jiang et al., TREM2 in Alzheimer's disease. Mol Neurobiol. Aug. 2013;48(1):180-5. doi: 10.1007/s12035-013-8424-8. Epub Feb. 14, 2013.
Jiang et al., TREM2 modifies microglial phenotype and provides neuroprotection in P301S tau transgenic mice. Neuropharmacology. Jun. 2016;105:196-206. doi: 10.1016/j.neuropharm.2016.01.028. Epub Jan. 21, 2016.
Jiang et al., TREM2 Overexpression has No Improvement on Neuropathology and Cognitive Impairment in Aging APPswe/PS1dE9 Mice. Mol Neurobiol. Mar. 2017;54(2):855-865. doi: 10.1007/s12035-016-9704-x. Epub Jan. 16, 2016.
Khodr et al., Targeting alpha-synuclein with a microRNA-embedded silencing vector in the rat substantia nigra: positive and negative effects. Brain Res. Mar. 6, 2014;1550:47-60. doi: 10.1016/j.brainres.2014.01.010. Epub Jan. 21, 2014.
Lazic et al., Cell-based therapies for disorders of the CNS. Expert Opin. Ther. Patents. 2005;15(10): 1361-76.
Ling et al., The Adeno-Associated Virus Genome Packaging Puzzle. J Mol Genet Med. Aug. 2015;9(3):175. doi: 10.4172/1747-0862.1000175. Epub Jul. 15, 2015. Author Manuscript, 10 pages.
Manno et al., Successful transduction of liver in hemophilia by AAV-Factor IX and limitations imposed by the host immune response. Nat Med. Mar. 2006; 12(3):342-7. doi: 10.1038/nm1358. Epub Feb. 12, 2006. Erratum in: Nat Med. May 2006;12(5):592. Rasko, John [corrected to Rasko, John JE]; Rustagi, Pradip K [added].
Molnar et al., Gene therapy in neurology: review of ongoing clinical trials. Clin. Invest. 2012;2(6): 639-52.
Naso et al., Adeno-Associated Virus (AAV) as a Vector for Gene Therapy. BioDrugs. Aug. 2017;31(4):317-334. doi: 10.1007/s40259-017-0234-5.
Niederkofler et al., Characterization of relevant mouse models for new biomarkers. 2019. QPS Austria GmbH. Poster #141. 1 page.
Rafi et al., Correction of sulfatide metabolism after transfer of prosaposin cDNA to cultured cells from a patient with SAP-1 deficiency. Am J Hum Genet. Jun. 1992;50(6):1252-8.
Renaud-Gabardos et al., Internal ribosome entry site-based vectors for combined gene therapy. World J Exp Med. Feb. 20, 2015;5(1):11-20. doi: 10.5493/wjem.v5.il.11.

(56) References Cited

OTHER PUBLICATIONS

Rothaug et al., LIMP-2 expression is critical for β-glucocerebrosidase activity and α-synuclein clearance. Proc Natl Acad Sci U S A. Oct. 28, 2014;111(43):15573-8. doi: 10.1073/pnas.1405700111. Epub Oct. 14, 2014.

Salmon et al., Safety profile of recombinant adeno-associated viral vectors: focus on alipogene tiparvovec (Glybera®). Expert Rev Clin Pharmacol. Jan. 2014;7(1):53-65. doi: 10.1586/17512433.2014.852065. Epub Nov. 25, 2013.

Savy et al., Impact of Inverted Terminal Repeat Integrity on rAAV8 Production Using the Baculovirus/Sf9 Cells System. Hum Gene Ther Methods. Oct. 2017;28(5):277-289. doi: 10.1089/hgtb.2016.133.

Shanks et al., Are animal models predictive for humans? Philos Ethics Humanit Med. Jan. 15, 2009;4:2. doi: 10.1186/1747-5341-4-2.

Sikora et al., Neurolysosomal pathology in human prosaposin deficiency suggests essential neurotrophic function of prosaposin. Acta Neuropathol. Feb. 2007;113(2):163-75. doi: 10.1007/s00401-006-0148-7. Epub Oct. 6, 2006.

Sinclair et al., Synonymous codon usage bias and the expression of human glucocerebrosidase in the methylotrophic yeast, *Pichia pastoris*. Protein Expr Purif. Oct. 2002;26(1):96-105. doi: 10.1016/s1046-5928(02)00526-0.

Takahashi et al., TREM2-transduced myeloid precursors mediate nervous tissue debris clearance and facilitate recovery in an animal model of multiple sclerosis. PLoS Med. Apr. 2007;4(4):e124. doi: 10.1371/journal.pmed.0040124.

Tamargo et al., The role of saposin C in Gaucher disease. Mol Genet Metab. Jul. 2012;106(3):257-63. doi: 10.1016/j.ymgme.2012.04.024. Epub May 5, 2012.

Ulrich et al., Elucidating the Role of TREM2 in Alzheimer's Disease. Neuron. Apr. 19, 2017;94(2):237-248. doi: 10.1016/j.neuron.2017.02.042.

UniProtKB Submission; Accession No. Q14108. "SCARB2—Lysosome membrane protein 2" Nov. 1, 1997. [online].

Wang et al., Adeno-associated virus type 2 DNA replication in vivo: mutation analyses of the D sequence in viral inverted terminal repeats. J Virol. Apr. 1997;71(4):3077-82. doi: 10.1128/JVI.71.4.3077-3082.1997.

Wang et al., Enhancing Transgene Expression from Recombinant AAV8 Vectors in Different Tissues Using Woodchuck Hepatitis Virus Post-Transcriptional Regulatory Element. Int J Med Sci. Apr. 1, 2016;13(4):286-91. doi: 10.7150/ijms.14152.

Wong et al., Lysosomal trafficking defects link Parkinson's disease with Gaucher's disease. Mov Disord. Nov. 2016;31(11):1610-1618. doi: 10.1002/mds.26802. Epub Sep. 13, 2016. Author Manuscript, 17 pages.

Xu et al., Extracellular progranulin protects cortical neurons from toxic insults by activating survival signaling. Neurobiol Aging. Dec. 2011;32(12):2326.e5-16. doi: 10.1016/j.neurobiolaging.2011.06.017. Epub Aug. 4, 2011. Author Manuscript, 20 pages.

Xu et al., Tau silencing by siRNA in the P301S mouse model of tauopathy. Curr Gene Ther. 2014;14(5):343-51. doi: 10.2174/1566523214051409261 60602.

Yu et al., The spectrum of mutations in progranulin: a collaborative study screening 545 cases of neurodegeneration. Arch Neurol. Feb. 2010;67(2):161-70. doi: 10.1001/archneurol.2009.328. Author Manuscript, 18 pages.

International Search Report and Written Opinion mailed Feb. 21, 2019 in connection with Application No. PCT/US2018/054223.

International Preliminary Report on Patentability mailed Apr. 16, 2020 in connection with Application No. PCT/US2018/054223.

Fath et al. Multiparameter RNA and codon optimization: a standardized tool to assess and enhance autologous mammalian gene expression. PLoS One. Mar. 3, 2011;6(3):e17596. doi: 10.1371/journal.pone.0017596. Erratum in: PLoS One. 2011;6(3). doi: 10.1371/annotation/039deb02-bbe7-406c-a876-341cc4f3fefa.

[No Author Listed] Can an ApoE Mutation Halt Alzheimer's Disease?, Nov. 4, 2019. Downloaded from online: https://www.alzforum.org/news/research-news/can-apoe-mutation-halt-alzheimers-disease. 14 pages.

[No Author Listed] GenBank NCBI Reference Sequence: "*Homo sapiens* granulin precursor (GRN), mRNA," NCBI Reference Sequence: NM_002087.3, Feb. 24, 2019. 6 pages.

Arrant et al., Progranulin Gene Therapy Improves Lysosomal Dysfunction and Microglial Pathology Associated with Frontotemporal Dementia and Neuronal Ceroid Lipofuscinosis. J Neurosci. Feb. 28, 2018;38(9):2341-2358. doi: 10.1523/JNEUROSCI.3081-17.2018. Epub Jan. 29, 2018.

Ciesielska et al., Cerebral infusion of AAV9 vector-encoding non-self proteins can elicit cell-mediated immune responses. Mol Ther. Jan. 2013;21(1):158-66. doi: 10.1038/mt.2012.167. Epub Aug. 28, 2012.

Deverman et al., Gene therapy for neurological disorders: progress and prospects. Nat Rev Drug Discov. Oct. 2018; 17(10):767. doi: 10.1038/nrd.2018.158. Epub Sep. 12, 2018. Erratum for: Nat Rev Drug Discov. Sep. 2018;17(9):641-659.

GenBank Accession No. AF043303.1, "Adeno-associated virus 2, complete genome", May 20, 2010 [online], 4 pages.

Indoh et al., Codon Optimization of Plant Fatty Acid Desaturase (FAD3) to Enhance Expression in Mammalian Cells, Mem. School. B. O. S. T. Kinki University, 2008, No. 22, pp. 33-41.

Samaranch et al., AAV9-mediated expression of a non-self protein in nonhuman primate central nervous system triggers widespread neuroinflammation driven by antigen-presenting cell transduction. Mol Ther. Feb. 2014;22(2):329-337. doi: 10.1038/mt.2013.266. Epub Nov. 21, 2013.

* cited by examiner

Intronic_eSIBR_Columbia_aSyn_CMVe_CBAp_GBA1_WPRE_bGH
10,849 bp

PrevailVector_BroadConservedSNCAshRNA_CMVe_CBAp_GRN_WPRE_bGH_MCS_121817
11,231 bp PrevailVector_0H_H1_aSynshRNA_CMVe_CBAp_GBA1_WPRE_bGH_4218nt
11,174 bp PrevailVector_FT3t_JetLong_mRNAiTMEM106B_GBA1_T2S_GRN_SyntheticpolyA_4364nt
11,320 bp

SEQUENCE LISTING

<160> NUMBER OF SEQ ID NOS: 69

<210> SEQ ID NO 1
<211> LENGTH: 3022
<212> TYPE: DNA
<213> ORGANISM: Artificial Sequence
<220> FEATURE:
<223> OTHER INFORMATION: Synthetic polynucleotide

<400> SEQUENCE: 1
attctggtgt gatccaggaa cagctgtctt ccagctctga aagagtgtgg tgtaaaggaa 60
ttcattagcc atggatgtat tcatgaaagg actttcaaag gccaaggagg gagttgtggc 120
tgctgctgag aaaaccaaac agggtgtggc agaagcagca ggaaagacaa aagagggtgt 180
tctctatgta ggctccaaaa ccaaggaggg agtggtgcat ggtgtggcaa cagtggctga 240
gaagaccaaa gagcaagtga caaatgttgg aggagcagtg gtgacgggtg tgacagcagt 300
agcccagaag acagtggagg gagcagggag cattgcagca gccactggct ttgtcaaaaa 360
ggaccagttg ggcaagaatg aagaaggagc cccacaggaa ggaattctgg aagatatgcc 420
tgtggatcct gacaatgagg cttatgaaat gccttctgag gaagggtatc aagactacga 480
acctgaagcc taagaaatat ctttgctccc agtttcttga gatctgctga cagatgttcc 540
atcctgtaca agtgctcagt tccaatgtgc ccagtcatga catttctcaa agtttttaca 600
gtgtatctcg aagtcttcca tcagcagtga ttgaagtatc tgtacctgcc cccactcagc 660
atttcggtgc ttccctttca ctgaagtgaa tacatggtag cagggtcttt gtgtgctgtg 720
gattttgtgg cttcaatcta cgatgttaaa acaaattaaa aacacctaag tgactaccac 780
ttatttctaa atcctcacta tttttttgtt gctgttgttc agaagttgtt agtgatttgc 840
tatcatatat tataagattt ttaggtgtct tttaatgata ctgtctaaga ataatgacgt 900
attgtgaaat ttgttaatat atataatact taaaaatatg tgagcatgaa actatgcacc 960
tataaatact aaatatgaaa ttttaccatt ttgcgatgtg ttttattcac ttgtgtttgt 1020
atataaatgg tgagaattaa aataaaacgt tatctcattg caaaaatatt ttattttat 1080 cccatctcac tttaataata aaaatcatgc ttataagcaa catgaattaa gaactgacac 1140
aaaggacaaa aatataaagt tattaatagc catttgaaga aggaggaatt ttagaagagg 1200
tagagaaaat ggaacattaa ccctacactc ggaattccct gaagcaacac tgccagaagt 1260
gtgttttggt atgcactggt tccttaagtg gctgtgatta attattgaaa gtggggtgtt 1320 gaagaccccca actactattg tagagtggtc tatttctccc ttcaatcctg tcaatgtttg 1380
ctttacgtat tttggggaac tgttgtttga tgtgtatgtg tttataattg ttatacattt 1440
ttaattgagc cttttattaa catatattgt tatttttgtc tcgaaataat tttttagtta 1500
aaatctattt tgtctgatat tggtgtgaat gctgtacctt tctgacaata aataatattc 1560
gaccatgaat aaaaaaaaaa aaaaagtggg ttcccgggaa ctaagcagtg tagaagatga 1620
ttttgactac accctcctta gagagccata agacacatta gcacatatta gcacattcaa 1680
ggctctgaga gaatgtggtt aactttgttt aactcagcat tcctcacttt tttttttaa 1740 tcatcagaaa ttctctctct ctctctctct ttttctctcg ctctcttttt tttttttttt 1800
ttacaggaaa tgcctttaaa catcgttgga actaccagag tcaccttaaa ggagatcaat 1860
tctctagact gataaaaatt tcatggcctc ctttaaatgt tgccaaatat atgaattcta 1920
ggatttttcc ttaggaaagg tttttctctt tcagggaaga tctattaact ccccatgggt 1980
gctgaaaata aacttgatgg tgaaaaactc tgtataaatt aatttaaaaa ttatttggtt 2040

-continued

```
tctcttttta attattctgg ggcatagtca tttctaaaag tcactagtag aaagtataat   2100

ttcaagacag aatattctag acatgctagc agtttatatg tattcatgag taatgtgata   2160

tatattgggc gctggtgagg aaggaaggag gaatgagtga ctataaggat ggttaccata   2220

gaaacttcct tttttaccta attgaagaga gactactaca gagtgctaag ctgcatgtgt   2280

catcttacac tagagagaaa tggtaagttt cttgttttat ttaagttatg tttaagcaag   2340

gaaaggattt gttattgaac agtatatttc aggaaggtta gaaagtggcg gttaggatat   2400

attttaaatc tacctaaagc agcatatttt aaaaatttaa aagtattggt attaaattaa   2460

gaaatagagg acagaactag actgatagca gtgacctaga acaatttgag attaggaaag   2520

ttgtgaccat gaatttaagg atttatgtgg atacaaattc tcctttaaag tgtttcttcc   2580

cttaatattt atctgacggt aatttttgag cagtgaatta ctttatatat cttaatagtt   2640

tatttgggac caaacactta aacaaaaagt tctttaagtc atataagcct tttcaggaag   2700

cttgtctcat attcactccc gagacattca cctgccaagt ggcctgagga tcaatccagt   2760

cctaggttta ttttgcagac ttacattctc ccaagttatt cagcctcata tgactccacg   2820

gtcggcttta ccaaaacagt tcagagtgca ctttggcaca caattgggaa cagaacaatc   2880

taatgtgtgg tttggtattc caagtggggt ctttttcaga atctctgcac tagtgtgaga   2940

tgcaaacatg tttcctcatc tttctggctt atccagtatg tagctatttg tgacataata   3000

aatatataca tatatgaaaa ta                                             3022
```

<210> SEQ ID NO 2
<211> LENGTH: 6514
<212> TYPE: DNA
<213> ORGANISM: Artificial Sequence
<220> FEATURE:
<223> OTHER INFORMATION: Synthetic polynucleotide

<400> SEQUENCE: 2

```
aggcgcggac gcaggttaca gcagcgcttg gcctctgctg atgccgtcgt tatcctaccc     60

ctcccccgtc ccagctctac ggcggccgcg cgctccaggc cggtcgctcc accccccggc    120

tcccgggact gtggactcca cgaccctgtc ctcggccctg tccgcgccga agcagcccgg    180

gactgcgcag cgccccgcgt gccgatcttt tcctaattca gcagcgattt aaccaagagc    240

ctggaatatt ttaaggagta ataagagaca tttacaaact attctctctg aagcctgcta    300

cctggaggca tcatctagat aatcagaacc ttggcttcca catcctcctc ccttgtctta    360

actacaaaca tttctttctg ctgacttcaa ctcctcagac atgggaaagt ctctttctca    420

tttgcctttg cattcaagca aagaagatgc ttatgatgga gtcacatctg aaaacatgag    480

gaatggactg gttaatagtg aagtccataa tgaagatgga agaaatggag atgtctctca    540

gtttccatat gtggaattta caggaagaga tagtgtcacc tgccctactt gtcagggaac    600

aggaagaatt cctagggggc aagaaaacca actggtggca ttgattccat atagtgatca    660

gagattaagg ccaagaagaa caaagctgta tgtgatggct tctgtgtttg tctgtctact    720

cctttctgga ttggctgtgt tttccttttt ccctcgctct atcgacgtga aatacattgg    780

tgtaaaatca gcctatgtca gttatgatgt tcagaagcgt acaatttatt taaatatcac    840

aaacacacta aatataacaa acaataacta ttactctgtc gaagttgaaa acatcactgc    900

ccaagttcaa ttttcaaaaa cagttattgg aaaggcacgc ttaaacaaca taaccattat    960

tggtccactt gatatgaaac aaattgatta cacagtacct accgttatag cagaggaaat   1020
```

-continued

```
gagttatatg tatgatttct gtactctgat atccatcaaa gtgcataaca tagtactcat   1080
gatgcaagtt actgtgacaa caacatactt tggccactct gaacagatat cccaggagag   1140
gtatcagtat gtcgactgtg gaagaaacac aacttatcag ttggggcagt ctgaatattt   1200
aaatgtactt cagccacaac agtaaaaact ggaagagatg gatttaaaga agaaatatct   1260
attgatattt cctatactct caatgaagag gtatttccta ataggagacc ttaaattgaa   1320
caaacctaaa gtttacactt ctaagagtac agttaaaagt atgtggacct gcagttcttg   1380
taactctcca ctctgtgtta atgatatatt tgtactagga tcttttactt gaatctaaat   1440
ttactggttg atttccttct ccagcctatc ccctacaggg aaaagctgat acttccccta   1500
tagtacaata aataattatt taaaagtcat agctccagtc actactgaaa acataatttt   1560
ggtgataaac ataatttgag aaacttaatt tctgaatgtt tttatagaaa attactgaaa   1620
gtctattact catggaagac ttttaaagaa taaccttttt tcctgtttta taaattccca   1680
ttgttatatg gtagtatttc agctacacaa tattttagct tttagctaga catttatagc   1740
ttttcatttg ttgaaatggt aatcatctgc atgtttttgt cacttatttc aggttagtga   1800
ttgcctaaca cttataagcc aaaataatct ttgcaaaatt ccatacctaa aattttgaaa   1860
gcccctaatg ttttcacaca tctttctgta ttagttatag ttttgtgaaa tctttgtgtg   1920
atcttcaaac attatcattt aatgtacaat actgtaaata aactgtgcat ggcttttata   1980
cagctttagt aaatgtcaaa taaagtggta cagactcatt acaacaagtt tctcataaaa   2040
atacaataaa taggaaaatg aaattcagaa acccatagac tgggaatagg ttccagttac   2100
agcttggatc tggcataaaa taaatttgaa ataaaatatt ttgatgctcc attttttat   2160
gttgcttttc atactaaaga atggtgtaga catgttttgc aactgttagg tacccagtta   2220
tcaattttat caatgtttta gaggaggaaa ttattttttt ggtagaaatt gttcaagaaa   2280
tccttaattg aatgtcatta aatgatggtg gccaaaataa aacctattta gaaatttaat   2340
cactttgcac atcacttgga atatgatgcc tctagtagtt actttttat agttttctac   2400
ttttggtttt atttaaaatt gttttcaaat atagattatt gacttattca actttgctgt   2460
tttatatttt cagtatcatt tttcattttt tttttttttt gtcttttcac ttaccaagtt   2520
ctagggacat ttaaaatatg tactaagtgt aggagtggtt atgataccaa aaaatgtagc   2580
tgggttgaga ttaatttcgt tctgttttct catgacagaa atcaggtttc cctttcccca   2640
cccctaagtg cctaacttag gtctgaaaca gcctgtttat tagtctgact ctctcaacca   2700
taaaacataa gctttattta attctgcctt taaacacact caggtttccc cttaattttc   2760
atattatttt ctgcaagttt tcttgagtat cttcaattcg ttgaatgtgg tttttggttt   2820
tttttgttt taacactagt cttcccttaa ttcattgcta actcaagcca tccttactat   2880
taaacccaaa tcagtccttt aagttcatta tggcctttct agtatttaaa aaaaaaaaaa   2940
tcattttcat ttttcttctg ctacgtttcc tgactactac tgcatacttc tctgatacag   3000
gttctgtttg tattttttat atcattctca ttttctcatt tgacatgatc tatgtctata   3060
tatgatatag gtcccctttt gtctcaaaat ttttaattat gtgacttcaa aaatcacctg   3120
tatctgtagt agggcttcca aatctgcttc tccatatgtg accagtcacc tgtctgcttt   3180
cacatttagc tagtgaacta cacatttact aaaatgtgta aattttacac atttagtgac   3240
tgtgtaaaat aaaaaaaaag ttattttatc atatcctttc tattatgttc ccatcctgtc   3300
ctcatgtccc atttacttta ttatcaccat tcatttcttc aaaattatct tttagatacg   3360
ctcatacaaa aatcaatcct tgttttcttg cttgtgtctt ttaaccttgg aaaattacat   3420
```

```
cgtgtaaatt aaacagattt ttctgatgat ctgtgcttct tatatactat tagagtgcat   3480

gatagtatct cctgaaaagg atggaaagta gaagcatttg cttttagtca cttaattttg   3540

aatctttttt cttcatcttt tgaattaatt tttttatta tatctacttt tagtggagtt   3600

tgagtcagaa aaaaacaaga atttgaaaca agtaaaaaga tagaagagaa ataaagatgg   3660

tatgtgacta ctttcagaga gagttaagta actgtcagaa taagcctgga acaaaacagg   3720

ctgtaaatta ataaaactac aaacacacat tcaggtgaag cagaagtata gccataaaac   3780

atctagaaag agtgaatgag gcttttagct tttcttaggt caatgtccag tgtgcttttt   3840

tccatgggaa taggataggt attaatacgc ttttctaaac tgctctcaga ccttatccag   3900

aggacatggt aaagatatgt tacagaaatt tttctgatac ttcctggaat aactttaagt   3960

tacaccctag tagactggtc attctaataa aatccagtac tataacaaac ctctgtatgt   4020

tgatagcaca ttggcccttt ttagagttct ttcctatgtt tttcttacgt gatttcccac   4080

agttccatga gtccaacaaa ggagagtgat aggctcctta tcttttagaa gaggaaggaa   4140

aggcatgaag aagttgaggg actggctgaa gatcacgtac ttactaagta gtacaactgg   4200

agcaagatca agtatctctg tctcccatat ctgtgttcta tcatttaaaa tatatattgg   4260

aaatccctgc tgactcagat tggtatgatt aaaaatgaga ggaaagttca aatagttagt   4320

agtgacaaac taatactgct ggactaagat tttggtagca ttgttttcta aaatatttta   4380

aatggagaat gaacacttat aaaatgcttt ggaacataat ctttagctta attttctgtt   4440

aaaatttagt accccttcat cattccaata aagataagac tgatccattg tctaaggaaa   4500

ttatttataa ataatagaga ttaatttatt tgagatttga aataagaata gtatgaaaat   4560

attagatacc acataaattg tttgaaatta ctgaataacc atcttaagta tggaacattt   4620

aaatggctat attttatttg tgtacagttt ttctgtgcct tgttaggcca gtgaagcaat   4680

tattttctct aagaaaatga caataaaata taacacactt cagattgtct gatttacagt   4740

ttggaaagga caccgcaatg ttcaaatagg taggagacca tcaaaaacac aattaaagta   4800

acatattagg agacttgaaa cttcagccta ataaatcctt catggttctt agccttatta   4860

ttgtgatata attctagata ttttcttgga gggcatgtgc ccaactctcc cgcaccccat   4920

tttgtttgtc ttttaaagtt cttagaataa acagttcttt atataataat tatattttat   4980

ttaagaaaat agtttgttag gtacttttta aaagatgtaa atttttaaat ttacaaatac   5040

atatgggtct ttgataagca ataggaattg aattacaagt tactagggtt ataagcaaaa   5100

ggttgcttac cataatgtca ttaggtcacg atttttagct cacatctgga agcagcaact   5160

acttggctca agtacatata agagtaatta gttttattct ctcttttta taaaatcggg   5220

tttcagatga gatgtttatc ttagactatt ttagggaaaa attttacatg tttgagatgg   5280

tggagtaaaa agactgttaa acatttcttt taaaaaatta tttttacatt acaacaatat   5340

atttatgatg tgttcagatc aaaaatttaa cttctgtgtc ccagatctac tttcaaagtg   5400

agattttcac ttgtcagctt aaatttctga ctagaactaa catttgtgta tttttgtgct   5460

tagtcggaat acaaatttca cagtggattt ttgaagtttg tccttaaatt ggataaaatc   5520

aagtgattaa agttactaaa gagataaaaa tggtaatttc catttttaaa agtaatttgg   5580

ttgtgtttat agttatttgt acaagtattt atcacagact ctaaattgaa aaatgtagta   5640

tgatctatat ttgaccctaa aaatgttgga ttaatttaac aaatatggca gatttttcat   5700

aactaagtct taagtcttct aaaaggaagc tgttaccctt ctgtttttaa ttacattaat   5760
```

```
tgaaatgtgt tttaagagat acaatttcag catattttat atattaaaaa acaaaaaagg   5820

attagtattg agccagtggc caaaaggtaa tattactacc atgtagactg ttatagttca   5880

aattgtccca cttcacccag aattttagaa actagaagtc tgggaggtac tatatcagct   5940

gtagttgggt aattccaagt gctgatagta ctattcatct tttttattat tgtgtcagat   6000

gaaacaaatg ccaagttgca aaatatgcag atttttatta tataatggtt ttaggcataa   6060

attattaaca agccatgcct tatgtgtttc atcttatatt tttctttaga actaaactat   6120

aacagatttt ggaaaatgat ttgacgtgct tgctcacttg attgacttgg tcagatattt   6180

gaatgatggt attacctaga ttctaatcct tgattctagt tatataataa ataatataga   6240

atatgaaaat atgtttgggc atttactgtt tatattatgt agtagcctcc atcatgacac   6300

acttactaca tttatgaatt gagcagttct gtaattgtaa ttattattgc tgttcatgta   6360

acaaaacatg cttataatag caaacaaata gaaatgcccc caaaatgcta ttttttttaat   6420

tcagttataa ctgttactct tgtagttgtg tatgacgcaa taaaatttgt aaaaaaattt   6480

cagcatgaaa aataaaattt gtatcactta tgta                               6514
```

```
<210> SEQ ID NO 3
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 3

tggaagactt cgagatacac tgt                                             23


<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4

acagtgtatc tcgaagtctt cca                                             23


<210> SEQ ID NO 5
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 5

tttagaaata agtggtagtc a                                               21


<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6

tgactaccac ttatttctaa a                                               21


<210> SEQ ID NO 7
<211> LENGTH: 19
<212> TYPE: DNA
<213> ORGANISM: Artificial Sequence
```

<220> FEATURE:
<223> OTHER INFORMATION: Synthetic polynucleotide

<400> SEQUENCE: 7
agggtatcaa gactacgaa 19

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8
ttcgtagtct tgataccct 19

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
gtgtactagg atcttttact tgaa 24

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
ttcaagtaaa agatcctagt acac 24

<210> SEQ ID NO 11
<211> LENGTH: 267
<212> TYPE: DNA
<213> ORGANISM: Artificial Sequence
<220> FEATURE:
<223> OTHER INFORMATION: Synthetic polynucleotide

<400> SEQUENCE: 11
gtgatatcac aaggtcccag ggctggggtc agaaattctc tcccgaggga atgaagccac 60
aggagccaag agcaggagga ccaaggccct ggcgaaggcc gtggcctcgt tcaagtaaaa 120
gatcctagta cagtgcaggt cccaatgtgt actaggatct tttacttgaa cggggacgcc 180
ggcatccggg ctcaggaccc ccctctctgc cagaggcacc aacaccagag ttcacaaatc 240
agtctcctgc cctttgcatg tagcaaa 267

<210> SEQ ID NO 12
<211> LENGTH: 267
<212> TYPE: DNA
<213> ORGANISM: Artificial Sequence
<220> FEATURE:
<223> OTHER INFORMATION: Synthetic polynucleotide

<400> SEQUENCE: 12
tttgctacat gcaaagggca ggagactgat ttgtgaactc tggtgttggt gcctctggca 60
gagagggggg tcctgagccc ggatgccggc gtccccgttc aagtaaaaga tcctagtaca 120
cattgggacc tgcactgtac taggatcttt tacttgaacg aggccacggc cttcgccagg 180
gccttggtcc tcctgctctt ggctcctgtg gcttcattcc ctcgggagag aatttctgac 240
cccagccctg ggaccttgtg atatcac 267

<210> SEQ ID NO 13
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 13
tattagatct gatggccgc 19

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
ctccatcact aggggttcct 20

<210> SEQ ID NO 15
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 15
agctctgggt atttaagccc gagtgagcac gcagggtctc cattttgaag cgggaggtta 60

<210> SEQ ID NO 16
<211> LENGTH: 145
<212> TYPE: DNA
<213> ORGANISM: Unknown
<220> FEATURE:
<223> OTHER INFORMATION: AAV2 ITR

<400> SEQUENCE: 16
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag agagggagtg gccaa 145

<210> SEQ ID NO 17
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 17
ctggaggctt gctttgggct gtatgctgtg gaagacttcg agatacactg tttttggcct 60
ctgactgaac agtgttctga agtcttccac aggacacaag gccctttatc agcactcaca 120
tggaacaaat ggccaccgtg ggaggatgac aa 152

<210> SEQ ID NO 18
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 18
ttgtcatcct cccacggtgg ccatttgttc catgtgagtg ctgataaagg gccttgtgtc 60
ctgtggaaga cttcagaaca ctgttcagtc agaggccaaa aacagtgtat ctcgaagtct 120
tccacagcat acagcccaaa gcaagcctcc ag 152

<210> SEQ ID NO 19
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 19
ttgtcatcct cccacggtgg ccatttgttc catgtgagtg ctagtaacag gccttgtgtc 60
cttttagaaa taagtggtag tcacatctgt ggcttcactt gactaccact tatttctaaa 120
gacaacagca tacagccttc agcaagcctc ca 152

<210> SEQ ID NO 20
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 20
tggaggcttg ctgaaggctg tatgctgttg tctttagaaa taagtggtag tcaagtgaag 60
ccacagatgt gactaccact tatttctaaa aggacacaag gcctgttact agcactcaca 120
tggaacaaat ggccaccgtg ggaggatgac aa 152

<210> SEQ ID NO 21
<211> LENGTH: 179
<212> TYPE: DNA
<213> ORGANISM: Artificial Sequence
<220> FEATURE:
<223> OTHER INFORMATION: Synthetic polynucleotide

<400> SEQUENCE: 21
tggaggcttg ctgaaggctg tatgctgttg tcctcgagtg agcgtagggt atcaagacta 60
cgaatactgt aaagccacag atgggtgttc gtagtcttga tacccttcgc ctactagagg 120
acacaaggcc tgttactagc actcacatgg aacaaatggc caccgtggga ggatgacaa 179

<210> SEQ ID NO 22
<211> LENGTH: 179
<212> TYPE: DNA
<213> ORGANISM: Artificial Sequence
<220> FEATURE:
<223> OTHER INFORMATION: Synthetic polynucleotide

<400> SEQUENCE: 22
ttgtcatcct cccacggtgg ccatttgttc catgtgagtg ctagtaacag gccttgtgtc 60
ctctagtagg cgaagggtat caagactacg aacacccatc tgtggcttta cagtattcgt 120
agtcttgata ccctacgctc actcgaggac aacagcatac agccttcagc aagcctcca 179

<210> SEQ ID NO 23
<211> LENGTH: 10960
<212> TYPE: DNA
<213> ORGANISM: Artificial Sequence
<220> FEATURE:

<223> OTHER INFORMATION: Synthetic polynucleotide

<400> SEQUENCE: 23

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tattttttaa ttattttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtcctggt ggcgaggggga gggggtggt cctcgaacgc   1140
cttgcagaac tggcctggat acagagtgga ccggctggcc ccatctggaa gacttcgaga   1200
tacactgttg tcttactgcg ctcaacagtg tatctcgaag tcttccaaat ggtgccagcc   1260
atcgcagcgg ggtgcaggaa atgggggcag cccccctttt tggctatcct tccacgtgtt   1320
ctttttgta tcttttgtgt ttcctagaaa acatctcagt caccaccttt ctgtggctgc   1380
gtgaaagcct tgaggggctc cgggagctag agcctctgct aaccatgttc atgccttctt   1440
ctttttccta cagctcctgg gcaacgtgct ggttattgtg ctgtctcatc attttggcaa   1500
agaattcctc gaagatccga agggaaagtc ttccacgact gtgggatccg ttcgaagata   1560
tcaccggttg agccaccatg gaattcagca gccccagcag agaggaatgc cccaagcctc   1620
tgagccgggt gtcaatcatg gccggatctc tgacaggact gctgctgctt caggccgtgt   1680
cttgggcttc tggcgctaga ccttgcatcc ccaagagctt cggctacagc agcgtcgtgt   1740
gcgtgtgcaa tgccacctac tgcgacagct tcgaccctcc tacctttcct gctctgggca   1800
ccttcagcag atacgagagc accagatccg gcagacggat ggaactgagc atggacccaa   1860
tccaggccaa tcacacaggc actggcctgc tgctgacact gcagcctgag cagaaattcc   1920
agaaagtgaa aggcttcggc ggagccatga cagatgccgc cgctctgaat atcctggctc   1980
tgtctccacc agctcagaac ctgctgctca agagctactt cagcgaggaa ggcatcggct   2040
acaacatcat cagagtgccc atggccagct gcgacttcag catcaggacc tacacctacg   2100
ccgacacacc cgacgatttc cagctgcaca acttcagcct gcctgaagag gacaccaagc   2160
tgaagatccc tctgatccac agagccctgc agctggcaca aagacccgtg tcactgctgg   2220
cctctccatg gacatctccc acctggctga aaacaaatgg cgccgtgaat ggcaagggca   2280
```

-continued

```
gcctgaaagg ccaacctggc gacatctacc accagacctg ggccagatac ttcgtgaagt   2340
tcctggacgc ctatgccgag cacaagctgc agttttgggc cgtgacagcc gagaacgaac   2400
cttctgctgg actgctgagc ggctacccct ttcagtgcct gggctttaca cccgagcacc   2460
agcgggactt tatcgcccgt gatctgggac ccacactggc caatagcacc caccataatg   2520
tgcggctgct gatgctggac gaccagagac tgcttctgcc ccactgggct aaagtggtgc   2580
tgacagatcc tgaggccgcc aaatacgtgc acggaatcgc cgtgcactgg tatctggact   2640
ttctggcccc tgccaaggcc acactgggag agacacacag actgttcccc aacaccatgc   2700
tgttcgccag cgaagcctgt gtgggcagca agttttggga acagagcgtg cggctcggca   2760
gctgggatag aggcatgcag tacagccaca gcatcatcac caacctgctg taccacgtcg   2820
tcggctggac cgactggaat ctggccctga atcctgaagg cggccctaac tgggtccgaa   2880
acttcgtgga cagccccatc atcgtggaca tcaccaagga caccttctac aagcagccca   2940
tgttctacca cctgggacac ttcagcaagt tcatccccga gggctctcag cgcgttggac   3000
tggtggcttc ccagaagaac gatctggacg ccgtggctct gatgcaccct gatggatctg   3060
ctgtggtggt ggtcctgaac cgcagcagca aagatgtgcc cctgaccatc aaggatcccg   3120
ccgtgggatt cctggaaaca atcagccctg gctactccat ccacacctac ctgtggcgta   3180
gacagtgaca attgttaatt aagtttaaac cctcgaggcc gcaagcttat cgataatcaa   3240
cctctggatt acaaaatttg tgaaagattg actggtattc ttaactatgt tgctcctttt   3300
acgctatgtg gatacgctgc tttaatgcct ttgtatcatg ctattgcttc ccgtatggct   3360
ttcattttct cctccttgta taaatcctgg ttgctgtctc tttatgagga gttgtggccc   3420
gttgtcaggc aacgtggcgt ggtgtgcact gtgtttgctg acgcaacccc cactggttgg   3480
ggcattgcca ccacctgtca gctcctttcc gggactttcg ctttccccct ccctattgcc   3540
acggcggaac tcatcgccgc ctgccttgcc cgctgctgga caggggctcg gctgttgggc   3600
actgacaatt ccgtggtgtt gtcggggaaa tcatcgtcct ttccttggct gctcgcctgt   3660
gttgccacct ggattctgcg cgggacgtcc ttctgctacg tcccttcggc cctcaatcca   3720
gcggaccttc cttcccgcgg cctgctgccg gctctgcggc ctcttccgcg tcttcgcctt   3780
cgccctcaga cgagtcggat ctccctttgg gccgcctccc cgcatcgata ccgtcgacta   3840
gagctcgctg atcagcctcg actgtgcctt ctagttgcca gccatctgtt gtttgcccct   3900
cccccgtgcc ttccttgacc ctggaaggtg ccactcccac tgtcctttcc taataaaatg   3960
aggaaattgc atcgcattgt ctgagtaggt gtcattctat tctggggggt ggggtggggc   4020
aggacagcaa gggggaggat tgggaagaca atagcaggca tgctggggag agatccacga   4080
taacaaacag ctttttgggg gtgaacatat tgactgaatt ccctgcaggt tggccactcc   4140
ctctctgcgc gctcgctcgc tcactgaggc cgcccgggca aagcccgggc gtcgggcgac   4200
ctttggtcgc ccggcctcag tgagcgagcg agcgcgcaga gagggagtgg ccaactccat   4260
cactaggggt tcctgcggcc gctcgtacgg tctcgaggaa ttcctgcagg ataacttgcc   4320
aacctcattc taaaatgtat atagaagccc aaaagacaat aacaaaaata ttcttgtaga   4380
acaaaatggg aaagaatgtt ccactaaata tcaagattta gagcaaagca tgagatgtgt   4440
ggggatagac agtgaggctg ataaaataga gtagagctca gaaacagacc cattgatata   4500
tgtaagtgac ctatgaaaaa aatatggcat tttacaatgg gaaaatgatg gtctttttct   4560
tttttagaaa aacagggaaa tatatttata tgtaaaaaat aaaagggaac ccatatgtca   4620
```

```
taccatacac acaaaaaaat tccagtgaat tataagtcta aatggagaag gcaaaacttt   4680
aaatctttta gaaaataata tagaagcatg cagaccagcc tggccaacat gatgaaaccc   4740
tctctactaa taataaaatc agtagaacta ctcaggacta ctttgagtgg gaagtccttt   4800
tctatgaaga cttctttggc caaaattagg ctctaaatgc aaggagatag tgcatcatgc   4860
ctggctgcac ttactgataa atgatgttat caccatcttt aaccaaatgc acaggaacaa   4920
gttatggtac tgatgtgctg gattgagaag gagctctact tccttgacag gacacatttg   4980
tatcaactta aaaaagcaga tttttgccag cagaactatt cattcagagg taggaaactt   5040
agaatagatg atgtcactga ttagcatggc ttccccatct ccacagctgc ttcccaccca   5100
ggttgcccac agttgagttt gtccagtgct cagggctgcc cactctcagt aagaagcccc   5160
acaccagccc ctctccaaat atgttggctg ttccttccat taaagtgacc ccactttaga   5220
gcagcaagtg gatttctgtt tcttacagtt caggaaggag gagtcagctg tgagaacctg   5280
gagcctgaga tgcttctaag tcccactgct actggggtca gggaagccag actccagcat   5340
cagcagtcag gagcactaag cccttgccaa catcctgttt ctcagagaaa ctgcttccat   5400
tataatggtt gtcctttttt aagctatcaa gccaaacaac cagtgtctac cattattctc   5460
atcacctgaa gccaagggtt ctagcaaaag tcaagctgtc ttgtaatggt tgatgtgcct   5520
ccagcttctg tcttcagtca ctccactctt agcctgctct gaatcaactc tgaccacagt   5580
tccctggagc ccctgccacc tgctgcccct gccaccttct ccatctgcag tgctgtgcag   5640
ccttctgcac tcttgcagag ctaataggtg gagacttgaa ggaagaggag gaaagtttct   5700
cataatagcc ttgctgcaag ctcaaatggg aggtgggcac tgtgcccagg agccttggag   5760
caaaggctgt gcccaacctc tgactgcatc caggtttggt cttgacagag ataagaagcc   5820
ctggcttttg gagccaaaat ctaggtcaga cttaggcagg attctcaaag tttatcagca   5880
gaacatgagg cagaagaccc tttctgctcc agcttcttca ggctcaacct tcatcagaat   5940
agatagaaag agaggctgtg agggttctta aaacagaagc aaatctgact cagagaataa   6000
acaacctcct agtaaactac agcttagaca gagcatctgg tggtgagtgt gctcagtgtc   6060
ctactcaact gtctggtatc agccctcatg aggacttctc ttctttccct catagacctc   6120
catctctgtt ttccttagcc tgcagaaatc tggatggcta ttcacagaat gcctgtgctt   6180
tcagagttgc atttttttctc tggtattctg gttcaagcat ttgaaggtag gaaaggttct   6240
ccaagtgcaa gaaagccagc cctgagcctc aactgcctgg ctagtgtggt cagtaggatg   6300
caaaggctgt tgaatgccac aaggccaaac tttaacctgt gtaccacaag cctagcagca   6360
gaggcagctc tgctcactgg aactctctgt cttctttctc ctgagccttt tcttttcctg   6420
agttttctag ctctcctcaa ccttacctct gccctaccca ggacaaaccc aagagccact   6480
gtttctgtga tgtcctctcc agccctaatt aggcatcatg acttcagcct gaccttccat   6540
gctcagaagc agtgctaatc cacttcagat gagctgctct atgcaacaca ggcagagcct   6600
acaaaccttt gcaccagagc cctccacata tcagtgtttg ttcatactca cttcaacagc   6660
aaatgtgact gctgagatta agattttaca caagatggtc tgtaatttca cagttagttt   6720
tatcccatta ggtatgaaag aattagcata attcccctta aacatgaatg aatcttagat   6780
tttttaataa atagttttgg aagtaaagac agagacatca ggagcacaag gaatagcctg   6840
agaggacaaa cagaacaaga aagagtctgg aaatacacag gatgttcttg gcctcctcaa   6900
agcaagtgca agcagatagt accagcagcc ccaggctatc agagcccagt gaagagaagt   6960
accatgaaag ccacagctct aaccaccctg ttccagagtg acagacagtc cccaagacaa   7020
```

```
gccagcctga gccagagaga gaactgcaag agaaagtttc taatttaggt tctgttagat   7080
tcagacaagt gcaggtcatc ctctctccac agctactcac ctctccagcc taacaaagcc   7140
tgcagtccac actccaaccc tggtgtctca cctcctagcc tctcccaaca tcctgctctc   7200
tgaccatctt ctgcatctct catctcacca tctcccactg tctacagcct actcttgcaa   7260
ctaccatctc attttctgac atcctgtcta catcttctgc catactctgc catctaccat   7320
accacctctt accatctacc acaccatctt ttatctccat ccctctcaga agcctccaag   7380
ctgaatcctg ctttatgtgt tcatctcagc ccctgcatgg aaagctgacc ccagaggcag   7440
aactattccc agagagcttg gccaagaaaa acaaaactac cagcctggcc aggctcagga   7500
gtagtaagct gcagtgtctg ttgtgttcta gcttcaacag ctgcaggagt tccactctca   7560
aatgctccac atttctcaca tcctcctgat tctggtcact acccatcttc aaagaacaga   7620
atatctcaca tcagcatact gtgaaggact agtcatgggt gcagctgctc agagctgcaa   7680
agtcattctg gatggtggag agcttacaaa catttcatga tgctcccccc gctctgatgg   7740
ctggagccca atccctacac agactcctgc tgtatgtgtt ttcctttcac tctgagccac   7800
agccagaggg caggcattca gtctcctctt caggctgggg ctggggcact gagaactcac   7860
ccaacacctt gctctcactc cttctgcaaa acaagaaaga gctttgtgct gcagtagcca   7920
tgaagaatga aaggaaggct ttaactaaaa aatgtcagag attattttca accccttact   7980
gtggatcacc agcaaggagg aaacacaaca cagagacatt ttttcccctc aaattatcaa   8040
aagaatcact gcatttgtta aagagagcaa ctgaatcagg aagcagagtt ttgaacatat   8100
cagaagttag gaatctgcat cagagacaaa tgcagtcatg gttgtttgct gcataccagc   8160
cctaatcatt agaagcctca tggacttcaa acatcattcc ctctgacaag atgctctagc   8220
ctaactccat gagataaaat aaatctgcct ttcagagcca aagaagagtc caccagcttc   8280
ttctcagtgt gaacaagagc tccagtcagg ttagtcagtc cagtgcagta gaggagacca   8340
gtctgcatcc tctaattttc aaaggcaaga agatttgttt accctggaca ccaggcacaa   8400
gtgaggtcac agagctctta gatatgcagt cctcatgagt gaggagacta aagcgcatgc   8460
catcaagact tcagtgtaga gaaaacctcc aaaaaagcct cctcactact tctggaatag   8520
ctcagaggcc gaggcggcct cggcctctgc ataaataaaa aaaattagtc agccatgggg   8580
cggagaatgg gcggaactgg gcggagttag gggcgggatg ggcggagtta ggggcgggac   8640
tatggttgct gactaattga gatgcatgct ttgcatactt ctgcctgctg gggagcctgg   8700
ggactttcca cacctggttg ctgactaatt gagatgcatg ctttgcatac ttctgcctgc   8760
tggggagcct ggggactttc cacaccctaa ctgacacaca ttccacagct gcattaatga   8820
atcggccaac gcgcggggag aggcggtttg cgtattgggc gctcttccgc ttcctcgctc   8880
actgactcgc tgcgctcggt cgttcggctg cggcgagcgg tatcagctca ctcaaaggcg   8940
gtaatacggt tatccacaga atcaggggat aacgcaggaa agaacatgtg agcaaaaggc   9000
cagcaaaagg ccaggaaccg taaaaaggcc gcgttgctgg cgtttttcca taggctccgc   9060
ccccctgacg agcatcacaa aaatcgacgc tcaagtcaga ggtggcgaaa cccgacagga   9120
ctataaagat accaggcgtt tccccctgga agctccctcg tgcgctctcc tgttccgacc   9180
ctgccgctta ccggatacct gtccgccttt ctcccttcgg gaagcgtggc gctttctcat   9240
agctcacgct gtaggtatct cagttcggtg taggtcgttc gctccaagct gggctgtgtg   9300
cacgaacccc ccgttcagcc cgaccgctgc gccttatccg gtaactatcg tcttgagtcc   9360
```

aacccggtaa gacacgactt atcgccactg gcagcagcca ctggtaacag gattagcaga 9420
gcgaggtatg taggcggtgc tacagagttc ttgaagtggt ggcctaacta cggctacact 9480
agaagaacag tatttggtat ctgcgctctg ctgaagccag ttaccttcgg aaaaagagtt 9540
ggtagctctt gatccggcaa acaaaccacc gctggtagcg gtggtttttt tgtttgcaag 9600
cagcagatta cgcgcagaaa aaaaggatct caagaagatc ctttgatctt ttctacgggg 9660
tctgacgctc agtggaacga aaactcacgt taagggattt tggtcatgag attatcaaaa 9720
aggatcttca cctagatcct tttaaattaa aaatgaagtt ttaaatcaat ctaaagtata 9780
tatgagtaaa cttggtctga cagttaccaa tgcttaatca gtgaggcacc tatctcagcg 9840
atctgtctat ttcgttcatc catagttgcc tgactcctgc aaaccacgtt gtgtctcaaa 9900
atctctgatg ttacattgca caagataaaa atatatcatc atgaacaata aaactgtctg 9960
cttacataaa cagtaataca aggggtgtta tgagccatat tcaacgggaa acgtcttgct 10020
cgaggccgcg attaaattcc aacatggatg ctgatttata tgggtataaa tgggctcgcg 10080
ataatgtcgg gcaatcaggt gcgacaatct atcgattgta tgggaagccc gatgcgccag 10140
agttgtttct gaaacatggc aaaggtagcg ttgccaatga tgttacagat gagatggtca 10200
gactaaactg gctgacggaa tttatgcctc ttccgaccat caagcatttt atccgtactc 10260
ctgatgatgc atggttactc accactgcga tccccgggaa aacagcattc caggtattag 10320
aagaatatcc tgattcaggt gaaaatattg ttgatgcgct ggcagtgttc ctgcgccggt 10380
tgcattcgat tcctgtttgt aattgtcctt ttaacagcga tcgcgtattt cgtctcgctc 10440
aggcgcaatc acgaatgaat aacggtttgg ttgatgcgag tgattttgat gacgagcgta 10500
atggctggcc tgttgaacaa gtctggaaag aaatgcataa gcttttgcca ttctcaccgg 10560
attcagtcgt cactcatggt gatttctcac ttgataacct tatttttgac gaggggaaat 10620
taataggttg tattgatgtt ggacgagtcg gaatcgcaga ccgataccag gatcttgcca 10680
tcctatggaa ctgcctcggt gagttttctc cttcattaca gaaacggctt tttcaaaaat 10740
atggtattga taatcctgat atgaataaat tgcagtttca tttgatgctc gatgagtttt 10800
tctaagggcg gcctgccacc atacccacgc cgaaacaagc gctcatgagc ccgaagtggc 10860
gagcccgatc ttccccatcg gtgatgtcgg cgatataggc gccagcaacc gcacctgtgg 10920
cgccggtgat gagggcgcgc caagtcgacg tccggcagtc 10960

<210> SEQ ID NO 24
<211> LENGTH: 10013
<212> TYPE: DNA
<213> ORGANISM: Artificial Sequence
<220> FEATURE:
<223> OTHER INFORMATION: Synthetic polynucleotide

<400> SEQUENCE: 24
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480

```
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttttaa ttattttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtttcttg tggctgcgtg aaagccttga ggggctccgg   1140
gagctagagc ctctgctaac catgttcatg ccttcttctt tttcctacag ctcctgggca   1200
acgtgctggt tattgtgctg tctcatcatt ttggcaaaga attcctcgaa gatccgaagg   1260
gaaagtcttc cacgactgtg ggatccgttc gaagatatca ccggttgagc caccatggac   1320
gtgttcatga agggcctgag caaggccaag gagggcgtgg tggccgccgc cgagaagacc   1380
aagcagggcg tggccgaggc cgccggcaag accaaggagg gcgtgctgta cgtgggcagc   1440
aagaccaagg agggcgtggt gcacggcgtg gccaccgtgg ccgagaagac caaggagcag   1500
gtgaccaacg tgggcggcgc cgtggtgacc ggcgtgaccg ccgtggccca gaagaccgtg   1560
gagggcgccg gcagcatcgc cgccgccacc ggcttcgtga agaaggacca gctgggcaag   1620
aacgaggagg gcgcccccca ggagggcatc ctggaggaca tgcccgtgga ccccgacaac   1680
gaggcctacg agatgcccag cgaggagggc taccaggact acgagcccga ggcctaagaa   1740
atatctttgc tcccagtttc ttgagatctg ctgacagatg ttccatcctg tacaagtgct   1800
cagttccaat gtgcccagtc atgacatttc tcaaagtttt tacagtgtat ctcgaagtct   1860
tccatcagca gtgattgaag tatctgtacc tgcccccact cagcatttcg gtgcttccct   1920
ttcactgaag tgaatacatg gtagcagggt ctttgtgtgc tgtggatttt gtggcttcaa   1980
tctacgatgt taaaacaaat taaaaacacc taagtgacta ccacttattt ctaaatcctc   2040
actatttttt tgttgctgtt gttcagaagt tgttagtgat ttgctatcat atattataag   2100
atttttaggt gtcttttaat gatactgtct aagaataatg acgtattgtg aaatttgtta   2160
atatatataa tacttaaaaa tatgtgagca tgaaactatg cacctataaa tactaaatat   2220
gaaattttac cattttgctg acaattgtta attaagttta aaccctcgag gccgcaagct   2280
tatcgataat caacctctgg attacaaaat ttgtgaaaga ttgactggta ttcttaacta   2340
tgttgctcct tttacgctat gtggatacgc tgctttaatg cctttgtatc atgctattgc   2400
ttcccgtatg gctttcattt tctcctcctt gtataaatcc tggttgctgt ctctttatga   2460
ggagttgtgg cccgttgtca ggcaacgtgg cgtggtgtgc actgtgtttg ctgacgcaac   2520
ccccactggt tggggcattg ccaccacctg tcagctcctt tccgggactt tcgctttccc   2580
cctccctatt gccacggcgg aactcatcgc cgcctgcctt gcccgctgct ggacaggggc   2640
tcggctgttg ggcactgaca attccgtggt gttgtcgggg aaatcatcgt cctttccttg   2700
gctgctcgcc tgtgttgcca cctggattct gcgcgggacg tccttctgct acgtcccttc   2760
ggccctcaat ccagcggacc ttccttcccg cggcctgctg ccggctctgc ggcctcttcc   2820
```

-continued

```
gcgtcttcgc cttcgccctc agacgagtcg gatctccctt tgggccgcct ccccgcatcg   2880
ataccgtcga ctagagctcg ctgatcagcc tcgactgtgc cttctagttg ccagccatct   2940
gttgtttgcc cctcccccgt gccttccttg accctggaag gtgccactcc cactgtcctt   3000
tcctaataaa atgaggaaat tgcatcgcat tgtctgagta ggtgtcattc tattctgggg   3060
ggtggggtgg ggcaggacag caagggggag gattgggaag acaatagcag gcatgctggg   3120
gagagatcca cgataacaaa cagctttttt ggggtgaaca tattgactga attccctgca   3180
ggttggccac tccctctctg cgcgctcgct cgctcactga ggccgcccgg gcaaagcccg   3240
ggcgtcgggc gacctttggt cgcccggcct cagtgagcga gcgagcgcgc agagagggag   3300
tggccaactc catcactagg ggttcctgcg gccgctcgta cggtctcgag gaattcctgc   3360
aggataactt gccaacctca ttctaaaatg tatatagaag cccaaaagac aataacaaaa   3420
atattcttgt agaacaaaat gggaaagaat gttccactaa atatcaagat ttagagcaaa   3480
gcatgagatg tgtggggata gacagtgagg ctgataaaat agagtagagc tcagaaacag   3540
acccattgat atatgtaagt gacctatgaa aaaaatatgg cattttacaa tgggaaaatg   3600
atggtctttt tctttttttag aaaaacaggg aaatatattt atatgtaaaa aataaaaggg   3660
aacccatatg tcataccata cacacaaaaa aattccagtg aattataagt ctaaatggag   3720
aaggcaaaac tttaaatctt ttagaaaata atatagaagc atgcagacca gcctggccaa   3780
catgatgaaa ccctctctac taataataaa atcagtagaa ctactcagga ctactttgag   3840
tgggaagtcc ttttctatga agacttcttt ggccaaaatt aggctctaaa tgcaaggaga   3900
tagtgcatca tgcctggctg cacttactga taaatgatgt tatcaccatc tttaaccaaa   3960
tgcacaggaa caagttatgg tactgatgtg ctggattgag aaggagctct acttccttga   4020
caggacacat ttgtatcaac ttaaaaaagc agatttttgc cagcagaact attcattcag   4080
aggtaggaaa cttagaatag atgatgtcac tgattagcat ggcttcccca tctccacagc   4140
tgcttcccac ccaggttgcc cacagttgag tttgtccagt gctcagggct gcccactctc   4200
agtaagaagc cccacaccag cccctctcca aatatgttgg ctgttccttc cattaaagtg   4260
accccacttt agagcagcaa gtggatttct gtttcttaca gttcaggaag gaggagtcag   4320
ctgtgagaac ctggagcctg agatgcttct aagtcccact gctactgggg tcagggaagc   4380
cagactccag catcagcagt caggagcact aagcccttgc caacatcctg tttctcagag   4440
aaactgcttc cattataatg gttgtccttt tttaagctat caagccaaac aaccagtgtc   4500
taccattatt ctcatcacct gaagccaagg gttctagcaa aagtcaagct gtcttgtaat   4560
ggttgatgtg cctccagctt ctgtcttcag tcactccact cttagcctgc tctgaatcaa   4620
ctctgaccac agttccctgg agcccctgcc acctgctgcc cctgccacct tctccatctg   4680
cagtgctgtg cagccttctg cactcttgca gagctaatag gtggagactt gaaggaagag   4740
gaggaaagtt tctcataata gccttgctgc aagctcaaat gggaggtggg cactgtgccc   4800
aggagccttg gagcaaaggc tgtgcccaac ctctgactgc atccaggttt ggtcttgaca   4860
gagataagaa gccctggctt ttggagccaa aatctaggtc agacttaggc aggattctca   4920
aagtttatca gcagaacatg aggcagaaga ccctttctgc tccagcttct tcaggctcaa   4980
ccttcatcag aatagataga aagagaggct gtgagggttc ttaaaacaga agcaaatctg   5040
actcagagaa taaacaacct cctagtaaac tacagcttag acagagcatc tggtggtgag   5100
tgtgctcagt gtcctactca actgtctggt atcagccctc atgaggactt ctcttctttc   5160
cctcatagac ctccatctct gttttcctta gcctgcagaa atctggatgg ctattcacag   5220
```

```
aatgcctgtg ctttcagagt tgcatttttt ctctggtatt ctggttcaag catttgaagg   5280
taggaaaggt tctccaagtg caagaaagcc agccctgagc ctcaactgcc tggctagtgt   5340
ggtcagtagg atgcaaaggc tgttgaatgc cacaaggcca aactttaacc tgtgtaccac   5400
aagcctagca gcagaggcag ctctgctcac tggaactctc tgtcttcttt ctcctgagcc   5460
ttttcttttc ctgagttttc tagctctcct caaccttacc tctgccctac ccaggacaaa   5520
cccaagagcc actgtttctg tgatgtcctc tccagcccta attaggcatc atgacttcag   5580
cctgaccttc catgctcaga agcagtgcta atccacttca gatgagctgc tctatgcaac   5640
acaggcagag cctacaaacc tttgcaccag agccctccac atatcagtgt ttgttcatac   5700
tcacttcaac agcaaatgtg actgctgaga ttaagatttt acacaagatg gtctgtaatt   5760
tcacagttag ttttatccca ttaggtatga aagaattagc ataattcccc ttaaacatga   5820
atgaatctta gattttttaa taaatagttt tggaagtaaa gacagagaca tcaggagcac   5880
aaggaatagc ctgagaggac aaacagaaca agaaagagtc tggaaataca caggatgttc   5940
ttggcctcct caaagcaagt gcaagcagat agtaccagca gccccaggct atcagagccc   6000
agtgaagaga agtaccatga aagccacagc tctaaccacc ctgttccaga gtgacagaca   6060
gtccccaaga caagccagcc tgagccagag agagaactgc aagagaaagt ttctaattta   6120
ggttctgtta gattcagaca agtgcaggtc atcctctctc cacagctact cacctctcca   6180
gcctaacaaa gcctgcagtc cacactccaa ccctggtgtc tcacctccta gcctctccca   6240
acatcctgct ctctgaccat cttctgcatc tctcatctca ccatctccca ctgtctacag   6300
cctactcttg caactaccat ctcattttct gacatcctgt ctacatcttc tgccatactc   6360
tgccatctac cataccacct cttaccatct accacaccat cttttatctc catccctctc   6420
agaagcctcc aagctgaatc ctgctttatg tgttcatctc agcccctgca tggaaagctg   6480
accccagagg cagaactatt cccagagagc ttggccaaga aaaacaaaac taccagcctg   6540
gccaggctca ggagtagtaa gctgcagtgt ctgttgtgtt ctagcttcaa cagctgcagg   6600
agttccactc tcaaatgctc cacatttctc acatcctcct gattctggtc actacccatc   6660
ttcaaagaac agaatatctc acatcagcat actgtgaagg actagtcatg ggtgcagctg   6720
ctcagagctg caaagtcatt ctggatggtg gagagcttac aaacatttca tgatgctccc   6780
cccgctctga tggctggagc ccaatcccta cacagactcc tgctgtatgt gttttccttt   6840
cactctgagc cacagccaga gggcaggcat tcagtctcct cttcaggctg gggctggggc   6900
actgagaact cacccaacac cttgctctca ctccttctgc aaaacaagaa agagctttgt   6960
gctgcagtag ccatgaagaa tgaaaggaag gctttaacta aaaaatgtca gagattattt   7020
tcaacccctt actgtggatc accagcaagg aggaaacaca acacagagac atttttttccc   7080
ctcaaattat caaaagaatc actgcatttg ttaaagagag caactgaatc aggaagcaga   7140
gttttgaaca tatcagaagt taggaatctg catcagagac aaatgcagtc atggttgttt   7200
gctgcatacc agccctaatc attagaagcc tcatggactt caaacatcat tccctctgac   7260
aagatgctct agcctaactc catgagataa aataaatctg cctttcagag ccaaagaaga   7320
gtccaccagc ttcttctcag tgtgaacaag agctccagtc aggttagtca gtccagtgca   7380
gtagaggaga ccagtctgca tcctctaatt ttcaaaggca agaagatttg tttaccctgg   7440
acaccaggca caagtgaggt cacagagctc ttagatatgc agtcctcatg agtgaggaga   7500
ctaaagcgca tgccatcaag acttcagtgt agagaaaacc tccaaaaaag cctcctcact   7560
```

```
acttctggaa tagctcagag gccgaggcgg cctcggcctc tgcataaata aaaaaaatta   7620
gtcagccatg gggcggagaa tgggcggaac tgggcggagt taggggcggg atgggcggag   7680
ttaggggcgg gactatggtt gctgactaat tgagatgcat gctttgcata cttctgcctg   7740
ctggggagcc tggggacttt ccacacctgg ttgctgacta attgagatgc atgctttgca   7800
tacttctgcc tgctggggag cctggggact ttccacaccc taactgacac acattccaca   7860
gctgcattaa tgaatcggcc aacgcgcggg gagaggcggt ttgcgtattg ggcgctcttc   7920
cgcttcctcg ctcactgact cgctgcgctc ggtcgttcgg ctgcggcgag cggtatcagc   7980
tcactcaaag gcggtaatac ggttatccac agaatcaggg gataacgcag gaaagaacat   8040
gtgagcaaaa ggccagcaaa aggccaggaa ccgtaaaaag gccgcgttgc tggcgttttt   8100
ccataggctc cgcccccctg acgagcatca caaaaatcga cgctcaagtc agaggtggcg   8160
aaacccgaca ggactataaa gataccaggc gtttccccct ggaagctccc tcgtgcgctc   8220
tcctgttccg accctgccgc ttaccggata cctgtccgcc tttctccctt cgggaagcgt   8280
ggcgctttct catagctcac gctgtaggta tctcagttcg gtgtaggtcg ttcgctccaa   8340
gctgggctgt gtgcacgaac cccccgttca gcccgaccgc tgcgccttat ccggtaacta   8400
tcgtcttgag tccaacccgg taagacacga cttatcgcca ctggcagcag ccactggtaa   8460
caggattagc agagcgaggt atgtaggcgg tgctacagag ttcttgaagt ggtggcctaa   8520
ctacggctac actagaagaa cagtatttgg tatctgcgct ctgctgaagc cagttacctt   8580
cggaaaaaga gttggtagct cttgatccgg caaacaaacc accgctggta gcggtggttt   8640
ttttgtttgc aagcagcaga ttacgcgcag aaaaaaagga tctcaagaag atcctttgat   8700
cttttctacg gggtctgacg ctcagtggaa cgaaaactca cgttaaggga ttttggtcat   8760
gagattatca aaaaggatct tcacctagat ccttttaaat taaaaatgaa gttttaaatc   8820
aatctaaagt atatatgagt aaacttggtc tgacagttac caatgcttaa tcagtgaggc   8880
acctatctca gcgatctgtc tatttcgttc atccatagtt gcctgactcc tgcaaaccac   8940
gttgtgtctc aaaatctctg atgttacatt gcacaagata aaaatatatc atcatgaaca   9000
ataaaactgt ctgcttacat aaacagtaat acaaggggtg ttatgagcca tattcaacgg   9060
gaaacgtctt gctcgaggcc gcgattaaat tccaacatgg atgctgattt atatgggtat   9120
aaatgggctc gcgataatgt cgggcaatca ggtgcgacaa tctatcgatt gtatgggaag   9180
cccgatgcgc cagagttgtt tctgaaacat ggcaaaggta gcgttgccaa tgatgttaca   9240
gatgagatgg tcagactaaa ctggctgacg gaatttatgc ctcttccgac catcaagcat   9300
tttatccgta ctcctgatga tgcatggtta ctcaccactg cgatccccgg gaaaacagca   9360
ttccaggtat tagaagaata tcctgattca ggtgaaaata ttgttgatgc gctggcagtg   9420
ttcctgcgcc ggttgcattc gattcctgtt tgtaattgtc cttttaacag cgatcgcgta   9480
tttcgtctcg ctcaggcgca atcacgaatg aataacggtt tggttgatgc gagtgatttt   9540
gatgacgagc gtaatggctg gcctgttgaa caagtctgga aagaaatgca taagcttttg   9600
ccattctcac cggattcagt cgtcactcat ggtgatttct cacttgataa ccttattttt   9660
gacgagggga aattaatagg ttgtattgat gttggacgag tcggaatcgc agaccgatac   9720
caggatcttg ccatcctatg gaactgcctc ggtgagtttt ctccttcatt acagaaacgg   9780
ctttttcaaa aatatggtat tgataatcct gatatgaata aattgcagtt tcatttgatg   9840
ctcgatgagt ttttctaagg gcggcctgcc accataccca cgccgaaaca agcgctcatg   9900
agcccgaagt ggcgagcccg atcttcccca tcggtgatgt cggcgatata ggcgccagca   9960
```

accgcacctg tggcgccggt gatgagggcg cgccaagtcg acgtccggca gtc 10013

<210> SEQ ID NO 25
<211> LENGTH: 10849
<212> TYPE: DNA
<213> ORGANISM: Artificial Sequence
<220> FEATURE:
<223> OTHER INFORMATION: Synthetic polynucleotide

<400> SEQUENCE: 25
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600
tacatgacct tatgggactt tcctacttgg cagtacatct acgtattagt catcgctatt 660
accatggtcg aggtgagccc cacgttctgc ttcactctcc ccatctcccc cccctcccca 720
cccccaattt tgtatttatt tattttttaa ttattttgtg cagcgatggg ggcggggggg 780 ggggggggc gcgcgccagg cggggcgggg cggggcgagg ggcggggcgg ggcgaggcgg 840
agaggtgcgg cggcagccaa tcagagcggc gcgctccgaa agtttccttt tatggcgagg 900
cggcggcggc ggcggcccta taaaaagcga agcgcgcggc gggcgggagt cgctgcgacg 960
ctgccttcgc cccgtgcccc gctccgccgc cgcctcgcgc cgcccgcccc ggctctgact 1020
gaccgcgtta ctcccacagg tgagcgggcg ggacggccct tctcctccgg gctgtaatta 1080
gcgcttggtt taatgacggc ttgtctggag gcttgctttg ggctgtatgc tgtggaagac 1140
ttcgagatac actgtttttg gcctctgact gaacagtgtt ctgaagtctt ccacaggaca 1200
caaggccctt tatcagcact cacatggaac aaatggccac cgtgggagga tgacaatttc 1260
tgtggctgcg tgaaagcctt gaggggctcc gggagctaga gcctctgcta accatgttca 1320
tgccttcttc tttttcctac agctcctggg caacgtgctg gttattgtgc tgtctcatca 1380
ttttggcaaa gaattcctcg aagatccgaa gggaaagtct tccacgactg tgggatccgt 1440
tcgaagatat caccggttga gccaccatgg aattcagcag ccccagcaga gaggaatgcc 1500
ccaagcctct gagccgggtg tcaatcatgg ccggatctct gacaggactg ctgctgcttc 1560
aggccgtgtc ttgggcttct ggcgctagac cttgcatccc caagagcttc ggctacagca 1620
gcgtcgtgtg cgtgtgcaat gccacctact gcgacagctt cgaccctcct acctttcctg 1680
ctctgggcac cttcagcaga tacgagagca ccagatccgg cagacggatg gaactgagca 1740
tgggacccat ccaggccaat cacacaggca ctggcctgct gctgacactg cagcctgagc 1800
agaaattcca gaaagtgaaa ggcttcggcg gagccatgac agatgccgcc gctctgaata 1860
tcctggctct gtctccacca gctcagaacc tgctgctcaa gagctacttc agcgaggaag 1920
gcatcggcta caacatcatc agagtgccca tggccagctg cgacttcagc atcaggacct 1980

-continued

```
acacctacgc cgacacaccc gacgatttcc agctgcacaa cttcagcctg cctgaagagg   2040

acaccaagct gaagatccct ctgatccaca gagccctgca gctggcacaa agacccgtgt   2100

cactgctggc ctctccatgg acatctccca cctggctgaa aacaaatggc gccgtgaatg   2160

gcaagggcag cctgaaaggc caacctggcg acatctacca ccagacctgg gccagatact   2220

tcgtgaagtt cctggacgcc tatgccgagc acaagctgca gttttgggcc gtgacagccg   2280

agaacgaacc ttctgctgga ctgctgagcg gctacccctt tcagtgcctg ggctttacac   2340

ccgagcacca gcgggacttt atcgcccgtg atctgggacc cacactggcc aatagcaccc   2400

accataatgt gcggctgctg atgctggacg accagagact gcttctgccc cactgggcta   2460

aagtggtgct gacagatcct gaggccgcca aatacgtgca cggaatcgcc gtgcactggt   2520

atctggactt tctggcccct gccaaggcca cactgggaga gacacacaga ctgttcccca   2580

acaccatgct gttcgccagc gaagcctgtg tgggcagcaa gttttgggaa cagagcgtgc   2640

ggctcggcag ctgggataga ggcatgcagt acagccacag catcatcacc aacctgctgt   2700

accacgtcgt cggctggacc gactggaatc tggccctgaa tcctgaaggc ggccctaact   2760

gggtccgaaa cttcgtggac agccccatca tcgtggacat caccaaggac accttctaca   2820

agcagcccat gttctaccac ctgggacact tcagcaagtt catccccgag ggctctcagc   2880

gcgttggact ggtggcttcc cagaagaacg atctggacgc cgtggctctg atgcaccctg   2940

atggatctgc tgtggtggtg gtcctgaacc gcagcagcaa agatgtgccc ctgaccatca   3000

aggatcccgc cgtgggattc ctggaaacaa tcagccctgg ctactccatc cacacctacc   3060

tgtggcgtag acagtgacaa ttgttaatta agtttaaacc ctcgaggccg caagcttatc   3120

gataatcaac ctctggatta caaaatttgt gaaagattga ctggtattct taactatgtt   3180

gctcctttta cgctatgtgg atacgctgct ttaatgcctt tgtatcatgc tattgcttcc   3240

cgtatggctt tcattttctc ctccttgtat aaatcctggt tgctgtctct ttatgaggag   3300

ttgtggcccg ttgtcaggca acgtggcgtg gtgtgcactg tgtttgctga cgcaaccccc   3360

actggttggg gcattgccac cacctgtcag ctcctttccg ggactttcgc tttccccctc   3420

cctattgcca cggcggaact catcgccgcc tgccttgccc gctgctggac aggggctcgg   3480

ctgttgggca ctgacaattc cgtggtgttg tcggggaaat catcgtcctt tccttggctg   3540

ctcgcctgtg ttgccacctg gattctgcgc gggacgtcct tctgctacgt cccttcggcc   3600

ctcaatccag cggaccttcc ttcccgcggc ctgctgccgg ctctgcggcc tcttccgcgt   3660

cttcgccttc gccctcagac gagtcggatc tccctttggg ccgcctcccc gcatcgatac   3720

cgtcgactag agctcgctga tcagcctcga ctgtgccttc tagttgccag ccatctgttg   3780

tttgcccctc ccccgtgcct tccttgaccc tggaaggtgc cactcccact gtcctttcct   3840

aataaaatga ggaaattgca tcgcattgtc tgagtaggtg tcattctatt ctggggggtg   3900

gggtggggca ggacagcaag ggggaggatt gggaagacaa tagcaggcat gctggggaga   3960

gatccacgat aacaaacagc tttttggggg tgaacatatt gactgaattc cctgcaggtt   4020

ggccactccc tctctgcgcg ctcgctcgct cactgaggcc gcccgggcaa agcccgggcg   4080

tcgggcgacc tttggtcgcc cggcctcagt gagcgagcga gcgcgcagag agggagtggc   4140

caactccatc actaggggtt cctgcggccg ctcgtacggt ctcgaggaat tcctgcagga   4200

taacttgcca acctcattct aaaatgtata tagaagccca aaagacaata acaaaaatat   4260

tcttgtagaa caaaatggga aagaatgttc cactaaatat caagatttag agcaaagcat   4320

gagatgtgtg ggatagaca gtgaggctga taaaatagag tagagctcag aaacagaccc   4380
```

```
attgatatat gtaagtgacc tatgaaaaaa atatggcatt ttacaatggg aaaatgatgg   4440
tctttttctt ttttagaaaa acagggaaat atatttatat gtaaaaaata aaagggaacc   4500
catatgtcat accatacaca caaaaaaatt ccagtgaatt ataagtctaa atggagaagg   4560
caaaacttta aatcttttag aaaataatat agaagcatgc agaccagcct ggccaacatg   4620
atgaaaccct ctctactaat aataaaatca gtagaactac tcaggactac tttgagtggg   4680
aagtcctttt ctatgaagac ttctttggcc aaaattaggc tctaaatgca aggagatagt   4740
gcatcatgcc tggctgcact tactgataaa tgatgttatc accatcttta accaaatgca   4800
caggaacaag ttatggtact gatgtgctgg attgagaagg agctctactt ccttgacagg   4860
acacatttgt atcaacttaa aaaagcagat ttttgccagc agaactattc attcagaggt   4920
aggaaactta gaatagatga tgtcactgat tagcatggct tccccatctc cacagctgct   4980
tcccacccag gttgcccaca gttgagtttg tccagtgctc agggctgccc actctcagta   5040
agaagcccca caccagcccc tctccaaata tgttggctgt tccttccatt aaagtgaccc   5100
cactttagag cagcaagtgg atttctgttt cttacagttc aggaaggagg agtcagctgt   5160
gagaacctgg agcctgagat gcttctaagt cccactgcta ctggggtcag ggaagccaga   5220
ctccagcatc agcagtcagg agcactaagc ccttgccaac atcctgtttc tcagagaaac   5280
tgcttccatt ataatggttg tcctttttta agctatcaag ccaaacaacc agtgtctacc   5340
attattctca tcacctgaag ccaagggttc tagcaaaagt caagctgtct tgtaatggtt   5400
gatgtgcctc cagcttctgt cttcagtcac tccactctta gcctgctctg aatcaactct   5460
gaccacagtt ccctggagcc cctgccacct gctgcccctg ccaccttctc catctgcagt   5520
gctgtgcagc cttctgcact cttgcagagc taataggtgg agacttgaag gaagaggagg   5580
aaagtttctc ataatagcct tgctgcaagc tcaaatggga ggtgggcact gtgcccagga   5640
gccttggagc aaaggctgtg cccaacctct gactgcatcc aggtttggtc ttgacagaga   5700
taagaagccc tggcttttgg agccaaaatc taggtcagac ttaggcagga ttctcaaagt   5760
ttatcagcag aacatgaggc agaagaccct ttctgctcca gcttcttcag gctcaacctt   5820
catcagaata gatagaaaga gaggctgtga gggttcttaa aacagaagca aatctgactc   5880
agagaataaa caacctccta gtaaactaca gcttagacag agcatctggt ggtgagtgtg   5940
ctcagtgtcc tactcaactg tctggtatca gccctcatga ggacttctct tctttccctc   6000
atagacctcc atctctgttt tccttagcct gcagaaatct ggatggctat tcacagaatg   6060
cctgtgcttt cagagttgca ttttttctct ggtattctgg ttcaagcatt tgaaggtagg   6120
aaaggttctc caagtgcaag aaagccagcc ctgagcctca actgcctggc tagtgtggtc   6180
agtaggatgc aaaggctgtt gaatgccaca aggccaaact ttaacctgtg taccacaagc   6240
ctagcagcag aggcagctct gctcactgga actctctgtc ttctttctcc tgagcctttt   6300
cttttcctga gttttctagc tctcctcaac cttacctctg ccctacccag gacaaaccca   6360
agagccactg tttctgtgat gtcctctcca gccctaatta ggcatcatga cttcagcctg   6420
accttccatg ctcagaagca gtgctaatcc acttcagatg agctgctcta tgcaacacag   6480
gcagagccta caaacctttg caccagagcc ctccacatat cagtgtttgt tcatactcac   6540
ttcaacagca aatgtgactg ctgagattaa gattttacac aagatggtct gtaatttcac   6600
agttagtttt atcccattag gtatgaaaga attagcataa ttccccttaa acatgaatga   6660
atcttagatt ttttaataaa tagttttgga agtaaagaca gagacatcag gagcacaagg   6720
```

```
aatagcctga gaggacaaac agaacaagaa agagtctgga aatacacagg atgttcttgg   6780
cctcctcaaa gcaagtgcaa gcagatagta ccagcagccc caggctatca gagcccagtg   6840
aagagaagta ccatgaaagc cacagctcta accaccctgt tccagagtga cagacagtcc   6900
ccaagacaag ccagcctgag ccagagagag aactgcaaga gaaagtttct aatttaggtt   6960
ctgttagatt cagacaagtg caggtcatcc tctctccaca gctactcacc tctccagcct   7020
aacaaagcct gcagtccaca ctccaaccct ggtgtctcac ctcctagcct ctcccaacat   7080
cctgctctct gaccatcttc tgcatctctc atctcaccat ctcccactgt ctacagccta   7140
ctcttgcaac taccatctca ttttctgaca tcctgtctac atcttctgcc atactctgcc   7200
atctaccata ccacctctta ccatctacca caccatcttt tatctccatc cctctcagaa   7260
gcctccaagc tgaatcctgc tttatgtgtt catctcagcc cctgcatgga aagctgaccc   7320
cagaggcaga actattccca gagagcttgg ccaagaaaaa caaaactacc agcctggcca   7380
ggctcaggag tagtaagctg cagtgtctgt tgtgttctag cttcaacagc tgcaggagtt   7440
ccactctcaa atgctccaca tttctcacat cctcctgatt ctggtcacta cccatcttca   7500
aagaacagaa tatctcacat cagcatactg tgaaggacta gtcatgggtg cagctgctca   7560
gagctgcaaa gtcattctgg atggtggaga gcttacaaac atttcatgat gctccccccg   7620
ctctgatggc tggagcccaa tccctacaca gactcctgct gtatgtgttt tcctttcact   7680
ctgagccaca gccagagggc aggcattcag tctcctcttc aggctggggc tggggcactg   7740
agaactcacc caacaccttg ctctcactcc ttctgcaaaa caagaaagag ctttgtgctg   7800
cagtagccat gaagaatgaa aggaaggctt taactaaaaa atgtcagaga ttattttcaa   7860
ccccttactg tggatcacca gcaaggagga aacacaacac agagacattt tttcccctca   7920
aattatcaaa agaatcactg catttgttaa agagagcaac tgaatcagga agcagagttt   7980
tgaacatatc agaagttagg aatctgcatc agagacaaat gcagtcatgg ttgtttgctg   8040
cataccagcc ctaatcatta gaagcctcat ggacttcaaa catcattccc tctgacaaga   8100
tgctctagcc taactccatg agataaaata aatctgcctt tcagagccaa agaagagtcc   8160
accagcttct tctcagtgtg aacaagagct ccagtcaggt tagtcagtcc agtgcagtag   8220
aggagaccag tctgcatcct ctaattttca aaggcaagaa gatttgttta ccctggacac   8280
caggcacaag tgaggtcaca gagctcttag atatgcagtc ctcatgagtg aggagactaa   8340
agcgcatgcc atcaagactt cagtgtagag aaaacctcca aaaaagcctc ctcactactt   8400
ctggaatagc tcagaggccg aggcggcctc ggcctctgca taaataaaaa aaattagtca   8460
gccatggggc ggagaatggg cggaactggg cggagttagg ggcgggatgg gcggagttag   8520
gggcgggact atggttgctg actaattgag atgcatgctt tgcatacttc tgcctgctgg   8580
ggagcctggg gactttccac acctggttgc tgactaattg agatgcatgc tttgcatact   8640
tctgcctgct ggggagcctg gggactttcc acaccctaac tgacacacat tccacagctg   8700
cattaatgaa tcggccaacg cgcggggaga ggcggtttgc gtattgggcg ctcttccgct   8760
tcctcgctca ctgactcgct gcgctcggtc gttcggctgc ggcgagcggt atcagctcac   8820
tcaaaggcgg taatacggtt atccacagaa tcaggggata acgcaggaaa gaacatgtga   8880
gcaaaaggcc agcaaaaggc caggaaccgt aaaaaggccg cgttgctggc gtttttccat   8940
aggctccgcc cccctgacga gcatcacaaa aatcgacgct caagtcagag gtggcgaaac   9000
ccgacaggac tataaagata ccaggcgttt ccccctggaa gctccctcgt gcgctctcct   9060
gttccgaccc tgccgcttac cggatacctg tccgcctttc tcccttcggg aagcgtggcg   9120
```

```
ctttctcata gctcacgctg taggtatctc agttcggtgt aggtcgttcg ctccaagctg   9180
ggctgtgtgc acgaaccccc cgttcagccc gaccgctgcg ccttatccgg taactatcgt   9240
cttgagtcca acccggtaag acacgactta tcgccactgg cagcagccac tggtaacagg   9300
attagcagag cgaggtatgt aggcggtgct acagagttct tgaagtggtg gcctaactac   9360
ggctacacta gaagaacagt atttggtatc tgcgctctgc tgaagccagt taccttcgga   9420
aaaagagttg gtagctcttg atccggcaaa caaaccaccg ctggtagcgg tggttttttt   9480
gtttgcaagc agcagattac gcgcagaaaa aaaggatctc aagaagatcc tttgatcttt   9540
tctacggggt ctgacgctca gtggaacgaa aactcacgtt aagggatttt ggtcatgaga   9600
ttatcaaaaa ggatcttcac ctagatcctt ttaaattaaa aatgaagttt taaatcaatc   9660
taaagtatat atgagtaaac ttggtctgac agttaccaat gcttaatcag tgaggcacct   9720
atctcagcga tctgtctatt tcgttcatcc atagttgcct gactcctgca aaccacgttg   9780
tgtctcaaaa tctctgatgt tacattgcac aagataaaaa tatatcatca tgaacaataa   9840
aactgtctgc ttacataaac agtaatacaa ggggtgttat gagccatatt caacgggaaa   9900
cgtcttgctc gaggccgcga ttaaattcca acatggatgc tgatttatat gggtataaat   9960
gggctcgcga taatgtcggg caatcaggtg cgacaatcta tcgattgtat gggaagcccg  10020
atgcgccaga gttgtttctg aaacatggca aaggtagcgt tgccaatgat gttacagatg  10080
agatggtcag actaaactgg ctgacggaat ttatgcctct tccgaccatc aagcatttta  10140
tccgtactcc tgatgatgca tggttactca ccactgcgat ccccgggaaa acagcattcc  10200
aggtattaga agaatatcct gattcaggtg aaaatattgt tgatgcgctg gcagtgttcc  10260
tgcgccggtt gcattcgatt cctgtttgta attgtccttt taacagcgat cgcgtatttc  10320
gtctcgctca ggcgcaatca cgaatgaata acggtttggt tgatgcgagt gattttgatg  10380
acgagcgtaa tggctggcct gttgaacaag tctggaaaga aatgcataag cttttgccat  10440
tctcaccgga ttcagtcgtc actcatggtg atttctcact tgataacctt atttttgacg  10500
aggggaaatt aataggttgt attgatgttg gacgagtcgg aatcgcagac cgataccagg  10560
atcttgccat cctatggaac tgcctcggtg agttttctcc ttcattacag aaacggcttt  10620
ttcaaaaata tggtattgat aatcctgata tgaataaatt gcagtttcat ttgatgctcg  10680
atgagttttt ctaagggcgg cctgccacca tacccacgcc gaaacaagcg ctcatgagcc  10740
cgaagtggcg agcccgatct tccccatcgg tgatgtcggc gatataggcg ccagcaaccg  10800
cacctgtggc gccggtgatg agggcgcgcc aagtcgacgt ccggcagtc              10849
```

<210> SEQ ID NO 26
<211> LENGTH: 11231
<212> TYPE: DNA
<213> ORGANISM: Artificial Sequence
<220> FEATURE:
<223> OTHER INFORMATION: Synthetic polynucleotide

<400> SEQUENCE: 26

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
ttgtcatcct cccacggtgg ccatttgttc catgtgagtg ctagtaacag gccttgtgtc    300
```

-continued

```
cttttagaaa taagtggtag tcacatctgt ggcttcactt gactaccact tatttctaaa    360
gacaacagca tacagccttc agcaagcctc cagtggtctc atacagaact tataagattc    420
ccaaatccaa agacatttca cgtttatggt gatttcccag aacacatagc gacatgcaaa    480
tattgcaggg cgccactccc ctgtccctca cagccatctt cctgccaggg cgcacgcgcg    540
ctgggtgttc ccgcctagtg acactgggcc cgcgattcct tggagcgggt tgatgacgtc    600
agcgtttccc atggtgaagc ttggatctga tccctaggtt ctagaaccgg tgacattcgg    660
taccctagtt attaatagta atcaattacg gggtcattag ttcatagccc atatatggag    720
ttccgcgtta cataacttac ggtaaatggc ccgcctggct gaccgcccaa cgacccccgc    780
ccattgacgt caataatgac gtatgttccc atagtaacgc caatagggac tttccattga    840
cgtcaatggg tggactattt acggtaaact gcccacttgg cagtacatca agtgtatcat    900
atgccaagta cgccccctat tgacgtcaat gacggtaaat ggcccgcctg gcattatgcc    960
cagtacatga ccttatggga ctttcctact tggcagtaca tctacgtatt agtcatcgct   1020
attaccatgg tcgaggtgag ccccacgttc tgcttcactc tccccatctc ccccccctcc   1080
ccacccccaa ttttgtattt atttattttt taattatttt gtgcagcgat gggggcgggg   1140
gggggggggg ggcgcgcgcc aggcggggcg gggcggggcg aggggcgggg cggggcgagg   1200
cggagaggtg cggcggcagc caatcagagc ggcgcgctcc gaaagtttcc ttttatggcg   1260
aggcggcggc ggcggcggcc ctataaaaag cgaagcgcgc ggcgggcggg agtcgctgcg   1320
acgctgcctt cgccccgtgc cccgctccgc cgccgcctcg cgccgcccgc cccggctctg   1380
actgaccgcg ttactcccac aggtgagcgg gcgggacggc ccttctcctc cgggctgtaa   1440
ttagcgcttg gtttaatgac ggcttgtttt ctgtggctgc gtgaaagcct tgaggggctc   1500
cgggagctag agcctctgct aaccatgttc atgccttctt cttttcccta cagctcctgg   1560
gcaacgtgct ggttattgtg ctgtctcatc attttggcaa agaattcctc gaagatccga   1620
agggaaagtc ttccacgact gtgggatccg ttcgaagata tcaccggttg agccaccatg   1680
tggaccctgg tgagctgggt ggccctgacc gccggcctgg tggccggcac ccgctgcccc   1740
gacggccagt tctgccccgt ggcctgctgc ctggaccccg gcggcgccag ctacagctgc   1800
tgccgccccc tgctggacaa gtggcccacc accctgagcc gccacctggg cggcccctgc   1860
caggtggacg cccactgcag cgccggccac agctgcatct tcaccgtgag cggcaccagc   1920
agctgctgcc ccttccccga ggccgtggcc tgcggcgacg gccaccactg ctgcccccgc   1980
ggcttccact gcagcgccga cggccgcagc tgcttccagc gcagcggcaa caacagcgtg   2040
ggcgccatcc agtgccccga cagccagttc gagtgccccg acttcagcac ctgctgcgtg   2100
atggtggacg gcagctgggg ctgctgcccc atgccccagg ccagctgctg cgaggaccgc   2160
gtgcactgct gcccccacgg cgccttctgc gacctggtgc acacccgctg catcaccccc   2220
accggcaccc accccctggc caagaagctg cccgcccagc gcaccaaccg cgccgtggcc   2280
ctgagcagca gcgtgatgtg ccccgacgcc cgcagccgct gccccgacgg cagcacctgc   2340
tgcgagctgc ccagcggcaa gtacggctgc tgccccatgc ccaacgccac ctgctgcagc   2400
gaccacctgc actgctgccc ccaggacacc gtgtgcgacc tgatccagag caagtgcctg   2460
agcaaggaga acgccaccac cgacctgctg accaagctgc ccgcccacac cgtgggcgac   2520
gtgaagtgcg acatggaggt gagctgcccc gacggctaca cctgctgccg cctgcagagc   2580
ggcgcctggg gctgctgccc cttcacccag gccgtgtgct gcgaggacca catccactgc   2640
tgccccgccg gcttcacctg cgacacccag aagggcacct gcgagcaggg cccccaccag   2700
```

```
gtgccctgga tggagaaggc ccccgcccac ctgagcctgc ccgacccccca ggccctgaag   2760
cgcgacgtgc cctgcgacaa cgtgagcagc tgccccagca gcgacacctg ctgccagctg   2820
accagcggcg agtggggctg ctgccccatc cccgaggccg tgtgctgcag cgaccaccag   2880
cactgctgcc cccagggcta cacctgcgtg gccgagggcc agtgccagcg cggcagcgag   2940
atcgtggccg gcctggagaa gatgcccgcc cgccgcgcca gcctgagcca cccccgcgac   3000
atcggctgcg accagcacac cagctgcccc gtgggccaga cctgctgccc cagcctgggc   3060
ggcagctggg cctgctgcca gctgccccac gccgtgtgct gcgaggaccg ccagcactgc   3120
tgccccgccg gctacacctg caacgtgaag gcccgcagct gcgagaagga ggtggtgagc   3180
gcccagcccg ccaccttcct ggcccgcagc cccccacgtgg gcgtgaagga cgtggagtgc   3240
ggcgagggcc acttctgcca cgacaaccag acctgctgcc gcgacaaccg ccagggctgg   3300
gcctgctgcc cctaccgcca gggcgtgtgc tgcgccgacc gccgccactg ctgccccgcc   3360
ggcttccgct gcgccgcccg cggcaccaag tgcctgcgcc gcgaggcccc ccgctgggac   3420
gcccccctgc gcgaccccgc cctgcgccag ctgctgtgac aattgttaat taagtttaaa   3480
ccctcgaggc cgcaagctta tcgataatca acctctggat tacaaaattt gtgaaagatt   3540
gactggtatt cttaactatg ttgctccttt tacgctatgt ggatacgctg ctttaatgcc   3600
tttgtatcat gctattgctt cccgtatggc tttcattttc tcctccttgt ataaatcctg   3660
gttgctgtct ctttatgagg agttgtggcc cgttgtcagg caacgtggcg tggtgtgcac   3720
tgtgtttgct gacgcaaccc ccactggttg gggcattgcc accacctgtc agctcctttc   3780
cgggactttc gctttccccc tccctattgc cacggcggaa ctcatcgccg cctgccttgc   3840
ccgctgctgg acaggggctc ggctgttggg cactgacaat tccgtggtgt tgtcggggaa   3900
atcatcgtcc tttccttggc tgctcgcctg tgttgccacc tggattctgc gcgggacgtc   3960
cttctgctac gtcccttcgg ccctcaatcc agcggacctt ccttcccgcg gcctgctgcc   4020
ggctctgcgg cctcttccgc gtcttcgcct tcgccctcag acgagtcgga tctccctttg   4080
ggccgcctcc ccgcatcgat accgtcgact agagctcgct gatcagcctc gactgtgcct   4140
tctagttgcc agccatctgt tgtttgcccc tcccccgtgc cttccttgac cctggaaggt   4200
gccactccca ctgtcctttc ctaataaaat gaggaaattg catcgcattg tctgagtagg   4260
tgtcattcta ttctgggggg tggggtgggg caggacagca agggggagga ttgggaagac   4320
aatagcaggc atgctgggga gagatccacg ataacaaaca gctttttttgg ggtgaacata   4380
ttgactgaat tccctgcagg ttggccactc cctctctgcg cgctcgctcg ctcactgagg   4440
ccgcccgggc aaagcccggg cgtcgggcga cctttggtcg cccggcctca gtgagcgagc   4500
gagcgcgcag agagggagtg gccaactcca tcactagggg ttcctgcggc cgctcgtacg   4560
gtctcgagga attcctgcag gataacttgc caacctcatt ctaaaatgta tatagaagcc   4620
caaaagacaa taacaaaaat attcttgtag aacaaaatgg gaaagaatgt tccactaaat   4680
atcaagattt agagcaaagc atgagatgtg tggggataga cagtgaggct gataaaatag   4740
agtagagctc agaaacagac ccattgatat atgtaagtga cctatgaaaa aaatatggca   4800
ttttacaatg ggaaaatgat ggtctttttc ttttttagaa aaacagggaa atatatttat   4860
atgtaaaaaa taaaagggaa cccatatgtc ataccataca cacaaaaaaa ttccagtgaa   4920
ttataagtct aaatggagaa ggcaaaactt taaatctttt agaaaataat atagaagcat   4980
gcagaccagc ctggccaaca tgatgaaacc ctctctacta ataataaaat cagtagaact   5040
```

-continued

```
actcaggact actttgagtg ggaagtcctt ttctatgaag acttctttgg ccaaaattag   5100
gctctaaatg caaggagata gtgcatcatg cctggctgca cttactgata aatgatgtta   5160
tcaccatctt taaccaaatg cacaggaaca agttatggta ctgatgtgct ggattgagaa   5220
ggagctctac ttccttgaca ggacacattt gtatcaactt aaaaaagcag atttttgcca   5280
gcagaactat tcattcagag gtaggaaact tagaatagat gatgtcactg attagcatgg   5340
cttccccatc tccacagctg cttcccaccc aggttgccca cagttgagtt tgtccagtgc   5400
tcagggctgc ccactctcag taagaagccc cacaccagcc cctctccaaa tatgttggct   5460
gttccttcca ttaaagtgac cccactttag agcagcaagt ggatttctgt ttcttacagt   5520
tcaggaagga ggagtcagct gtgagaacct ggagcctgag atgcttctaa gtcccactgc   5580
tactggggtc agggaagcca gactccagca tcagcagtca ggagcactaa gcccttgcca   5640
acatcctgtt tctcagagaa actgcttcca ttataatggt tgtccttttt taagctatca   5700
agccaaacaa ccagtgtcta ccattattct catcacctga agccaagggt tctagcaaaa   5760
gtcaagctgt cttgtaatgg ttgatgtgcc tccagcttct gtcttcagtc actccactct   5820
tagcctgctc tgaatcaact ctgaccacag ttccctggag cccctgccac ctgctgcccc   5880
tgccaccttc tccatctgca gtgctgtgca gccttctgca ctcttgcaga gctaataggt   5940
ggagacttga aggaagagga ggaaagtttc tcataatagc cttgctgcaa gctcaaatgg   6000
gaggtgggca ctgtgcccag gagccttgga gcaaaggctg tgcccaacct ctgactgcat   6060
ccaggtttgg tcttgacaga gataagaagc cctggctttt ggagccaaaa tctaggtcag   6120
acttaggcag gattctcaaa gtttatcagc agaacatgag gcagaagacc ctttctgctc   6180
cagcttcttc aggctcaacc ttcatcagaa tagatagaaa gagaggctgt gagggttctt   6240
aaaacagaag caaatctgac tcagagaata aacaacctcc tagtaaacta cagcttagac   6300
agagcatctg gtggtgagtg tgctcagtgt cctactcaac tgtctggtat cagccctcat   6360
gaggacttct cttctttccc tcatagacct ccatctctgt tttccttagc ctgcagaaat   6420
ctggatggct attcacagaa tgcctgtgct ttcagagttg catttttttct ctggtattct   6480
ggttcaagca tttgaaggta ggaaaggttc tccaagtgca agaaagccag ccctgagcct   6540
caactgcctg gctagtgtgg tcagtaggat gcaaaggctg ttgaatgcca caaggccaaa   6600
ctttaacctg tgtaccacaa gcctagcagc agaggcagct ctgctcactg gaactctctg   6660
tcttctttct cctgagcctt ttcttttcct gagttttcta gctctcctca accttacctc   6720
tgccctaccc aggacaaacc caagagccac tgtttctgtg atgtcctctc cagccctaat   6780
taggcatcat gacttcagcc tgaccttcca tgctcagaag cagtgctaat ccacttcaga   6840
tgagctgctc tatgcaacac aggcagagcc tacaaacctt tgcaccagag ccctccacat   6900
atcagtgttt gttcatactc acttcaacag caaatgtgac tgctgagatt aagattttac   6960
acaagatggt ctgtaatttc acagttagtt ttatcccatt aggtatgaaa gaattagcat   7020
aattcccctt aaacatgaat gaatcttaga ttttttaata aatagttttg gaagtaaaga   7080
cagagacatc aggagcacaa ggaatagcct gagaggacaa acagaacaag aaagagtctg   7140
gaaatacaca ggatgttctt ggcctcctca aagcaagtgc aagcagatag taccagcagc   7200
cccaggctat cagagcccag tgaagagaag taccatgaaa gccacagctc taaccaccct   7260
gttccagagt gacagacagt ccccaagaca agccagcctg agccagagag agaactgcaa   7320
gagaaagttt ctaatttagg ttctgttaga ttcagacaag tgcaggtcat cctctctcca   7380
cagctactca cctctccagc ctaacaaagc ctgcagtcca cactccaacc ctggtgtctc   7440
```

```
acctcctagc ctctcccaac atcctgctct ctgaccatct tctgcatctc tcatctcacc   7500
atctcccact gtctacagcc tactcttgca actaccatct cattttctga catcctgtct   7560
acatcttctg ccatactctg ccatctacca taccacctct taccatctac cacaccatct   7620
tttatctcca tccctctcag aagcctccaa gctgaatcct gctttatgtg ttcatctcag   7680
cccctgcatg gaaagctgac cccagaggca gaactattcc cagagagctt ggccaagaaa   7740
aacaaaacta ccagcctggc caggctcagg agtagtaagc tgcagtgtct gttgtgttct   7800
agcttcaaca gctgcaggag ttccactctc aaatgctcca catttctcac atcctcctga   7860
ttctggtcac tacccatctt caaagaacag aatatctcac atcagcatac tgtgaaggac   7920
tagtcatggg tgcagctgct cagagctgca aagtcattct ggatggtgga gagcttacaa   7980
acatttcatg atgctccccc cgctctgatg gctggagccc aatccctaca cagactcctg   8040
ctgtatgtgt tttcctttca ctctgagcca cagccagagg gcaggcattc agtctcctct   8100
tcaggctggg gctggggcac tgagaactca cccaacacct tgctctcact ccttctgcaa   8160
aacaagaaag agctttgtgc tgcagtagcc atgaagaatg aaaggaaggc tttaactaaa   8220
aaatgtcaga gattattttc aaccccttac tgtggatcac cagcaaggag gaaacacaac   8280
acagagacat tttttcccct caaattatca aaagaatcac tgcatttgtt aaagagagca   8340
actgaatcag gaagcagagt tttgaacata tcagaagtta ggaatctgca tcagagacaa   8400
atgcagtcat ggttgtttgc tgcataccag ccctaatcat tagaagcctc atggacttca   8460
aacatcattc cctctgacaa gatgctctag cctaactcca tgagataaaa taaatctgcc   8520
tttcagagcc aaagaagagt ccaccagctt cttctcagtg tgaacaagag ctccagtcag   8580
gttagtcagt ccagtgcagt agaggagacc agtctgcatc ctctaatttt caaaggcaag   8640
aagatttgtt taccctggac accaggcaca agtgaggtca cagagctctt agatatgcag   8700
tcctcatgag tgaggagact aaagcgcatg ccatcaagac ttcagtgtag agaaaacctc   8760
caaaaaagcc tcctcactac ttctggaata gctcagaggc cgaggcggcc tcggcctctg   8820
cataaataaa aaaaattagt cagccatggg gcggagaatg ggcggaactg ggcggagtta   8880
ggggcgggat gggcggagtt aggggcggga ctatggttgc tgactaattg agatgcatgc   8940
tttgcatact tctgcctgct ggggagcctg gggactttcc acacctggtt gctgactaat   9000
tgagatgcat gctttgcata cttctgcctg ctggggagcc tggggacttt ccacacccta   9060
actgacacac attccacagc tgcattaatg aatcggccaa cgcgcgggga gaggcggttt   9120
gcgtattggg cgctcttccg cttcctcgct cactgactcg ctgcgctcgg tcgttcggct   9180
gcggcgagcg gtatcagctc actcaaaggc ggtaatacgg ttatccacag aatcagggga   9240
taacgcagga aagaacatgt gagcaaaagg ccagcaaaag gccaggaacc gtaaaaaggc   9300
cgcgttgctg gcgtttttcc ataggctccg cccccctgac gagcatcaca aaaatcgacg   9360
ctcaagtcag aggtggcgaa acccgacagg actataaaga taccaggcgt ttccccctgg   9420
aagctccctc gtgcgctctc ctgttccgac cctgccgctt accggatacc tgtccgcctt   9480
tctcccttcg ggaagcgtgg cgctttctca tagctcacgc tgtaggtatc tcagttcggt   9540
gtaggtcgtt cgctccaagc tgggctgtgt gcacgaaccc cccgttcagc ccgaccgctg   9600
cgccttatcc ggtaactatc gtcttgagtc caacccggta agacacgact tatcgccact   9660
ggcagcagcc actggtaaca ggattagcag agcgaggtat gtaggcggtg ctacagagtt   9720
cttgaagtgg tggcctaact acggctacac tagaagaaca gtatttggta tctgcgctct   9780
```

gctgaagcca gttaccttcg gaaaaagagt tggtagctct tgatccggca aacaaaccac 9840
cgctggtagc ggtggttttt ttgtttgcaa gcagcagatt acgcgcagaa aaaaaggatc 9900
tcaagaagat cctttgatct tttctacggg gtctgacgct cagtggaacg aaaactcacg 9960
ttaagggatt ttggtcatga gattatcaaa aaggatcttc acctagatcc ttttaaatta 10020
aaaatgaagt tttaaatcaa tctaaagtat atatgagtaa acttggtctg acagttacca 10080
atgcttaatc agtgaggcac ctatctcagc gatctgtcta tttcgttcat ccatagttgc 10140
ctgactcctg caaaccacgt tgtgtctcaa aatctctgat gttacattgc acaagataaa 10200
aatatatcat catgaacaat aaaactgtct gcttacataa acagtaatac aaggggtgtt 10260
atgagccata ttcaacggga aacgtcttgc tcgaggccgc gattaaattc caacatggat 10320
gctgatttat atgggtataa atgggctcgc gataatgtcg ggcaatcagg tgcgacaatc 10380
tatcgattgt atgggaagcc cgatgcgcca gagttgtttc tgaaacatgg caaaggtagc 10440
gttgccaatg atgttacaga tgagatggtc agactaaact ggctgacgga atttatgcct 10500
cttccgacca tcaagcattt tatccgtact cctgatgatg catggttact caccactgcg 10560
atccccggga aaacagcatt ccaggtatta gaagaatatc ctgattcagg tgaaaatatt 10620
gttgatgcgc tggcagtgtt cctgcgccgg ttgcattcga ttcctgtttg taattgtcct 10680
tttaacagcg atcgcgtatt tcgtctcgct caggcgcaat cacgaatgaa taacggtttg 10740
gttgatgcga gtgattttga tgacgagcgt aatggctggc ctgttgaaca agtctggaaa 10800
gaaatgcata agcttttgcc attctcaccg gattcagtcg tcactcatgg tgatttctca 10860
cttgataacc ttatttttga cgaggggaaa ttaataggtt gtattgatgt tggacgagtc 10920
ggaatcgcag accgatacca ggatcttgcc atcctatgga actgcctcgg tgagttttct 10980
ccttcattac agaaacggct ttttcaaaaa tatggtattg ataatcctga tatgaataaa 11040
ttgcagtttc atttgatgct cgatgagttt ttctaagggc ggcctgccac catacccacg 11100
ccgaaacaag cgctcatgag cccgaagtgg cgagcccgat cttccccatc ggtgatgtcg 11160
gcgatatagg cgccagcaac cgcacctgtg gcgccggtga tgagggcgcg ccaagtcgac 11220
gtccggcagt c 11231

<210> SEQ ID NO 27
<211> LENGTH: 10876
<212> TYPE: DNA
<213> ORGANISM: Artificial Sequence
<220> FEATURE:
<223> OTHER INFORMATION: Synthetic polynucleotide

<400> SEQUENCE: 27
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctgctag ctctgggtat ttaagcccga gtgagcacgc 180
agggtctcca ttttgaagcg ggaggttacg cgttcgtcga ctactagtgg gtaccagagc 240
tccctaggtt ctagaaccgg tgacgtctcc catggtgaag cttggatctg aattcggtac 300
cctagttatt aatagtaatc aattacgggg tcattagttc atagcccata tatggagttc 360
cgcgttacat aacttacggt aaatggcccg cctggctgac cgcccaacga cccccgccca 420
ttgacgtcaa taatgacgta tgttcccata gtaacgccaa tagggacttt ccattgacgt 480
caatgggtgg actatttacg gtaaactgcc cacttggcag tacatcaagt gtatcatatg 540
ccaagtacgc cccctattga cgtcaatgac ggtaaatggc ccgcctggca ttatgcccag 600

```
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttttaa ttattttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctcagc gctgtaatta   1080
gcgcttggtt taatgacggc ttgttggagg cttgctgaag gctgtatgct gttgtcctcg   1140
agtgagcgta gggtatcaag actacgaata ctgtaaagcc acagatgggt gttcgtagtc   1200
ttgataccct tcgcctacta gaggacacaa ggcctgttac tagcactcac atggaacaaa   1260
tggccaccgt gggaggatga caatttctgt ggctgcgtga aagccttgag ggctccgggg   1320
agctagagcc tctgctaacc atgttcatgc cttcttcttt ttcctacagc tcctgggcaa   1380
cgtgctggtt attgtgctgt ctcatcattt tggcaaagaa ttcctcgaag atccgaaggg   1440
aaagtcttcc acgactgtgg gatccgttcg aagatatcac cggttgagcc accatggaat   1500
tcagcagccc cagcagagag gaatgcccca agcctctgag ccgggtgtca atcatggccg   1560
gatctctgac aggactgctg ctgcttcagg ccgtgtcttg ggcttctggc gctagacctt   1620
gcatccccaa gagcttcggc tacagcagcg tcgtgtgcgt gtgcaatgcc acctactgcg   1680
acagcttcga ccctcctacc tttcctgctc tgggcacctt cagcagatac gagagcacca   1740
gatccggcag acggatggaa ctgagcatgg gacccatcca ggccaatcac acaggcactg   1800
gcctgctgct gacactgcag cctgagcaga aattccagaa agtgaaaggc ttcggcggag   1860
ccatgacaga tgccgccgct ctgaatatcc tggctctgtc tccaccagct cagaacctgc   1920
tgctcaagag ctacttcagc gaggaaggca tcggctacaa catcatcaga gtgcccatgg   1980
ccagctgcga cttcagcatc aggacctaca cctacgccga cacacccgac gatttccagc   2040
tgcacaactt cagcctgcct gaagaggaca ccaagctgaa gatccctctg atccacagag   2100
ccctgcagct ggcacaaaga cccgtgtcac tgctggcctc tccatggaca tctcccacct   2160
ggctgaaaac aaatggcgcc gtgaatggca agggcagcct gaaaggccaa cctggcgaca   2220
tctaccacca gacctgggcc agatacttcg tgaagttcct ggacgcctat gccgagcaca   2280
agctgcagtt ttgggccgtg acagccgaga acgaaccttc tgctggactg ctgagcggct   2340
acccctttca gtgcctgggc tttacacccg agcaccagcg ggactttatc gcccgtgatc   2400
tgggacccac actggccaat agcacccacc ataatgtgcg gctgctgatg ctggacgacc   2460
agagactgct tctgccccac tgggctaaag tggtgctgac agatcctgag gccgccaaat   2520
acgtgcacgg aatcgccgtg cactggtatc tggactttct ggcccctgcc aaggccacac   2580
tgggagagac acacagactg ttccccaaca ccatgctgtt cgccagcgaa gcctgtgtgg   2640
gcagcaagtt ttgggaacag agcgtgcggc tcggcagctg ggatagaggc atgcagtaca   2700
gccacagcat catcaccaac ctgctgtacc acgtcgtcgg ctggaccgac tggaatctgg   2760
ccctgaatcc tgaaggcggc cctaactggg tccgaaactt cgtggacagc cccatcatcg   2820
tggacatcac caaggacacc ttctacaagc agcccatgtt ctaccacctg ggacacttca   2880
gcaagttcat ccccgagggc tctcagcgcg ttggactggt ggcttcccag aagaacgatc   2940
```

-continued

```
tggacgccgt ggctctgatg caccctgatg gatctgctgt ggtggtggtc ctgaaccgca   3000
gcagcaaaga tgtgcccctg accatcaagg atcccgccgt gggattcctg gaaacaatca   3060
gccctggcta ctccatccac acctacctgt ggcgtagaca gtgacaattg ttaattaagt   3120
ttaaaccctc gaggccgcaa gcttatcgat aatcaacctc tggattacaa aatttgtgaa   3180
agattgactg gtattcttaa ctatgttgct ccttttacgc tatgtggata cgctgcttta   3240
atgcctttgt atcatgctat tgcttcccgt atggctttca ttttctcctc cttgtataaa   3300
tcctggttgc tgtctcttta tgaggagttg tggcccgttg tcaggcaacg tggcgtggtg   3360
tgcactgtgt ttgctgacgc aacccccact ggttggggca ttgccaccac ctgtcagctc   3420
ctttccggga ctttcgcttt ccccctccct attgccacgg cggaactcat cgccgcctgc   3480
cttgcccgct gctggacagg ggctcggctg ttgggcactg acaattccgt ggtgttgtcg   3540
gggaaatcat cgtcctttcc ttggctgctc gcctgtgttg ccacctggat tctgcgcggg   3600
acgtccttct gctacgtccc ttcggccctc aatccagcgg accttccttc ccgcggcctg   3660
ctgccggctc tgcggcctct tccgcgtctt cgccttcgcc ctcagacgag tcggatctcc   3720
ctttgggccg cctccccgca tcgataccgt cgactagagc tcgctgatca gcctcgactg   3780
tgccttctag ttgccagcca tctgttgttt gcccctcccc cgtgccttcc ttgaccctgg   3840
aaggtgccac tcccactgtc ctttcctaat aaaatgagga aattgcatcg cattgtctga   3900
gtaggtgtca ttctattctg gggggtgggg tggggcagga cagcaagggg gaggattggg   3960
aagacaatag caggcatgct ggggagagat ccacgataac aaacagcttt tttggggtga   4020
acatattgac tgaattccct gcaggttggc cactccctct ctgcgcgctc gctcgctcac   4080
tgaggccgcc cgggcaaagc ccgggcgtcg ggcgaccttt ggtcgcccgg cctcagtgag   4140
cgagcgagcg cgcagagagg gagtggccaa ctccatcact aggggttcct gcggccgctc   4200
gtacggtctc gaggaattcc tgcaggataa cttgccaacc tcattctaaa atgtatatag   4260
aagcccaaaa gacaataaca aaaatattct tgtagaacaa aatgggaaag aatgttccac   4320
taaatatcaa gatttagagc aaagcatgag atgtgtgggg atagacagtg aggctgataa   4380
aatagagtag agctcagaaa cagacccatt gatatatgta agtgacctat gaaaaaaata   4440
tggcatttta caatgggaaa atgatggtct tttcttttt tagaaaaaca gggaaatata   4500
tttatatgta aaaaataaaa gggaacccat atgtcatacc atacacacaa aaaaattcca   4560
gtgaattata agtctaaatg gagaaggcaa aactttaaat cttttagaaa ataatataga   4620
agcatgcaga ccagcctggc caacatgatg aaaccctctc tactaataat aaaatcagta   4680
gaactactca ggactacttt gagtgggaag tccttttcta tgaagacttc tttggccaaa   4740
attaggctct aaatgcaagg agatagtgca tcatgcctgg ctgcacttac tgataaatga   4800
tgttatcacc atctttaacc aaatgcacag gaacaagtta tggtactgat gtgctggatt   4860
gagaaggagc tctacttcct tgacaggaca catttgtatc aacttaaaaa agcagatttt   4920
tgccagcaga actattcatt cagaggtagg aaacttagaa tagatgatgt cactgattag   4980
catggcttcc ccatctccac agctgcttcc cacccaggtt gcccacagtt gagtttgtcc   5040
agtgctcagg gctgcccact ctcagtaaga agccccacac cagcccctct ccaaatatgt   5100
tggctgttcc ttccattaaa gtgaccccac tttagagcag caagtggatt tctgtttctt   5160
acagttcagg aaggaggagt cagctgtgag aacctggagc ctgagatgct tctaagtccc   5220
actgctactg gggtcaggga agccagactc cagcatcagc agtcaggagc actaagccct   5280
tgccaacatc ctgtttctca gagaaactgc ttccattata atggttgtcc tttttaagc   5340
```

```
tatcaagcca aacaaccagt gtctaccatt attctcatca cctgaagcca agggttctag   5400
caaaagtcaa gctgtcttgt aatggttgat gtgcctccag cttctgtctt cagtcactcc   5460
actcttagcc tgctctgaat caactctgac cacagttccc tggagcccct gccacctgct   5520
gcccctgcca ccttctccat ctgcagtgct gtgcagcctt ctgcactctt gcagagctaa   5580
taggtggaga cttgaaggaa gaggaggaaa gtttctcata atagccttgc tgcaagctca   5640
aatgggaggt gggcactgtg cccaggagcc ttggagcaaa ggctgtgccc aacctctgac   5700
tgcatccagg tttggtcttg acagagataa gaagccctgg cttttggagc caaaatctag   5760
gtcagactta ggcaggattc tcaaagttta tcagcagaac atgaggcaga agaccctttc   5820
tgctccagct tcttcaggct caaccttcat cagaatagat agaaagagag gctgtgaggg   5880
ttcttaaaac agaagcaaat ctgactcaga gaataaacaa cctcctagta aactacagct   5940
tagacagagc atctggtggt gagtgtgctc agtgtcctac tcaactgtct ggtatcagcc   6000
ctcatgagga cttctcttct ttccctcata gacctccatc tctgttttcc ttagcctgca   6060
gaaatctgga tggctattca cagaatgcct gtgctttcag agttgcattt tttctctggt   6120
attctggttc aagcatttga aggtaggaaa ggttctccaa gtgcaagaaa gccagccctg   6180
agcctcaact gcctggctag tgtggtcagt aggatgcaaa ggctgttgaa tgccacaagg   6240
ccaaacttta acctgtgtac cacaagccta gcagcagagg cagctctgct cactggaact   6300
ctctgtcttc tttctcctga gccttttctt ttcctgagtt ttctagctct cctcaacctt   6360
acctctgccc tacccaggac aaacccaaga gccactgttt ctgtgatgtc ctctccagcc   6420
ctaattaggc atcatgactt cagcctgacc ttccatgctc agaagcagtg ctaatccact   6480
tcagatgagc tgctctatgc aacacaggca gagcctacaa acctttgcac cagagccctc   6540
cacatatcag tgtttgttca tactcacttc aacagcaaat gtgactgctg agattaagat   6600
tttacacaag atggtctgta atttcacagt tagttttatc ccattaggta tgaaagaatt   6660
agcataattc cccttaaaca tgaatgaatc ttagattttt taataaatag ttttggaagt   6720
aaagacagag acatcaggag cacaaggaat agcctgagag gacaaacaga acaagaaaga   6780
gtctggaaat acacaggatg ttcttggcct cctcaaagca agtgcaagca gatagtacca   6840
gcagccccag gctatcagag cccagtgaag agaagtacca tgaaagccac agctctaacc   6900
accctgttcc agagtgacag acagtcccca agacaagcca gcctgagcca gagagagaac   6960
tgcaagagaa agtttctaat ttaggttctg ttagattcag acaagtgcag gtcatcctct   7020
ctccacagct actcacctct ccagcctaac aaagcctgca gtccacactc caaccctggt   7080
gtctcacctc ctagcctctc ccaacatcct gctctctgac catcttctgc atctctcatc   7140
tcaccatctc ccactgtcta cagcctactc ttgcaactac catctcattt tctgacatcc   7200
tgtctacatc ttctgccata ctctgccatc taccatacca cctcttacca tctaccacac   7260
catcttttat ctccatccct ctcagaagcc tccaagctga atcctgcttt atgtgttcat   7320
ctcagcccct gcatggaaag ctgaccccag aggcagaact attcccagag agcttggcca   7380
agaaaaacaa aactaccagc ctggccaggc tcaggagtag taagctgcag tgtctgttgt   7440
gttctagctt caacagctgc aggagttcca ctctcaaatg ctccacattt ctcacatcct   7500
cctgattctg gtcactaccc atcttcaaag aacagaatat ctcacatcag catactgtga   7560
aggactagtc atgggtgcag ctgctcagag ctgcaaagtc attctggatg gtggagagct   7620
tacaaacatt tcatgatgct ccccccgctc tgatggctgg agcccaatcc ctacacagac   7680
```

-continued

```
tcctgctgta tgtgttttcc tttcactctg agccacagcc agagggcagg cattcagtct   7740
cctcttcagg ctggggctgg ggcactgaga actcacccaa caccttgctc tcactccttc   7800
tgcaaaacaa gaaagagctt tgtgctgcag tagccatgaa gaatgaaagg aaggctttaa   7860
ctaaaaaatg tcagagatta ttttcaaccc cttactgtgg atcaccagca aggaggaaac   7920
acaacacaga gacatttttt cccctcaaat tatcaaaaga atcactgcat ttgttaaaga   7980
gagcaactga atcaggaagc agagttttga acatatcaga agttaggaat ctgcatcaga   8040
gacaaatgca gtcatggttg tttgctgcat accagcccta atcattagaa gcctcatgga   8100
cttcaaacat cattccctct gacaagatgc tctagcctaa ctccatgaga taaaataaat   8160
ctgcctttca gagccaaaga agagtccacc agcttcttct cagtgtgaac aagagctcca   8220
gtcaggttag tcagtccagt gcagtagagg agaccagtct gcatcctcta attttcaaag   8280
gcaagaagat ttgtttaccc tggacaccag gcacaagtga ggtcacagag ctcttagata   8340
tgcagtcctc atgagtgagg agactaaagc gcatgccatc aagacttcag tgtagagaaa   8400
acctccaaaa aagcctcctc actacttctg gaatagctca gaggccgagg cggcctcggc   8460
ctctgcataa ataaaaaaaa ttagtcagcc atggggcgga gaatgggcgg aactgggcgg   8520
agttaggggc gggatgggcg gagttagggg cgggactatg gttgctgact aattgagatg   8580
catgctttgc atacttctgc ctgctgggga gcctggggac tttccacacc tggttgctga   8640
ctaattgaga tgcatgcttt gcatacttct gcctgctggg gagcctgggg actttccaca   8700
ccctaactga cacacattcc acagctgcat taatgaatcg gccaacgcgc ggggagaggc   8760
ggtttgcgta ttgggcgctc ttccgcttcc tcgctcactg actcgctgcg ctcggtcgtt   8820
cggctgcggc gagcggtatc agctcactca aaggcggtaa tacggttatc cacagaatca   8880
ggggataacg caggaaagaa catgtgagca aaaggccagc aaaaggccag gaaccgtaaa   8940
aaggccgcgt tgctggcgtt tttccatagg ctccgccccc ctgacgagca tcacaaaaat   9000
cgacgctcaa gtcagaggtg gcgaaacccg acaggactat aaagatacca ggcgtttccc   9060
cctggaagct ccctcgtgcg ctctcctgtt ccgaccctgc cgcttaccgg atacctgtcc   9120
gcctttctcc cttcgggaag cgtggcgctt tctcatagct cacgctgtag gtatctcagt   9180
tcggtgtagg tcgttcgctc caagctgggc tgtgtgcacg aaccccccgt tcagcccgac   9240
cgctgcgcct tatccggtaa ctatcgtctt gagtccaacc cggtaagaca cgacttatcg   9300
ccactggcag cagccactgg taacaggatt agcagagcga ggtatgtagg cggtgctaca   9360
gagttcttga agtggtggcc taactacggc tacactagaa gaacagtatt tggtatctgc   9420
gctctgctga agccagttac cttcggaaaa agagttggta gctcttgatc cggcaaacaa   9480
accaccgctg gtagcggtgg tttttttgtt tgcaagcagc agattacgcg cagaaaaaaa   9540
ggatctcaag aagatccttt gatcttttct acggggtctg acgctcagtg gaacgaaaac   9600
tcacgttaag ggattttggt catgagatta tcaaaaagga tcttcaccta gatcctttta   9660
aattaaaaat gaagttttaa atcaatctaa agtatatatg agtaaacttg gtctgacagt   9720
taccaatgct taatcagtga ggcacctatc tcagcgatct gtctatttcg ttcatccata   9780
gttgcctgac tcctgcaaac cacgttgtgt ctcaaaatct ctgatgttac attgcacaag   9840
ataaaaatat atcatcatga acaataaaac tgtctgctta cataaacagt aatacaaggg   9900
gtgttatgag ccatattcaa cgggaaacgt cttgctcgag gccgcgatta aattccaaca   9960
tggatgctga tttatatggg tataaatggg ctcgcgataa tgtcgggcaa tcaggtgcga  10020
caatctatcg attgtatggg aagcccgatg cgccagagtt gtttctgaaa catggcaaag  10080
```

```
gtagcgttgc caatgatgtt acagatgaga tggtcagact aaactggctg acggaattta  10140

tgcctcttcc gaccatcaag cattttatcc gtactcctga tgatgcatgg ttactcacca  10200

ctgcgatccc cgggaaaaca gcattccagg tattagaaga atatcctgat tcaggtgaaa  10260

atattgttga tgcgctggca gtgttcctgc gccggttgca ttcgattcct gtttgtaatt  10320

gtccttttaa cagcgatcgc gtatttcgtc tcgctcaggc gcaatcacga atgaataacg  10380

gtttggttga tgcgagtgat tttgatgacg agcgtaatgg ctggcctgtt gaacaagtct  10440

ggaaagaaat gcataagctt ttgccattct caccggattc agtcgtcact catggtgatt  10500

tctcacttga taaccttatt tttgacgagg ggaaattaat aggttgtatt gatgttggac  10560

gagtcggaat cgcagaccga taccaggatc ttgccatcct atggaactgc ctcggtgagt  10620

tttctccttc attacagaaa cggctttttc aaaaatatgg tattgataat cctgatatga  10680

ataaattgca gtttcatttg atgctcgatg agtttttcta agggcggcct gccaccatac  10740

ccacgccgaa acaagcgctc atgagcccga agtggcgagc ccgatcttcc ccatcggtga  10800

tgtcggcgat ataggcgcca gcaaccgcac ctgtggcgcc ggtgatgagg gcgcgccaag  10860

tcgacgtccg gcagtc                                                  10876
```

<210> SEQ ID NO 28
<211> LENGTH: 10849
<212> TYPE: DNA
<213> ORGANISM: Artificial Sequence
<220> FEATURE:
<223> OTHER INFORMATION: Synthetic polynucleotide

<400> SEQUENCE: 28

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

cctagttatt aatagtaatc aattacgggg tcattagttc atagcccata tatggagttc    360

cgcgttacat aacttacggt aaatggcccg cctggctgac cgcccaacga cccccgccca    420

ttgacgtcaa taatgacgta tgttcccata gtaacgccaa tagggacttt ccattgacgt    480

caatgggtgg actatttacg gtaaactgcc cacttggcag tacatcaagt gtatcatatg    540

ccaagtacgc cccctattga cgtcaatgac ggtaaatggc ccgcctggca ttatgcccag    600

tacatgacct tatgggactt tcctacttgg cagtacatct acgtattagt catcgctatt    660

accatggtcg aggtgagccc cacgttctgc ttcactctcc ccatctcccc cccctcccca    720

cccccaattt tgtatttatt tatttttaa ttattttgtg cagcgatggg ggcggggggg    780

gggggggggc gcgcgccagg cggggcgggg cggggcgagg ggcggggcgg ggcgaggcgg    840

agaggtgcgg cggcagccaa tcagagcggc gcgctccgaa agtttccttt tatggcgagg    900

cggcggcggc ggcggcccta taaaaagcga agcgcgcggc gggcgggagt cgctgcgacg    960

ctgccttcgc cccgtgcccc gctccgccgc cgcctcgcgc cgcccgcccc ggctctgact   1020

gaccgcgtta ctcccacagg tgagcgggcg ggacggccct tctcctcagc gctgtaatta   1080

gcgcttggtt taatgacggc ttgtttggagg cttgctgaag gctgtatgct gttgtcttta   1140

gaaataagtg gtagtcaagt gaagccacag atgtgactac cacttatttc taaaaggaca   1200
```

-continued

```
caaggcctgt tactagcact cacatggaac aaatggccac cgtgggagga tgacaatttc   1260
tgtggctgcg tgaaagcctt gaggggctcc gggagctaga gcctctgcta accatgttca   1320
tgccttcttc tttttcctac agctcctggg caacgtgctg gttattgtgc tgtctcatca   1380
ttttggcaaa gaattcctcg aagatccgaa gggaaagtct tccacgactg tgggatccgt   1440
tcgaagatat caccggttga gccaccatgg aattcagcag ccccagcaga gaggaatgcc   1500
ccaagcctct gagccgggtg tcaatcatgg ccggatctct gacaggactg ctgctgcttc   1560
aggccgtgtc ttgggcttct ggcgctagac cttgcatccc caagagcttc ggctacagca   1620
gcgtcgtgtg cgtgtgcaat gccacctact gcgacagctt cgaccctcct acctttcctg   1680
ctctgggcac cttcagcaga tacgagagca ccagatccgg cagacggatg gaactgagca   1740
tgggacccat ccaggccaat cacacaggca ctggcctgct gctgacactg cagcctgagc   1800
agaaattcca gaaagtgaaa ggcttcggcg gagccatgac agatgccgcc gctctgaata   1860
tcctggctct gtctccacca gctcagaacc tgctgctcaa gagctacttc agcgaggaag   1920
gcatcggcta caacatcatc agagtgccca tggccagctg cgacttcagc atcaggacct   1980
acacctacgc cgacacaccc gacgatttcc agctgcacaa cttcagcctg cctgaagagg   2040
acaccaagct gaagatccct ctgatccaca gagccctgca gctggcacaa agacccgtgt   2100
cactgctggc ctctccatgg acatctccca cctggctgaa aacaaatggc gccgtgaatg   2160
gcaagggcag cctgaaaggc caacctggcg acatctacca ccagacctgg gccagatact   2220
tcgtgaagtt cctggacgcc tatgccgagc acaagctgca gttttgggcc gtgacagccg   2280
agaacgaacc ttctgctgga ctgctgagcg gctacccctt tcagtgcctg ggctttacac   2340
ccgagcacca gcgggacttt atcgcccgtg atctgggacc cacactggcc aatagcaccc   2400
accataatgt gcggctgctg atgctggacg accagagact gcttctgccc cactgggcta   2460
aagtggtgct gacagatcct gaggccgcca aatacgtgca cggaatcgcc gtgcactggt   2520
atctggactt tctggcccct gccaaggcca cactgggaga gacacacaga ctgttcccca   2580
acaccatgct gttcgccagc gaagcctgtg tgggcagcaa gttttgggaa cagagcgtgc   2640
ggctcggcag ctgggataga ggcatgcagt acagccacag catcatcacc aacctgctgt   2700
accacgtcgt cggctggacc gactggaatc tggccctgaa tcctgaaggc ggccctaact   2760
gggtccgaaa cttcgtggac agccccatca tcgtggacat caccaaggac accttctaca   2820
agcagcccat gttctaccac ctgggacact tcagcaagtt catccccgag ggctctcagc   2880
gcgttggact ggtggcttcc cagaagaacg atctggacgc cgtggctctg atgcaccctg   2940
atggatctgc tgtggtggtg gtcctgaacc gcagcagcaa agatgtgccc ctgaccatca   3000
aggatcccgc cgtgggattc ctggaaacaa tcagccctgg ctactccatc cacacctacc   3060
tgtggcgtag acagtgacaa ttgttaatta agtttaaacc ctcgaggccg caagcttatc   3120
gataatcaac ctctggatta caaaatttgt gaaagattga ctggtattct taactatgtt   3180
gctcctttta cgctatgtgg atacgctgct ttaatgcctt tgtatcatgc tattgcttcc   3240
cgtatggctt tcattttctc ctccttgtat aaatcctggt tgctgtctct ttatgaggag   3300
ttgtggcccg ttgtcaggca acgtggcgtg gtgtgcactg tgtttgctga cgcaaccccc   3360
actggttggg gcattgccac cacctgtcag ctcctttccg ggactttcgc tttccccctc   3420
cctattgcca cggcggaact catcgccgcc tgccttgccc gctgctggac aggggctcgg   3480
ctgttgggca ctgacaattc cgtggtgttg tcggggaaat catcgtcctt tccttggctg   3540
ctcgcctgtg ttgccacctg gattctgcgc gggacgtcct tctgctacgt cccttcggcc   3600
```

```
ctcaatccag cggaccttcc ttcccgcggc ctgctgccgg ctctgcggcc tcttccgcgt   3660
cttcgccttc gccctcagac gagtcggatc tccctttggg ccgcctcccc gcatcgatac   3720
cgtcgactag agctcgctga tcagcctcga ctgtgccttc tagttgccag ccatctgttg   3780
tttgcccctc ccccgtgcct tccttgaccc tggaaggtgc cactcccact gtcctttcct   3840
aataaaatga ggaaattgca tcgcattgtc tgagtaggtg tcattctatt ctggggggtg   3900
gggtggggca ggacagcaag ggggaggatt gggaagacaa tagcaggcat gctggggaga   3960
gatccacgat aacaaacagc tttttggggg tgaacatatt gactgaattc cctgcaggtt   4020
ggccactccc tctctgcgcg ctcgctcgct cactgaggcc gcccgggcaa agcccgggcg   4080
tcgggcgacc tttggtcgcc cggcctcagt gagcgagcga gcgcgcagag agggagtggc   4140
caactccatc actaggggtt cctgcggccg ctcgtacggt ctcgaggaat tcctgcagga   4200
taacttgcca acctcattct aaaatgtata tagaagccca aaagacaata acaaaaatat   4260
tcttgtagaa caaaatggga aagaatgttc cactaaatat caagatttag agcaaagcat   4320
gagatgtgtg gggatagaca gtgaggctga taaaatagag tagagctcag aaacagaccc   4380
attgatatat gtaagtgacc tatgaaaaaa atatggcatt ttacaatggg aaaatgatgg   4440
tctttttctt ttttagaaaa acagggaaat atatttatat gtaaaaaata aaagggaacc   4500
catatgtcat accatacaca caaaaaaatt ccagtgaatt ataagtctaa atggagaagg   4560
caaaacttta aatcttttag aaaataatat agaagcatgc agaccagcct ggccaacatg   4620
atgaaaccct ctctactaat aataaaatca gtagaactac tcaggactac tttgagtggg   4680
aagtcctttt ctatgaagac ttctttggcc aaaattaggc tctaaatgca aggagatagt   4740
gcatcatgcc tggctgcact tactgataaa tgatgttatc accatcttta accaaatgca   4800
caggaacaag ttatggtact gatgtgctgg attgagaagg agctctactt ccttgacagg   4860
acacatttgt atcaacttaa aaaagcagat ttttgccagc agaactattc attcagaggt   4920
aggaaactta gaatagatga tgtcactgat tagcatggct tccccatctc cacagctgct   4980
tcccacccag gttgcccaca gttgagtttg tccagtgctc agggctgccc actctcagta   5040
agaagcccca caccagcccc tctccaaata tgttggctgt tccttccatt aaagtgaccc   5100
cactttagag cagcaagtgg atttctgttt cttacagttc aggaaggagg agtcagctgt   5160
gagaacctgg agcctgagat gcttctaagt cccactgcta ctggggtcag ggaagccaga   5220
ctccagcatc agcagtcagg agcactaagc ccttgccaac atcctgtttc tcagagaaac   5280
tgcttccatt ataatggttg tcctttttta agctatcaag ccaaacaacc agtgtctacc   5340
attattctca tcacctgaag ccaagggttc tagcaaaagt caagctgtct tgtaatggtt   5400
gatgtgcctc cagcttctgt cttcagtcac tccactctta gcctgctctg aatcaactct   5460
gaccacagtt ccctggagcc cctgccacct gctgcccctg ccaccttctc catctgcagt   5520
gctgtgcagc cttctgcact cttgcagagc taataggtgg agacttgaag gaagaggagg   5580
aaagtttctc ataatagcct tgctgcaagc tcaaatggga ggtgggcact gtgcccagga   5640
gccttggagc aaaggctgtg cccaacctct gactgcatcc aggtttggtc ttgacagaga   5700
taagaagccc tggcttttgg agccaaaatc taggtcagac ttaggcagga ttctcaaagt   5760
ttatcagcag aacatgaggc agaagaccct ttctgctcca gcttcttcag gctcaacctt   5820
catcagaata gatagaaaga gaggctgtga gggttcttaa aacagaagca aatctgactc   5880
agagaataaa caacctccta gtaaactaca gcttagacag agcatctggt ggtgagtgtg   5940
```

```
ctcagtgtcc tactcaactg tctggtatca gccctcatga ggacttctct tctttccctc   6000
atagacctcc atctctgttt tccttagcct gcagaaatct ggatggctat tcacagaatg   6060
cctgtgcttt cagagttgca ttttttctct ggtattctgg ttcaagcatt tgaaggtagg   6120
aaaggttctc caagtgcaag aaagccagcc ctgagcctca actgcctggc tagtgtggtc   6180
agtaggatgc aaaggctgtt gaatgccaca aggccaaact ttaacctgtg taccacaagc   6240
ctagcagcag aggcagctct gctcactgga actctctgtc ttctttctcc tgagcctttt   6300
cttttcctga gttttctagc tctcctcaac cttacctctg ccctacccag gacaaaccca   6360
agagccactg tttctgtgat gtcctctcca gccctaatta ggcatcatga cttcagcctg   6420
accttccatg ctcagaagca gtgctaatcc acttcagatg agctgctcta tgcaacacag   6480
gcagagccta caaacctttg caccagagcc ctccacatat cagtgtttgt tcatactcac   6540
ttcaacagca aatgtgactg ctgagattaa gattttacac aagatggtct gtaatttcac   6600
agttagtttt atcccattag gtatgaaaga attagcataa ttccccttaa acatgaatga   6660
atcttagatt ttttaataaa tagttttgga agtaaagaca gagacatcag gagcacaagg   6720
aatagcctga gaggacaaac agaacaagaa agagtctgga aatacacagg atgttcttgg   6780
cctcctcaaa gcaagtgcaa gcagatagta ccagcagccc caggctatca gagcccagtg   6840
aagagaagta ccatgaaagc cacagctcta accaccctgt tccagagtga cagacagtcc   6900
ccaagacaag ccagcctgag ccagagagag aactgcaaga gaaagtttct aatttaggtt   6960
ctgttagatt cagacaagtg caggtcatcc tctctccaca gctactcacc tctccagcct   7020
aacaaagcct gcagtccaca ctccaaccct ggtgtctcac ctcctagcct ctcccaacat   7080
cctgctctct gaccatcttc tgcatctctc atctcaccat ctcccactgt ctacagccta   7140
ctcttgcaac taccatctca ttttctgaca tcctgtctac atcttctgcc atactctgcc   7200
atctaccata ccacctctta ccatctacca caccatcttt tatctccatc cctctcagaa   7260
gcctccaagc tgaatcctgc tttatgtgtt catctcagcc cctgcatgga aagctgaccc   7320
cagaggcaga actattccca gagagcttgg ccaagaaaaa caaaactacc agcctggcca   7380
ggctcaggag tagtaagctg cagtgtctgt tgtgttctag cttcaacagc tgcaggagtt   7440
ccactctcaa atgctccaca tttctcacat cctcctgatt ctggtcacta cccatcttca   7500
aagaacagaa tatctcacat cagcatactg tgaaggacta gtcatgggtg cagctgctca   7560
gagctgcaaa gtcattctgg atggtggaga gcttacaaac atttcatgat gctccccccg   7620
ctctgatggc tggagcccaa tccctacaca gactcctgct gtatgtgttt tcctttcact   7680
ctgagccaca gccagagggc aggcattcag tctcctcttc aggctggggc tggggcactg   7740
agaactcacc caacaccttg ctctcactcc ttctgcaaaa caagaaagag ctttgtgctg   7800
cagtagccat gaagaatgaa aggaaggctt taactaaaaa atgtcagaga ttattttcaa   7860
ccccttactg tggatcacca gcaaggagga aacacaacac agagacattt tttcccctca   7920
aattatcaaa agaatcactg catttgttaa agagagcaac tgaatcagga agcagagttt   7980
tgaacatatc agaagttagg aatctgcatc agagacaaat gcagtcatgg ttgtttgctg   8040
cataccagcc ctaatcatta gaagcctcat ggacttcaaa catcattccc tctgacaaga   8100
tgctctagcc taactccatg agataaaata aatctgcctt tcagagccaa agaagagtcc   8160
accagcttct tctcagtgtg aacaagagct ccagtcaggt tagtcagtcc agtgcagtag   8220
aggagaccag tctgcatcct ctaattttca aaggcaagaa gatttgttta ccctggacac   8280
caggcacaag tgaggtcaca gagctcttag atatgcagtc ctcatgagtg aggagactaa   8340
```

```
agcgcatgcc atcaagactt cagtgtagag aaaacctcca aaaaagcctc ctcactactt    8400
ctggaatagc tcagaggccg aggcggcctc ggcctctgca taaataaaaa aaattagtca    8460
gccatggggc ggagaatggg cggaactggg cggagttagg ggcgggatgg gcggagttag    8520
gggcgggact atggttgctg actaattgag atgcatgctt tgcatacttc tgcctgctgg    8580
ggagcctggg gactttccac acctggttgc tgactaattg agatgcatgc tttgcatact    8640
tctgcctgct ggggagcctg gggactttcc acaccctaac tgacacacat tccacagctg    8700
cattaatgaa tcggccaacg cgcggggaga ggcggtttgc gtattgggcg ctcttccgct    8760
tcctcgctca ctgactcgct gcgctcggtc gttcggctgc ggcgagcggt atcagctcac    8820
tcaaaggcgg taatacggtt atccacagaa tcaggggata acgcaggaaa gaacatgtga    8880
gcaaaaggcc agcaaaaggc caggaaccgt aaaaaggccg cgttgctggc gtttttccat    8940
aggctccgcc cccctgacga gcatcacaaa aatcgacgct caagtcagag gtggcgaaac    9000
ccgacaggac tataaagata ccaggcgttt ccccctggaa gctccctcgt gcgctctcct    9060
gttccgaccc tgccgcttac cggatacctg tccgcctttc tcccttcggg aagcgtggcg    9120
ctttctcata gctcacgctg taggtatctc agttcggtgt aggtcgttcg ctccaagctg    9180
ggctgtgtgc acgaaccccc cgttcagccc gaccgctgcg ccttatccgg taactatcgt    9240
cttgagtcca acccggtaag acacgactta tcgccactgg cagcagccac tggtaacagg    9300
attagcagag cgaggtatgt aggcggtgct acagagttct tgaagtggtg gcctaactac    9360
ggctacacta gaagaacagt atttggtatc tgcgctctgc tgaagccagt taccttcgga    9420
aaaagagttg gtagctcttg atccggcaaa caaaccaccg ctggtagcgg tggttttttt    9480
gtttgcaagc agcagattac gcgcagaaaa aaaggatctc aagaagatcc tttgatcttt    9540
tctacggggt ctgacgctca gtggaacgaa aactcacgtt aagggatttt ggtcatgaga    9600
ttatcaaaaa ggatcttcac ctagatcctt ttaaattaaa aatgaagttt taaatcaatc    9660
taaagtatat atgagtaaac ttggtctgac agttaccaat gcttaatcag tgaggcacct    9720
atctcagcga tctgtctatt tcgttcatcc atagttgcct gactcctgca aaccacgttg    9780
tgtctcaaaa tctctgatgt tacattgcac aagataaaaa tatatcatca tgaacaataa    9840
aactgtctgc ttacataaac agtaatacaa ggggtgttat gagccatatt caacgggaaa    9900
cgtcttgctc gaggccgcga ttaaattcca acatggatgc tgatttatat gggtataaat    9960
gggctcgcga taatgtcggg caatcaggtg cgacaatcta tcgattgtat gggaagcccg   10020
atgcgccaga gttgtttctg aaacatggca aaggtagcgt tgccaatgat gttacagatg   10080
agatggtcag actaaactgg ctgacggaat ttatgcctct tccgaccatc aagcatttta   10140
tccgtactcc tgatgatgca tggttactca ccactgcgat ccccgggaaa acagcattcc   10200
aggtattaga agaatatcct gattcaggtg aaaatattgt tgatgcgctg gcagtgttcc   10260
tgcgccggtt gcattcgatt cctgtttgta attgtccttt taacagcgat cgcgtatttc   10320
gtctcgctca ggcgcaatca cgaatgaata acggtttggt tgatgcgagt gattttgatg   10380
acgagcgtaa tggctggcct gttgaacaag tctggaaaga aatgcataag cttttgccat   10440
tctcaccgga ttcagtcgtc actcatggtg atttctcact tgataacctt atttttgacg   10500
aggggaaatt aataggttgt attgatgttg gacgagtcgg aatcgcagac cgataccagg   10560
atcttgccat cctatggaac tgcctcggtg agttttctcc ttcattacag aaacggcttt   10620
ttcaaaaata tggtattgat aatcctgata tgaataaatt gcagtttcat ttgatgctcg   10680
```

```
atgagttttt ctaagggcgg cctgccacca tacccacgcc gaaacaagcg ctcatgagcc  10740

cgaagtggcg agcccgatct tccccatcgg tgatgtcggc gatataggcg ccagcaaccg  10800

cacctgtggc gccggtgatg agggcgcgcc aagtcgacgt ccggcagtc             10849
```

```
<210> SEQ ID NO 29
<211> LENGTH: 11188
<212> TYPE: DNA
<213> ORGANISM: Artificial Sequence
<220> FEATURE:
<223> OTHER INFORMATION: Synthetic polynucleotide

<400> SEQUENCE: 29

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactatt agatctgatg gccgcgctag ctctgggtat ttaagcccga gtgagcacgc    180

agggtctcca ttttgaagcg ggaggttacg cgttcgtcga ctactagtgg gtaccagagc    240

gtggtgactg agatgttttc taggaaacac aaaagataca aaaaagaaca cgtggaagga    300

tagccaaaaa ggggggctgc cccatttcc tgcaccccgc tgcgatggct ggcaccattt    360

ggaagacttc gagatacact gttgagcgca gtaagacaac agtgtatctc gaagtcttcc    420

agatggggcc agccggtcca ctctgtatcc aggccagttc tgcaaggcgt tcgaggacca    480

ccccctccc ctcgccacca gggtggtctc atacagaact tataagattc ccaaatccaa    540

agacatttca cgtttatggt gatttcccag aacacatagc gacatgcaaa tattgcaggg    600

cgccactccc ctgtccctca cagccatctt cctgccaggg cgcacgcgcg ctgggtgttc    660

ccgcctagtg acactgggcc cgcgattcct tggagcgggt tgatgacgtc agcgtttccc    720

atggtgaatc cctaggttct agaaccggtg acgtctccca tggtgaagct tggatctgaa    780

ttcggtacct agttattaat agtaatcaat tacggggtca ttagttcata gcccatatat    840

ggagttccgc gttacataac ttacggtaaa tggcccgcct ggctgaccgc ccaacgaccc    900

ccgcccattg acgtcaataa tgacgtatgt tcccatagta acgccaatag ggactttcca    960

ttgacgtcaa tgggtggagt atttacggta aactgcccac ttggcagtac atcaagtgta   1020

tcatatgcca agtacgcccc ctattgacgt caatgacggt aaatggcccg cctggcatta   1080

tgcccagtac atgaccttat gggactttcc tacttggcag tacatctacg tattagtcat   1140

cgctattacc atggtcgagg tgagccccac gttctgcttc actctcccca tctccccccc   1200

ctccccaccc ccaattttgt atttatttat tttttaatta ttttgtgcag cgatgggggc   1260

gggggggggg ggggggcgcg cgccaggcgg ggcggggcgg ggcgaggggc ggggcggggc   1320

gaggcggaga ggtgcggcgg cagccaatca gagcggcgcg ctccgaaagt ttccttttat   1380

ggcgaggcgg cggcggcggc ggccctataa aaagcgaagc gcgcggcggg cgggagtcgc   1440

tgcgacgctg ccttcgcccc gtgccccgct ccgccgccgc ctcgcgccgc ccgccccggc   1500

tctgactgac cgcgttactc ccacaggtga gcgggcggga cggcccttct cctccgggct   1560

gtaattagcg cttggtttaa tgacggcttg tttcttttct gtggctgcgt gaaagccttg   1620

aggggctccg ggagctagag cctctgctaa ccatgttcat gccttcttct ttttcctaca   1680

gctcctgggc aacgtgctgg ttattgtgct gtctcatcat tttggcaaag aattcctcga   1740

agatccgaag ggaaagtctt ccacgactgt gggatccgtt cgaagatatc accggttgag   1800

ccaccatgga attcagcagc cccagcagag aggaatgccc caagcctctg agccgggtgt   1860

caatcatggc cggatctctg acaggactgc tgctgcttca ggccgtgtct tgggcttctg   1920
```

```
gcgctagacc ttgcatcccc aagagcttcg gctacagcag cgtcgtgtgc gtgtgcaatg   1980
ccacctactg cgacagcttc gaccctccta cctttcctgc tctgggcacc ttcagcagat   2040
acgagagcac cagatccggc agacggatgg aactgagcat gggacccatc caggccaatc   2100
acacaggcac tggcctgctg ctgacactgc agcctgagca gaaattccag aaagtgaaag   2160
gcttcggcgg agccatgaca gatgccgccg ctctgaatat cctggctctg tctccaccag   2220
ctcagaacct gctgctcaag agctacttca gcgaggaagg catcggctac aacatcatca   2280
gagtgcccat ggccagctgc gacttcagca tcaggaccta cacctacgcc gacacacccg   2340
acgatttcca gctgcacaac ttcagcctgc ctgaagagga caccaagctg aagatccctc   2400
tgatccacag agccctgcag ctggcacaaa gacccgtgtc actgctggcc tctccatgga   2460
catctcccac ctggctgaaa acaaatggcg ccgtgaatgg caagggcagc ctgaaaggcc   2520
aacctggcga catctaccac cagacctggg ccagatactt cgtgaagttc ctggacgcct   2580
atgccgagca caagctgcag ttttgggccg tgacagccga gaacgaacct tctgctggac   2640
tgctgagcgg ctaccccttt cagtgcctgg gctttacacc cgagcaccag cgggacttta   2700
tcgcccgtga tctgggaccc acactggcca atagcaccca ccataatgtg cggctgctga   2760
tgctggacga ccagagactg cttctgcccc actgggctaa agtggtgctg acagatcctg   2820
aggccgccaa atacgtgcac ggaatcgccg tgcactggta tctggacttt ctggcccctg   2880
ccaaggccac actgggagag acacacagac tgttccccaa caccatgctg ttcgccagcg   2940
aagcctgtgt gggcagcaag ttttgggaac agagcgtgcg gctcggcagc tgggatagag   3000
gcatgcagta cagccacagc atcatcacca acctgctgta ccacgtcgtc ggctggaccg   3060
actggaatct ggccctgaat cctgaaggcg gccctaactg ggtccgaaac ttcgtggaca   3120
gccccatcat cgtggacatc accaaggaca ccttctacaa gcagcccatg ttctaccacc   3180
tgggacactt cagcaagttc atccccgagg gctctcagcg cgttggactg gtggcttccc   3240
agaagaacga tctggacgcc gtggctctga tgcaccctga tggatctgct gtggtggtgg   3300
tcctgaaccg cagcagcaaa gatgtgcccc tgaccatcaa ggatcccgcc gtgggattcc   3360
tggaaacaat cagccctggc tactccatcc acacctacct gtggcgtaga cagtgacaat   3420
tgttaattaa gtttaaaccc tcgaggccgc aagcttatcg ataatcaacc tctggattac   3480
aaaatttgtg aaagattgac tggtattctt aactatgttg ctccttttac gctatgtgga   3540
tacgctgctt taatgccttt gtatcatgct attgcttccc gtatggcttt cattttctcc   3600
tccttgtata aatcctggtt gctgtctctt tatgaggagt tgtggcccgt tgtcaggcaa   3660
cgtggcgtgg tgtgcactgt gtttgctgac gcaaccccca ctggttgggg cattgccacc   3720
acctgtcagc tcctttccgg gactttcgct ttccccctcc ctattgccac ggcggaactc   3780
atcgccgcct gccttgcccg ctgctggaca ggggctcggc tgttgggcac tgacaattcc   3840
gtggtgttgt cggggaaatc atcgtccttt ccttggctgc tcgcctgtgt tgccacctgg   3900
attctgcgcg ggacgtcctt ctgctacgtc ccttcggccc tcaatccagc ggaccttcct   3960
tcccgcggcc tgctgccggc tctgcggcct cttccgcgtc ttcgccttcg ccctcagacg   4020
agtcggatct ccctttgggc cgcctccccg catcgatacc gtcgactaga gctcgctgat   4080
cagcctcgac tgtgccttct agttgccagc catctgttgt ttgcccctcc cccgtgcctt   4140
ccttgaccct ggaaggtgcc actcccactg tcctttccta ataaaatgag gaaattgcat   4200
cgcattgtct gagtaggtgt cattctattc tggggggtgg ggtggggcag gacagcaagg   4260
```

```
gggaggattg ggaagacaat agcaggcatg ctggggagag atccacgata acaaacagct   4320
tttttggggt gaacatattg actgaattcc ctgcaggttg gccactccct ctctgcgcgc   4380
tcgctcgctc actgaggccg cccgggcaaa gcccgggcgt cgggcgacct ttggtcgccc   4440
ggcctcagtg agcgagcgag cgcgcagaga gggagtggcc aactccatca ctaggggttc   4500
ctgcggccgc tcgtacggtc tcgaggaatt cctgcaggat aacttgccaa cctcattcta   4560
aaatgtatat agaagcccaa aagacaataa caaaaatatt cttgtagaac aaaatgggaa   4620
agaatgttcc actaaatatc aagatttaga gcaaagcatg agatgtgtgg ggatagacag   4680
tgaggctgat aaaatagagt agagctcaga aacagaccca ttgatatatg taagtgacct   4740
atgaaaaaaa tatggcattt tacaatggga aaatgatggt ctttttcttt tttagaaaaa   4800
cagggaaata tatttatatg taaaaaataa aagggaaccc atatgtcata ccatacacac   4860
aaaaaaattc cagtgaatta taagtctaaa tggagaaggc aaaactttaa atcttttaga   4920
aaataatata gaagcatgca gaccagcctg gccaacatga tgaaaccctc tctactaata   4980
ataaaatcag tagaactact caggactact ttgagtggga agtccttttc tatgaagact   5040
tctttggcca aaattaggct ctaaatgcaa ggagatagtg catcatgcct ggctgcactt   5100
actgataaat gatgttatca ccatctttaa ccaaatgcac aggaacaagt tatggtactg   5160
atgtgctgga ttgagaagga gctctacttc cttgacagga cacatttgta tcaacttaaa   5220
aaagcagatt tttgccagca gaactattca ttcagaggta ggaaacttag aatagatgat   5280
gtcactgatt agcatggctt ccccatctcc acagctgctt cccacccagg ttgcccacag   5340
ttgagtttgt ccagtgctca gggctgccca ctctcagtaa gaagccccac accagcccct   5400
ctccaaatat gttggctgtt ccttccatta aagtgacccc actttagagc agcaagtgga   5460
tttctgtttc ttacagttca ggaaggagga gtcagctgtg agaacctgga gcctgagatg   5520
cttctaagtc ccactgctac tggggtcagg gaagccagac tccagcatca gcagtcagga   5580
gcactaagcc cttgccaaca tcctgtttct cagagaaact gcttccatta taatggttgt   5640
cctttttaa gctatcaagc caaacaacca gtgtctacca ttattctcat cacctgaagc   5700
caagggttct agcaaaagtc aagctgtctt gtaatggttg atgtgcctcc agcttctgtc   5760
ttcagtcact ccactcttag cctgctctga atcaactctg accacagttc cctggagccc   5820
ctgccacctg ctgcccctgc caccttctcc atctgcagtg ctgtgcagcc ttctgcactc   5880
ttgcagagct aataggtgga gacttgaagg aagaggagga aagtttctca taatagcctt   5940
gctgcaagct caaatgggag gtgggcactg tgcccaggag ccttggagca aaggctgtgc   6000
ccaacctctg actgcatcca ggtttggtct tgacagagat aagaagccct ggcttttgga   6060
gccaaaatct aggtcagact taggcaggat tctcaaagtt tatcagcaga acatgaggca   6120
gaagaccctt tctgctccag cttcttcagg ctcaaccttc atcagaatag atagaaagag   6180
aggctgtgag ggttcttaaa acagaagcaa atctgactca gagaataaac aacctcctag   6240
taaactacag cttagacaga gcatctggtg gtgagtgtgc tcagtgtcct actcaactgt   6300
ctggtatcag ccctcatgag gacttctctt ctttccctca tagacctcca tctctgtttt   6360
ccttagcctg cagaaatctg gatggctatt cacagaatgc ctgtgctttc agagttgcat   6420
tttttctctg gtattctggt tcaagcattt gaaggtagga aaggttctcc aagtgcaaga   6480
aagccagccc tgagcctcaa ctgcctggct agtgtggtca gtaggatgca aaggctgttg   6540
aatgccacaa ggccaaactt taacctgtgt accacaagcc tagcagcaga ggcagctctg   6600
ctcactggaa ctctctgtct tctttctcct gagccttttc ttttcctgag ttttctagct   6660
```

-continued

```
ctcctcaacc ttacctctgc cctacccagg acaaacccaa gagccactgt ttctgtgatg   6720
tcctctccag ccctaattag gcatcatgac ttcagcctga ccttccatgc tcagaagcag   6780
tgctaatcca cttcagatga gctgctctat gcaacacagg cagagcctac aaacctttgc   6840
accagagccc tccacatatc agtgtttgtt catactcact tcaacagcaa atgtgactgc   6900
tgagattaag attttacaca agatggtctg taatttcaca gttagtttta tcccattagg   6960
tatgaaagaa ttagcataat tccccttaaa catgaatgaa tcttagattt tttaataaat   7020
agttttggaa gtaaagacag agacatcagg agcacaagga atagcctgag aggacaaaca   7080
gaacaagaaa gagtctggaa atacacagga tgttcttggc ctcctcaaag caagtgcaag   7140
cagatagtac cagcagcccc aggctatcag agcccagtga agagaagtac catgaaagcc   7200
acagctctaa ccaccctgtt ccagagtgac agacagtccc caagacaagc cagcctgagc   7260
cagagagaga actgcaagag aaagtttcta atttaggttc tgttagattc agacaagtgc   7320
aggtcatcct ctctccacag ctactcacct ctccagccta acaaagcctg cagtccacac   7380
tccaaccctg gtgtctcacc tcctagcctc tcccaacatc ctgctctctg accatcttct   7440
gcatctctca tctcaccatc tcccactgtc tacagcctac tcttgcaact accatctcat   7500
tttctgacat cctgtctaca tcttctgcca tactctgcca tctaccatac cacctcttac   7560
catctaccac accatctttt atctccatcc ctctcagaag cctccaagct gaatcctgct   7620
ttatgtgttc atctcagccc ctgcatggaa agctgacccc agaggcagaa ctattcccag   7680
agagcttggc caagaaaaac aaaactacca gcctggccag gctcaggagt agtaagctgc   7740
agtgtctgtt gtgttctagc ttcaacagct gcaggagttc cactctcaaa tgctccacat   7800
ttctcacatc ctcctgattc tggtcactac ccatcttcaa agaacagaat atctcacatc   7860
agcatactgt gaaggactag tcatgggtgc agctgctcag agctgcaaag tcattctgga   7920
tggtggagag cttacaaaca tttcatgatg ctccccccgc tctgatggct ggagcccaat   7980
ccctacacag actcctgctg tatgtgtttt cctttcactc tgagccacag ccagagggca   8040
ggcattcagt ctcctcttca ggctggggct ggggcactga gaactcaccc aacaccttgc   8100
tctcactcct tctgcaaaac aagaaagagc tttgtgctgc agtagccatg aagaatgaaa   8160
ggaaggcttt aactaaaaaa tgtcagagat tattttcaac cccttactgt ggatcaccag   8220
caaggaggaa acacaacaca gagacatttt ttcccctcaa attatcaaaa gaatcactgc   8280
atttgttaaa gagagcaact gaatcaggaa gcagagtttt gaacatatca gaagttagga   8340
atctgcatca gagacaaatg cagtcatggt tgtttgctgc ataccagccc taatcattag   8400
aagcctcatg gacttcaaac atcattccct ctgacaagat gctctagcct aactccatga   8460
gataaaataa atctgccttt cagagccaaa gaagagtcca ccagcttctt ctcagtgtga   8520
acaagagctc cagtcaggtt agtcagtcca gtgcagtaga ggagaccagt ctgcatcctc   8580
taattttcaa aggcaagaag atttgtttac cctggacacc aggcacaagt gaggtcacag   8640
agctcttaga tatgcagtcc tcatgagtga ggagactaaa gcgcatgcca tcaagacttc   8700
agtgtagaga aaacctccaa aaaagcctcc tcactacttc tggaatagct cagaggccga   8760
ggcggcctcg gcctctgcat aaataaaaaa aattagtcag ccatggggcg gagaatgggc   8820
ggaactgggc ggagttaggg gcgggatggg cggagttagg ggcgggacta tggttgctga   8880
ctaattgaga tgcatgcttt gcatacttct gcctgctggg gagcctgggg actttccaca   8940
cctggttgct gactaattga gatgcatgct ttgcatactt ctgcctgctg gggagcctgg   9000
```

```
ggactttcca caccctaact gacacacatt ccacagctgc attaatgaat cggccaacgc   9060
gcggggagag gcggtttgcg tattgggcgc tcttccgctt cctcgctcac tgactcgctg   9120
cgctcggtcg ttcggctgcg gcgagcggta tcagctcact caaaggcggt aatacggtta   9180
tccacagaat caggggataa cgcaggaaag aacatgtgag caaaaggcca gcaaaaggcc   9240
aggaaccgta aaaaggccgc gttgctggcg tttttccata ggctccgccc ccctgacgag   9300
catcacaaaa atcgacgctc aagtcagagg tggcgaaacc cgacaggact ataaagatac   9360
caggcgtttc cccctggaag ctccctcgtg cgctctcctg ttccgaccct gccgcttacc   9420
ggatacctgt ccgcctttct cccttcggga agcgtggcgc tttctcatag ctcacgctgt   9480
aggtatctca gttcggtgta ggtcgttcgc tccaagctgg gctgtgtgca cgaacccccc   9540
gttcagcccg accgctgcgc cttatccggt aactatcgtc ttgagtccaa cccggtaaga   9600
cacgacttat cgccactggc agcagccact ggtaacagga ttagcagagc gaggtatgta   9660
ggcggtgcta cagagttctt gaagtggtgg cctaactacg gctacactag aagaacagta   9720
tttggtatct gcgctctgct gaagccagtt accttcggaa aaagagttgg tagctcttga   9780
tccggcaaac aaaccaccgc tggtagcggt ggtttttttg tttgcaagca gcagattacg   9840
cgcagaaaaa aaggatctca agaagatcct ttgatctttt ctacggggtc tgacgctcag   9900
tggaacgaaa actcacgtta agggattttg gtcatgagat tatcaaaaag gatcttcacc   9960
tagatccttt taaattaaaa atgaagtttt aaatcaatct aaagtatata tgagtaaact  10020
tggtctgaca gttaccaatg cttaatcagt gaggcaccta tctcagcgat ctgtctattt  10080
cgttcatcca tagttgcctg actcctgcaa accacgttgt gtctcaaaat ctctgatgtt  10140
acattgcaca agataaaaat atatcatcat gaacaataaa actgtctgct tacataaaca  10200
gtaatacaag gggtgttatg agccatattc aacgggaaac gtcttgctcg aggccgcgat  10260
taaattccaa catggatgct gatttatatg ggtataaatg ggctcgcgat aatgtcgggc  10320
aatcaggtgc gacaatctat cgattgtatg ggaagcccga tgcgccagag ttgtttctga  10380
aacatggcaa aggtagcgtt gccaatgatg ttacagatga gatggtcaga ctaaactggc  10440
tgacggaatt tatgcctctt ccgaccatca agcattttat ccgtactcct gatgatgcat  10500
ggttactcac cactgcgatc cccgggaaaa cagcattcca ggtattagaa gaatatcctg  10560
attcaggtga aaatattgtt gatgcgctgg cagtgttcct gcgccggttg cattcgattc  10620
ctgtttgtaa ttgtcctttt aacagcgatc gcgtatttcg tctcgctcag gcgcaatcac  10680
gaatgaataa cggtttggtt gatgcgagtg attttgatga cgagcgtaat ggctggcctg  10740
ttgaacaagt ctggaaagaa atgcataagc ttttgccatt ctcaccggat tcagtcgtca  10800
ctcatggtga tttctcactt gataacctta tttttgacga ggggaaatta ataggttgta  10860
ttgatgttgg acgagtcgga atcgcagacc gataccagga tcttgccatc ctatggaact  10920
gcctcggtga gttttctcct tcattacaga aacggctttt tcaaaaatat ggtattgata  10980
atcctgatat gaataaattg cagtttcatt tgatgctcga tgagtttttc taagggcggc  11040
ctgccaccat acccacgccg aaacaagcgc tcatgagccc gaagtggcga gcccgatctt  11100
ccccatcggt gatgtcggcg atataggcgc cagcaaccgc acctgtggcg ccggtgatga  11160
gggcgcgcca agtcgacgtc cggcagtc                                    11188
```

<210> SEQ ID NO 30
<211> LENGTH: 11174
<212> TYPE: DNA
<213> ORGANISM: Artificial Sequence
<220> FEATURE:
<223> OTHER INFORMATION: Synthetic polynucleotide

<400> SEQUENCE: 30

```
ttggccactc cctctctgcg cgctcgctcg ctcactgagg ccgggcgacc aaaggtcgcc      60

cgacgcccgg gctttgcccg ggcggcctca gtgagcgagc gagcgcgcag agagggagtg     120

gccaactcca tcactagggg ttcctgctag ctctgggtat ttaagcccga gtgagcacgc     180

agggtctcca ttttgaagcg ggaggttacg cgttcgtcga ctactagtgg gtaccagagc     240

tccctaggtt ctagaaccgg tgacgtcggt ggtgactgag atgttttcta ggaaacacaa     300

aagatacaaa aaagaacacg tggaaggata gccaaaaagg ggggctgccc ccatttcctg     360

caccccgctg cgatggctgg caccatttgg aagacttcga gatacactgt tgagcgcagt     420

aagacaacag tgtatctcga agtcttccag atggggccag ccggtccact ctgtatccag     480

gccagttctg caaggcgttc gaggaccacc cccctcccct cgccaccagg gtggtctcat     540

acagaactta taagattccc aaatccaaag acatttcacg tttatggtga tttcccagaa     600

cacatagcga catgcaaata ttgcagggcg ccactcccct gtccctcaca gccatcttcc     660

tgccagggcg cacgcgcgct gggtgttccc gcctagtgac actgggcccg cgattccttg     720

gagcgggttg atgacgtcag cgtttcccat ggtgaagctt ggatctgaat tcggtaccct     780

agttattaat agtaatcaat tacggggtca ttagttcata gcccatatat ggagttccgc     840

gttacataac ttacggtaaa tggcccgcct ggctgaccgc ccaacgaccc ccgcccattg     900

acgtcaataa tgacgtatgt tcccatagta acgccaatag ggactttcca ttgacgtcaa     960

tgggtggact atttacggta aactgcccac ttggcagtac atcaagtgta tcatatgcca    1020

agtacgcccc ctattgacgt caatgacggt aaatggcccg cctggcatta tgcccagtac    1080

atgaccttat gggactttcc tacttggcag tacatctacg tattagtcat cgctattacc    1140

atggtcgagg tgagccccac gttctgcttc actctcccca tctccccccc ctccccaccc    1200

ccaattttgt atttatttat tttttaatta ttttgtgcag cgatgggggc gggggggggg    1260

ggggggcgcg cgccaggcgg ggcggggcgg ggcgaggggc ggggcggggc gaggcggaga    1320

ggtgcggcgg cagccaatca gagcggcgcg ctccgaaagt ttccttttat ggcgaggcgg    1380

cggcggcggc ggccctataa aaagcgaagc gcgcggcggg cgggagtcgc tgcgacgctg    1440

ccttcgcccc gtgccccgct ccgccgccgc ctcgcgccgc ccgccccggc tctgactgac    1500

cgcgttactc ccacaggtga gcgggcggga cggcccttct cctccgggct gtaattagcg    1560

cttggtttaa tgacggcttg ttttctgtgg ctgcgtgaaa gccttgaggg gctccgggag    1620

ctagagcctc tgctaaccat gttcatgcct tcttcttttt cctacagctc ctgggcaacg    1680

tgctggttat tgtgctgtct catcattttg gcaaagaatt cctcgaagat ccgaagggaa    1740

agtcttccac gactgtggga tccgttcgaa gatatcaccg gttgagccac catggaattc    1800

agcagcccca gcagagagga atgccccaag cctctgagcc gggtgtcaat catggccgga    1860

tctctgacag gactgctgct gcttcaggcc gtgtcttggg cttctggcgc tagaccttgc    1920

atccccaaga gcttcggcta cagcagcgtc gtgtgcgtgt gcaatgccac ctactgcgac    1980

agcttcgacc ctcctacctt tcctgctctg ggcaccttca gcagatacga gagcaccaga    2040

tccggcagac ggatggaact gagcatggga cccatccagg ccaatcacac aggcactggc    2100

ctgctgctga cactgcagcc tgagcagaaa ttccagaaag tgaaaggctt cggcggagcc    2160

atgacagatg ccgccgctct gaatatcctg gctctgtctc caccagctca gaacctgctg    2220
```

```
ctcaagagct acttcagcga ggaaggcatc ggctacaaca tcatcagagt gcccatggcc   2280
agctgcgact tcagcatcag gacctacacc tacgccgaca cacccgacga tttccagctg   2340
cacaacttca gcctgcctga agaggacacc aagctgaaga tccctctgat ccacagagcc   2400
ctgcagctgg cacaaagacc cgtgtcactg ctggcctctc catggacatc tcccacctgg   2460
ctgaaaacaa atggcgccgt gaatggcaag ggcagcctga aaggccaacc tggcgacatc   2520
taccaccaga cctgggccag atacttcgtg aagttcctgg acgcctatgc cgagcacaag   2580
ctgcagtttt gggccgtgac agccgagaac gaaccttctg ctggactgct gagcggctac   2640
ccctttcagt gcctgggctt tacacccgag caccagcggg actttatcgc ccgtgatctg   2700
ggacccacac tggccaatag cacccaccat aatgtgcggc tgctgatgct ggacgaccag   2760
agactgcttc tgccccactg ggctaaagtg gtgctgacag atcctgaggc cgccaaatac   2820
gtgcacggaa tcgccgtgca ctggtatctg gactttctgg cccctgccaa ggccacactg   2880
ggagagacac acagactgtt ccccaacacc atgctgttcg ccagcgaagc ctgtgtgggc   2940
agcaagtttt gggaacagag cgtgcggctc ggcagctggg atagaggcat gcagtacagc   3000
cacagcatca tcaccaacct gctgtaccac gtcgtcggct ggaccgactg gaatctggcc   3060
ctgaatcctg aaggcggccc taactgggtc cgaaacttcg tggacagccc catcatcgtg   3120
gacatcacca aggacacctt ctacaagcag cccatgttct accacctggg acacttcagc   3180
aagttcatcc ccgagggctc tcagcgcgtt ggactggtgg cttcccagaa gaacgatctg   3240
gacgccgtgg ctctgatgca ccctgatgga tctgctgtgg tggtggtcct gaaccgcagc   3300
agcaaagatg tgcccctgac catcaaggat cccgccgtgg gattcctgga aacaatcagc   3360
cctggctact ccatccacac ctacctgtgg cgtagacagt gacaattgtt aattaagttt   3420
aaaccctcga ggccgcaagc ttatcgataa tcaacctctg gattacaaaa tttgtgaaag   3480
attgactggt attcttaact atgttgctcc ttttacgcta tgtggatacg ctgctttaat   3540
gcctttgtat catgctattg cttcccgtat ggctttcatt ttctcctcct tgtataaatc   3600
ctggttgctg tctctttatg aggagttgtg gcccgttgtc aggcaacgtg gcgtggtgtg   3660
cactgtgttt gctgacgcaa cccccactgg ttggggcatt gccaccacct gtcagctcct   3720
ttccgggact ttcgctttcc ccctccctat tgccacggcg gaactcatcg ccgcctgcct   3780
tgcccgctgc tggacagggg ctcggctgtt gggcactgac aattccgtgg tgttgtcggg   3840
gaaatcatcg tcctttcctt ggctgctcgc ctgtgttgcc acctggattc tgcgcgggac   3900
gtccttctgc tacgtccctt cggccctcaa tccagcggac cttccttccc gcggcctgct   3960
gccggctctg cggcctcttc cgcgtcttcg ccttcgccct cagacgagtc ggatctccct   4020
ttgggccgcc tccccgcatc gataccgtcg actagagctc gctgatcagc ctcgactgtg   4080
ccttctagtt gccagccatc tgttgtttgc ccctcccccg tgccttcctt gaccctggaa   4140
ggtgccactc ccactgtcct ttcctaataa aatgaggaaa ttgcatcgca ttgtctgagt   4200
aggtgtcatt ctattctggg gggtggggtg gggcaggaca gcaaggggga ggattgggaa   4260
gacaatagca ggcatgctgg ggagagatcc acgataacaa acagcttttt tggggtgaac   4320
atattgactg aattccctgc aggttggcca ctccctctct gcgcgctcgc tcgctcactg   4380
aggccgcccg ggcaaagccc gggcgtcggg cgacctttgg tcgcccggcc tcagtgagcg   4440
agcgagcgcg cagagaggga gtggccaact ccatcactag gggttcctgc ggccgctcgt   4500
acggtctcga ggaattcctg caggataact tgccaacctc attctaaaat gtatatagaa   4560
gcccaaaaga caataacaaa aatattcttg tagaacaaaa tgggaaagaa tgttccacta   4620
```

```
aatatcaaga tttagagcaa agcatgagat gtgtggggat agacagtgag gctgataaaa   4680
tagagtagag ctcagaaaca gacccattga tatatgtaag tgacctatga aaaaaatatg   4740
gcattttaca atgggaaaat gatggtcttt ttctttttta gaaaaacagg gaaatatatt   4800
tatatgtaaa aaataaaagg gaacccatat gtcataccat acacacaaaa aaattccagt   4860
gaattataag tctaaatgga gaaggcaaaa ctttaaatct tttagaaaat aatatagaag   4920
catgcagacc agcctggcca acatgatgaa accctctcta ctaataataa aatcagtaga   4980
actactcagg actactttga gtgggaagtc cttttctatg aagacttctt tggccaaaat   5040
taggctctaa atgcaaggag atagtgcatc atgcctggct gcacttactg ataaatgatg   5100
ttatcaccat ctttaaccaa atgcacagga acaagttatg gtactgatgt gctggattga   5160
gaaggagctc tacttccttg acaggacaca tttgtatcaa cttaaaaaag cagatttttg   5220
ccagcagaac tattcattca gaggtaggaa acttagaata gatgatgtca ctgattagca   5280
tggcttcccc atctccacag ctgcttccca cccaggttgc ccacagttga gtttgtccag   5340
tgctcagggc tgcccactct cagtaagaag ccccacacca gcccctctcc aaatatgttg   5400
gctgttcctt ccattaaagt gaccccactt tagagcagca agtggatttc tgtttcttac   5460
agttcaggaa ggaggagtca gctgtgagaa cctggagcct gagatgcttc taagtcccac   5520
tgctactggg gtcagggaag ccagactcca gcatcagcag tcaggagcac taagcccttg   5580
ccaacatcct gtttctcaga gaaactgctt ccattataat ggttgtcctt ttttaagcta   5640
tcaagccaaa caaccagtgt ctaccattat tctcatcacc tgaagccaag ggttctagca   5700
aaagtcaagc tgtcttgtaa tggttgatgt gcctccagct tctgtcttca gtcactccac   5760
tcttagcctg ctctgaatca actctgacca cagttccctg gagcccctgc cacctgctgc   5820
ccctgccacc ttctccatct gcagtgctgt gcagccttct gcactcttgc agagctaata   5880
ggtggagact tgaaggaaga ggaggaaagt ttctcataat agccttgctg caagctcaaa   5940
tgggaggtgg gcactgtgcc caggagcctt ggagcaaagg ctgtgcccaa cctctgactg   6000
catccaggtt tggtcttgac agagataaga agccctggct tttggagcca aaatctaggt   6060
cagacttagg caggattctc aaagtttatc agcagaacat gaggcagaag accctttctg   6120
ctccagcttc ttcaggctca accttcatca gaatagatag aaagagaggc tgtgagggtt   6180
cttaaaacag aagcaaatct gactcagaga ataaacaacc tcctagtaaa ctacagctta   6240
gacagagcat ctggtggtga gtgtgctcag tgtcctactc aactgtctgg tatcagccct   6300
catgaggact tctcttcttt ccctcataga cctccatctc tgttttcctt agcctgcaga   6360
aatctggatg gctattcaca gaatgcctgt gctttcagag ttgcattttt tctctggtat   6420
tctggttcaa gcatttgaag gtaggaaagg ttctccaagt gcaagaaagc cagccctgag   6480
cctcaactgc ctggctagtg tggtcagtag gatgcaaagg ctgttgaatg ccacaaggcc   6540
aaactttaac ctgtgtacca caagcctagc agcagaggca gctctgctca ctggaactct   6600
ctgtcttctt tctcctgagc cttttctttt cctgagtttt ctagctctcc tcaaccttac   6660
ctctgcccta cccaggacaa acccaagagc cactgtttct gtgatgtcct ctccagccct   6720
aattaggcat catgacttca gcctgacctt ccatgctcag aagcagtgct aatccacttc   6780
agatgagctg ctctatgcaa cacaggcaga gcctacaaac ctttgcacca gagccctcca   6840
catatcagtg tttgttcata ctcacttcaa cagcaaatgt gactgctgag attaagattt   6900
tacacaagat ggtctgtaat ttcacagtta gttttatccc attaggtatg aaagaattag   6960
```

```
cataattccc cttaaacatg aatgaatctt agatttttta ataaatagtt ttggaagtaa   7020
agacagagac atcaggagca caaggaatag cctgagagga caaacagaac aagaaagagt   7080
ctggaaatac acaggatgtt cttggcctcc tcaaagcaag tgcaagcaga tagtaccagc   7140
agccccaggc tatcagagcc cagtgaagag aagtaccatg aaagccacag ctctaaccac   7200
cctgttccag agtgacagac agtccccaag acaagccagc ctgagccaga gagagaactg   7260
caagagaaag tttctaattt aggttctgtt agattcagac aagtgcaggt catcctctct   7320
ccacagctac tcacctctcc agcctaacaa agcctgcagt ccacactcca accctggtgt   7380
ctcacctcct agcctctccc aacatcctgc tctctgacca tcttctgcat ctctcatctc   7440
accatctccc actgtctaca gcctactctt gcaactacca tctcattttc tgacatcctg   7500
tctacatctt ctgccatact ctgccatcta ccataccacc tcttaccatc taccacacca   7560
tcttttatct ccatccctct cagaagcctc caagctgaat cctgctttat gtgttcatct   7620
cagcccctgc atggaaagct gaccccagag gcagaactat tcccagagag cttggccaag   7680
aaaaacaaaa ctaccagcct ggccaggctc aggagtagta agctgcagtg tctgttgtgt   7740
tctagcttca acagctgcag gagttccact ctcaaatgct ccacatttct cacatcctcc   7800
tgattctggt cactacccat cttcaaagaa cagaatatct cacatcagca tactgtgaag   7860
gactagtcat gggtgcagct gctcagagct gcaaagtcat tctggatggt ggagagctta   7920
caaacatttc atgatgctcc ccccgctctg atggctggag cccaatccct acacagactc   7980
ctgctgtatg tgttttcctt tcactctgag ccacagccag agggcaggca ttcagtctcc   8040
tcttcaggct ggggctgggg cactgagaac tcacccaaca ccttgctctc actccttctg   8100
caaaacaaga aagagctttg tgctgcagta gccatgaaga atgaaaggaa ggctttaact   8160
aaaaaatgtc agagattatt ttcaacccct tactgtggat caccagcaag gaggaaacac   8220
aacacagaga catttttttcc cctcaaatta tcaaaagaat cactgcattt gttaaagaga   8280
gcaactgaat caggaagcag agttttgaac atatcagaag ttaggaatct gcatcagaga   8340
caaatgcagt catggttgtt tgctgcatac cagccctaat cattagaagc ctcatggact   8400
tcaaacatca ttccctctga caagatgctc tagcctaact ccatgagata aaataaatct   8460
gcctttcaga gccaaagaag agtccaccag cttcttctca gtgtgaacaa gagctccagt   8520
caggttagtc agtccagtgc agtagaggag accagtctgc atcctctaat tttcaaaggc   8580
aagaagattt gtttaccctg gacaccaggc acaagtgagg tcacagagct cttagatatg   8640
cagtcctcat gagtgaggag actaaagcgc atgccatcaa gacttcagtg tagagaaaac   8700
ctccaaaaaa gcctcctcac tacttctgga atagctcaga ggccgaggcg gcctcggcct   8760
ctgcataaat aaaaaaaatt agtcagccat ggggcggaga atgggcggaa ctgggcggag   8820
ttaggggcgg gatgggcgga gttaggggcg ggactatggt tgctgactaa ttgagatgca   8880
tgctttgcat acttctgcct gctggggagc ctggggactt tccacacctg gttgctgact   8940
aattgagatg catgctttgc atacttctgc ctgctgggga gcctggggac tttccacacc   9000
ctaactgaca cacattccac agctgcatta atgaatcggc caacgcgcgg ggagaggcgg   9060
tttgcgtatt gggcgctctt ccgcttcctc gctcactgac tcgctgcgct cggtcgttcg   9120
gctgcggcga gcggtatcag ctcactcaaa ggcggtaata cggttatcca cagaatcagg   9180
ggataacgca ggaaagaaca tgtgagcaaa aggccagcaa aaggccagga accgtaaaaa   9240
ggccgcgttg ctggcgtttt tccataggct ccgcccccct gacgagcatc acaaaaatcg   9300
acgctcaagt cagaggtggc gaaacccgac aggactataa agataccagg cgtttccccc   9360
```

```
tggaagctcc ctcgtgcgct ctcctgttcc gaccctgccg cttaccggat acctgtccgc   9420

ctttctccct tcgggaagcg tggcgctttc tcatagctca cgctgtaggt atctcagttc   9480

ggtgtaggtc gttcgctcca agctgggctg tgtgcacgaa ccccccgttc agcccgaccg   9540

ctgcgcctta tccggtaact atcgtcttga gtccaacccg gtaagacacg acttatcgcc   9600

actggcagca gccactggta acaggattag cagagcgagg tatgtaggcg gtgctacaga   9660

gttcttgaag tggtggccta actacggcta cactagaaga acagtatttg gtatctgcgc   9720

tctgctgaag ccagttacct tcggaaaaag agttggtagc tcttgatccg gcaaacaaac   9780

caccgctggt agcggtggtt tttttgtttg caagcagcag attacgcgca gaaaaaaagg   9840

atctcaagaa gatcctttga tcttttctac ggggtctgac gctcagtgga acgaaaactc   9900

acgttaaggg attttggtca tgagattatc aaaaaggatc ttcacctaga tccttttaaa   9960

ttaaaaatga agttttaaat caatctaaag tatatatgag taaacttggt ctgacagtta  10020

ccaatgctta atcagtgagg cacctatctc agcgatctgt ctatttcgtt catccatagt  10080

tgcctgactc ctgcaaacca cgttgtgtct caaaatctct gatgttacat tgcacaagat  10140

aaaaatatat catcatgaac aataaaactg tctgcttaca taaacagtaa tacaaggggt  10200

gttatgagcc atattcaacg ggaaacgtct tgctcgaggc cgcgattaaa ttccaacatg  10260

gatgctgatt tatatgggta taaatgggct cgcgataatg tcgggcaatc aggtgcgaca  10320

atctatcgat tgtatgggaa gcccgatgcg ccagagttgt ttctgaaaca tggcaaaggt  10380

agcgttgcca atgatgttac agatgagatg gtcagactaa actggctgac ggaatttatg  10440

cctcttccga ccatcaagca ttttatccgt actcctgatg atgcatggtt actcaccact  10500

gcgatccccg ggaaaacagc attccaggta ttagaagaat atcctgattc aggtgaaaat  10560

attgttgatg cgctggcagt gttcctgcgc cggttgcatt cgattcctgt ttgtaattgt  10620

ccttttaaca gcgatcgcgt atttcgtctc gctcaggcgc aatcacgaat gaataacggt  10680

ttggttgatg cgagtgattt tgatgacgag cgtaatggct ggcctgttga acaagtctgg  10740

aaagaaatgc ataagctttt gccattctca ccggattcag tcgtcactca tggtgatttc  10800

tcacttgata accttatttt tgacgagggg aaattaatag gttgtattga tgttggacga  10860

gtcggaatcg cagaccgata ccaggatctt gccatcctat ggaactgcct cggtgagttt  10920

tctccttcat tacagaaacg gctttttcaa aaatatggta ttgataatcc tgatatgaat  10980

aaattgcagt ttcatttgat gctcgatgag tttttctaag ggcggcctgc caccataccc  11040

acgccgaaac aagcgctcat gagcccgaag tggcgagccc gatcttcccc atcggtgatg  11100

tcggcgatat aggcgccagc aaccgcacct gtggcgccgg tgatgagggc gcgccaagtc  11160

gacgtccggc agtc                                                    11174
```

<210> SEQ ID NO 31
<211> LENGTH: 10841
<212> TYPE: DNA
<213> ORGANISM: Artificial Sequence
<220> FEATURE:
<223> OTHER INFORMATION: Synthetic polynucleotide

<400> SEQUENCE: 31

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180
```

```
agggtctcca ttttgaagcg ggaggttacg cgttcgtcga ctactagtgg gtaccagagc    240
tccctaggtt ctagaaccgg tgacgtctcc catggtgaag cttggatctg aattcggtac    300
cctagttatt aatagtaatc aattacgggg tcattagttc atagcccata tatggagttc    360
cgcgttacat aacttacggt aaatggcccg cctggctgac cgcccaacga cccccgccca    420
ttgacgtcaa taatgacgta tgttcccata gtaacgccaa tagggacttt ccattgacgt    480
caatgggtgg actatttacg gtaaactgcc cacttggcag tacatcaagt gtatcatatg    540
ccaagtacgc cccctattga cgtcaatgac ggtaaatggc ccgcctggca ttatgcccag    600
tacatgacct tatgggactt tcctacttgg cagtacatct acgtattagt catcgctatt    660
accatggtcg aggtgagccc cacgttctgc ttcactctcc ccatctcccc cccctcccca    720
cccccaattt tgtatttatt tatttttaa ttattttgtg cagcgatggg ggcggggggg    780
gggggggggc gcgcgccagg cggggcgggg cggggcgagg ggcggggcgg ggcgaggcgg    840
agaggtgcgg cggcagccaa tcagagcggc gcgctccgaa agtttccttt tatggcgagg    900
cggcggcggc ggcggcccta taaaaagcga agcgcgcggc gggcgggagt cgctgcgacg    960
ctgccttcgc cccgtgcccc gctccgccgc cgcctcgcgc cgcccgcccc ggctctgact   1020
gaccgcgtta ctcccacagg tgagcgggcg ggacggccct tctcctccgg gctgtaatta   1080
gcgcttggtt taatgacggc ttgtctggag gcttgctttg ggctgtatgc tgagggtatc   1140
aagactacga attttggcct ctgactgatt cgtagcttat accctcagga cacaaggccc   1200
tttatcagca ctcacatgga acaaatggcc accgtgggag gatgacaatt tctgtggctg   1260
cgtgaaagcc ttgaggggct ccgggagcta gagcctctgc taaccatgtt catgccttct   1320
tctttttcct acagctcctg ggcaacgtgc tggttattgt gctgtctcat cattttggca   1380
aagaattcct cgaagatccg aagggaaagt cttccacgac tgtgggatcc gttcgaagat   1440
atcaccggtt gagccaccat ggaattcagc agccccagca gagaggaatg ccccaagcct   1500
ctgagccggg tgtcaatcat ggccggatct ctgacaggac tgctgctgct tcaggccgtg   1560
tcttgggctt ctggcgctag accttgcatc cccaagagct tcggctacag cagcgtcgtg   1620
tgcgtgtgca atgccaccta ctgcgacagc ttcgaccctc ctacctttcc tgctctgggc   1680
accttcagca gatacgagag caccagatcc ggcagacgga tggaactgag catgggaccc   1740
atccaggcca atcacacagg cactggcctg ctgctgacac tgcagcctga gcagaaattc   1800
cagaaagtga aaggcttcgg cggagccatg acagatgccg ccgctctgaa tatcctggct   1860
ctgtctccac cagctcagaa cctgctgctc aagagctact tcagcgagga aggcatcggc   1920
tacaacatca tcagagtgcc catggccagc tgcgacttca gcatcaggac ctacacctac   1980
gccgacacac ccgacgattt ccagctgcac aacttcagcc tgcctgaaga ggacaccaag   2040
ctgaagatcc ctctgatcca cagagccctg cagctggcac aaagacccgt gtcactgctg   2100
gcctctccat ggacatctcc cacctggctg aaaacaaatg gcgccgtgaa tggcaagggc   2160
agcctgaaag gccaacctgg cgacatctac caccagacct gggccagata cttcgtgaag   2220
ttcctggacg cctatgccga gcacaagctg cagttttggg ccgtgacagc cgagaacgaa   2280
ccttctgctg gactgctgag cggctacccc tttcagtgcc tgggctttac acccgagcac   2340
cagcgggact ttatcgcccg tgatctggga cccacactgg ccaatagcac ccaccataat   2400
gtgcggctgc tgatgctgga cgaccagaga ctgcttctgc cccactgggc taaagtggtg   2460
ctgacagatc ctgaggccgc caaatacgtg cacggaatcg ccgtgcactg gtatctggac   2520
tttctggccc ctgccaaggc cacactggga gagacacaca gactgttccc caacaccatg   2580
```

```
ctgttcgcca gcgaagcctg tgtgggcagc aagttttggg aacagagcgt gcggctcggc   2640
agctgggata gaggcatgca gtacagccac agcatcatca ccaacctgct gtaccacgtc   2700
gtcggctgga ccgactggaa tctggccctg aatcctgaag gcggccctaa ctgggtccga   2760
aacttcgtgg acagccccat catcgtggac atcaccaagg acaccttcta caagcagccc   2820
atgttctacc acctgggaca cttcagcaag ttcatccccg agggctctca gcgcgttgga   2880
ctggtggctt cccagaagaa cgatctggac gccgtggctc tgatgcaccc tgatggatct   2940
gctgtggtgg tggtcctgaa ccgcagcagc aaagatgtgc ccctgaccat caaggatccc   3000
gccgtgggat tcctggaaac aatcagccct ggctactcca tccacaccta cctgtggcgt   3060
agacagtgac aattgttaat taagtttaaa ccctcgaggc cgcaagctta tcgataatca   3120
acctctggat tacaaaattt gtgaaagatt gactggtatt cttaactatg ttgctccttt   3180
tacgctatgt ggatacgctg ctttaatgcc tttgtatcat gctattgctt cccgtatggc   3240
tttcattttc tcctccttgt ataaatcctg gttgctgtct ctttatgagg agttgtggcc   3300
cgttgtcagg caacgtggcg tggtgtgcac tgtgtttgct gacgcaaccc ccactggttg   3360
gggcattgcc accacctgtc agctcctttc cgggactttc gctttccccc tccctattgc   3420
cacggcggaa ctcatcgccg cctgccttgc ccgctgctgg acaggggctc ggctgttggg   3480
cactgacaat tccgtggtgt tgtcggggaa atcatcgtcc tttccttggc tgctcgcctg   3540
tgttgccacc tggattctgc gcgggacgtc cttctgctac gtcccttcgg ccctcaatcc   3600
agcggacctt ccttcccgcg gcctgctgcc ggctctgcgg cctcttccgc gtcttcgcct   3660
tcgccctcag acgagtcgga tctccctttg ggccgcctcc ccgcatcgat accgtcgact   3720
agagctcgct gatcagcctc gactgtgcct tctagttgcc agccatctgt tgtttgcccc   3780
tcccccgtgc cttccttgac cctggaaggt gccactccca ctgtcctttc ctaataaaat   3840
gaggaaattg catcgcattg tctgagtagg tgtcattcta ttctgggggg tggggtgggg   3900
caggacagca agggggagga ttgggaagac aatagcaggc atgctgggga gagatccacg   3960
ataacaaaca gctttttttgg ggtgaacata ttgactgaat tccctgcagg ttggccactc   4020
cctctctgcg cgctcgctcg ctcactgagg ccgcccgggc aaagcccggg cgtcgggcga   4080
cctttggtcg cccggcctca gtgagcgagc gagcgcgcag agagggagtg gccaactcca   4140
tcactagggg ttcctgcggc cgctcgtacg gtctcgagga attcctgcag gataacttgc   4200
caacctcatt ctaaaatgta tatagaagcc caaaagacaa taacaaaaat attcttgtag   4260
aacaaaatgg gaaagaatgt tccactaaat atcaagattt agagcaaagc atgagatgtg   4320
tggggataga cagtgaggct gataaaatag agtagagctc agaaacagac ccattgatat   4380
atgtaagtga cctatgaaaa aaatatggca ttttacaatg ggaaaatgat ggtctttttc   4440
tttttagaa aaacagggaa atatatttat atgtaaaaaa taaaagggaa cccatatgtc   4500
ataccataca cacaaaaaaa ttccagtgaa ttataagtct aaatggagaa ggcaaaactt   4560
taaatctttt agaaaataat atagaagcat gcagaccagc ctggccaaca tgatgaaacc   4620
ctctctacta ataataaaat cagtagaact actcaggact actttgagtg ggaagtcctt   4680
ttctatgaag acttctttgg ccaaaattag gctctaaatg caaggagata gtgcatcatg   4740
cctggctgca cttactgata aatgatgtta tcaccatctt taaccaaatg cacaggaaca   4800
agttatggta ctgatgtgct ggattgagaa ggagctctac ttccttgaca ggacacattt   4860
gtatcaactt aaaaaagcag atttttgcca gcagaactat tcattcagag gtaggaaact   4920
```

-continued

```
tagaatagat gatgtcactg attagcatgg cttccccatc tccacagctg cttcccaccc   4980
aggttgccca cagttgagtt tgtccagtgc tcagggctgc ccactctcag taagaagccc   5040
cacaccagcc cctctccaaa tatgttggct gttccttcca ttaaagtgac cccactttag   5100
agcagcaagt ggatttctgt ttcttacagt tcaggaagga ggagtcagct gtgagaacct   5160
ggagcctgag atgcttctaa gtcccactgc tactggggtc agggaagcca gactccagca   5220
tcagcagtca ggagcactaa gcccttgcca acatcctgtt tctcagagaa actgcttcca   5280
ttataatggt tgtccttttt taagctatca agccaaacaa ccagtgtcta ccattattct   5340
catcacctga agccaagggt tctagcaaaa gtcaagctgt cttgtaatgg ttgatgtgcc   5400
tccagcttct gtcttcagtc actccactct tagcctgctc tgaatcaact ctgaccacag   5460
ttccctggag cccctgccac ctgctgcccc tgccaccttc tccatctgca gtgctgtgca   5520
gccttctgca ctcttgcaga gctaataggt ggagacttga aggaagagga ggaaagtttc   5580
tcataatagc cttgctgcaa gctcaaatgg gaggtgggca ctgtgcccag gagccttgga   5640
gcaaaggctg tgcccaacct ctgactgcat ccaggtttgg tcttgacaga gataagaagc   5700
cctggctttt ggagccaaaa tctaggtcag acttaggcag gattctcaaa gtttatcagc   5760
agaacatgag gcagaagacc ctttctgctc cagcttcttc aggctcaacc ttcatcagaa   5820
tagatagaaa gagaggctgt gagggttctt aaaacagaag caaatctgac tcagagaata   5880
aacaacctcc tagtaaacta cagcttagac agagcatctg gtggtgagtg tgctcagtgt   5940
cctactcaac tgtctggtat cagccctcat gaggacttct cttctttccc tcatagacct   6000
ccatctctgt tttccttagc ctgcagaaat ctggatggct attcacagaa tgcctgtgct   6060
ttcagagttg catttttttct ctggtattct ggttcaagca tttgaaggta ggaaaggttc   6120
tccaagtgca agaaagccag ccctgagcct caactgcctg gctagtgtgg tcagtaggat   6180
gcaaaggctg ttgaatgcca caaggccaaa ctttaacctg tgtaccacaa gcctagcagc   6240
agaggcagct ctgctcactg gaactctctg tcttctttct cctgagcctt ttcttttcct   6300
gagttttcta gctctcctca accttacctc tgccctaccc aggacaaacc caagagccac   6360
tgtttctgtg atgtcctctc cagccctaat taggcatcat gacttcagcc tgaccttcca   6420
tgctcagaag cagtgctaat ccacttcaga tgagctgctc tatgcaacac aggcagagcc   6480
tacaaacctt tgcaccagag ccctccacat atcagtgttt gttcatactc acttcaacag   6540
caaatgtgac tgctgagatt aagattttac acaagatggt ctgtaatttc acagttagtt   6600
ttatcccatt aggtatgaaa gaattagcat aattcccctt aaacatgaat gaatcttaga   6660
ttttttaata aatagttttg gaagtaaaga cagagacatc aggagcacaa ggaatagcct   6720
gagaggacaa acagaacaag aaagagtctg gaaatacaca ggatgttctt ggcctcctca   6780
aagcaagtgc aagcagatag taccagcagc cccaggctat cagagcccag tgaagagaag   6840
taccatgaaa gccacagctc taaccaccct gttccagagt gacagacagt ccccaagaca   6900
agccagcctg agccagagag agaactgcaa gagaaagttt ctaatttagg ttctgttaga   6960
ttcagacaag tgcaggtcat cctctctcca cagctactca cctctccagc ctaacaaagc   7020
ctgcagtcca cactccaacc ctggtgtctc acctcctagc ctctcccaac atcctgctct   7080
ctgaccatct tctgcatctc tcatctcacc atctcccact gtctacagcc tactcttgca   7140
actaccatct cattttctga catcctgtct acatcttctg ccatactctg ccatctacca   7200
taccacctct taccatctac cacaccatct tttatctcca tccctctcag aagcctccaa   7260
gctgaatcct gctttatgtg ttcatctcag cccctgcatg gaaagctgac cccagaggca   7320
```

gaactattcc cagagagctt ggccaagaaa aacaaaacta ccagcctggc caggctcagg 7380
agtagtaagc tgcagtgtct gttgtgttct agcttcaaca gctgcaggag ttccactctc 7440
aaatgctcca catttctcac atcctcctga ttctggtcac tacccatctt caaagaacag 7500
aatatctcac atcagcatac tgtgaaggac tagtcatggg tgcagctgct cagagctgca 7560
aagtcattct ggatggtgga gagcttacaa acatttcatg atgctccccc cgctctgatg 7620
gctggagccc aatccctaca cagactcctg ctgtatgtgt tttcctttca ctctgagcca 7680
cagccagagg gcaggcattc agtctcctct tcaggctggg gctggggcac tgagaactca 7740
cccaacacct tgctctcact ccttctgcaa aacaagaaag agctttgtgc tgcagtagcc 7800
atgaagaatg aaaggaaggc tttaactaaa aaatgtcaga gattattttc aaccccttac 7860
tgtggatcac cagcaaggag gaaacacaac acagagacat tttttcccct caaattatca 7920
aaagaatcac tgcatttgtt aaagagagca actgaatcag gaagcagagt tttgaacata 7980
tcagaagtta ggaatctgca tcagagacaa atgcagtcat ggttgtttgc tgcataccag 8040
ccctaatcat tagaagcctc atggacttca aacatcattc cctctgacaa gatgctctag 8100
cctaactcca tgagataaaa taaatctgcc tttcagagcc aaagaagagt ccaccagctt 8160
cttctcagtg tgaacaagag ctccagtcag gttagtcagt ccagtgcagt agaggagacc 8220
agtctgcatc ctctaatttt caaaggcaag aagatttgtt taccctggac accaggcaca 8280
agtgaggtca cagagctctt agatatgcag tcctcatgag tgaggagact aaagcgcatg 8340
ccatcaagac ttcagtgtag agaaaacctc caaaaaagcc tcctcactac ttctggaata 8400
gctcagaggc cgaggcggcc tcggcctctg cataaataaa aaaaattagt cagccatggg 8460
gcggagaatg ggcggaactg ggcggagtta ggggcgggat gggcggagtt aggggcggga 8520
ctatggttgc tgactaattg agatgcatgc tttgcatact tctgcctgct ggggagcctg 8580
gggactttcc acacctggtt gctgactaat tgagatgcat gctttgcata cttctgcctg 8640
ctggggagcc tggggacttt ccacacccta actgacacac attccacagc tgcattaatg 8700
aatcggccaa cgcgcgggga gaggcggttt gcgtattggg cgctcttccg cttcctcgct 8760
cactgactcg ctgcgctcgg tcgttcggct gcggcgagcg gtatcagctc actcaaaggc 8820
ggtaatacgg ttatccacag aatcagggga taacgcagga aagaacatgt gagcaaaagg 8880
ccagcaaaag gccaggaacc gtaaaaaggc cgcgttgctg gcgtttttcc ataggctccg 8940
cccccctgac gagcatcaca aaaatcgacg ctcaagtcag aggtggcgaa acccgacagg 9000
actataaaga taccaggcgt ttccccctgg aagctccctc gtgcgctctc ctgttccgac 9060
cctgccgctt accggatacc tgtccgcctt tctcccttcg ggaagcgtgg cgctttctca 9120
tagctcacgc tgtaggtatc tcagttcggt gtaggtcgtt cgctccaagc tgggctgtgt 9180
gcacgaaccc cccgttcagc ccgaccgctg cgccttatcc ggtaactatc gtcttgagtc 9240
caacccggta agacacgact tatcgccact ggcagcagcc actggtaaca ggattagcag 9300
agcgaggtat gtaggcggtg ctacagagtt cttgaagtgg tggcctaact acggctacac 9360
tagaagaaca gtatttggta tctgcgctct gctgaagcca gttaccttcg gaaaaagagt 9420
tggtagctct tgatccggca aacaaaccac cgctggtagc ggtggttttt ttgtttgcaa 9480
gcagcagatt acgcgcagaa aaaaaggatc tcaagaagat cctttgatct tttctacggg 9540
gtctgacgct cagtggaacg aaaactcacg ttaagggatt ttggtcatga gattatcaaa 9600
aaggatcttc acctagatcc ttttaaatta aaaatgaagt tttaaatcaa tctaaagtat 9660
atatgagtaa acttggtctg acagttacca atgcttaatc agtgaggcac ctatctcagc 9720
gatctgtcta tttcgttcat ccatagttgc ctgactcctg caaaccacgt tgtgtctcaa 9780
aatctctgat gttacattgc acaagataaa aatatatcat catgaacaat aaaactgtct 9840
gcttacataa acagtaatac aaggggtgtt atgagccata ttcaacggga aacgtcttgc 9900
tcgaggccgc gattaaattc caacatggat gctgatttat atgggtataa atgggctcgc 9960
gataatgtcg ggcaatcagg tgcgacaatc tatcgattgt atgggaagcc cgatgcgcca 10020
gagttgtttc tgaaacatgg caaaggtagc gttgccaatg atgttacaga tgagatggtc 10080
agactaaact ggctgacgga atttatgcct cttccgacca tcaagcattt tatccgtact 10140
cctgatgatg catggttact caccactgcg atccccggga aaacagcatt ccaggtatta 10200
gaagaatatc ctgattcagg tgaaaatatt gttgatgcgc tggcagtgtt cctgcgccgg 10260
ttgcattcga ttcctgtttg taattgtcct tttaacagcg atcgcgtatt tcgtctcgct 10320
caggcgcaat cacgaatgaa taacggtttg gttgatgcga gtgattttga tgacgagcgt 10380
aatggctggc ctgttgaaca agtctggaaa gaaatgcata agcttttgcc attctcaccg 10440
gattcagtcg tcactcatgg tgatttctca cttgataacc ttatttttga cgaggggaaa 10500
ttaataggtt gtattgatgt tggacgagtc ggaatcgcag accgatacca ggatcttgcc 10560
atcctatgga actgcctcgg tgagttttct ccttcattac agaaacggct ttttcaaaaa 10620
tatggtattg ataatcctga tatgaataaa ttgcagtttc atttgatgct cgatgagttt 10680
ttctaagggc ggcctgccac catacccacg ccgaaacaag cgctcatgag cccgaagtgg 10740
cgagcccgat cttccccatc ggtgatgtcg gcgatatagg cgccagcaac cgcacctgtg 10800
gcgccggtga tgagggcgcg ccaagtcgac gtccggcagt c 10841

<210> SEQ ID NO 32
<211> LENGTH: 11187
<212> TYPE: DNA
<213> ORGANISM: Artificial Sequence
<220> FEATURE:
<223> OTHER INFORMATION: Synthetic polynucleotide

<400> SEQUENCE: 32
ctagaaccgg tgacgtctcc catggtgaag cttggatctg aattcggtac ctagttataa 60
tagtaatcaa ttacggggtc attagttcat agcccatata tggagttccg cgttacataa 120
cttacggtaa atggcccgcc tggctgaccg cccaacgacc cccgcccatt gacgtcaata 180
atgacgtatg ttcccatagt aacgccaata gggactttcc attgacgtca atgggtggag 240
tatttacggt aaactgccca cttggcagta catcaagtgt atcatatgcc aagtacgccc 300
cctattgacg tcaatgacgg taaatggccc gcctggcatt atgcccagta catgacctta 360
tgggactttc ctacttggca gtacatctac gtattagtca tcgctattac catggtcgag 420
gtgagcccca cgttctgctt cactctcccc atctcccccc cctccccacc cccaattttg 480
tatttattta tttttaatt attttgtgca gcgatggggg cggggggggg gggggggcgc 540
gcgccaggcg gggcggggcg gggcgagggg cggggcgggg cgaggcggag aggtgcggcg 600
gcagccaatc agagcggcgc gctccgaaag tttcctttta tggcgaggcg gcggcggcgg 660
cggccctata aaaagcgaag cgcgcggcgg gcgggagtcg ctgcgacgct gccttcgccc 720
cgtgccccgc tccgccgccg cctcgcgccg cccgccccgg ctctgactga ccgcgttact 780
cccacaggtg agcgggcggg acggcccttc tcctccgggc tgtaattagc gcttggttta 840
atgacggctt gtttcttttc tgtggctgcg tgaaagcctt gaggggctcc gggagctaga 900

```
gcctctgcta accatgttca tgccttcttc tttttcctac agctcctggg caacgtgctg    960
gttattgtgc tgtctcatca ttttggcaaa gaattcctcg aagatccgaa gggaaagtct   1020
tccacgactg tgggatccgt tcgaagatat caccggttga gccaccatgg aattcagcag   1080
ccccagcaga gaggaatgcc ccaagcctct gagccgggtg tcaatcatgg ccggatctct   1140
gacaggactg ctgctgcttc aggccgtgtc ttgggcttct ggcgctagac cttgcatccc   1200
caagagcttc ggctacagca gcgtcgtgtg cgtgtgcaat gccacctact gcgacagctt   1260
cgaccctcct acctttcctg ctctgggcac cttcagcaga tacgagagca ccagatccgg   1320
cagacggatg gaactgagca tgggacccat ccaggccaat cacacaggca ctggcctgct   1380
gctgacactg cagcctgagc agaaattcca gaaagtgaaa ggcttcggcg gagccatgac   1440
agatgccgcc gctctgaata tcctggctct gtctccacca gctcagaacc tgctgctcaa   1500
gagctacttc agcgaggaag gcatcggcta caacatcatc agagtgccca tggccagctg   1560
cgacttcagc atcaggacct acacctacgc cgacacaccc gacgatttcc agctgcacaa   1620
cttcagcctg cctgaagagg acaccaagct gaagatccct ctgatccaca gagccctgca   1680
gctggcacaa agacccgtgt cactgctggc ctctccatgg acatctccca cctggctgaa   1740
aacaaatggc gccgtgaatg gcaagggcag cctgaaaggc caacctggcg acatctacca   1800
ccagacctgg gccagatact tcgtgaagtt cctggacgcc tatgccgagc acaagctgca   1860
gttttgggcc gtgacagccg agaacgaacc ttctgctgga ctgctgagcg gctacccctt   1920
tcagtgcctg ggctttacac ccgagcacca gcgggacttt atcgcccgtg atctgggacc   1980
cacactggcc aatagcaccc accataatgt gcggctgctg atgctggacg accagagact   2040
gcttctgccc cactgggcta aagtggtgct gacagatcct gaggccgcca aatacgtgca   2100
cggaatcgcc gtgcactggt atctggactt tctggcccct gccaaggcca cactgggaga   2160
gacacacaga ctgttcccca acaccatgct gttcgccagc gaagcctgtg tgggcagcaa   2220
gttttgggaa cagagcgtgc ggctcggcag ctgggataga ggcatgcagt acagccacag   2280
catcatcacc aacctgctgt accacgtcgt cggctggacc gactggaatc tggccctgaa   2340
tcctgaaggc ggccctaact gggtccgaaa cttcgtggac agccccatca tcgtggacat   2400
caccaaggac accttctaca agcagcccat gttctaccac ctgggacact tcagcaagtt   2460
catccccgag ggctctcagc gcgttggact ggtggcttcc cagaagaacg atctggacgc   2520
cgtggctctg atgcaccctg atggatctgc tgtggtggtg gtcctgaacc gcagcagcaa   2580
agatgtgccc ctgaccatca aggatcccgc cgtgggattc ctggaaacaa tcagccctgg   2640
ctactccatc cacacctacc tgtggcgtag acagtgacaa ttgttaatta agtttaaacc   2700
ctcgaggccg caagcttatc gataatcaac ctctggatta caaaatttgt gaaagattga   2760
ctggtattct taactatgtt gctcctttta cgctatgtgg atacgctgct ttaatgcctt   2820
tgtatcatgc tattgcttcc cgtatggctt tcattttctc ctccttgtat aaatcctggt   2880
tgctgtctct ttatgaggag ttgtggcccg ttgtcaggca acgtggcgtg gtgtgcactg   2940
tgtttgctga cgcaaccccc actggttggg gcattgccac cacctgtcag ctcctttccg   3000
ggactttcgc tttccccctc cctattgcca cggcggaact catcgccgcc tgccttgccc   3060
gctgctggac aggggctcgg ctgttgggca ctgacaattc cgtggtgttg tcggggaaat   3120
catcgtcctt tccttggctg ctcgcctgtg ttgccacctg gattctgcgc gggacgtcct   3180
tctgctacgt cccttcggcc ctcaatccag cggaccttcc ttcccgcggc ctgctgccgg   3240
```

```
ctctgcggcc tcttccgcgt cttcgccttc gccctcagac gagtcggatc tccctttggg   3300
ccgcctcccc gcatcgatac cgtcgactag agctcgctga tcagcctcga ctgtgccttc   3360
tagttgccag ccatctgttg tttgcccctc ccccgtgcct tccttgaccc tggaaggtgc   3420
cactcccact gtcctttcct aataaaatga ggaaattgca tcgcattgtc tgagtaggtg   3480
tcattctatt ctggggggtg gggtggggca ggacagcaag ggggaggatt gggaagacaa   3540
tagcaggcat gctggggaga gatccacgat aacaaacagc tttttggggg tgaacatatt   3600
gactgaattc cctgcaggtt ggccactccc tctctgcgcg ctcgctcgct cactgaggcc   3660
gcccgggcaa agcccgggcg tcgggcgacc tttggtcgcc cggcctcagt gagcgagcga   3720
gcgcgcagag agggagtggc caactccatc actaggggtt cctgcggccg ctcgtacggt   3780
ctcgaggaat tcctgcagga taacttgcca acctcattct aaaatgtata tagaagccca   3840
aaagacaata acaaaaatat tcttgtagaa caaaatggga aagaatgttc cactaaatat   3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatgg tctttttctt ttttagaaaa acagggaaat atatttatat   4080
gtaaaaaata aaagggaacc catatgtcat accatacaca caaaaaaatt ccagtgaatt   4140
ataagtctaa atggagaagg caaaacttta aatcttttag aaaataatat agaagcatgc   4200
agaccagcct ggccaacatg atgaaaccct ctctactaat aataaaatca gtagaactac   4260
tcaggactac tttgagtggg aagtcctttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc   4620
agggctgccc actctcagta agaagcccca caccagcccc tctccaaata tgttggctgt   4680
tccttccatt aaagtgaccc cactttagag cagcaagtgg atttctgttt cttacagttc   4740
aggaaggagg agtcagctgt gagaacctgg agcctgagat gcttctaagt cccactgcta   4800
ctggggtcag ggaagccaga ctccagcatc agcagtcagg agcactaagc ccttgccaac   4860
atcctgtttc tcagagaaac tgcttccatt ataatggttg tcctttttta agctatcaag   4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
gcctgctctg aatcaactct gaccacagtt ccctggagcc cctgccacct gctgcccctg   5100
ccaccttctc catctgcagt gctgtgcagc cttctgcact cttgcagagc taataggtgg   5160
agacttgaag gaagaggagg aaagtttctc ataatagcct tgctgcaagc tcaaatggga   5220
ggtgggcact gtgcccagga gccttggagc aaaggctgtg cccaacctct gactgcatcc   5280
aggtttggtc ttgacagaga taagaagccc tggcttttgg agccaaaatc taggtcagac   5340
ttaggcagga ttctcaaagt ttatcagcag aacatgaggc agaagaccct ttctgctcca   5400
gcttcttcag gctcaacctt catcagaata gatagaaaga gaggctgtga gggttcttaa   5460
aacagaagca aatctgactc agagaataaa caacctccta gtaaactaca gcttagacag   5520
agcatctggt ggtgagtgtg ctcagtgtcc tactcaactg tctggtatca gccctcatga   5580
ggacttctct tctttccctc atagacctcc atctctgttt tccttagcct gcagaaatct   5640
```

```
ggatggctat tcacagaatg cctgtgcttt cagagttgca ttttttctct ggtattctgg   5700
ttcaagcatt tgaaggtagg aaaggttctc caagtgcaag aaagccagcc ctgagcctca   5760
actgcctggc tagtgtggtc agtaggatgc aaaggctgtt gaatgccaca aggccaaact   5820
ttaacctgtg taccacaagc ctagcagcag aggcagctct gctcactgga actctctgtc   5880
ttctttctcc tgagcctttt cttttcctga gttttctagc tctcctcaac cttacctctg   5940
ccctacccag gacaaaccca agagccactg tttctgtgat gtcctctcca gccctaatta   6000
ggcatcatga cttcagcctg accttccatg ctcagaagca gtgctaatcc acttcagatg   6060
agctgctcta tgcaacacag gcagagccta caaacctttg caccagagcc ctccacatat   6120
cagtgtttgt tcatactcac ttcaacagca aatgtgactg ctgagattaa gattttacac   6180
aagatggtct gtaatttcac agttagtttt atcccattag gtatgaaaga attagcataa   6240
ttccccttaa acatgaatga atcttagatt ttttaataaa tagttttgga agtaaagaca   6300
gagacatcag gagcacaagg aatagcctga gaggacaaac agaacaagaa agagtctgga   6360
aatacacagg atgttcttgg cctcctcaaa gcaagtgcaa gcagatagta ccagcagccc   6420
caggctatca gagcccagtg aagagaagta ccatgaaagc cacagctcta accaccctgt   6480
tccagagtga cagacagtcc ccaagacaag ccagcctgag ccagagagag aactgcaaga   6540
gaaagtttct aatttaggtt ctgttagatt cagacaagtg caggtcatcc tctctccaca   6600
gctactcacc tctccagcct aacaaagcct gcagtccaca ctccaaccct ggtgtctcac   6660
ctcctagcct ctcccaacat cctgctctct gaccatcttc tgcatctctc atctcaccat   6720
ctcccactgt ctacagccta ctcttgcaac taccatctca ttttctgaca tcctgtctac   6780
atcttctgcc atactctgcc atctaccata ccacctctta ccatctacca caccatcttt   6840
tatctccatc cctctcagaa gcctccaagc tgaatcctgc tttatgtgtt catctcagcc   6900
cctgcatgga aagctgaccc cagaggcaga actattccca gagagcttgg ccaagaaaaa   6960
caaaactacc agcctggcca ggctcaggag tagtaagctg cagtgtctgt tgtgttctag   7020
cttcaacagc tgcaggagtt ccactctcaa atgctccaca tttctcacat cctcctgatt   7080
ctggtcacta cccatcttca aagaacagaa tatctcacat cagcatactg tgaaggacta   7140
gtcatgggtg cagctgctca gagctgcaaa gtcattctgg atggtggaga gcttacaaac   7200
atttcatgat gctccccccg ctctgatggc tggagcccaa tccctacaca gactcctgct   7260
gtatgtgttt tcctttcact ctgagccaca gccagagggc aggcattcag tctcctcttc   7320
aggctggggc tggggcactg agaactcacc caacaccttg ctctcactcc ttctgcaaaa   7380
caagaaagag ctttgtgctg cagtagccat gaagaatgaa aggaaggctt taactaaaaa   7440
atgtcagaga ttattttcaa ccccttactg tggatcacca gcaaggagga aacacaacac   7500
agagacattt tttcccctca aattatcaaa agaatcactg catttgttaa agagagcaac   7560
tgaatcagga agcagagttt tgaacatatc agaagttagg aatctgcatc agagacaaat   7620
gcagtcatgg ttgtttgctg cataccagcc ctaatcatta gaagcctcat ggacttcaaa   7680
catcattccc tctgacaaga tgctctagcc taactccatg agataaaata aatctgcctt   7740
tcagagccaa agaagagtcc accagcttct tctcagtgtg aacaagagct ccagtcaggt   7800
tagtcagtcc agtgcagtag aggagaccag tctgcatcct ctaattttca aaggcaagaa   7860
gatttgttta ccctggacac caggcacaag tgaggtcaca gagctcttag atatgcagtc   7920
ctcatgagtg aggagactaa agcgcatgcc atcaagactt cagtgtagag aaaacctcca   7980
```

```
aaaaagcctc ctcactactt ctggaatagc tcagaggccg aggcggcctc ggcctctgca   8040
taaataaaaa aaattagtca gccatggggc ggagaatggg cggaactggg cggagttagg   8100
ggcgggatgg gcggagttag gggcgggact atggttgctg actaattgag atgcatgctt   8160
tgcatacttc tgcctgctgg ggagcctggg gactttccac acctggttgc tgactaattg   8220
agatgcatgc tttgcatact tctgcctgct ggggagcctg gggactttcc acaccctaac   8280
tgacacacat tccacagctg cattaatgaa tcggccaacg cgcggggaga ggcggtttgc   8340
gtattgggcg ctcttccgct tcctcgctca ctgactcgct gcgctcggtc gttcggctgc   8400
ggcgagcggt atcagctcac tcaaaggcgg taatacggtt atccacagaa tcaggggata   8460
acgcaggaaa gaacatgtga gcaaaaggcc agcaaaaggc caggaaccgt aaaaaggccg   8520
cgttgctggc gtttttccat aggctccgcc cccctgacga gcatcacaaa aatcgacgct   8580
caagtcagag gtggcgaaac ccgacaggac tataaagata ccaggcgttt ccccctggaa   8640
gctccctcgt gcgctctcct gttccgaccc tgccgcttac cggatacctg tccgcctttc   8700
tcccttcggg aagcgtggcg ctttctcata gctcacgctg taggtatctc agttcggtgt   8760
aggtcgttcg ctccaagctg ggctgtgtgc acgaaccccc cgttcagccc gaccgctgcg   8820
ccttatccgg taactatcgt cttgagtcca acccggtaag acacgactta tcgccactgg   8880
cagcagccac tggtaacagg attagcagag cgaggtatgt aggcggtgct acagagttct   8940
tgaagtggtg gcctaactac ggctacacta gaagaacagt atttggtatc tgcgctctgc   9000
tgaagccagt taccttcgga aaaagagttg gtagctcttg atccggcaaa caaaccaccg   9060
ctggtagcgg tggttttttt gtttgcaagc agcagattac gcgcagaaaa aaaggatctc   9120
aagaagatcc tttgatcttt tctacggggt ctgacgctca gtggaacgaa aactcacgtt   9180
aagggatttt ggtcatgaga ttatcaaaaa ggatcttcac ctagatcctt ttaaattaaa   9240
aatgaagttt taaatcaatc taaagtatat atgagtaaac ttggtctgac agttaccaat   9300
gcttaatcag tgaggcacct atctcagcga tctgtctatt tcgttcatcc atagttgcct   9360
gactcctgca aaccacgttg tgtctcaaaa tctctgatgt tacattgcac aagataaaaa   9420
tatatcatca tgaacaataa aactgtctgc ttacataaac agtaatacaa ggggtgttat   9480
gagccatatt caacgggaaa cgtcttgctc gaggccgcga ttaaattcca acatggatgc   9540
tgatttatat gggtataaat gggctcgcga taatgtcggg caatcaggtg cgacaatcta   9600
tcgattgtat gggaagcccg atgcgccaga gttgtttctg aaacatggca aaggtagcgt   9660
tgccaatgat gttacagatg agatggtcag actaaactgg ctgacggaat ttatgcctct   9720
tccgaccatc aagcatttta tccgtactcc tgatgatgca tggttactca ccactgcgat   9780
ccccgggaaa acagcattcc aggtattaga agaatatcct gattcaggtg aaaatattgt   9840
tgatgcgctg gcagtgttcc tgcgccggtt gcattcgatt cctgtttgta attgtccttt   9900
taacagcgat cgcgtatttc gtctcgctca ggcgcaatca cgaatgaata acggtttggt   9960
tgatgcgagt gattttgatg acgagcgtaa tggctggcct gttgaacaag tctggaaaga  10020
aatgcataag cttttgccat tctcaccgga ttcagtcgtc actcatggtg atttctcact  10080
tgataacctt atttttgacg aggggaaatt aataggttgt attgatgttg gacgagtcgg  10140
aatcgcagac cgataccagg atcttgccat cctatggaac tgcctcggtg agttttctcc  10200
ttcattacag aaacggcttt ttcaaaaata tggtattgat aatcctgata tgaataaatt  10260
gcagtttcat ttgatgctcg atgagttttt ctaagggcgg cctgccacca tacccacgcc  10320
gaaacaagcg ctcatgagcc cgaagtggcg agcccgatct tccccatcgg tgatgtcggc  10380
```

```
gatataggcg ccagcaaccg cacctgtggc gccggtgatg agggcgcgcc aagtcgacgt  10440
ccggcagtct tggccactcc ctctctgcgc gctcgctcgc tcactgaggc cgggcgacca  10500
aaggtcgccc gacgcccggg ctttgcccgg gcggcctcag tgagcgagcg agcgcgcaga  10560
gagggagtgg ccaactccat cactaggggt tcctgctagc tctgggtatt taagcccgag  10620
tgagcacgca gggtctccat tttgaagcgg gaggttacgc gttcgtcgac tactagtggg  10680
taccagagcg tggtgactga gatgttttct aggaaacaca aaagatacaa aaaagaacac  10740
gtggaaggat agccaaaaag gggggctgcc cccatttcct gcaccccgct gcgatggctg  10800
gcaccatttg gaagacttcg agatacactg ttgagcgcag taagacaaca gtgtatctcg  10860
aagtcttcca gatggggcca gccggtccac tctgtatcca ggccagttct gcaaggcgtt  10920
cgaggaccac ccccctcccc tcgccaccag ggtggtctca tacagaactt ataagattcc  10980
caaatccaaa gacatttcac gtttatggtg atttcccaga acacatagcg acatgcaaat  11040
attgcagggc gccactcccc tgtccctcac agccatcttc ctgccagggc gcacgcgcgc  11100
tgggtgttcc cgcctagtga cactgggccc gcgattcctt ggagcgggtt gatgacgtca  11160
gcgtttccca tggtgaatcc ctaggtt                                     11187
```

<210> SEQ ID NO 33
<211> LENGTH: 10996
<212> TYPE: DNA
<213> ORGANISM: Artificial Sequence
<220> FEATURE:
<223> OTHER INFORMATION: Synthetic polynucleotide

<400> SEQUENCE: 33

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtccta gtaggcgaag ggtatcaaga ctacgaacac    300
ccatctgtgg ctttacagta ttcgtagtct tgatacccta cgctcactcg aggtggtctc    360
atacagaact tataagattc ccaaatccaa agacatttca cgtttatggt gatttcccag    420
aacacatagc gacatgcaaa tattgcaggg cgccactccc ctgtccctca cagccatctt    480
cctgccaggg cgcacgcgcg ctgggtgttc ccgcctagtg acactgggcc cgcgattcct    540
tggagcgggt tgatgacgtc agcgtttccc atggtgaagc ttggatctga attcggtacc    600
ctagttatta atagtaatca attacggggt cattagttca tagcccatat atggagttcc    660
gcgttacata acttacggta aatggcccgc ctggctgacc gcccaacgac ccccgcccat    720
tgacgtcaat aatgacgtat gttcccatag taacgccaat agggactttc cattgacgtc    780
aatgggtgga ctatttacgg taaactgccc acttggcagt acatcaagtg tatcatatgc    840
caagtacgcc ccctattgac gtcaatgacg gtaaatggcc cgcctggcat tatgcccagt    900
acatgacctt atgggacttt cctacttggc agtacatcta cgtattagtc atcgctatta    960
ccatggtcga ggtgagcccc acgttctgct tcactctccc catctccccc ccctccccac   1020
ccccaatttt gtatttattt atttttttaat tattttgtgc agcgatgggg gcgggggggg   1080
gggggggcg cgcgccaggc ggggcggggc ggggcgaggg gcggggcggg gcgaggcgga   1140
gaggtgcggc ggcagccaat cagagcggcg cgctccgaaa gtttcctttt atggcgaggc   1200
```

-continued

```
ggcggcggcg gcggccctat aaaaagcgaa gcgcgcggcg ggcgggagtc gctgcgacgc   1260
tgccttcgcc ccgtgccccg ctccgccgcc gcctcgcgcc gcccgccccg gctctgactg   1320
accgcgttac tcccacaggt gagcgggcgg gacggccctt ctcctccggg ctgtaattag   1380
cgcttggttt aatgacggct tgttttctgt ggctgcgtga aagccttgag gggctccggg   1440
agctagagcc tctgctaacc atgttcatgc cttcttcttt ttcctacagc tcctgggcaa   1500
cgtgctggtt attgtgctgt ctcatcattt tggcaaagaa ttcctcgaag atccgaaggg   1560
aaagtcttcc acgactgtgg gatccgttcg aagatatcac cggttgagcc accatggaat   1620
tcagcagccc cagcagagag gaatgcccca agcctctgag ccgggtgtca atcatggccg   1680
gatctctgac aggactgctg ctgcttcagg ccgtgtcttg ggcttctggc gctagacctt   1740
gcatccccaa gagcttcggc tacagcagcg tcgtgtgcgt gtgcaatgcc acctactgcg   1800
acagcttcga ccctcctacc tttcctgctc tgggcacctt cagcagatac gagagcacca   1860
gatccggcag acggatggaa ctgagcatgg gacccatcca ggccaatcac acaggcactg   1920
gcctgctgct gacactgcag cctgagcaga aattccagaa agtgaaaggc ttcggcggag   1980
ccatgacaga tgccgccgct ctgaatatcc tggctctgtc tccaccagct cagaacctgc   2040
tgctcaagag ctacttcagc gaggaaggca tcggctacaa catcatcaga gtgcccatgg   2100
ccagctgcga cttcagcatc aggacctaca cctacgccga cacacccgac gatttccagc   2160
tgcacaactt cagcctgcct gaagaggaca ccaagctgaa gatccctctg atccacagag   2220
ccctgcagct ggcacaaaga cccgtgtcac tgctggcctc tccatggaca tctcccacct   2280
ggctgaaaac aaatggcgcc gtgaatggca agggcagcct gaaaggccaa cctggcgaca   2340
tctaccacca gacctgggcc agatacttcg tgaagttcct ggacgcctat gccgagcaca   2400
agctgcagtt ttgggccgtg acagccgaga acgaaccttc tgctggactg ctgagcggct   2460
accccttca gtgcctgggc tttacacccg agcaccagcg ggactttatc gcccgtgatc   2520
tgggacccac actggccaat agcacccacc ataatgtgcg gctgctgatg ctggacgacc   2580
agagactgct tctgccccac tgggctaaag tggtgctgac agatcctgag gccgccaaat   2640
acgtgcacgg aatcgccgtg cactggtatc tggactttct ggcccctgcc aaggccacac   2700
tgggagagac acacagactg ttccccaaca ccatgctgtt cgccagcgaa gcctgtgtgg   2760
gcagcaagtt ttgggaacag agcgtgcggc tcggcagctg ggatagaggc atgcagtaca   2820
gccacagcat catcaccaac ctgctgtacc acgtcgtcgg ctggaccgac tggaatctgg   2880
ccctgaatcc tgaaggcggc cctaactggg tccgaaactt cgtggacagc cccatcatcg   2940
tggacatcac caaggacacc ttctacaagc agcccatgtt ctaccacctg ggacacttca   3000
gcaagttcat ccccgagggc tctcagcgcg ttggactggt ggcttcccag aagaacgatc   3060
tggacgccgt ggctctgatg caccctgatg gatctgctgt ggtggtggtc ctgaaccgca   3120
gcagcaaaga tgtgcccctg accatcaagg atcccgccgt gggattcctg gaaacaatca   3180
gccctggcta ctccatccac acctacctgt ggcgtagaca gtgacaattg ttaattaagt   3240
ttaaaccctc gaggccgcaa gcttatcgat aatcaacctc tggattacaa aatttgtgaa   3300
agattgactg gtattcttaa ctatgttgct ccttttacgc tatgtggata cgctgcttta   3360
atgcctttgt atcatgctat tgcttcccgt atggctttca ttttctcctc cttgtataaa   3420
tcctggttgc tgtctcttta tgaggagttg tggcccgttg tcaggcaacg tggcgtggtg   3480
tgcactgtgt ttgctgacgc aacccccact ggttggggca ttgccaccac ctgtcagctc   3540
ctttccggga ctttcgcttt ccccctccct attgccacgg cggaactcat cgccgcctgc   3600
```

-continued

```
cttgcccgct gctggacagg ggctcggctg ttgggcactg acaattccgt ggtgttgtcg   3660

gggaaatcat cgtcctttcc ttggctgctc gcctgtgttg ccacctggat tctgcgcggg   3720

acgtccttct gctacgtccc ttcggccctc aatccagcgg accttccttc ccgcggcctg   3780

ctgccggctc tgcggcctct tccgcgtctt cgccttcgcc ctcagacgag tcggatctcc   3840

ctttgggccg cctccccgca tcgataccgt cgactagagc tcgctgatca gcctcgactg   3900

tgccttctag ttgccagcca tctgttgttt gcccctcccc cgtgccttcc ttgaccctgg   3960

aaggtgccac tcccactgtc ctttcctaat aaaatgagga aattgcatcg cattgtctga   4020

gtaggtgtca ttctattctg gggggtgggg tggggcagga cagcaagggg gaggattggg   4080

aagacaatag caggcatgct ggggagagat ccacgataac aaacagcttt tttggggtga   4140

acatattgac tgaattccct gcaggttggc cactccctct ctgcgcgctc gctcgctcac   4200

tgaggccgcc cgggcaaagc ccgggcgtcg ggcgaccttt ggtcgcccgg cctcagtgag   4260

cgagcgagcg cgcagagagg gagtggccaa ctccatcact aggggttcct gcggccgctc   4320

gtacggtctc gaggaattcc tgcaggataa cttgccaacc tcattctaaa atgtatatag   4380

aagcccaaaa gacaataaca aaaatattct tgtagaacaa aatgggaaag aatgttccac   4440

taaatatcaa gatttagagc aaagcatgag atgtgtgggg atagacagtg aggctgataa   4500

aatagagtag agctcagaaa cagacccatt gatatatgta agtgacctat gaaaaaaata   4560

tggcatttta caatgggaaa atgatggtct tttctttttt tagaaaaaca gggaaatata   4620

tttatatgta aaaaataaaa gggaacccat atgtcatacc atacacacaa aaaaattcca   4680

gtgaattata agtctaaatg gagaaggcaa aactttaaat cttttagaaa ataatataga   4740

agcatgcaga ccagcctggc caacatgatg aaaccctctc tactaataat aaaatcagta   4800

gaactactca ggactacttt gagtgggaag tccttttcta tgaagacttc tttggccaaa   4860

attaggctct aaatgcaagg agatagtgca tcatgcctgg ctgcacttac tgataaatga   4920

tgttatcacc atctttaacc aaatgcacag gaacaagtta tggtactgat gtgctggatt   4980

gagaaggagc tctacttcct tgacaggaca catttgtatc aacttaaaaa agcagatttt   5040

tgccagcaga actattcatt cagaggtagg aaacttagaa tagatgatgt cactgattag   5100

catggcttcc ccatctccac agctgcttcc cacccaggtt gcccacagtt gagtttgtcc   5160

agtgctcagg gctgcccact ctcagtaaga agccccacac cagcccctct ccaaatatgt   5220

tggctgttcc ttccattaaa gtgaccccac tttagagcag caagtggatt tctgtttctt   5280

acagttcagg aaggaggagt cagctgtgag aacctggagc ctgagatgct tctaagtccc   5340

actgctactg gggtcaggga agccagactc cagcatcagc agtcaggagc actaagccct   5400

tgccaacatc ctgtttctca gagaaactgc ttccattata atggttgtcc ttttttaagc   5460

tatcaagcca aacaaccagt gtctaccatt attctcatca cctgaagcca agggttctag   5520

caaaagtcaa gctgtcttgt aatggttgat gtgcctccag cttctgtctt cagtcactcc   5580

actcttagcc tgctctgaat caactctgac cacagttccc tggagcccct gccacctgct   5640

gcccctgcca ccttctccat ctgcagtgct gtgcagcctt ctgcactctt gcagagctaa   5700

taggtggaga cttgaaggaa gaggaggaaa gtttctcata atagccttgc tgcaagctca   5760

aatgggaggt gggcactgtg cccaggagcc ttggagcaaa ggctgtgccc aacctctgac   5820

tgcatccagg tttggtcttg acagagataa gaagccctgg cttttggagc caaaatctag   5880

gtcagactta ggcaggattc tcaaagttta tcagcagaac atgaggcaga agaccctttc   5940
```

-continued

```
tgctccagct tcttcaggct caaccttcat cagaatagat agaaagagag gctgtgaggg   6000
ttcttaaaac agaagcaaat ctgactcaga gaataaacaa cctcctagta aactacagct   6060
tagacagagc atctggtggt gagtgtgctc agtgtcctac tcaactgtct ggtatcagcc   6120
ctcatgagga cttctcttct ttccctcata gacctccatc tctgttttcc ttagcctgca   6180
gaaatctgga tggctattca cagaatgcct gtgctttcag agttgcattt ttctctggt    6240
attctggttc aagcatttga aggtaggaaa ggttctccaa gtgcaagaaa gccagccctg   6300
agcctcaact gcctggctag tgtggtcagt aggatgcaaa ggctgttgaa tgccacaagg   6360
ccaaacttta acctgtgtac cacaagccta gcagcagagg cagctctgct cactggaact   6420
ctctgtcttc tttctcctga gccttttctt ttcctgagtt ttctagctct cctcaacctt   6480
acctctgccc tacccaggac aaacccaaga gccactgttt ctgtgatgtc ctctccagcc   6540
ctaattaggc atcatgactt cagcctgacc ttccatgctc agaagcagtg ctaatccact   6600
tcagatgagc tgctctatgc aacacaggca gagcctacaa acctttgcac cagagccctc   6660
cacatatcag tgtttgttca tactcacttc aacagcaaat gtgactgctg agattaagat   6720
tttacacaag atggtctgta atttcacagt tagttttatc ccattaggta tgaaagaatt   6780
agcataattc cccttaaaca tgaatgaatc ttagattttt taataaatag ttttggaagt   6840
aaagacagag acatcaggag cacaaggaat agcctgagag gacaaacaga acaagaaaga   6900
gtctggaaat acacaggatg ttcttggcct cctcaaagca agtgcaagca gatagtacca   6960
gcagccccag gctatcagag cccagtgaag agaagtacca tgaaagccac agctctaacc   7020
accctgttcc agagtgacag acagtcccca agacaagcca gcctgagcca gagagagaac   7080
tgcaagagaa agtttctaat ttaggttctg ttagattcag acaagtgcag gtcatcctct   7140
ctccacagct actcacctct ccagcctaac aaagcctgca gtccacactc caaccctggt   7200
gtctcacctc ctagcctctc ccaacatcct gctctctgac catcttctgc atctctcatc   7260
tcaccatctc ccactgtcta cagcctactc ttgcaactac catctcattt tctgacatcc   7320
tgtctacatc ttctgccata ctctgccatc taccatacca cctcttacca tctaccacac   7380
catcttttat ctccatccct ctcagaagcc tccaagctga atcctgcttt atgtgttcat   7440
ctcagcccct gcatggaaag ctgaccccag aggcagaact attcccagag agcttggcca   7500
agaaaaacaa aactaccagc ctggccaggc tcaggagtag taagctgcag tgtctgttgt   7560
gttctagctt caacagctgc aggagttcca ctctcaaatg ctccacattt ctcacatcct   7620
cctgattctg gtcactaccc atcttcaaag aacagaatat ctcacatcag catactgtga   7680
aggactagtc atgggtgcag ctgctcagag ctgcaaagtc attctggatg gtggagagct   7740
tacaaacatt tcatgatgct ccccccgctc tgatggctgg agcccaatcc ctacacagac   7800
tcctgctgta tgtgttttcc tttcactctg agccacagcc agagggcagg cattcagtct   7860
cctcttcagg ctggggctgg ggcactgaga actcacccaa caccttgctc tcactccttc   7920
tgcaaaacaa gaaagagctt tgtgctgcag tagccatgaa gaatgaaagg aaggctttaa   7980
ctaaaaaatg tcagagatta ttttcaaccc cttactgtgg atcaccagca aggaggaaac   8040
acaacacaga gacatttttt cccctcaaat tatcaaaaga atcactgcat ttgttaaaga   8100
gagcaactga atcaggaagc agagttttga acatatcaga agttaggaat ctgcatcaga   8160
gacaaatgca gtcatggttg tttgctgcat accagcccta atcattagaa gcctcatgga   8220
cttcaaacat cattccctct gacaagatgc tctagcctaa ctccatgaga taaaataaat   8280
ctgcctttca gagccaaaga agagtccacc agcttcttct cagtgtgaac aagagctcca   8340
```

```
gtcaggttag tcagtccagt gcagtagagg agaccagtct gcatcctcta attttcaaag   8400
gcaagaagat ttgtttaccc tggacaccag gcacaagtga ggtcacagag ctcttagata   8460
tgcagtcctc atgagtgagg agactaaagc gcatgccatc aagacttcag tgtagagaaa   8520
acctccaaaa aagcctcctc actacttctg gaatagctca gaggccgagg cggcctcggc   8580
ctctgcataa ataaaaaaaa ttagtcagcc atggggcgga gaatgggcgg aactgggcgg   8640
agttaggggc gggatgggcg gagttagggg cgggactatg gttgctgact aattgagatg   8700
catgctttgc atacttctgc ctgctgggga gcctggggac tttccacacc tggttgctga   8760
ctaattgaga tgcatgcttt gcatacttct gcctgctggg gagcctgggg actttccaca   8820
ccctaactga cacacattcc acagctgcat taatgaatcg gccaacgcgc ggggagaggc   8880
ggtttgcgta ttgggcgctc ttccgcttcc tcgctcactg actcgctgcg ctcggtcgtt   8940
cggctgcggc gagcggtatc agctcactca aaggcggtaa tacggttatc cacagaatca   9000
ggggataacg caggaaagaa catgtgagca aaaggccagc aaaaggccag gaaccgtaaa   9060
aaggccgcgt tgctggcgtt tttccatagg ctccgccccc ctgacgagca tcacaaaaat   9120
cgacgctcaa gtcagaggtg gcgaaacccg acaggactat aaagatacca ggcgtttccc   9180
cctggaagct ccctcgtgcg ctctcctgtt ccgaccctgc cgcttaccgg atacctgtcc   9240
gcctttctcc cttcgggaag cgtggcgctt tctcatagct cacgctgtag gtatctcagt   9300
tcggtgtagg tcgttcgctc caagctgggc tgtgtgcacg aaccccccgt tcagcccgac   9360
cgctgcgcct tatccggtaa ctatcgtctt gagtccaacc cggtaagaca cgacttatcg   9420
ccactggcag cagccactgg taacaggatt agcagagcga ggtatgtagg cggtgctaca   9480
gagttcttga agtggtggcc taactacggc tacactagaa gaacagtatt tggtatctgc   9540
gctctgctga agccagttac cttcggaaaa agagttggta gctcttgatc cggcaaacaa   9600
accaccgctg gtagcggtgg tttttttgtt tgcaagcagc agattacgcg cagaaaaaaa   9660
ggatctcaag aagatccttt gatcttttct acggggtctg acgctcagtg gaacgaaaac   9720
tcacgttaag ggattttggt catgagatta tcaaaaagga tcttcaccta gatcctttta   9780
aattaaaaat gaagttttaa atcaatctaa agtatatatg agtaaacttg gtctgacagt   9840
taccaatgct taatcagtga ggcacctatc tcagcgatct gtctatttcg ttcatccata   9900
gttgcctgac tcctgcaaac cacgttgtgt ctcaaaatct ctgatgttac attgcacaag   9960
ataaaaatat atcatcatga acaataaaac tgtctgctta cataaacagt aatacaaggg  10020
gtgttatgag ccatattcaa cgggaaacgt cttgctcgag gccgcgatta aattccaaca  10080
tggatgctga tttatatggg tataaatggg ctcgcgataa tgtcgggcaa tcaggtgcga  10140
caatctatcg attgtatggg aagcccgatg cgccagagtt gtttctgaaa catggcaaag  10200
gtagcgttgc caatgatgtt acagatgaga tggtcagact aaactggctg acggaattta  10260
tgcctcttcc gaccatcaag cattttatcc gtactcctga tgatgcatgg ttactcacca  10320
ctgcgatccc cgggaaaaca gcattccagg tattagaaga atatcctgat tcaggtgaaa  10380
atattgttga tgcgctggca gtgttcctgc gccggttgca ttcgattcct gtttgtaatt  10440
gtccttttaa cagcgatcgc gtatttcgtc tcgctcaggc gcaatcacga atgaataacg  10500
gtttggttga tgcgagtgat tttgatgacg agcgtaatgg ctggcctgtt gaacaagtct  10560
ggaaagaaat gcataagctt ttgccattct caccggattc agtcgtcact catggtgatt  10620
tctcacttga taaccttatt tttgacgagg ggaaattaat aggttgtatt gatgttggac  10680
```

```
gagtcggaat cgcagaccga taccaggatc ttgccatcct atggaactgc ctcggtgagt  10740

tttctccttc attacagaaa cggctttttc aaaaatatgg tattgataat cctgatatga  10800

ataaattgca gtttcatttg atgctcgatg agtttttcta agggcggcct gccaccatac  10860

ccacgccgaa acaagcgctc atgagcccga agtggcgagc ccgatcttcc ccatcggtga  10920

tgtcggcgat ataggcgcca gcaaccgcac ctgtggcgcc ggtgatgagg gcgcgccaag  10980

tcgacgtccg gcagtc                                                  10996
```

<210> SEQ ID NO 34
<211> LENGTH: 10845
<212> TYPE: DNA
<213> ORGANISM: Artificial Sequence
<220> FEATURE:
<223> OTHER INFORMATION: Synthetic polynucleotide

<400> SEQUENCE: 34

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300

cctagttatt aatagtaatc aattacgggg tcattagttc atagcccata tatggagttc    360

cgcgttacat aacttacggt aaatggcccg cctggctgac cgcccaacga cccccgccca    420

ttgacgtcaa taatgacgta tgttcccata gtaacgccaa tagggacttt ccattgacgt    480

caatgggtgg actatttacg gtaaactgcc cacttggcag tacatcaagt gtatcatatg    540

ccaagtacgc cccctattga cgtcaatgac ggtaaatggc ccgcctggca ttatgcccag    600

tacatgacct tatgggactt tcctacttgg cagtacatct acgtattagt catcgctatt    660

accatggtcg aggtgagccc cacgttctgc ttcactctcc ccatctcccc cccctcccca    720

cccccaattt tgtatttatt tatttttaa ttattttgtg cagcgatggg ggcggggggg    780

gggggggggc gcgcgccagg cggggcgggg cggggcgagg ggcggggcgg ggcgaggcgg    840

agaggtgcgg cggcagccaa tcagagcggc gcgctccgaa agtttccttt tatggcgagg    900

cggcggcggc ggcggcccta taaaaagcga agcgcgcggc gggcgggagt cgctgcgacg    960

ctgccttcgc cccgtgcccc gctccgccgc cgcctcgcgc cgcccgcccc ggctctgact   1020

gaccgcgtta ctcccacagg tgagcgggcg ggacggccct tctcctccgg gctgtaatta   1080

gcgcttggtt taatgacggc ttgtctggag gcttgctttg ggctgtatgc tgtttagaaa   1140

taagtggtag tcattttggc ctctgactga tgactacact atttctaaac aggacacaag   1200

gccctttatc agcactcaca tggaacaaat ggccaccgtg ggaggatgac aatttctgtg   1260

gctgcgtgaa agccttgagg ggctccggga gctagagcct ctgctaacca tgttcatgcc   1320

ttcttctttt tcctacagct cctgggcaac gtgctggtta ttgtgctgtc tcatcatttt   1380

ggcaaagaat tcctcgaaga tccgaaggga aagtcttcca cgactgtggg atccgttcga   1440

agatatcacc ggttgagcca ccatggaatt cagcagcccc agcagagagg aatgccccaa   1500

gcctctgagc cgggtgtcaa tcatggccgg atctctgaca ggactgctgc tgcttcaggc   1560

cgtgtcttgg gcttctggcg ctagaccttg catccccaag agcttcggct acagcagcgt   1620

cgtgtgcgtg tgcaatgcca cctactgcga cagcttcgac cctcctacct ttcctgctct   1680

gggcaccttc agcagatacg agagcaccag atccggcaga cggatggaac tgagcatggg   1740
```

```
acccatccag gccaatcaca caggcactgg cctgctgctg acactgcagc ctgagcagaa   1800
attccagaaa gtgaaaggct tcggcggagc catgacagat gccgccgctc tgaatatcct   1860
ggctctgtct ccaccagctc agaacctgct gctcaagagc tacttcagcg aggaaggcat   1920
cggctacaac atcatcagag tgcccatggc cagctgcgac ttcagcatca ggacctacac   1980
ctacgccgac acacccgacg atttccagct gcacaacttc agcctgcctg aagaggacac   2040
caagctgaag atccctctga tccacagagc cctgcagctg gcacaaagac ccgtgtcact   2100
gctggcctct ccatggacat ctcccacctg gctgaaaaca aatggcgccg tgaatggcaa   2160
gggcagcctg aaaggccaac ctggcgacat ctaccaccag acctgggcca gatacttcgt   2220
gaagttcctg gacgcctatg ccgagcacaa gctgcagttt tgggccgtga cagccgagaa   2280
cgaaccttct gctggactgc tgagcggcta cccctttcag tgcctgggct ttacacccga   2340
gcaccagcgg gactttatcg cccgtgatct gggacccaca ctggccaata gcacccacca   2400
taatgtgcgg ctgctgatgc tggacgacca gagactgctt ctgccccact gggctaaagt   2460
ggtgctgaca gatcctgagg ccgccaaata cgtgcacgga atcgccgtgc actggtatct   2520
ggactttctg gcccctgcca aggccacact gggagagaca cacagactgt tccccaacac   2580
catgctgttc gccagcgaag cctgtgtggg cagcaagttt tgggaacaga gcgtgcggct   2640
cggcagctgg gatagaggca tgcagtacag ccacagcatc atcaccaacc tgctgtacca   2700
cgtcgtcggc tggaccgact ggaatctggc cctgaatcct gaaggcggcc ctaactgggt   2760
ccgaaacttc gtggacagcc ccatcatcgt ggacatcacc aaggacacct tctacaagca   2820
gcccatgttc taccacctgg gacacttcag caagttcatc cccgagggct ctcagcgcgt   2880
tggactggtg gcttcccaga agaacgatct ggacgccgtg gctctgatgc accctgatgg   2940
atctgctgtg gtggtggtcc tgaaccgcag cagcaaagat gtgcccctga ccatcaagga   3000
tcccgccgtg ggattcctgg aaacaatcag ccctggctac tccatccaca cctacctgtg   3060
gcgtagacag tgacaattgt taattaagtt taaaccctcg aggccgcaag cttatcgata   3120
atcaacctct ggattacaaa atttgtgaaa gattgactgg tattcttaac tatgttgctc   3180
cttttacgct atgtggatac gctgctttaa tgcctttgta tcatgctatt gcttcccgta   3240
tggctttcat tttctcctcc ttgtataaat cctggttgct gtctctttat gaggagttgt   3300
ggcccgttgt caggcaacgt ggcgtggtgt gcactgtgtt tgctgacgca acccccactg   3360
gttggggcat tgccaccacc tgtcagctcc tttccgggac tttcgctttc cccctcccta   3420
ttgccacggc ggaactcatc gccgcctgcc ttgcccgctg ctggacaggg gctcggctgt   3480
tgggcactga caattccgtg gtgttgtcgg ggaaatcatc gtcctttcct tggctgctcg   3540
cctgtgttgc cacctggatt ctgcgcggga cgtccttctg ctacgtccct tcggccctca   3600
atccagcgga ccttccttcc cgcggcctgc tgccggctct gcggcctctt ccgcgtcttc   3660
gccttcgccc tcagacgagt cggatctccc tttgggccgc ctccccgcat cgataccgtc   3720
gactagagct cgctgatcag cctcgactgt gccttctagt tgccagccat ctgttgtttg   3780
cccctccccc gtgccttcct tgaccctgga aggtgccact cccactgtcc tttcctaata   3840
aaatgaggaa attgcatcgc attgtctgag taggtgtcat tctattctgg ggggtggggt   3900
ggggcaggac agcaaggggg aggattggga agacaatagc aggcatgctg gggagagatc   3960
cacgataaca aacagctttt ttggggtgaa catattgact gaattccctg caggttggcc   4020
actccctctc tgcgcgctcg ctcgctcact gaggccgccc gggcaaagcc cgggcgtcgg   4080
```

```
gcgacctttg gtcgcccggc ctcagtgagc gagcgagcgc gcagagaggg agtggccaac   4140
tccatcacta ggggttcctg cggccgctcg tacggtctcg aggaattcct gcaggataac   4200
ttgccaacct cattctaaaa tgtatataga agcccaaaag acaataacaa aaatattctt   4260
gtagaacaaa atgggaaaga atgttccact aaatatcaag atttagagca aagcatgaga   4320
tgtgtgggga tagacagtga ggctgataaa atagagtaga gctcagaaac agacccattg   4380
atatatgtaa gtgacctatg aaaaaaatat ggcattttac aatgggaaaa tgatggtctt   4440
tttctttttt agaaaaacag ggaaatatat ttatatgtaa aaaataaaag ggaacccata   4500
tgtcatacca tacacacaaa aaaattccag tgaattataa gtctaaatgg agaaggcaaa   4560
actttaaatc ttttagaaaa taatatagaa gcatgcagac cagcctggcc aacatgatga   4620
aaccctctct actaataata aaatcagtag aactactcag gactactttg agtgggaagt   4680
ccttttctat gaagacttct ttggccaaaa ttaggctcta aatgcaagga gatagtgcat   4740
catgcctggc tgcacttact gataaatgat gttatcacca tctttaacca aatgcacagg   4800
aacaagttat ggtactgatg tgctggattg agaaggagct ctacttcctt gacaggacac   4860
atttgtatca acttaaaaaa gcagattttt gccagcagaa ctattcattc agaggtagga   4920
aacttagaat agatgatgtc actgattagc atggcttccc catctccaca gctgcttccc   4980
acccaggttg cccacagttg agtttgtcca gtgctcaggg ctgcccactc tcagtaagaa   5040
gccccacacc agcccctctc caaatatgtt ggctgttcct tccattaaag tgaccccact   5100
ttagagcagc aagtggattt ctgtttctta cagttcagga aggaggagtc agctgtgaga   5160
acctggagcc tgagatgctt ctaagtccca ctgctactgg ggtcagggaa gccagactcc   5220
agcatcagca gtcaggagca ctaagccctt gccaacatcc tgtttctcag agaaactgct   5280
tccattataa tggttgtcct tttttaagct atcaagccaa acaaccagtg tctaccatta   5340
ttctcatcac ctgaagccaa gggttctagc aaaagtcaag ctgtcttgta atggttgatg   5400
tgcctccagc ttctgtcttc agtcactcca ctcttagcct gctctgaatc aactctgacc   5460
acagttccct ggagcccctg ccacctgctg cccctgccac cttctccatc tgcagtgctg   5520
tgcagccttc tgcactcttg cagagctaat aggtggagac ttgaaggaag aggaggaaag   5580
tttctcataa tagccttgct gcaagctcaa atgggaggtg ggcactgtgc ccaggagcct   5640
tggagcaaag gctgtgccca acctctgact gcatccaggt ttggtcttga cagagataag   5700
aagccctggc ttttggagcc aaaatctagg tcagacttag gcaggattct caaagtttat   5760
cagcagaaca tgaggcagaa gaccctttct gctccagctt cttcaggctc aaccttcatc   5820
agaatagata gaaagagagg ctgtgagggt tcttaaaaca gaagcaaatc tgactcagag   5880
aataaacaac ctcctagtaa actacagctt agacagagca tctggtggtg agtgtgctca   5940
gtgtcctact caactgtctg gtatcagccc tcatgaggac ttctcttctt tccctcatag   6000
acctccatct ctgttttcct tagcctgcag aaatctggat ggctattcac agaatgcctg   6060
tgctttcaga gttgcatttt ttctctggta ttctggttca agcatttgaa ggtaggaaag   6120
gttctccaag tgcaagaaag ccagccctga gcctcaactg cctggctagt gtggtcagta   6180
ggatgcaaag gctgttgaat gccacaaggc caaactttaa cctgtgtacc acaagcctag   6240
cagcagaggc agctctgctc actggaactc tctgtcttct ttctcctgag ccttttcttt   6300
tcctgagttt tctagctctc ctcaacctta cctctgccct acccaggaca aacccaagag   6360
ccactgtttc tgtgatgtcc tctccagccc taattaggca tcatgacttc agcctgacct   6420
tccatgctca gaagcagtgc taatccactt cagatgagct gctctatgca acacaggcag   6480
```

```
agcctacaaa cctttgcacc agagccctcc acatatcagt gtttgttcat actcacttca   6540
acagcaaatg tgactgctga gattaagatt ttacacaaga tggtctgtaa tttcacagtt   6600
agttttatcc cattaggtat gaaagaatta gcataattcc ccttaaacat gaatgaatct   6660
tagatttttt aataaatagt tttggaagta aagacagaga catcaggagc acaaggaata   6720
gcctgagagg acaaacagaa caagaaagag tctggaaata cacaggatgt tcttggcctc   6780
ctcaaagcaa gtgcaagcag atagtaccag cagccccagg ctatcagagc ccagtgaaga   6840
gaagtaccat gaaagccaca gctctaacca ccctgttcca gagtgacaga cagtccccaa   6900
gacaagccag cctgagccag agagagaact gcaagagaaa gtttctaatt taggttctgt   6960
tagattcaga caagtgcagg tcatcctctc tccacagcta ctcacctctc cagcctaaca   7020
aagcctgcag tccacactcc aaccctggtg tctcacctcc tagcctctcc caacatcctg   7080
ctctctgacc atcttctgca tctctcatct caccatctcc cactgtctac agcctactct   7140
tgcaactacc atctcatttt ctgacatcct gtctacatct tctgccatac tctgccatct   7200
accataccac ctcttaccat ctaccacacc atcttttatc tccatccctc tcagaagcct   7260
ccaagctgaa tcctgcttta tgtgttcatc tcagcccctg catggaaagc tgaccccaga   7320
ggcagaacta ttcccagaga gcttggccaa gaaaaacaaa actaccagcc tggccaggct   7380
caggagtagt aagctgcagt gtctgttgtg ttctagcttc aacagctgca ggagttccac   7440
tctcaaatgc tccacatttc tcacatcctc ctgattctgg tcactaccca tcttcaaaga   7500
acagaatatc tcacatcagc atactgtgaa ggactagtca tgggtgcagc tgctcagagc   7560
tgcaaagtca ttctggatgg tggagagctt acaaacattt catgatgctc cccccgctct   7620
gatggctgga gcccaatccc tacacagact cctgctgtat gtgttttcct ttcactctga   7680
gccacagcca gagggcaggc attcagtctc ctcttcaggc tggggctggg gcactgagaa   7740
ctcacccaac accttgctct cactccttct gcaaaacaag aaagagcttt gtgctgcagt   7800
agccatgaag aatgaaagga aggctttaac taaaaaatgt cagagattat tttcaacccc   7860
ttactgtgga tcaccagcaa ggaggaaaca caacacagag acattttttc ccctcaaatt   7920
atcaaaagaa tcactgcatt tgttaaagag agcaactgaa tcaggaagca gagttttgaa   7980
catatcagaa gttaggaatc tgcatcagag acaaatgcag tcatggttgt ttgctgcata   8040
ccagccctaa tcattagaag cctcatggac ttcaaacatc attccctctg acaagatgct   8100
ctagcctaac tccatgagat aaaataaatc tgcctttcag agccaaagaa gagtccacca   8160
gcttcttctc agtgtgaaca agagctccag tcaggttagt cagtccagtg cagtagagga   8220
gaccagtctg catcctctaa ttttcaaagg caagaagatt tgtttaccct ggacaccagg   8280
cacaagtgag gtcacagagc tcttagatat gcagtcctca tgagtgagga gactaaagcg   8340
catgccatca agacttcagt gtagagaaaa cctccaaaaa agcctcctca ctacttctgg   8400
aatagctcag aggccgaggc ggcctcggcc tctgcataaa taaaaaaaat tagtcagcca   8460
tggggcggag aatgggcgga actgggcgga gttaggggcg ggatgggcgg agttaggggc   8520
gggactatgg ttgctgacta attgagatgc atgctttgca tacttctgcc tgctggggag   8580
cctggggact ttccacacct ggttgctgac taattgagat gcatgctttg catacttctg   8640
cctgctgggg agcctgggga ctttccacac cctaactgac acacattcca cagctgcatt   8700
aatgaatcgg ccaacgcgcg gggagaggcg gtttgcgtat tgggcgctct tccgcttcct   8760
cgctcactga ctcgctgcgc tcggtcgttc ggctgcggcg agcggtatca gctcactcaa   8820
```

```
aggcggtaat acggttatcc acagaatcag gggataacgc aggaaagaac atgtgagcaa   8880
aaggccagca aaaggccagg aaccgtaaaa aggccgcgtt gctggcgttt ttccataggc   8940
tccgcccccc tgacgagcat cacaaaaatc gacgctcaag tcagaggtgg cgaaacccga   9000
caggactata aagataccag gcgtttcccc ctggaagctc cctcgtgcgc tctcctgttc   9060
cgaccctgcc gcttaccgga tacctgtccg cctttctccc ttcgggaagc gtggcgcttt   9120
ctcatagctc acgctgtagg tatctcagtt cggtgtaggt cgttcgctcc aagctgggct   9180
gtgtgcacga accccccgtt cagcccgacc gctgcgcctt atccggtaac tatcgtcttg   9240
agtccaaccc ggtaagacac gacttatcgc cactggcagc agccactggt aacaggatta   9300
gcagagcgag gtatgtaggc ggtgctacag agttcttgaa gtggtggcct aactacggct   9360
acactagaag aacagtattt ggtatctgcg ctctgctgaa gccagttacc ttcggaaaaa   9420
gagttggtag ctcttgatcc ggcaaacaaa ccaccgctgg tagcggtggt ttttttgttt   9480
gcaagcagca gattacgcgc agaaaaaaag gatctcaaga agatcctttg atcttttcta   9540
cggggtctga cgctcagtgg aacgaaaact cacgttaagg gattttggtc atgagattat   9600
caaaaaggat cttcacctag atccttttaa attaaaaatg aagttttaaa tcaatctaaa   9660
gtatatatga gtaaacttgg tctgacagtt accaatgctt aatcagtgag gcacctatct   9720
cagcgatctg tctatttcgt tcatccatag ttgcctgact cctgcaaacc acgttgtgtc   9780
tcaaaatctc tgatgttaca ttgcacaaga taaaaatata tcatcatgaa caataaaact   9840
gtctgcttac ataaacagta atacaagggg tgttatgagc catattcaac gggaaacgtc   9900
ttgctcgagg ccgcgattaa attccaacat ggatgctgat ttatatgggt ataaatgggc   9960
tcgcgataat gtcgggcaat caggtgcgac aatctatcga ttgtatggga agcccgatgc  10020
gccagagttg tttctgaaac atggcaaagg tagcgttgcc aatgatgtta cagatgagat  10080
ggtcagacta aactggctga cggaatttat gcctcttccg accatcaagc attttatccg  10140
tactcctgat gatgcatggt tactcaccac tgcgatcccc gggaaaacag cattccaggt  10200
attagaagaa tatcctgatt caggtgaaaa tattgttgat gcgctggcag tgttcctgcg  10260
ccggttgcat tcgattcctg tttgtaattg tccttttaac agcgatcgcg tatttcgtct  10320
cgctcaggcg caatcacgaa tgaataacgg tttggttgat gcgagtgatt ttgatgacga  10380
gcgtaatggc tggcctgttg aacaagtctg gaaagaaatg cataagcttt tgccattctc  10440
accggattca gtcgtcactc atggtgattt ctcacttgat aaccttattt ttgacgaggg  10500
gaaattaata ggttgtattg atgttggacg agtcggaatc gcagaccgat accaggatct  10560
tgccatccta tggaactgcc tcggtgagtt ttctccttca ttacagaaac ggctttttca  10620
aaaatatggt attgataatc ctgatatgaa taaattgcag tttcatttga tgctcgatga  10680
gtttttctaa gggcggcctg ccaccatacc cacgccgaaa caagcgctca tgagcccgaa  10740
gtggcgagcc cgatcttccc catcggtgat gtcggcgata taggcgccag caaccgcacc  10800
tgtggcgccg gtgatgaggg cgcgccaagt cgacgtccgg cagtc                  10845
```

<210> SEQ ID NO 35
<211> LENGTH: 11320
<212> TYPE: DNA
<213> ORGANISM: Artificial Sequence
<220> FEATURE:
<223> OTHER INFORMATION: Synthetic polynucleotide

<400> SEQUENCE: 35

```
ttggccactc cctctctgcg cgctcgctcg ctcactgagg ccgggcgacc aaaggtcgcc     60
```

```
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
tccctaggtt ctagaaccgg tgacgtctcc catggtgaag cttggatctg agggcggagt    300
tagggcggag ccaatcagcg tgcgccgttc cgaaagttgc cttttatggc tgggcggaga    360
atgggcggtg aacgccgatg attatataag gacgcgccgg gtgtggcaca gctagttccg    420
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgtga tatcacaagg tcccagggct ggggtcagaa attctctccc    600
gagggaatga agccacagga gccaagagca ggaggaccaa ggccctggcg aaggccgtgg    660
cctcgttcaa gtaaaagatc ctagtacagt gcaggtccca atgtgtacta ggatctttta    720
cttgaacggg gacgccggca tccgggctca ggacccccct ctctgccaga ggcaccaaca    780
ccagagttca caaatcagtc tcctgccctt tgcatgtagc aaagcagccc taggaatgca    840
tctagacaat tgtactaacc ttcttctctt tcctctcctg acagtccgga aagccaccat    900
ggaattcagc agccccagca gagaggaatg ccccaagcct ctgagccggg tgtcaatcat    960
ggccggatct ctgacaggac tgctgctgct tcaggccgtg tcttgggctt ctggcgctag   1020
accttgcatc cccaagagct tcggctacag cagcgtcgtg tgcgtgtgca atgccaccta   1080
ctgcgacagc ttcgaccctc ctacctttcc tgctctgggc accttcagca gatacgagag   1140
caccagatcc ggcagacgga tggaactgag catgggaccc atccaggcca atcacacagg   1200
cactggcctg ctgctgacac tgcagcctga gcagaaattc cagaaagtga aaggcttcgg   1260
cggagccatg acagatgccg ccgctctgaa tatcctggct ctgtctccac cagctcagaa   1320
cctgctgctc aagagctact tcagcgagga aggcatcggc tacaacatca tcagagtgcc   1380
catggccagc tgcgacttca gcatcaggac ctacacctac gccgacacac ccgacgattt   1440
ccagctgcac aacttcagcc tgcctgaaga ggacaccaag ctgaagatcc ctctgatcca   1500
cagagccctg cagctggcac aaagacccgt gtcactgctg gcctctccat ggacatctcc   1560
cacctggctg aaaacaaatg gcgccgtgaa tggcaagggc agcctgaaag gccaacctgg   1620
cgacatctac caccagacct gggccagata cttcgtgaag ttcctggacg cctatgccga   1680
gcacaagctg cagttttggg ccgtgacagc cgagaacgaa ccttctgctg gactgctgag   1740
cggctacccc tttcagtgcc tgggctttac acccgagcac cagcgggact ttatcgcccg   1800
tgatctggga cccacactgg ccaatagcac ccaccataat gtgcggctgc tgatgctgga   1860
cgaccagaga ctgcttctgc cccactgggc taaagtggtg ctgacagatc ctgaggccgc   1920
caaatacgtg cacggaatcg ccgtgcactg gtatctggac tttctggccc ctgccaaggc   1980
cacactggga gagacacaca gactgttccc caacaccatg ctgttcgcca gcgaagcctg   2040
tgtgggcagc aagttttggg aacagagcgt gcggctcggc agctgggata gaggcatgca   2100
gtacagccac agcatcatca ccaacctgct gtaccacgtc gtcggctgga ccgactggaa   2160
tctggccctg aatcctgaag gcggccctaa ctgggtccga aacttcgtgg acagccccat   2220
catcgtggac atcaccaagg acaccttcta caagcagccc atgttctacc acctgggaca   2280
cttcagcaag ttcatccccg agggctctca gcgcgttgga ctggtggctt cccagaagaa   2340
cgatctggac gccgtggctc tgatgcaccc tgatggatct gctgtggtgg tggtcctgaa   2400
```

```
ccgcagcagc aaagatgtgc ccctgaccat caaggatccc gccgtgggat tcctggaaac   2460
aatcagccct ggctactcca tccacaccta cctgtggcgt agacaggagg gcagaggaag   2520
tcttctgaca tgcggagacg tggaagagaa tcccggccct atgtggaccc tggtgagctg   2580
ggtggccctg accgccggcc tggtggccgg cacccgctgc cccgacggcc agttctgccc   2640
cgtggcctgc tgcctggacc ccggcggcgc cagctacagc tgctgccgcc ccctgctgga   2700
caagtggccc accaccctga gccgccacct gggcggcccc tgccaggtgg acgcccactg   2760
cagcgccggc cacagctgca tcttcaccgt gagcggcacc agcagctgct gccccttccc   2820
cgaggccgtg gcctgcggcg acggccacca ctgctgcccc cgcggcttcc actgcagcgc   2880
cgacggccgc agctgcttcc agcgcagcgg caacaacagc gtgggcgcca tccagtgccc   2940
cgacagccag ttcgagtgcc ccgacttcag cacctgctgc gtgatggtgg acggcagctg   3000
gggctgctgc cccatgcccc aggccagctg ctgcgaggac cgcgtgcact gctgccccca   3060
cggcgccttc tgcgacctgg tgcacacccg ctgcatcacc cccaccggca cccacccccct   3120
ggccaagaag ctgcccgccc agcgcaccaa ccgcgccgtg gccctgagca gcagcgtgat   3180
gtgccccgac gcccgcagcc gctgccccga cggcagcacc tgctgcgagc tgcccagcgg   3240
caagtacggc tgctgcccca tgcccaacgc cacctgctgc agcgaccacc tgcactgctg   3300
cccccaggac accgtgtgcg acctgatcca gagcaagtgc ctgagcaagg agaacgccac   3360
caccgacctg ctgaccaagc tgcccgccca caccgtgggc gacgtgaagt gcgacatgga   3420
ggtgagctgc cccgacggct acacctgctg ccgcctgcag agcggcgcct ggggctgctg   3480
cccctcacc caggccgtgt gctgcgagga ccacatccac tgctgccccg ccggcttcac   3540
ctgcgacacc cagaagggca cctgcgagca gggcccccac caggtgccct ggatggagaa   3600
ggcccccgcc cacctgagcc tgcccgaccc ccaggccctg aagcgcgacg tgccctgcga   3660
caacgtgagc agctgcccca gcagcgacac ctgctgccag ctgaccagcg gcgagtgggg   3720
ctgctgcccc atccccgagg ccgtgtgctg cagcgaccac cagcactgct gcccccaggg   3780
ctacacctgc gtggccgagg gccagtgcca gcgcggcagc gagatcgtgg ccggcctgga   3840
gaagatgccc gcccgccgcg ccagcctgag ccacccccgc gacatcggct gcgaccagca   3900
caccagctgc cccgtgggcc agacctgctg ccccagcctg ggcggcagct gggcctgctg   3960
ccagctgccc cacgccgtgt gctgcgagga ccgccagcac tgctgccccg ccggctacac   4020
ctgcaacgtg aaggcccgca gctgcgagaa ggaggtggtg agcgcccagc ccgccacctt   4080
cctggcccgc agcccccacg tgggcgtgaa ggacgtggag tgcggcgagg gccacttctg   4140
ccacgacaac cagacctgct gccgcgacaa ccgccagggc tgggcctgct gcccctaccg   4200
ccagggcgtg tgctgcgccg accgccgcca ctgctgcccc gccggcttcc gctgcgccgc   4260
ccgcggcacc aagtgcctgc gccgcgaggc cccccgctgg gacgcccccc tgcgcgaccc   4320
cgccctgcgc cagctgctgt gacaattgtt aattaagttt aaaccctcga ggccgcaagc   4380
aataaaatat ctttattttc attacatctg tgtgttggtt ttttgtgtgg agatccacga   4440
taacaaacag ctttttttggg gtgaacatat tgactgaatt ccctgcaggt tggccactcc   4500
ctctctgcgc gctcgctcgc tcactgaggc cgcccgggca aagcccgggc gtcgggcgac   4560
ctttggtcgc ccggcctcag tgagcgagcg agcgcgcaga gagggagtgg ccaactccat   4620
cactaggggt tcctgcggcc gctcgtacgg tctcgaggaa ttcctgcagg ataacttgcc   4680
aacctcattc taaaatgtat atagaagccc aaaagacaat aacaaaaata ttcttgtaga   4740
acaaaatggg aaagaatgtt ccactaaata tcaagattta gagcaaagca tgagatgtgt   4800
```

```
ggggatagac agtgaggctg ataaaataga gtagagctca gaaacagacc cattgatata   4860
tgtaagtgac ctatgaaaaa aatatggcat tttacaatgg gaaaatgatg gtctttttct   4920
tttttagaaa aacagggaaa tatatttata tgtaaaaaat aaaagggaac ccatatgtca   4980
taccatacac acaaaaaaat tccagtgaat tataagtcta aatggagaag gcaaaacttt   5040
aaatctttta gaaaataata tagaagcatg cagaccagcc tggccaacat gatgaaaccc   5100
tctctactaa taataaaatc agtagaacta ctcaggacta ctttgagtgg gaagtccttt   5160
tctatgaaga cttctttggc caaaattagg ctctaaatgc aaggagatag tgcatcatgc   5220
ctggctgcac ttactgataa atgatgttat caccatcttt aaccaaatgc acaggaacaa   5280
gttatggtac tgatgtgctg gattgagaag gagctctact tccttgacag gacacatttg   5340
tatcaactta aaaaagcaga tttttgccag cagaactatt cattcagagg taggaaactt   5400
agaatagatg atgtcactga ttagcatggc ttccccatct ccacagctgc ttcccaccca   5460
ggttgcccac agttgagttt gtccagtgct cagggctgcc cactctcagt aagaagcccc   5520
acaccagccc ctctccaaat atgttggctg ttccttccat taaagtgacc ccactttaga   5580
gcagcaagtg gatttctgtt tcttacagtt caggaaggag gagtcagctg tgagaacctg   5640
gagcctgaga tgcttctaag tcccactgct actggggtca gggaagccag actccagcat   5700
cagcagtcag gagcactaag cccttgccaa catcctgttt ctcagagaaa ctgcttccat   5760
tataatggtt gtcctttttt aagctatcaa gccaaacaac cagtgtctac cattattctc   5820
atcacctgaa gccaagggtt ctagcaaaag tcaagctgtc ttgtaatggt tgatgtgcct   5880
ccagcttctg tcttcagtca ctccactctt agcctgctct gaatcaactc tgaccacagt   5940
tccctggagc ccctgccacc tgctgcccct gccaccttct ccatctgcag tgctgtgcag   6000
ccttctgcac tcttgcagag ctaataggtg gagacttgaa ggaagaggag gaaagtttct   6060
cataatagcc ttgctgcaag ctcaaatggg aggtgggcac tgtgcccagg agccttggag   6120
caaaggctgt gcccaacctc tgactgcatc caggtttggt cttgacagag ataagaagcc   6180
ctggcttttg gagccaaaat ctaggtcaga cttaggcagg attctcaaag tttatcagca   6240
gaacatgagg cagaagaccc tttctgctcc agcttcttca ggctcaacct tcatcagaat   6300
agatagaaag agaggctgtg agggttctta aaacagaagc aaatctgact cagagaataa   6360
acaacctcct agtaaactac agcttagaca gagcatctgg tggtgagtgt gctcagtgtc   6420
ctactcaact gtctggtatc agccctcatg aggacttctc ttctttccct catagacctc   6480
catctctgtt ttccttagcc tgcagaaatc tggatggcta ttcacagaat gcctgtgctt   6540
tcagagttgc atttttttctc tggtattctg gttcaagcat ttgaaggtag gaaaggttct   6600
ccaagtgcaa gaaagccagc cctgagcctc aactgcctgg ctagtgtggt cagtaggatg   6660
caaaggctgt tgaatgccac aaggccaaac tttaacctgt gtaccacaag cctagcagca   6720
gaggcagctc tgctcactgg aactctctgt cttctttctc ctgagccttt tcttttcctg   6780
agttttctag ctctcctcaa ccttacctct gccctaccca ggacaaaccc aagagccact   6840
gtttctgtga tgtcctctcc agccctaatt aggcatcatg acttcagcct gaccttccat   6900
gctcagaagc agtgctaatc cacttcagat gagctgctct atgcaacaca ggcagagcct   6960
acaaaccttt gcaccagagc cctccacata tcagtgtttg ttcatactca cttcaacagc   7020
aaatgtgact gctgagatta agattttaca caagatggtc tgtaatttca cagttagttt   7080
tatcccatta ggtatgaaag aattagcata attcccctta aacatgaatg aatcttagat   7140
```

```
tttttaataa atagttttgg aagtaaagac agagacatca ggagcacaag gaatagcctg   7200
agaggacaaa cagaacaaga aagagtctgg aaatacacag gatgttcttg gcctcctcaa   7260
agcaagtgca agcagatagt accagcagcc ccaggctatc agagcccagt gaagagaagt   7320
accatgaaag ccacagctct aaccaccctg ttccagagtg acagacagtc cccaagacaa   7380
gccagcctga gccagagaga gaactgcaag agaaagtttc taatttaggt tctgttagat   7440
tcagacaagt gcaggtcatc ctctctccac agctactcac ctctccagcc taacaaagcc   7500
tgcagtccac actccaaccc tggtgtctca cctcctagcc tctcccaaca tcctgctctc   7560
tgaccatctt ctgcatctct catctcacca tctcccactg tctacagcct actcttgcaa   7620
ctaccatctc attttctgac atcctgtcta catcttctgc catactctgc catctaccat   7680
accacctctt accatctacc acaccatctt ttatctccat ccctctcaga agcctccaag   7740
ctgaatcctg ctttatgtgt tcatctcagc ccctgcatgg aaagctgacc ccagaggcag   7800
aactattccc agagagcttg gccaagaaaa acaaaactac cagcctggcc aggctcagga   7860
gtagtaagct gcagtgtctg ttgtgttcta gcttcaacag ctgcaggagt tccactctca   7920
aatgctccac atttctcaca tcctcctgat tctggtcact acccatcttc aaagaacaga   7980
atatctcaca tcagcatact gtgaaggact agtcatgggt gcagctgctc agagctgcaa   8040
agtcattctg gatggtggag agcttacaaa catttcatga tgctcccccc gctctgatgg   8100
ctggagccca atccctacac agactcctgc tgtatgtgtt ttcctttcac tctgagccac   8160
agccagaggg caggcattca gtctcctctt caggctgggg ctggggcact gagaactcac   8220
ccaacacctt gctctcactc cttctgcaaa acaagaaaga gctttgtgct gcagtagcca   8280
tgaagaatga aaggaaggct ttaactaaaa aatgtcagag attattttca accccttact   8340
gtggatcacc agcaaggagg aaacacaaca cagagacatt ttttcccctc aaattatcaa   8400
aagaatcact gcatttgtta aagagagcaa ctgaatcagg aagcagagtt ttgaacatat   8460
cagaagttag gaatctgcat cagagacaaa tgcagtcatg gttgtttgct gcataccagc   8520
cctaatcatt agaagcctca tggacttcaa acatcattcc ctctgacaag atgctctagc   8580
ctaactccat gagataaaat aaatctgcct ttcagagcca aagaagagtc caccagcttc   8640
ttctcagtgt gaacaagagc tccagtcagg ttagtcagtc cagtgcagta gaggagacca   8700
gtctgcatcc tctaattttc aaaggcaaga agatttgttt accctggaca ccaggcacaa   8760
gtgaggtcac agagctctta gatatgcagt cctcatgagt gaggagacta aagcgcatgc   8820
catcaagact tcagtgtaga gaaaacctcc aaaaaagcct cctcactact tctggaatag   8880
ctcagaggcc gaggcggcct cggcctctgc ataaataaaa aaaattagtc agccatgggg   8940
cggagaatgg gcggaactgg gcggagttag gggcgggatg ggcggagtta ggggcgggac   9000
tatggttgct gactaattga gatgcatgct ttgcatactt ctgcctgctg gggagcctgg   9060
ggactttcca cacctggttg ctgactaatt gagatgcatg ctttgcatac ttctgcctgc   9120
tggggagcct ggggactttc cacaccctaa ctgacacaca ttccacagct gcattaatga   9180
atcggccaac gcgcggggag aggcggtttg cgtattgggc gctcttccgc ttcctcgctc   9240
actgactcgc tgcgctcggt cgttcggctg cggcgagcgg tatcagctca ctcaaaggcg   9300
gtaatacggt tatccacaga atcaggggat aacgcaggaa agaacatgtg agcaaaaggc   9360
cagcaaaagg ccaggaaccg taaaaaggcc gcgttgctgg cgtttttcca taggctccgc   9420
ccccctgacg agcatcacaa aaatcgacgc tcaagtcaga ggtggcgaaa cccgacagga   9480
ctataaagat accaggcgtt tccccctgga agctccctcg tgcgctctcc tgttccgacc   9540
```

```
ctgccgctta ccggatacct gtccgccttt ctcccttcgg gaagcgtggc gctttctcat   9600

agctcacgct gtaggtatct cagttcggtg taggtcgttc gctccaagct gggctgtgtg   9660

cacgaacccc ccgttcagcc cgaccgctgc gccttatccg gtaactatcg tcttgagtcc   9720

aacccggtaa gacacgactt atcgccactg gcagcagcca ctggtaacag gattagcaga   9780

gcgaggtatg taggcggtgc tacagagttc ttgaagtggt ggcctaacta cggctacact   9840

agaagaacag tatttggtat ctgcgctctg ctgaagccag ttaccttcgg aaaaagagtt   9900

ggtagctctt gatccggcaa acaaaccacc gctggtagcg gtggtttttt tgtttgcaag   9960

cagcagatta cgcgcagaaa aaaaggatct caagaagatc ctttgatctt ttctacgggg  10020

tctgacgctc agtggaacga aaactcacgt taagggattt tggtcatgag attatcaaaa  10080

aggatcttca cctagatcct tttaaattaa aaatgaagtt ttaaatcaat ctaaagtata  10140

tatgagtaaa cttggtctga cagttaccaa tgcttaatca gtgaggcacc tatctcagcg  10200

atctgtctat ttcgttcatc catagttgcc tgactcctgc aaaccacgtt gtgtctcaaa  10260

atctctgatg ttacattgca caagataaaa atatatcatc atgaacaata aaactgtctg  10320

cttacataaa cagtaataca aggggtgtta tgagccatat tcaacgggaa acgtcttgct  10380

cgaggccgcg attaaattcc aacatggatg ctgatttata tgggtataaa tgggctcgcg  10440

ataatgtcgg gcaatcaggt gcgacaatct atcgattgta tgggaagccc gatgcgccag  10500

agttgtttct gaaacatggc aaaggtagcg ttgccaatga tgttacagat gagatggtca  10560

gactaaactg gctgacggaa tttatgcctc ttccgaccat caagcatttt atccgtactc  10620

ctgatgatgc atggttactc accactgcga tccccgggaa aacagcattc caggtattag  10680

aagaatatcc tgattcaggt gaaaatattg ttgatgcgct ggcagtgttc ctgcgccggt  10740

tgcattcgat tcctgtttgt aattgtcctt ttaacagcga tcgcgtattt cgtctcgctc  10800

aggcgcaatc acgaatgaat aacggtttgg ttgatgcgag tgattttgat gacgagcgta  10860

atggctggcc tgttgaacaa gtctggaaag aaatgcataa gcttttgcca ttctcaccgg  10920

attcagtcgt cactcatggt gatttctcac ttgataacct tatttttgac gaggggaaat  10980

taataggttg tattgatgtt ggacgagtcg gaatcgcaga ccgataccag gatcttgcca  11040

tcctatggaa ctgcctcggt gagttttctc cttcattaca gaaacggctt tttcaaaaat  11100

atggtattga taatcctgat atgaataaat tgcagtttca tttgatgctc gatgagtttt  11160

tctaagggcg gcctgccacc atacccacgc cgaaacaagc gctcatgagc ccgaagtggc  11220

gagcccgatc ttccccatcg gtgatgtcgg cgatataggc gccagcaacc gcacctgtgg  11280

cgccggtgat gagggcgcgc caagtcgacg tccggcagtc                        11320
```

<210> SEQ ID NO 36
<211> LENGTH: 3793
<212> TYPE: DNA
<213> ORGANISM: Artificial Sequence
<220> FEATURE:
<223> OTHER INFORMATION: Synthetic polynucleotide

<400> SEQUENCE: 36

```
tctcattaga agtgaggcgg ggccggccaa atcgaatgga caccgggtaa ttagcagggt     60

tacccagata ctccagcacc tctttcccgt cggccgtgta cctgccattc acgtccatgc    120

cattgatggc cagcactgca tgacccactg cagaggtgaa gctaacggtc agcgaaggtg    180

cagcccgggg attccgccga ggggacaagg gacccgacac aaccccttt  cccccaaccc    240
```

```
cgcacctaca accagcccac ttctacagca ctggggccct cccacccccg cacccgccac    300
gggcccgagc ctagcccacc tcggatgccg tcccgctggc cgaaagcaac caacacacgc    360
tcatcgtgta gcttgagcag cagatccagc ggataactga aagttttctc agcctcagcc    420
cgtggcgcgt agctgtccaa ctggtaaatc aagccgccag ctttgttcac cacatacaca    480
ctaaaaatcg ccatcgctgc cttgccgctc ggaaactggt attcagcctc tacccgacgg    540
cccctccccg gaaccgcatc acagcacttg ccgccggccc caccccagcc tcctcctcct    600
cctcctcctc ctcccgcgcc ccccgtgcag ccacctgctg cacttgcgca ctgggagcga    660
cacgctcggg cataagtagt gccgaaaagt tagctgccga gacctggtgg attgcttttc    720
gtttatcagt gcaggaaaac agcgctatag tactgcgtca caactagcgc agactccggc    780
agtatttagg cggtgcggct tgggaactag aatccacttc ctgtcttccg cctcaggcta    840
gagggcgagc gcttcgccgt gggacttctt ctgcctggct ccgcctcttg ccccggaagt    900
actcacagcg gacggtggtt tttgggcccg tttctgagca gcgcttcctt tttgtccgac    960
atcttgacga ggctgcggtg tctgctgcta ttctccgagc ttcgcaatgg taagcttcag   1020
gggtgtgaag tcgccggcgt tcttgggttt gaggactcag tggggagagc cttcggcggg   1080
agcgctcctt ggcctgccgg cctcggttgc agggcgggcg cggttattgc ttggcccatg   1140
tgctctggtg gtggagtttg cgggggctga gggcgcagta ttaggggact ttggcgctat   1200
ttgaggacct ggttgcattc ccgctgccct cctacagccg cctaaggacg acaagaagaa   1260
gaaggacgct ggaaagtcgg ccaagaaaga caaagaccca gtgaacaaat ccgggggcaa   1320
ggccaaaaag aaggtagaaa taagacctct ctgaaagaga ctaggggtaa ctctctcgta   1380
atcctctagt aataggtaac ttgtatagta agtggttttt caggtgtaga tttctagagt   1440
caaaatgtga gagtttatct tcccgtcacc actcgttctt tttcccatta ggatcatgaa   1500
aatgggtctg ttgtgcgaag tgtctgccgc tgtgcctgct gtgttatttt taactgatct   1560
agtggggctc ggcccctgtt tgaaggccaa aaacgtgtcg gtgttttttt tttgtttttg   1620
ttttagtaat gtgtaattta tccttgataa cggtggaaca gatttctctg acgcagatta   1680
ctcgagaggg aaagggtgct tctgccagaa atactaactt gtttctgttt tgttttggtg   1740
agcagaagtg gtccaaaggc aaagttcggg acaagctcaa taacttagtc ttgtttgaca   1800
aagctaccta tgataaactc tgtaaggaag ttcccaacta taaacttata accccagctg   1860
tggtctctga gagactgaag attcgaggct ccctggccag ggcagccctt caggagctcc   1920
ttagtaaagg tgaggggtgt atcctacatg tgtgtttttg taggttaaat tgtcttgacc   1980
atgttaagca tcttcagtgg ttttgctgga aaagcagaat taaaaaaaaa aagcgtggct   2040
tgaccattgg ctgttagtaa tgtaattctg acgtcttact cctgatcctg agatgaattc   2100
tcagggttct tagccacttt tgtgccgtgg accctgtggc agtttagtga agcccaagga   2160
tcttttatgt ttcgagtaaa tggatgcata gaattacagg gacaaccgtt tttgaaataa   2220
ttagattact attttgaaac aactttgaaa atgtttaaaa cctttatggt aaatattttg   2280
ttgatgtatt aaattttaaa accagaaatt tagtacggtc tactcagtag tatggtctga   2340
ttaccataat tccacaataa taaggctcag ctaactatag tgactgaacg tctataattc   2400
tagcactttg ggaggccaag gcgggtgaat caacggaggt caggagttaa agaccagcct   2460
ggccaatatg gtgaaaacct gctctactga aagttagctg gacgtggggg cacacgtctg   2520
taatcccagc tactcaggat gctgaggcat gaggatccct tgaacccagg agatggaggt   2580
ggcagtgagc cgagatgaca ccactgcact ccagccttag tgacagcaaa agactgtctc   2640
```

```
agaaaggggg ggggggtgga agataatgga gccctaattt aaaggaaaag taaggataga   2700

tgatccgtta aaaacttgga ttctcggtta ccgaacgtca gattaagcaa ttctggagcc   2760

aggtgcagtg gtacccttgt atttctagct acttgggagg ccaaagcagg aggatcattt   2820

gagccaagga gttttaagac cattctgggc acctctgaga gaactctgtc tttttgtttt   2880

ccttttcttt aaatagagat gcggttttgc catgttgccc aggctggtct cctgggctca   2940

agagatccac ctgtccaaag tgctgggatt acaggcatga gcctctgcac ccggccaaaa   3000

caaaccttac tagagtctca ttctgttgcc caggttggag tgcggagggg cagtcttggc   3060

tcaatgcaac caccaattcc tgggttcagg tggtcctcac ctcagcttcc caagtagctg   3120

gaattacaag catgtgccac catgcccagc taatttttgt atttttggta gagatggggt   3180

ttcaccttgt tggccaggct ggtgtgcaac tccttacctc aagctatctg cccgtctcca   3240

cctcccaaag cagtgggatt ataagcatga gccaccgcgc ccagccaaaa accttactag   3300

tttctattgt agcatctgtt aagcatctca tcgtgctatt ctctccccct aggacttatc   3360

aaactggttt caaagcacag agctcaagta atttacacca gaaataccaa gggtggagat   3420

gctccagctg ctggtgaaga tgcatgaata ggtgagtagg aatgtgtggg ctcatggtgt   3480

aggaggtaga tacaaagctt tatggttctg attcttttaa ttttttttta caggtccaac   3540

cagctgtaca tttggaaaaa taaaacttta ttaaatcaaa tgaatgagta tgtctgtttc   3600

ctaagaaaga caatgataaa gaatttggtg gaaggtataa taggggtttg ttgactttgc   3660

ttttagcctc atggtagttg gtagagagca tgattagctt ttttctgtat gtgactgctt   3720

cttcattgct gcagcttcag ttttgaattg atgtctgaaa ggaaataaag ggttaacacg   3780

atgatgaagg gtg                                                      3793
```

<210> SEQ ID NO 37
<211> LENGTH: 6762
<212> TYPE: DNA
<213> ORGANISM: Artificial Sequence
<220> FEATURE:
<223> OTHER INFORMATION: Synthetic polynucleotide

<400> SEQUENCE: 37

```
ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca ggatggctga gccccgccag gagttcgaag tgatggaaga    360

tcacgctggg acgtacgggt tgggggacag gaaagatcag gggggctaca ccatgcacca    420

agaccaagag ggtgacacgg acgctggcct gaaagaatct cccctgcaga cccccactga    480

ggacggatct gaggaaccgg gctctgaaac ctctgatgct aagagcactc caacagcgga    540

agatgtgaca gcacccttag tggatgaggg agctcccggc aagcaggctg ccgcgcagcc    600

ccacacggag atcccagaag gaaccacagc tgaagaagca ggcattggag acacccccag    660

cctggaagac gaagctgctg gtcacgtgac ccaagagcct gaaagtggta aggtggtcca    720

ggaaggcttc ctccgagagc caggcccccc aggtctgagc caccagctca tgtccggcat    780

gcctggggct cccctcctgc ctgagggccc cagagaggcc acacgccaac cttcggggac    840
```

```
aggacctgag gacacagagg gcggccgcca cgcccctgag ctgctcaagc accagcttct    900

aggagacctg caccaggagg ggccgccgct gaagggggca gggggcaaag agaggccggg    960

gagcaaggag gaggtggatg aagaccgcga cgtcgatgag tcctccccc aagactcccc    1020

tccctccaag gcctccccag cccaagatgg gcggcctccc cagacagccg ccagagaagc   1080

caccagcatc ccaggcttcc cagcggaggg tgccatcccc ctccctgtgg atttcctctc   1140

caaagtttcc acagagatcc cagcctcaga gcccgacggg cccagtgtag ggcgggccaa   1200

agggcaggat gccccctgg agttcacgtt tcacgtggaa atcacaccca acgtgcagaa    1260

ggagcaggcg cactcggagg agcatttggg aagggctgca tttccagggg cccctggaga   1320

ggggccagag gcccggggcc cctctttggg agaggacaca aaagaggctg accttccaga   1380

gccctctgaa aagcagcctg ctgctgctcc gcgggggaag cccgtcagcc gggtccctca   1440

actcaaagct cgcatggtca gtaaaagcaa agacgggact ggaagcgatg acaaaaaagc   1500

caagacatcc acacgttcct ctgctaaaac cttgaaaaat aggccttgcc ttagccccaa   1560

acaccccact cctggtagct cagaccctct gatccaaccc tccagccctg ctgtgtgccc   1620

agagccacct tcctctccta aatacgtctc ttctgtcact tcccgaactg gcagttctgg   1680

agcaaaggag atgaaactca agggggctga tggtaaaacg aagatcgcca caccgcgggg   1740

agcagcccct ccaggccaga agggccaggc caacgccacc aggattccag caaaaacccc   1800

gcccgctcca aagacaccac ccagctctgg tgaacctcca aaatcagggg atcgcagcgg   1860

ctacagcagc cccggctccc caggcactcc cggcagccgc tcccgcaccc cgtcccttcc   1920

aaccccaccc acccgggagc ccaagaaggt ggcagtggtc cgtactccac ccaagtcgcc   1980

gtcttccgcc aagagccgcc tgcagacagc cccgtgccc atgccagacc tgaagaatgt    2040

caagtccaag atcggctcca ctgagaacct gaagcaccag ccgggaggcg ggaaggtgca   2100

gataattaat aagaagctgg atcttagcaa cgtccagtcc aagtgtggct caaaggataa   2160

tatcaaacac gtcccgggag gcggcagtgt gcaaatagtc tacaaaccag ttgacctgag   2220

caaggtgacc tccaagtgtg gctcattagg caacatccat cataaaccag gaggtggcca   2280

ggtggaagta aaatctgaga agcttgactt caaggacaga gtccagtcga agattgggtc   2340

cctggacaat atcacccacg tccctggcgg aggaaataaa aagattgaaa cccacaagct   2400

gaccttccgc gagaacgcca aagccaagac agaccacggg gcggagatcg tgtacaagtc   2460

gccagtggtg tctggggaca cgtctccacg gcatctcagc aatgtctcct ccaccggcag   2520

catcgacatg gtagactcgc cccagctcgc cacgctagct gacgaggtgt ctgcctccct   2580

ggccaagcag ggtttgtgat caggcccctg gggcggtcaa taattgtgga gaggagagaa   2640

tgagagagtg tggaaaaaaa aagaataatg acccggcccc cgccctctgc ccccagctgc   2700

tcctcgcagt tcggttaatt ggttaatcac ttaacctgct tttgtcactc ggctttggct   2760

cgggacttca aaatcagtga tgggagtaag agcaaatttc atctttccaa attgatgggt   2820

gggctagtaa taaaatattt aaaaaaaaac attcaaaaac atggccacat ccaacatttc   2880

ctcaggcaat tccttttgat tctttttct tccccctcca tgtagaagag ggagaaggag    2940

aggctctgaa agctgcttct gggggatttc aagggactgg gggtgccaac cacctctggc   3000

cctgttgtgg gggtgtcaca gaggcagtgg cagcaacaaa ggatttgaaa cttggtgtgt   3060

tcgtggagcc acaggcagac gatgtcaacc ttgtgtgagt gtgacggggg ttggggtggg   3120

gcgggaggcc acgggggagg ccgaggcagg ggctgggcag aggggagagg aagcacaaga   3180

agtgggagtg ggagaggaag ccacgtgctg gagagtagac atcccctcc ttgccgctgg    3240
```

```
gagagccaag gcctatgcca cctgcagcgt ctgagcggcc gcctgtcctt ggtggccggg   3300
ggtgggggcc tgctgtgggt cagtgtgcca ccctctgcag ggcagcctgt gggagaaggg   3360
acagcgggta aaaagagaag gcaagctggc aggagggtgg cacttcgtgg atgacctcct   3420
tagaaaagac tgaccttgat gtcttgagag cgctggcctc ttcctccctc cctgcagggt   3480
agggggcctg agttgagggg cttccctctg ctccacagaa accctgtttt attgagttct   3540
gaaggttgga actgctgcca tgattttggc cactttgcag acctgggact ttagggctaa   3600
ccagttctct ttgtaaggac ttgtgcctct tgggagacgt ccacccgttt ccaagcctgg   3660
gccactggca tctctggagt gtgtggggt ctgggaggca ggtcccgagc cccctgtcct    3720
tcccacggcc actgcagtca ccccgtctgc gccgctgtgc tgttgtctgc cgtgagagcc   3780
caatcactgc ctatacccct catcacacgt cacaatgtcc cgaattccca gcctcaccac   3840
cccttctcag taatgaccct ggttggttgc aggaggtacc tactccatac tgagggtgaa   3900
attaagggaa ggcaaagtcc aggcacaaga gtgggacccc agcctctcac tctcagttcc   3960
actcatccaa ctgggaccct caccacgaat ctcatgatct gattcggttc cctgtctcct   4020
cctcccgtca cagatgtgag ccagggcact gctcagctgt gaccctaggt gtttctgcct   4080
tgttgacatg gagagagccc tttcccctga gaaggcctgg ccccttcctg tgctgagccc   4140
acagcagcag gctgggtgtc ttggttgtca gtggtggcac caggatggaa gggcaaggca   4200
cccagggcag gcccacagtc ccgctgtccc ccacttgcac cctagcttgt agctgccaac   4260
ctcccagaca gcccagcccg ctgctcagct ccacatgcat agtatcagcc ctccacaccc   4320
gacaaagggg aacacacccc cttggaaatg gttcttttcc cccagtccca gctggaagcc   4380
atgctgtctg ttctgctgga gcagctgaac atatacatag atgttgccct gccctcccca   4440
tctgcaccct gttgagttgt agttggattt gtctgtttat gcttggattc accagagtga   4500
ctatgatagt gaaaagaaaa aaaaaaaaaa aaaaggacgc atgtatcttg aaatgcttgt   4560
aaagaggttt ctaacccacc ctcacgaggt gtctctcacc cccacactgg gactcgtgtg   4620
gcctgtgtgg tgccaccctg ctggggcctc ccaagttttg aaaggctttc ctcagcacct   4680
gggacccaac agagaccagc ttctagcagc taaggaggcc gttcagctgt gacgaaggcc   4740
tgaagcacag gattaggact gaagcgatga tgtccccttc cctacttccc cttggggctc   4800
cctgtgtcag ggcacagact aggtcttgtg gctggtctgg cttgcggcgc gaggatggtt   4860
ctctctggtc atagcccgaa gtctcatggc agtcccaaag gaggcttaca actcctgcat   4920
cacaagaaaa aggaagccac tgccagctgg ggggatctgc agctcccaga agctccgtga   4980
gcctcagcca cccctcagac tgggttcctc tccaagctcg ccctctggag gggcagcgca   5040
gcctcccacc aagggccctg cgaccacagc agggattggg atgaattgcc tgtcctggat   5100
ctgctctaga ggcccaagct gcctgcctga ggaaggatga cttgacaagt caggagacac   5160
tgttcccaaa gccttgacca gagcacctca gcccgctgac cttgcacaaa ctccatctgc   5220
tgccatgaga aaagggaagc cgcctttgca aaacattgct gcctaaagaa actcagcagc   5280
ctcaggccca attctgccac ttctggtttg ggtacagtta aaggcaaccc tgagggactt   5340
ggcagtagaa atccagggcc tcccctgggg ctggcagctt cgtgtgcagc tagagcttta   5400
cctgaaagga agtctctggg cccagaactc tccaccaaga gcctccctgc cgttcgctga   5460
gtcccagcaa ttctcctaag ttgaagggat ctgagaagga gaaggaaatg tggggtagat   5520
ttggtggtgg ttagagatat gcccccctca ttactgccaa cagtttcggc tgcatttctt   5580
```

```
cacgcacctc ggttcctctt cctgaagttc ttgtgccctg ctcttcagca ccatgggcct   5640

tcttatacgg aaggctctgg gatctccccc ttgtggggca ggctcttggg gccagcctaa   5700

gatcatggtt tagggtgatc agtgctggca gataaattga aaaggcacgc tggcttgtga   5760

tcttaaatga ggacaatccc cccagggctg ggcactcctc ccctcccctc acttctccca   5820

cctgcagagc cagtgtcctt gggtgggcta gataggatat actgtatgcc ggctccttca   5880

agctgctgac tcactttatc aatagttcca tttaaattga cttcagtggt gagactgtat   5940

cctgtttgct attgcttgtt gtgctatggg gggagggggg aggaatgtgt aagatagtta   6000

acatgggcaa agggagatct tggggtgcag cacttaaact gcctcgtaac ccttttcatg   6060

atttcaacca catttgctag agggagggag cagccacgga gttagaggcc cttggggttt   6120

ctcttttcca ctgacaggct ttcccaggca gctggctagt tcattccctc cccagccagg   6180

tgcaggcgta ggaatatgga catctggttg ctttggcctg ctgccctctt tcaggggtcc   6240

taagcccaca atcatgcctc cctaagacct tggcatcctt ccctctaagc cgttggcacc   6300

tctgtgccac ctctcacact ggctccagac acacagcctg tgcttttgga gctgagatca   6360

ctcgcttcac cctcctcatc tttgttctcc aagtaaagcc acgaggtcgg ggcgagggca   6420

gaggtgatca cctgcgtgtc ccatctacag acctgcagct tcataaaact tctgatttct   6480

cttcagcttt gaaaagggtt accctgggca ctggcctaga gcctcacctc ctaatagact   6540

tagccccatg agtttgccat gttgagcagg actatttctg gcacttgcaa gtcccatgat   6600

ttcttcggta attctgaggg tggggggagg gacatgaaat catcttagct tagctttctg   6660

tctgtgaatg tctatatagt gtattgtgtg ttttaacaaa tgatttacac tgactgttgc   6720

tgtaaaagtg aatttggaaa taaagttatt actctgatta aa                      6762
```

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38

```
ataccttcca ccaaattctt ta                                              22
```

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 39

```
taaagaattt ggtggaaggt at                                              22
```

<210> SEQ ID NO 40
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 40

```
ctggaggctt gctttgggct gtatgctgat accttccacc aaattcttta ttttggcctc     60

tgactgataa agaattgtgg aaggtatcag gacacaaggc cctttatcag cactcacatg    120

gaacaaatgg ccaccgtggg aggatgacaa                                     150
```

<210> SEQ ID NO 41
<211> LENGTH: 150
<212> TYPE: DNA
<213> ORGANISM: Artificial Sequence
<220> FEATURE:
<223> OTHER INFORMATION: Synthetic polynucleotide

<400> SEQUENCE: 41
ttgtcatcct cccacggtgg ccatttgttc catgtgagtg ctgataaagg gccttgtgtc 60
ctgatacctt ccacaattct ttatcagtca gaggccaaaa taaagaattt ggtggaaggt 120
atcagcatac agcccaaagc aagcctccag 150

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
ataagtcctt tactaaggag c 21

<210> SEQ ID NO 43
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 43
gctccttagt aaaggactta t 21

<210> SEQ ID NO 44
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 44
ctggaggctt gctttgggct gtatgctgat aagtccttta ctaaggagct tttggcctct 60
gactgagctc cttgtaagga cttatcagga cacaaggccc tttatcagca ctcacatgga 120
acaaatggcc accgtgggag gatgacaa 148

<210> SEQ ID NO 45
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 45
ttgtcatcct cccacggtgg ccatttgttc catgtgagtg ctgataaagg gccttgtgtc 60
ctgataagtc cttacaagga gctcagtcag aggccaaaag ctccttagta aaggacttat 120
cagcatacag cccaaagcaa gcctccag 148

<210> SEQ ID NO 46
<211> LENGTH: 21
<212> TYPE: DNA
<213> ORGANISM: Artificial Sequence
<220> FEATURE:

<223> OTHER INFORMATION: Synthetic polynucleotide

<400> SEQUENCE: 46
gattttgaag tcccgagcca a 21

<210> SEQ ID NO 47
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 47
ttggctcggg acttcaaaat c 21

<210> SEQ ID NO 48
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 48
ctggaggctt gctttgggct gtatgctgga ttttgaagtc ccgagccaat tttggcctct 60
gactgattgg ctcggattca aaatccagga cacaaggccc tttatcagca ctcacatgga 120
acaaatggcc accgtgggag gatgacaa 148

<210> SEQ ID NO 49
<211> LENGTH: 148
<212> TYPE: DNA
<213> ORGANISM: Artificial Sequence
<220> FEATURE:
<223> OTHER INFORMATION: Synthetic polynucleotide

<400> SEQUENCE: 49
ttgtcatcct cccacggtgg ccatttgttc catgtgagtg ctgataaagg gccttgtgtc 60
ctggattttg aatccgagcc aatcagtcag aggccaaaat tggctcggga cttcaaaatc 120
cagcatacag cccaaagcaa gcctccag 148

<210> SEQ ID NO 50
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 50
ggaaatgttg gatgtggcca tgt 23

<210> SEQ ID NO 51
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 51
acatggccac atccaacatt tcc 23

<210> SEQ ID NO 52
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 52
ctggaggctt gctttgggct gtatgctggg aaatgttgga tgtggccatg tttttggcct 60
ctgactgaac atggcacacc aacatttccc aggacacaag gccctttatc agcactcaca 120
tggaacaaat ggccaccgtg ggaggatgac aa 152

<210> SEQ ID NO 53
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 53
ttgtcatcct cccacggtgg ccatttgttc catgtgagtg ctgataaagg gccttgtgtc 60
ctgggaaatg ttggtgtgcc atgttcagtc agaggccaaa aacatggcca catccaacat 120
ttcccagcat acagcccaaa gcaagcctcc ag 152

<210> SEQ ID NO 54
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 54
ggtgcagata attaataagt tcgcttatta attatctgca ccttc 45

<210> SEQ ID NO 55
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 55
gaaggtgcag ataattaata agcgaactta ttaattatct gcacc 45

<210> SEQ ID NO 56
<211> LENGTH: 139
<212> TYPE: DNA
<213> ORGANISM: Artificial Sequence
<220> FEATURE:
<223> OTHER INFORMATION: Synthetic polynucleotide

<400> SEQUENCE: 56
tggaggcttg ctgaaggctg tatgctgttg tcggtgcaga taattaataa gttcgcttat 60
taattatctg caccttcagg acacaaggcc tgttactagc actcacatgg aacaaatggc 120
caccgtggga ggatgacaa 139

<210> SEQ ID NO 57
<211> LENGTH: 139
<212> TYPE: DNA
<213> ORGANISM: Artificial Sequence
<220> FEATURE:
<223> OTHER INFORMATION: Synthetic polynucleotide

<400> SEQUENCE: 57
ttgtcatcct cccacggtgg ccatttgttc catgtgagtg ctagtaacag gccttgtgtc 60

```
ctgaaggtgc agataattaa taagcgaact tattaattat ctgcaccgac aacagcatac    120

agccttcagc aagcctcca                                                  139


<210> SEQ ID NO 58
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 58

ttgtagacta tttgcacact g                                               21


<210> SEQ ID NO 59
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 59

cagtgtgcaa atagtctaca a                                               21


<210> SEQ ID NO 60
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 60

ttgtcatcct cccacggtgg ccatttgttc catgtgagtg ctagtaacag gccttgtgtc     60

ctttgtagac tatttgcaca ctgcatctgt ggcttcactc agtgtgcaaa tagtctacaa    120

gacaacagca tacagccttc agcaagcctc ca                                  152


<210> SEQ ID NO 61
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 61

tggaggcttg ctgaaggctg tatgctgttg tcttgtagac tatttgcaca ctgagtgaag     60

ccacagatgc agtgtgcaaa tagtctacaa aggacacaag gcctgttact agcactcaca    120

tggaacaaat ggccaccgtg ggaggatgac aa                                  152


<210> SEQ ID NO 62
<211> LENGTH: 4321
<212> TYPE: DNA
<213> ORGANISM: Artificial Sequence
<220> FEATURE:
<223> OTHER INFORMATION: Synthetic polynucleotide

<400> SEQUENCE: 62

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

tccctaggtt ctagaaccgg tgacgtctcc catggtgaag cttggatctg aattcggtac    300
```

-continued

```
cctagttatt aatagtaatc aattacgggg tcattagttc atagcccata tatggagttc    360

cgcgttacat aacttacggt aaatggcccg cctggctgac cgcccaacga cccccgccca    420

ttgacgtcaa taatgacgta tgttcccata gtaacgccaa tagggacttt ccattgacgt    480

caatgggtgg actatttacg gtaaactgcc cacttggcag tacatcaagt gtatcatatg    540

ccaagtacgc cccctattga cgtcaatgac ggtaaatggc ccgcctggca ttatgcccag    600

tacatgacct tatgggactt tcctacttgg cagtacatct acgtattagt catcgctatt    660

accatggtcg aggtgagccc cacgttctgc ttcactctcc ccatctcccc cccctcccca    720

cccccaattt tgtatttatt tattttttaa ttattttgtg cagcgatggg ggcggggggg    780

gggggggggc gcgcgccagg cggggcgggg cggggcgagg ggcggggcgg ggcgaggcgg    840

agaggtgcgg cggcagccaa tcagagcggc gcgctccgaa agtttccttt tatggcgagg    900

cggcggcggc ggcggcccta taaaaagcga agcgcgcggc gggcgggagt cgctgcgacg    960

ctgccttcgc cccgtgcccc gctccgccgc cgcctcgcgc cgcccgcccc ggctctgact   1020

gaccgcgtta ctcccacagg tgagcgggcg ggacggccct tctcctcagc gctgtaatta   1080

gcgcttggtt taatgacggc ttgttggagg cttgctgaag gctgtatgct gttgtcggtg   1140

cagataatta ataagttcgc ttattaatta tctgcacctt caggacacaa ggcctgttac   1200

tagcactcac atggaacaaa tggccaccgt gggaggatga caatttctgt ggctgcgtga   1260

aagccttgag gggctccggg agctagagcc tctgctaacc atgttcatgc cttcttcttt   1320

ttcctacagc tcctgggcaa cgtgctggtt attgtgctgt ctcatcattt tggcaaagaa   1380

ttcctcgaag atccgaaggg aaagtcttcc acgactgtgg gatccgttcg aagatatcac   1440

cggttgagcc accatgtgga ccctggtgag ctgggtggcc ctgaccgccg gcctggtggc   1500

cggcacccgc tgccccgacg gccagttctg ccccgtggcc tgctgcctgg accccggcgg   1560

cgccagctac agctgctgcc gcccccctgct ggacaagtgg cccaccaccc tgagccgcca   1620

cctgggcggc ccctgccagg tggacgccca ctgcagcgcc ggccacagct gcatcttcac   1680

cgtgagcggc accagcagct gctgcccctt ccccgaggcc gtggcctgcg gcgacggcca   1740

ccactgctgc ccccgcggct tccactgcag cgccgacggc cgcagctgct tccagcgcag   1800

cggcaacaac agcgtgggcg ccatccagtg ccccgacagc cagttcgagt gccccgactt   1860

cagcacctgc tgcgtgatgg tggacggcag ctggggctgc tgccccatgc cccaggccag   1920

ctgctgcgag gaccgcgtgc actgctgccc ccacggcgcc ttctgcgacc tggtgcacac   1980

ccgctgcatc acccccaccg gcacccaccc cctggccaag aagctgcccg cccagcgcac   2040

caaccgcgcc gtggccctga gcagcagcgt gatgtgcccc gacgcccgca gccgctgccc   2100

cgacggcagc acctgctgcg agctgcccag cggcaagtac ggctgctgcc ccatgcccaa   2160

cgccacctgc tgcagcgacc acctgcactg ctgcccccag gacaccgtgt gcgacctgat   2220

ccagagcaag tgcctgagca aggagaacgc caccaccgac ctgctgacca agctgcccgc   2280

ccacaccgtg ggcgacgtga agtgcgacat ggaggtgagc tgccccgacg gctacacctg   2340

ctgccgcctg cagagcggcg cctggggctg ctgccccttc acccaggccg tgtgctgcga   2400

ggaccacatc cactgctgcc ccgccggctt cacctgcgac acccagaagg gcacctgcga   2460

gcagggcccc caccaggtgc cctggatgga gaaggccccc gcccacctga gcctgcccga   2520

cccccaggcc ctgaagcgcg acgtgccctg cgacaacgtg agcagctgcc ccagcagcga   2580

cacctgctgc cagctgacca gcggcgagtg ggctgctgc cccatccccg aggccgtgtg   2640
```

```
ctgcagcgac caccagcact gctgccccca gggctacacc tgcgtggccg agggccagtg   2700

ccagcgcggc agcgagatcg tggccggcct ggagaagatg cccgcccgcc gcgccagcct   2760

gagccacccc cgcgacatcg gctgcgacca gcacaccagc tgccccgtgg gccagacctg   2820

ctgccccagc ctgggcggca gctgggcctg ctgccagctg ccccacgccg tgtgctgcga   2880

ggaccgccag cactgctgcc ccgccggcta cacctgcaac gtgaaggccc gcagctgcga   2940

gaaggaggtg gtgagcgccc agcccgccac cttcctggcc cgcagccccc acgtgggcgt   3000

gaaggacgtg gagtgcggcg agggccactt ctgccacgac aaccagacct gctgccgcga   3060

caaccgccag ggctgggcct gctgccccta ccgccagggc gtgtgctgcg ccgaccgccg   3120

ccactgctgc cccgccggct tccgctgcgc cgcccgcggc accaagtgcc tgcgccgcga   3180

ggcccccccgc tgggacgccc ccctgcgcga ccccgccctg cgccagctgc tgtgacaatt   3240

gttaattaag tttaaaccct cgaggccgca agcttatcga taatcaacct ctggattaca   3300

aaatttgtga aagattgact ggtattctta actatgttgc tccttttacg ctatgtggat   3360

acgctgcttt aatgcctttg tatcatgcta ttgcttcccg tatggctttc attttctcct   3420

ccttgtataa atcctggttg ctgtctcttt atgaggagtt gtggcccgtt gtcaggcaac   3480

gtggcgtggt gtgcactgtg tttgctgacg caacccccac tggttggggc attgccacca   3540

cctgtcagct cctttccggg actttcgctt tccccctccc tattgccacg gcggaactca   3600

tcgccgcctg ccttgcccgc tgctggacag gggctcggct gttgggcact gacaattccg   3660

tggtgttgtc ggggaaatca tcgtcctttc cttggctgct cgcctgtgtt gccacctgga   3720

ttctgcgcgg gacgtccttc tgctacgtcc cttcggccct caatccagcg gaccttcctt   3780

cccgcggcct gctgccggct ctgcggcctc ttccgcgtct tcgccttcgc cctcagacga   3840

gtcggatctc cctttgggcc gcctccccgc atcgataccg tcgactagag ctcgctgatc   3900

agcctcgact gtgccttcta gttgccagcc atctgttgtt tgcccctccc ccgtgccttc   3960

cttgaccctg gaaggtgcca ctcccactgt cctttcctaa taaaatgagg aaattgcatc   4020

gcattgtctg agtaggtgtc attctattct ggggggtggg gtggggcagg acagcaaggg   4080

ggaggattgg gaagacaata gcaggcatgc tggggagaga tccacgataa caaacagctt   4140

ttttggggtg aacatattga ctgaattccc tgcaggttgg ccactccctc tctgcgcgct   4200

cgctcgctca ctgaggccgc ccgggcaaag cccgggcgtc gggcgacctt tggtcgcccg   4260

gcctcagtga gcgagcgagc gcgcagagag ggagtggcca actccatcac taggggttcc   4320

t                                                                  4321
```

<210> SEQ ID NO 63
<211> LENGTH: 4552
<212> TYPE: DNA
<213> ORGANISM: Artificial Sequence
<220> FEATURE:
<223> OTHER INFORMATION: Synthetic polynucleotide

<400> SEQUENCE: 63

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctgctag ctctgggtat ttaagcccga gtgagcacgc    180

agggtctcca ttttgaagcg ggaggttacg cgttcgtcga ctactagtgg gtaccagagc    240

aaaaaaattg tcatcctccc acggtggcca tttgttccat gtgagtgcta gtaacaggcc    300

ttgtgtcctt tgtagactat ttgcacactg catctgtggc ttcactcagt gtgcaaatag    360
```

```
tctacaagac aacagcatac agccttcagc aagcctccag tggtctcata cagaacttat    420
aagattccca aatccaaaga catttcacgt ttatggtgat ttcccagaac acatagcgac    480
atgcaaatat tgcagggcgc cactcccctg tccctcacag ccatcttcct gccagggcgc    540
acgcgcgctg ggtgttcccg cctagtgaca ctgggcccgc gattccttgg agcgggttga    600
tgacgtcagc gtttcccatg gtgaagcttg gatctgatcc ctaggttcta gaaccggtga    660
cattcggtac cctagttatt aatagtaatc aattacgggg tcattagttc atagcccata    720
tatggagttc cgcgttacat aacttacggt aaatggcccg cctggctgac cgcccaacga    780
cccccgccca ttgacgtcaa taatgacgta tgttcccata gtaacgccaa tagggacttt    840
ccattgacgt caatgggtgg actatttacg gtaaactgcc cacttggcag tacatcaagt    900
gtatcatatg ccaagtacgc cccctattga cgtcaatgac ggtaaatggc ccgcctggca    960
ttatgcccag tacatgacct tatgggactt tcctacttgg cagtacatct acgtattagt   1020
catcgctatt accatggtcg aggtgagccc cacgttctgc ttcactctcc ccatctcccc   1080
cccctcccca cccccaattt tgtatttatt tattttttaa ttattttgtg cagcgatggg   1140
ggcggggggg gggggggggc gcgcgccagg cggggcgggg cggggcgagg ggcggggcgg   1200
ggcgaggcgg agaggtgcgg cggcagccaa tcagagcggc gcgctccgaa agtttccttt   1260
tatggcgagg cggcggcggc ggcggcccta taaaaagcga agcgcgcggc gggcgggagt   1320
cgctgcgacg ctgccttcgc cccgtgcccc gctccgccgc cgcctcgcgc cgcccgcccc   1380
ggctctgact gaccgcgtta ctcccacagg tgagcgggcg ggacggccct tctcctccgg   1440
gctgtaatta gcgcttggtt taatgacggc ttgttttctg tggctgcgtg aaagccttga   1500
ggggctccgg gagctagagc ctctgctaac catgttcatg ccttcttctt tttcctacag   1560
ctcctgggca acgtgctggt tattgtgctg tctcatcatt ttggcaaaga attcctcgaa   1620
gatccgaagg gaaagtcttc cacgactgtg ggatccgttc gaagatatca ccggttgagc   1680
caccatgtgg accctggtga gctgggtggc cctgaccgcc ggcctggtgg ccggcacccg   1740
ctgccccgac ggccagttct gccccgtggc ctgctgcctg gaccccggcg gcgccagcta   1800
cagctgctgc cgcccccctgc tggacaagtg gcccaccacc ctgagccgcc acctgggcgg   1860
cccctgccag gtggacgccc actgcagcgc cggccacagc tgcatcttca ccgtgagcgg   1920
caccagcagc tgctgcccct tccccgaggc cgtggcctgc ggcgacggcc accactgctg   1980
cccccgcggc ttccactgca gcgccgacgg ccgcagctgc ttccagcgca gcggcaacaa   2040
cagcgtgggc gccatccagt gccccgacag ccagttcgag tgccccgact tcagcacctg   2100
ctgcgtgatg gtggacggca gctggggctg ctgccccatg ccccaggcca gctgctgcga   2160
ggaccgcgtg cactgctgcc cccacggcgc cttctgcgac ctggtgcaca cccgctgcat   2220
cacccccacc ggcacccacc ccctggccaa gaagctgccc gcccagcgca ccaaccgcgc   2280
cgtggccctg agcagcagcg tgatgtgccc cgacgcccgc agccgctgcc ccgacggcag   2340
cacctgctgc gagctgccca gcggcaagta cggctgctgc cccatgccca acgccacctg   2400
ctgcagcgac cacctgcact gctgccccca ggacaccgtg tgcgacctga tccagagcaa   2460
gtgcctgagc aaggagaacg ccaccaccga cctgctgacc aagctgcccg cccacaccgt   2520
gggcgacgtg aagtgcgaca tggaggtgag ctgccccgac ggctacacct gctgccgcct   2580
gcagagcggc gcctggggct gctgcccctt cacccaggcc gtgtgctgcg aggaccacat   2640
ccactgctgc cccgccggct tcacctgcga cacccagaag ggcacctgcg agcagggccc   2700
```

```
ccaccaggtg ccctggatgg agaaggcccc cgcccacctg agcctgcccg acccccaggc   2760

cctgaagcgc gacgtgccct gcgacaacgt gagcagctgc cccagcagcg acacctgctg   2820

ccagctgacc agcggcgagt ggggctgctg ccccatcccc gaggccgtgt gctgcagcga   2880

ccaccagcac tgctgccccc agggctacac ctgcgtggcc gagggccagt gccagcgcgg   2940

cagcgagatc gtggccggcc tggagaagat gcccgcccgc cgcgccagcc tgagccaccc   3000

ccgcgacatc ggctgcgacc agcacaccag ctgccccgtg ggccagacct gctgccccag   3060

cctgggcggc agctgggcct gctgccagct gccccacgcc gtgtgctgcg aggaccgcca   3120

gcactgctgc cccgccggct acacctgcaa cgtgaaggcc cgcagctgcg agaaggaggt   3180

ggtgagcgcc cagcccgcca ccttcctggc ccgcagcccc cacgtgggcg tgaaggacgt   3240

ggagtgcggc gagggccact tctgccacga caaccagacc tgctgccgcg acaaccgcca   3300

gggctgggcc tgctgcccct accgccaggg cgtgtgctgc gccgaccgcc gccactgctg   3360

ccccgccggc ttccgctgcg ccgcccgcgg caccaagtgc ctgcgccgcg aggccccccg   3420

ctgggacgcc cccctgcgcg accccgccct gcgccagctg ctgtgacaat tgttaattaa   3480

gtttaaaccc tcgaggccgc aagcttatcg ataatcaacc tctggattac aaaatttgtg   3540

aaagattgac tggtattctt aactatgttg ctccttttac gctatgtgga tacgctgctt   3600

taatgccttt gtatcatgct attgcttccc gtatggcttt cattttctcc tccttgtata   3660

aatcctggtt gctgtctctt tatgaggagt tgtggcccgt tgtcaggcaa cgtggcgtgg   3720

tgtgcactgt gtttgctgac gcaaccccca ctggttgggg cattgccacc acctgtcagc   3780

tcctttccgg gactttcgct ttccccctcc ctattgccac ggcggaactc atcgccgcct   3840

gccttgcccg ctgctggaca ggggctcggc tgttgggcac tgacaattcc gtggtgttgt   3900

cggggaaatc atcgtccttt ccttggctgc tcgcctgtgt tgccacctgg attctgcgcg   3960

ggacgtcctt ctgctacgtc ccttcggccc tcaatccagc ggaccttcct tcccgcggcc   4020

tgctgccggc tctgcggcct cttccgcgtc ttcgccttcg ccctcagacg agtcggatct   4080

ccctttgggc cgcctccccg catcgatacc gtcgactaga gctcgctgat cagcctcgac   4140

tgtgccttct agttgccagc catctgttgt ttgcccctcc cccgtgcctt ccttgaccct   4200

ggaaggtgcc actcccactg tcctttccta ataaaatgag gaaattgcat cgcattgtct   4260

gagtaggtgt cattctattc tggggggtgg ggtggggcag gacagcaagg gggaggattg   4320

ggaagacaat agcaggcatg ctggggagag atccacgata acaaacagct tttttggggt   4380

gaacatattg actgaattcc ctgcaggttg gccactccct ctctgcgcgc tcgctcgctc   4440

actgaggccg cccgggcaaa gcccgggcgt cgggcgacct ttggtcgccc ggcctcagtg   4500

agcgagcgag cgcgcagaga gggagtggcc aactccatca ctaggggttc ct           4552
```

<210> SEQ ID NO 64
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 64

```
aagagggtgt tctctatgta ggc                                          23
```

<210> SEQ ID NO 65
<211> LENGTH: 22
<212> TYPE: DNA
<213> ORGANISM: Artificial Sequence

```
<220> FEATURE:
<223> OTHER INFORMATION: Synthetic polynucleotide

<400> SEQUENCE: 65

gctcctccaa catttgtcac tt                                             22


<210> SEQ ID NO 66
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 66

acacagtacc taccgttata gca                                            23


<210> SEQ ID NO 67
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 67

tgttgtcaca gtaacttgca tca                                            23


<210> SEQ ID NO 68
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 68

ctgggctaca ctgagcacc                                                 19


<210> SEQ ID NO 69
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 69

aagtggtcgt tgagggcaat g                                              21
```

GENE THERAPY FOR NEURODEGENERATIVE DISORDERS

RELATED APPLICATIONS

This application claims the benefit under 35 U.S.C. 119(e) of U.S. Provisional Application Ser. No. 62/567,303, filed Oct. 3, 2017, entitled "GENE THERAPIES FOR LYSOSOMAL DISORDERS", and 62/567,305, filed Oct. 3, 2017, entitled "GENE THERAPIES FOR LYSOSOMAL DISORDERS", the entire contents of each of which are incorporated herein by reference.

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies as described below, chaperone-like small molecule drugs that bind to defective Gcase and improve stability, and substrate reduction therapy that block the production of substrate that accumulate in Gaucher disease leading to symptoms and findings. However, other aspects of Gaucher disease (particularly those affecting the skeleton and brain) appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms-which include gait difficulty, a tremor at rest, rigidity, and often depression, sleep difficulties, and cognitive decline-correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

In some aspects, the disclosure is based on expression constructs encoding one or more inhibitory RNA (e.g., shRNA, miRNA, etc.) that targets a PD-associated gene (e.g., α-Synuclein (α-Syn), transmembrane protein 106B (TMEM106B), ribosomal protein s25 (RPS25), microtubule-associated protein tau (MAPT), or a combination thereof). In some aspects, the disclosure is based on expression constructs (e.g., vectors) encoding Gcase (or a portion thereof) and one or more additional gene products from PD-associated genes (e.g., α-Syn). Without wishing to be bound by any particular theory, combinations of gene products described herein act together (e.g., synergistically) to reduce one or more signs and symptoms of PD when expressed in a subject.

Accordingly, in some aspects, the disclosure provides an isolated nucleic acid encoding an inhibitory RNA that targets SNCA (e.g., a portion of SCNA) and inhibits expression and/or activity of α-Syn. In some aspects, the disclosure provides an isolated nucleic acid comprising an expression construct encoding a first gene product and a second gene product, wherein each gene product independently is selected from the gene products, or portions thereof, set forth in Table 1.

Accordingly, in some aspects, the disclosure provides an isolated nucleic acid encoding an inhibitory RNA that targets TMEM106B (e.g., a portion of TMEM106B) and inhibits expression and/or activity of TMEM106B. In some aspects, the disclosure provides an isolated nucleic acid comprising an expression construct encoding a first gene product and a second gene product, wherein each gene product independently is selected from the gene products, or portions thereof, set forth in Table 1.

Accordingly, in some aspects, the disclosure provides an isolated nucleic acid encoding an inhibitory RNA that targets a gene encoding RPS25 (e.g., a portion of a gene encoding RPS25) and inhibits expression and/or activity of RPS25. In some aspects, the disclosure provides an isolated nucleic acid comprising an expression construct encoding a first gene product and a second gene product, wherein each gene product independently is selected from the gene products, or portions thereof, set forth in Table 1.

Accordingly, in some aspects, the disclosure provides an isolated nucleic acid encoding an inhibitory RNA that targets MAPT (e.g., a portion of a gene encoding MAPT) and inhibits expression and/or activity of MAPT. In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product or a second gene product is an interfering nucleic acid (e.g., shRNA, miRNA, dsRNA, etc.). In some embodiments, an interfering nucleic acid inhibits expression of α-Synuclein (α-Synuclein). In some embodiments, the first gene product is a Gcase protein, and the second gene product is an interfering nucleic acid (e.g., shRNA, miRNA, dsRNA, etc.) that inhibits expression of α-Syn (e.g., an interfering nucleic acid that targets SCNA).

In some embodiments, an interfering nucleic acid inhibits expression of TMEM106B. In some embodiments, the first gene product is a Gcase protein, and the second gene product is an interfering nucleic acid (e.g., shRNA, miRNA, dsRNA, etc.) that inhibits expression of TMEM106B (e.g., an interfering nucleic acid that targets TMEM106B).

In some embodiments, an interfering nucleic acid inhibits expression of RPS25. In some embodiments, the first gene product is a Gcase protein, and the second gene product is an interfering nucleic acid (e.g., shRNA, miRNA, dsRNA, etc.) that inhibits expression of a gene encoding RPS25 (e.g., an interfering nucleic acid that targets RPS25 encoding sequence).

In some embodiments, an interfering nucleic acid inhibits expression of MAPT. In some embodiments, the first gene product is a Gcase protein, and the second gene product is an interfering nucleic acid (e.g., shRNA, miRNA, dsRNA, etc.) that inhibits expression of MAPT (e.g., an interfering nucleic acid that targets MAPT).

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter or a RNA pol III promoter (e.g., U6).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments. ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 16). In some embodiments, the ITR having the modified D region is the 5' ITR of the rAAV vector. In some embodiments, a modified "D" region comprises an "S" sequence, for example as set forth in SEQ ID NO: 13. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 13 or 14.

In some embodiments, an isolated nucleic acid (e.g., an rAAV vector) comprises a TRY region. In some embodiments, a TRY region comprises the sequence set forth in SEQ ID NO: 16.

In some embodiments, an isolated nucleic acid described by the disclosure comprises or consists of the sequence set forth in SEQ ID NO: 1-67.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector or a Baculovirus vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain harrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna magna injection, or any combination thereof. In some embodiments, direct injection to the CNS of a subject comprises convection enhanced delivery (CED).

In some embodiments, administration comprises peripheral injection. In some embodiments, peripheral injection is intravenous injection.

DETAILED DESCRIPTION

Figure 1:
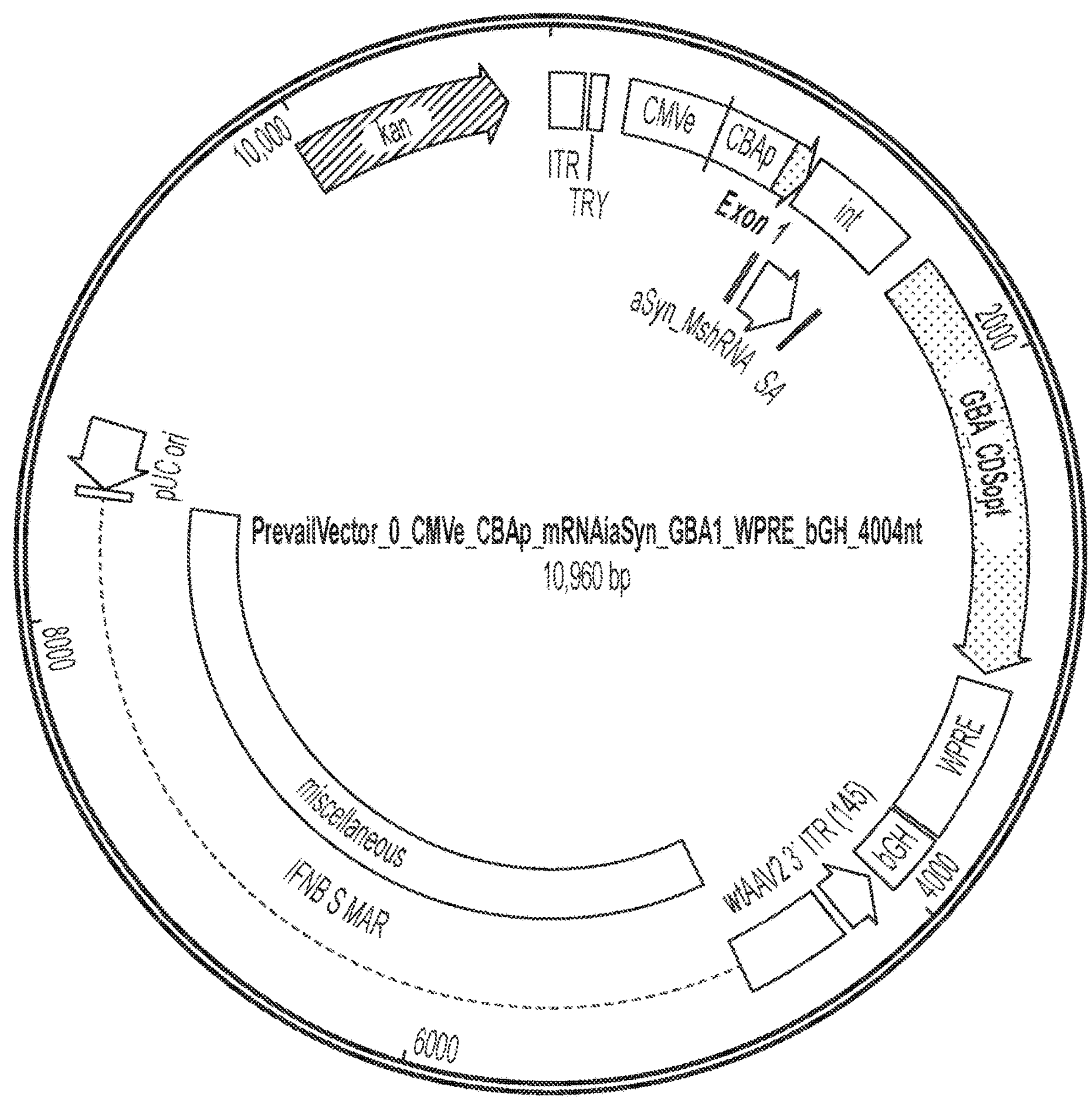
FIG. 1 is a schematic depicting one embodiment of a vector comprising an expression construct encoding Gcase (e.g., GBA1 or a portion thereof) and an inhibitory RNA targeting SCNA.
Figure 2:
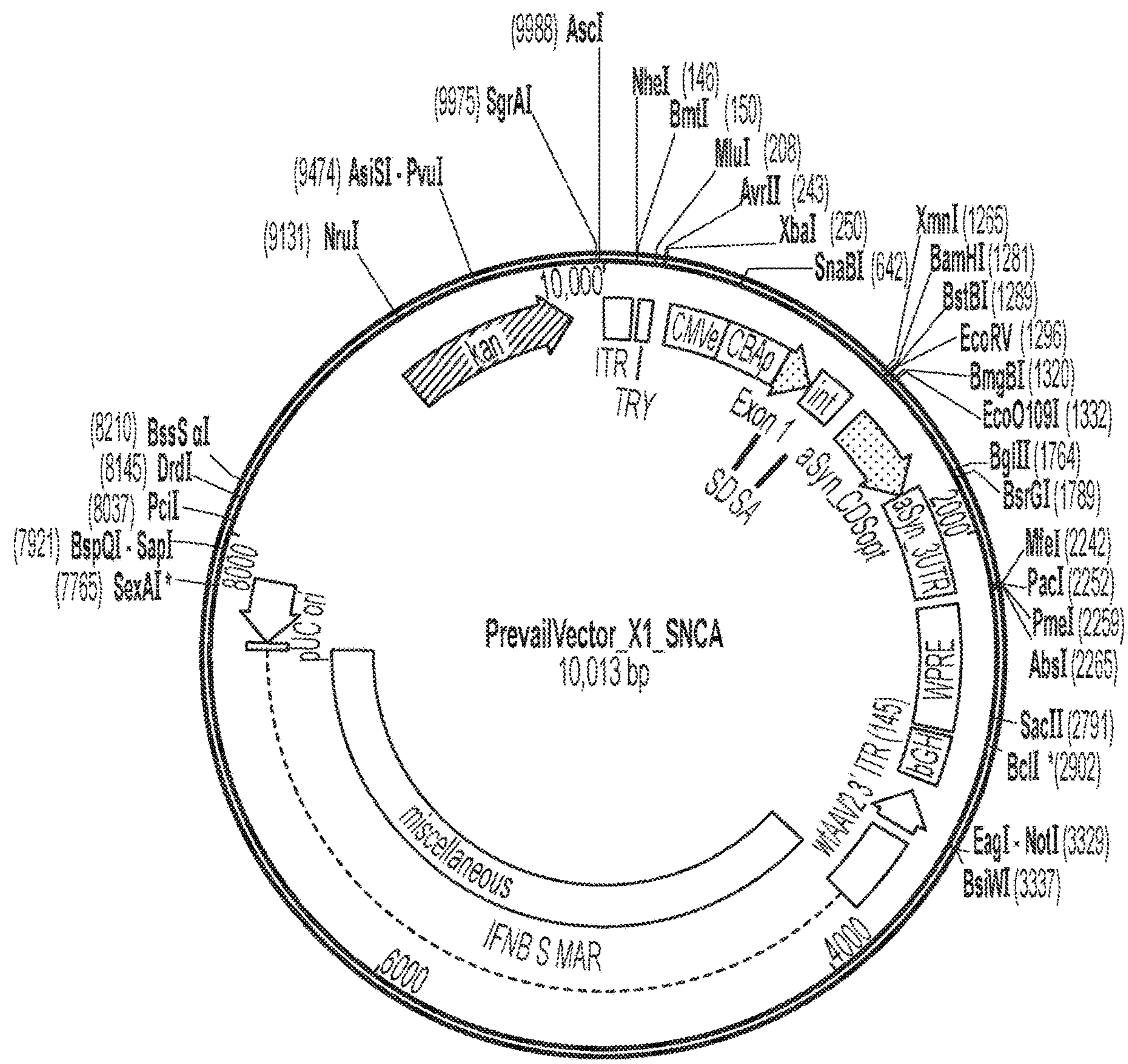
FIG. 2 is a schematic depicting one embodiment of a plasmid comprising an rAAV vector that includes an expression construct encoding SCNA.
Figure 3:
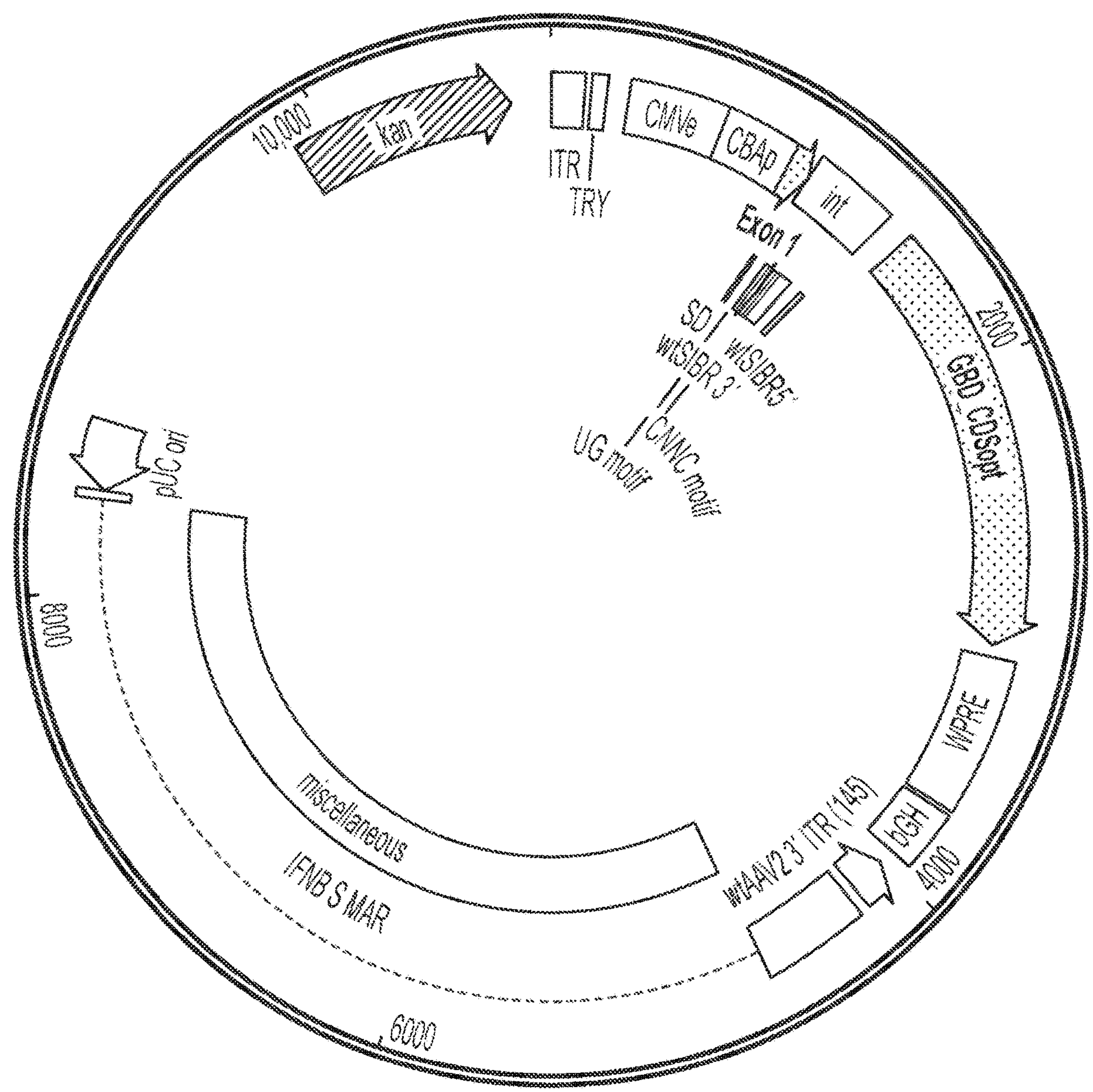
FIG. 3 is a schematic depicting one embodiment of a plasmid comprising an rAAV vector that includes an expression construct encoding an inhibitory RNA targeting SCNA. The inhibitory RNA is positioned within an intron between the promoter sequence and the Gcase encoding sequence.
Figure 4:
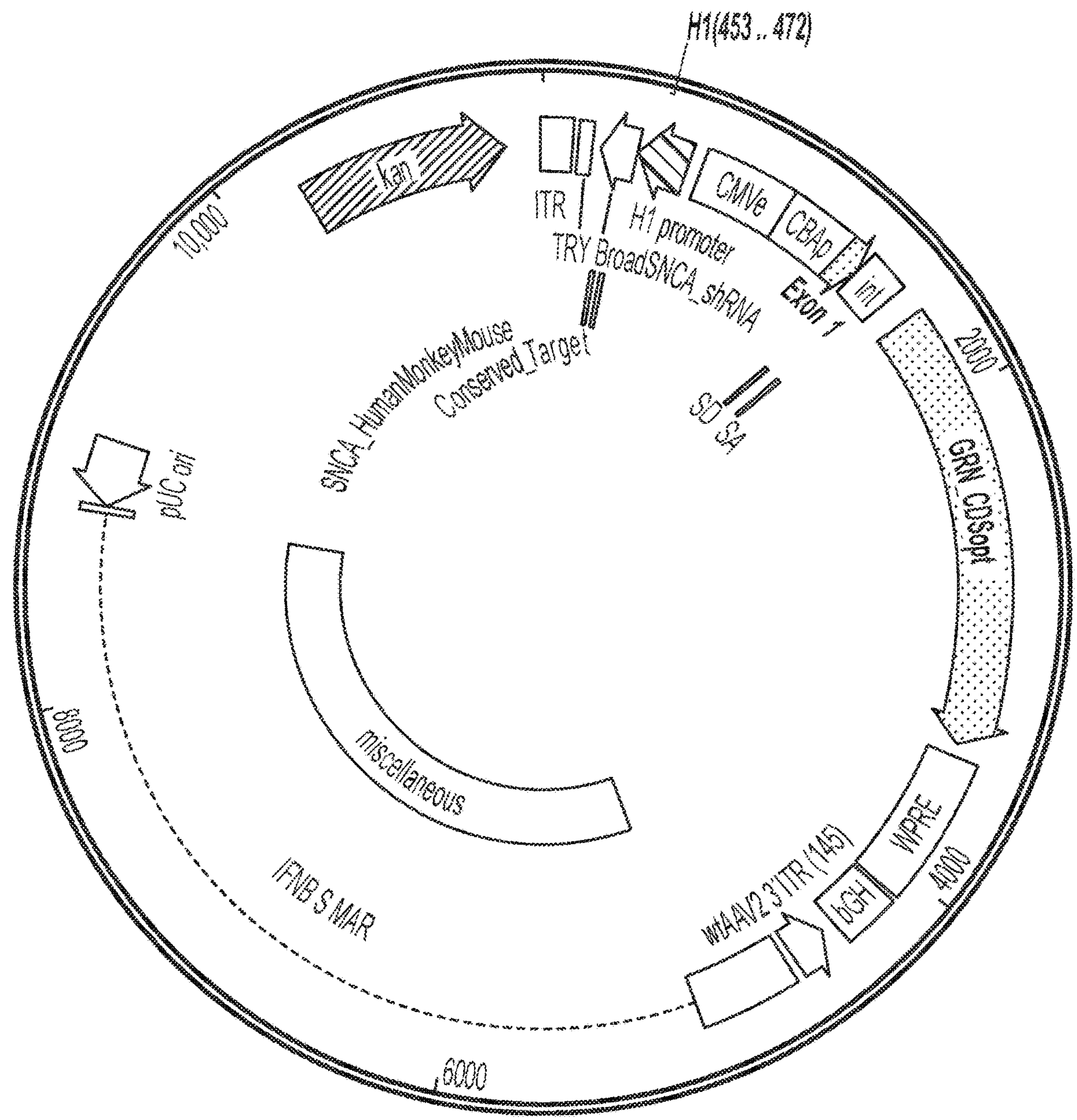
FIG. 4 is a schematic depicting one embodiment of a plasmid comprising an rAAV vector that includes an expression construct encoding progranulin (PGRN) and an inhibitory RNA targeting SCNA. The inhibitory RNA is positioned within an intron between the promoter sequence and the Gcase encoding sequence.
Figure 5:
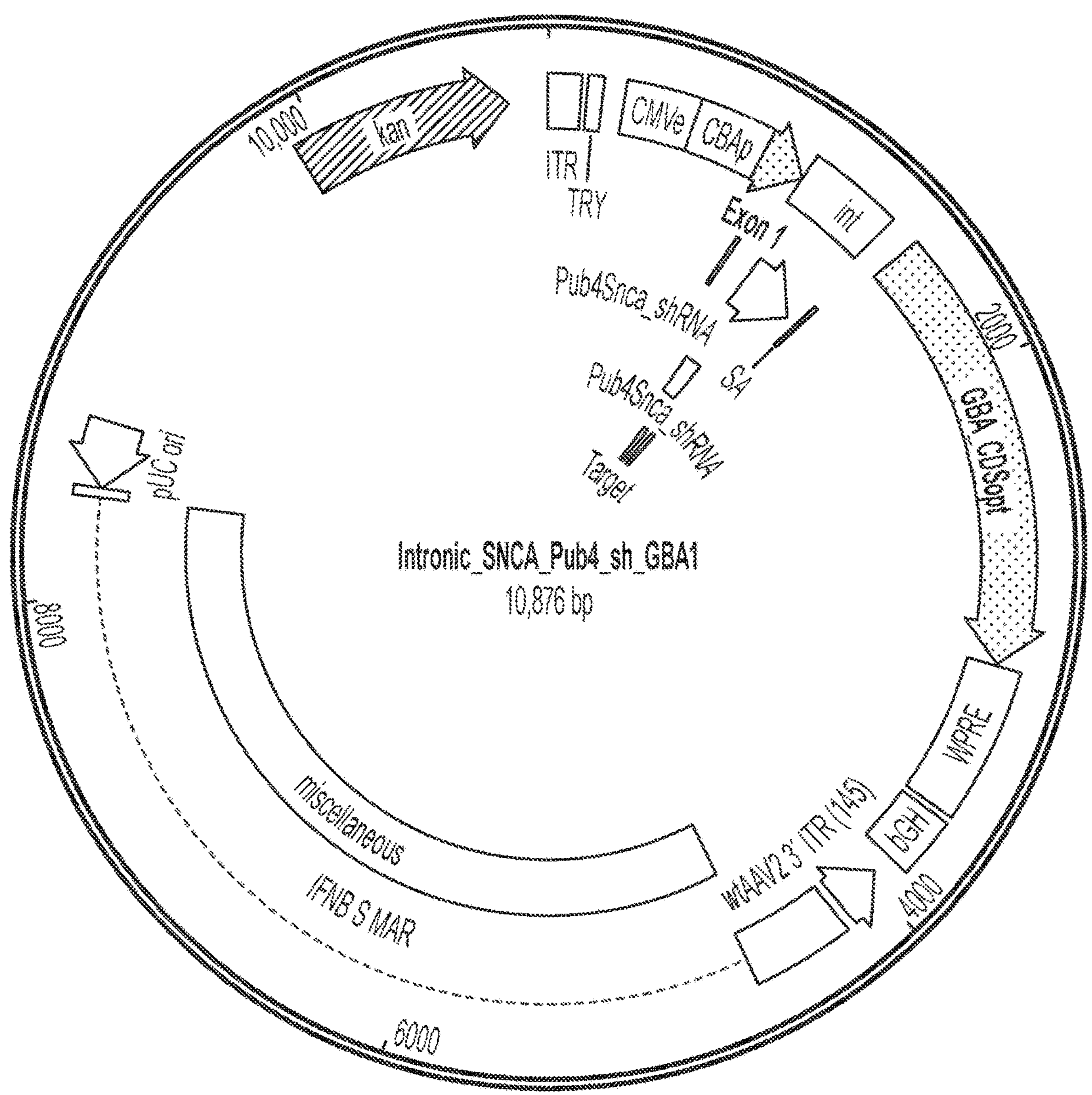
FIG. 5 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 6:
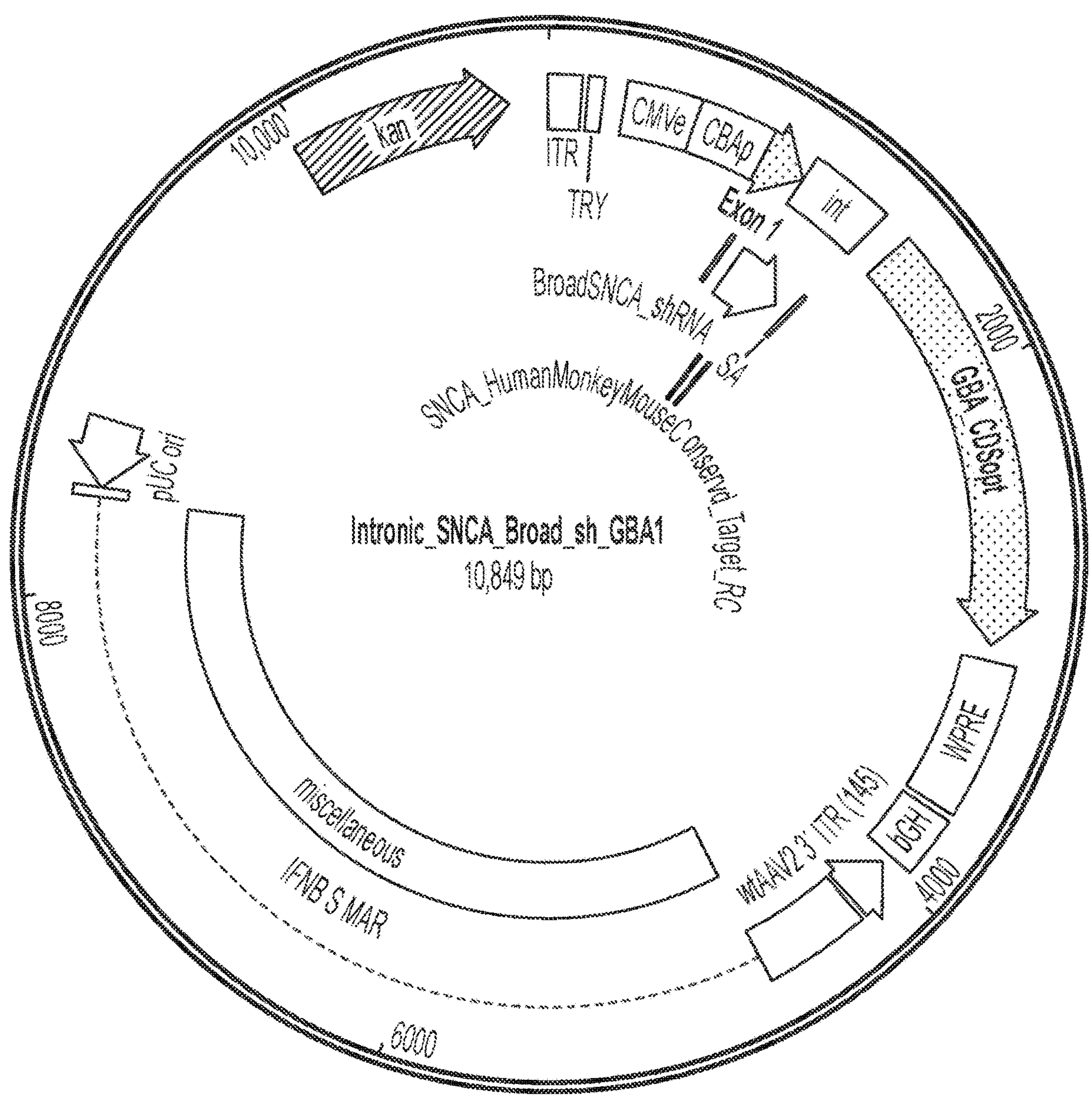
FIG. 6 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 7:
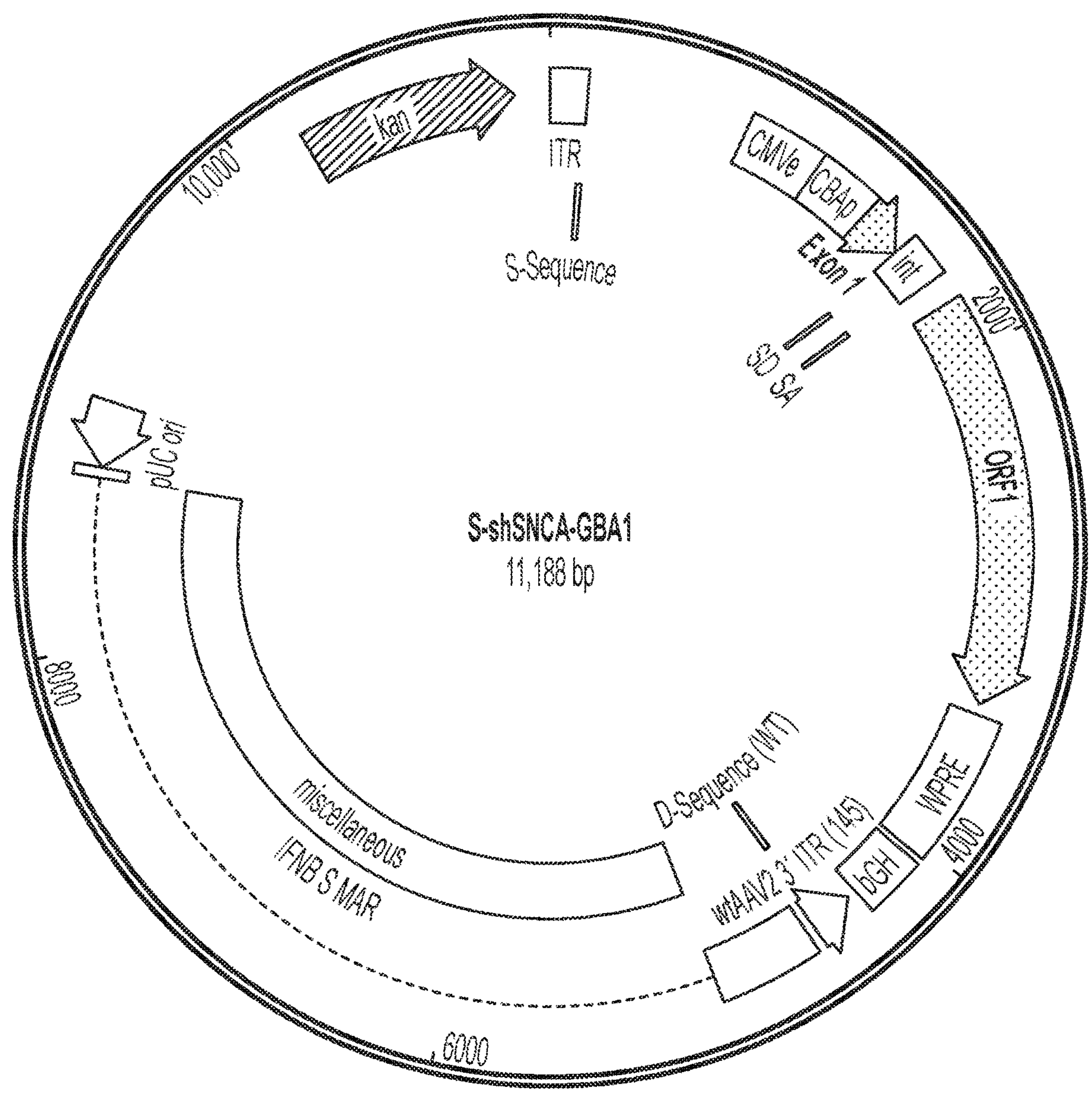
FIG. 7 is a schematic depicting one embodiment of a plasmid comprising an rAAV vector that includes an expression construct encoding Gcase (GBA1) and an inhibitory RNA targeting SCNA. The "D" sequence of the 3'ITR is positioned on the "outside" of the vector.
Figure 8:
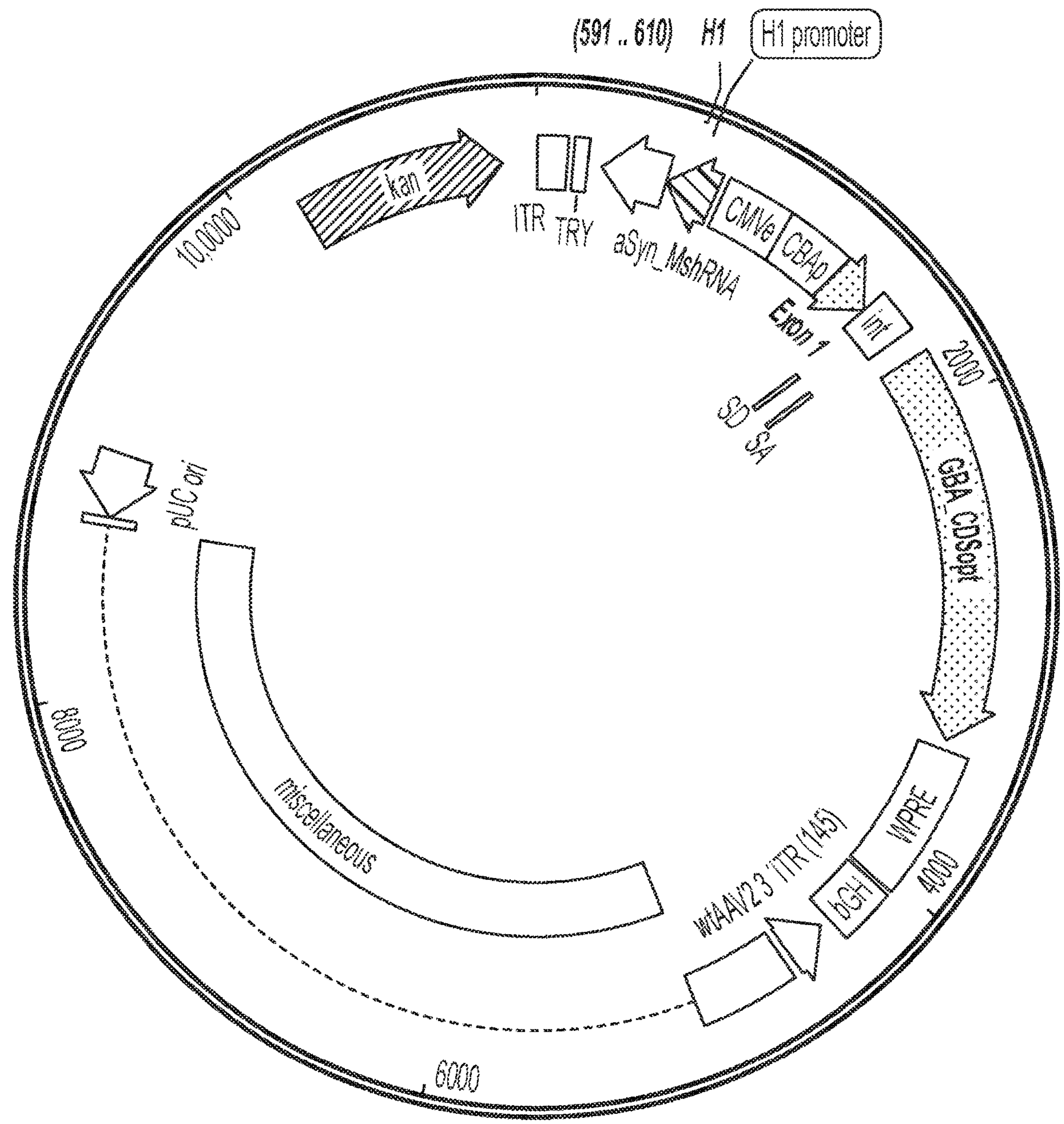
FIG. 8 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 9:
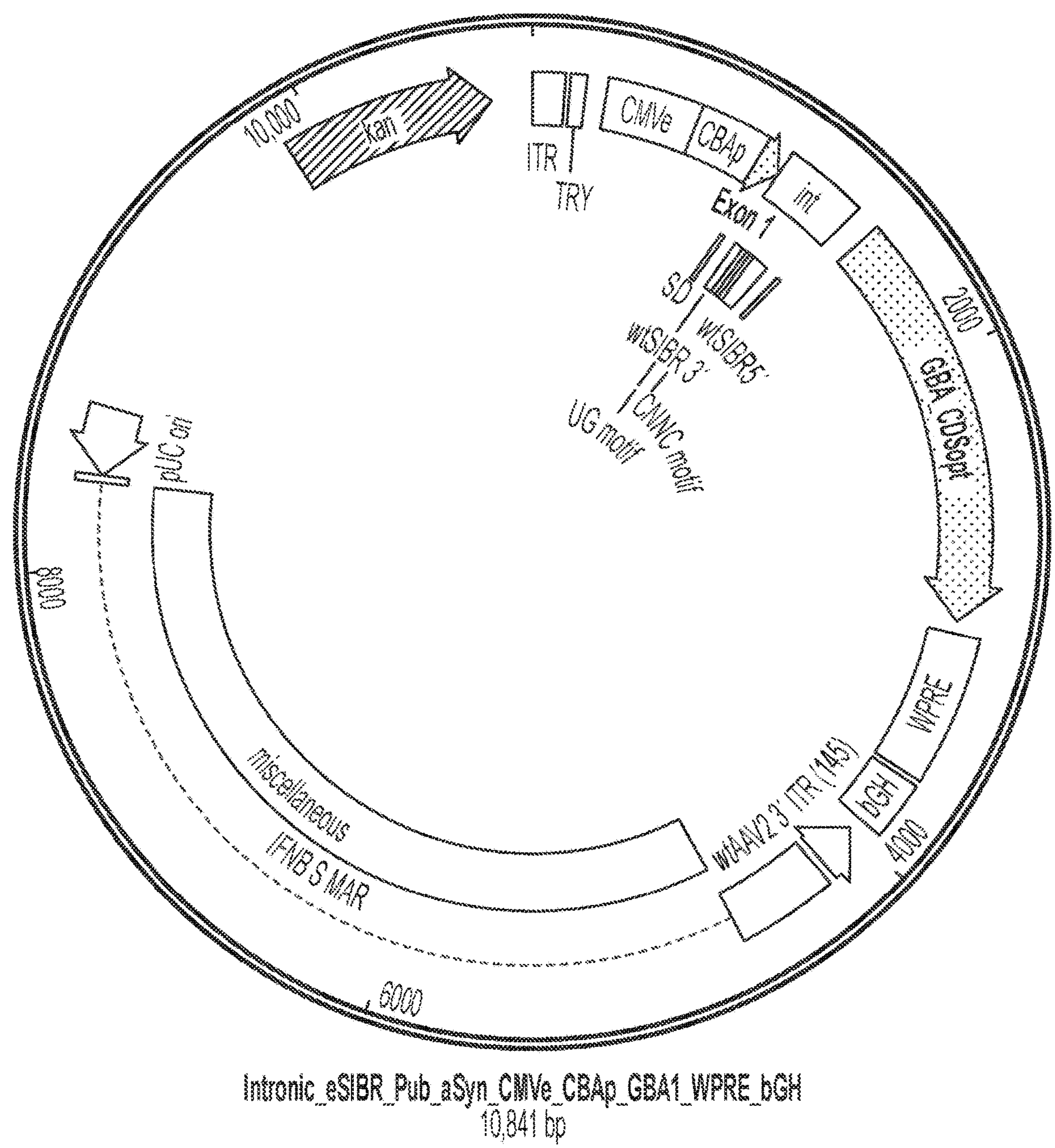
FIG. 9 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 10:
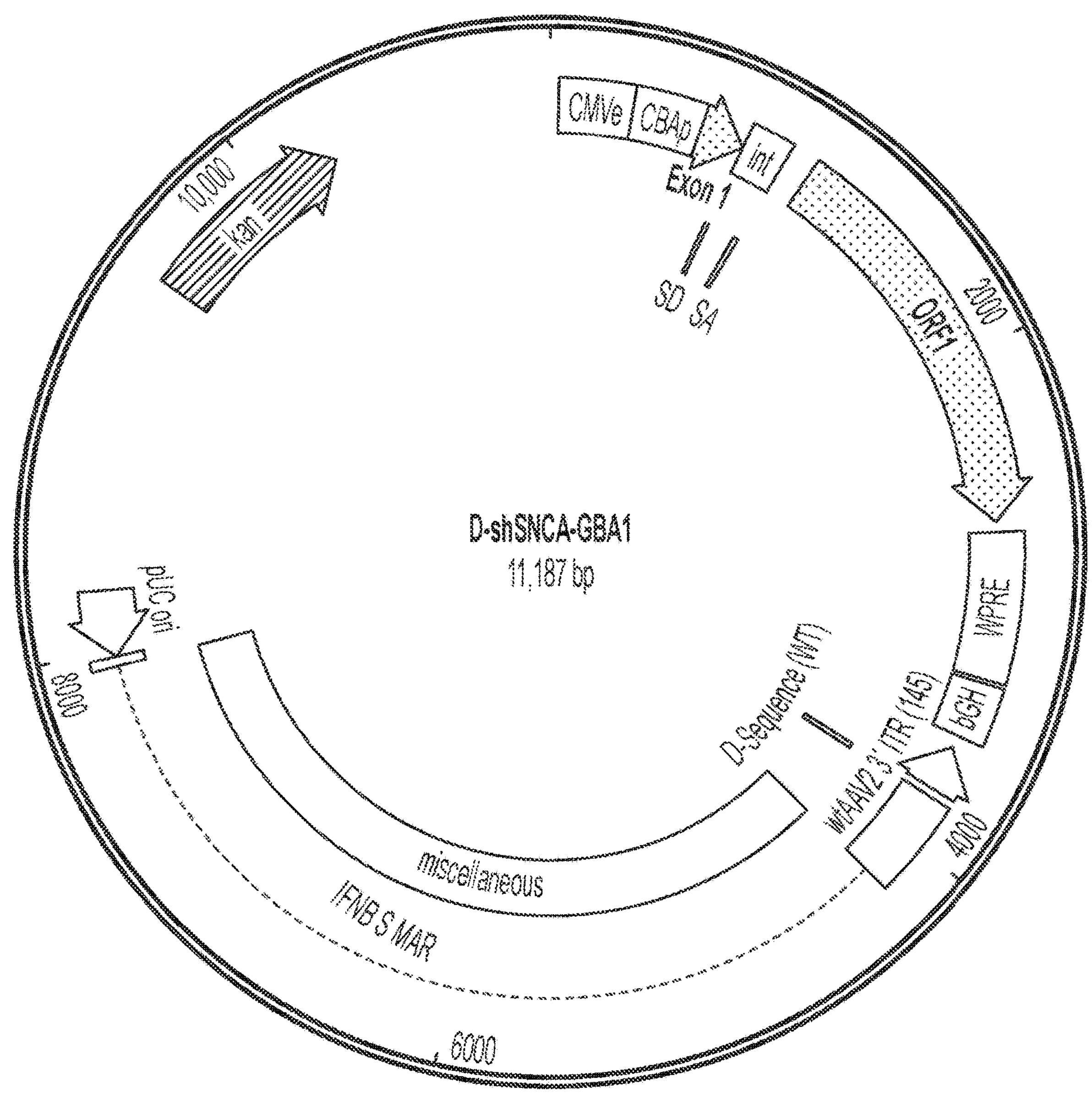
FIG. 10 is a schematic depicting one embodiment of a plasmid comprising an rAAV vector that includes an expression construct encoding Gcase (GBA1) and an inhibitory RNA targeting SCNA.
Figure 11:
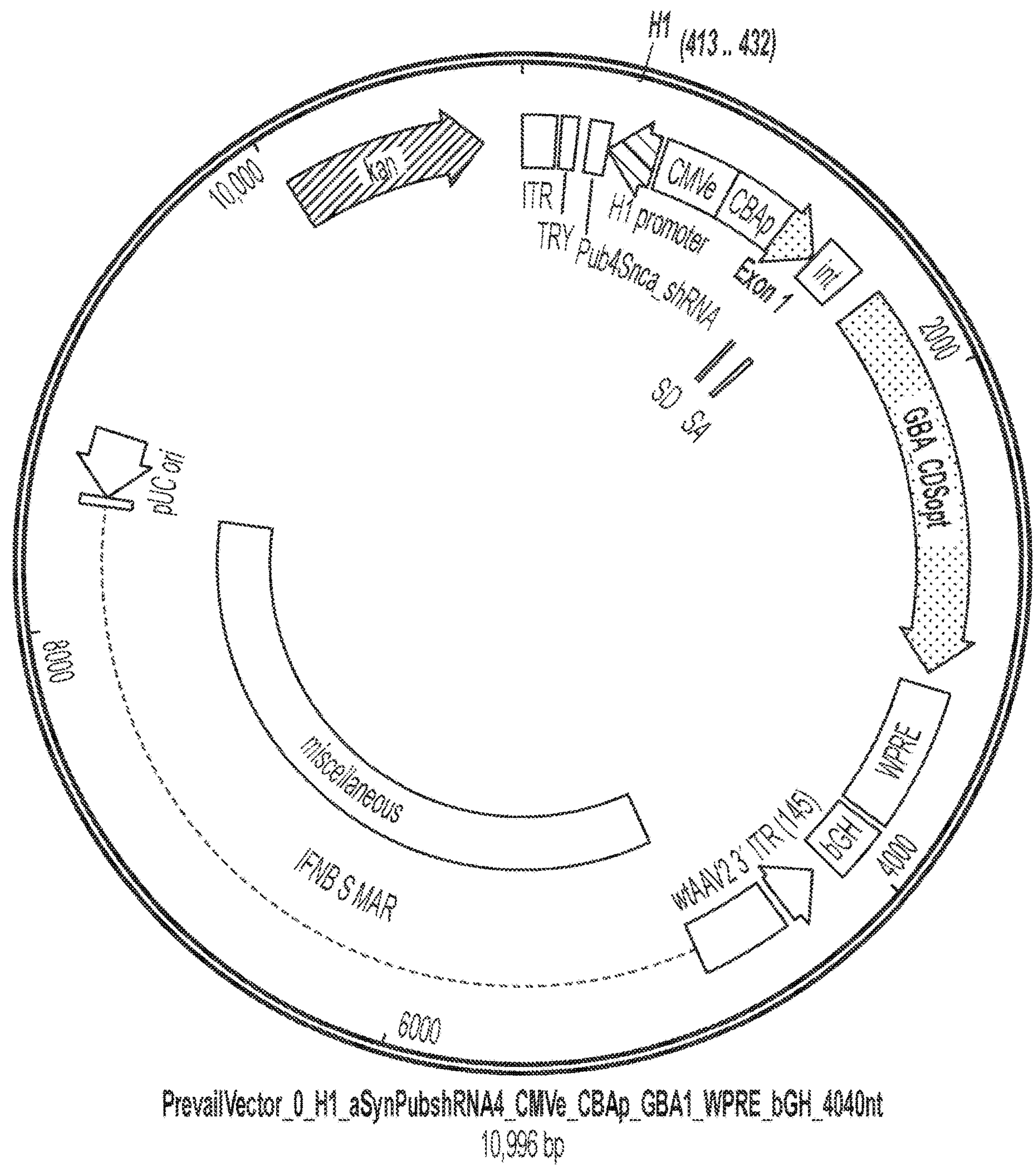
FIG. 11 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 12:
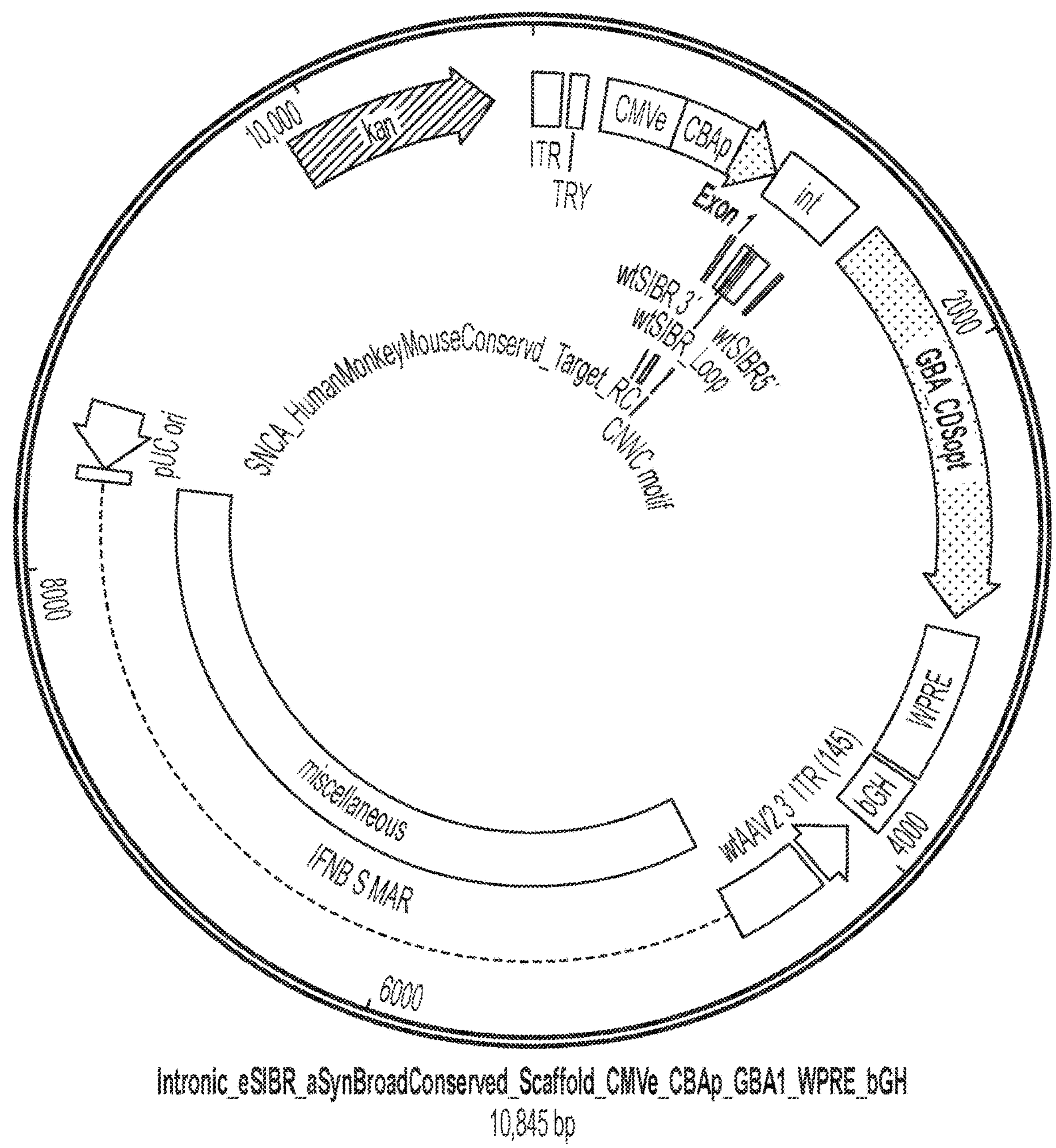
FIG. 12 is a schematic depicting one embodiment of a plasmid comprising an rAAV vector that includes an expression construct encoding Gcase (GBA1) and an inhibitory RNA targeting SCNA. The inhibitory RNA is positioned within an intron between the promoter sequence and the Gcase encoding sequence.
Figure 13:
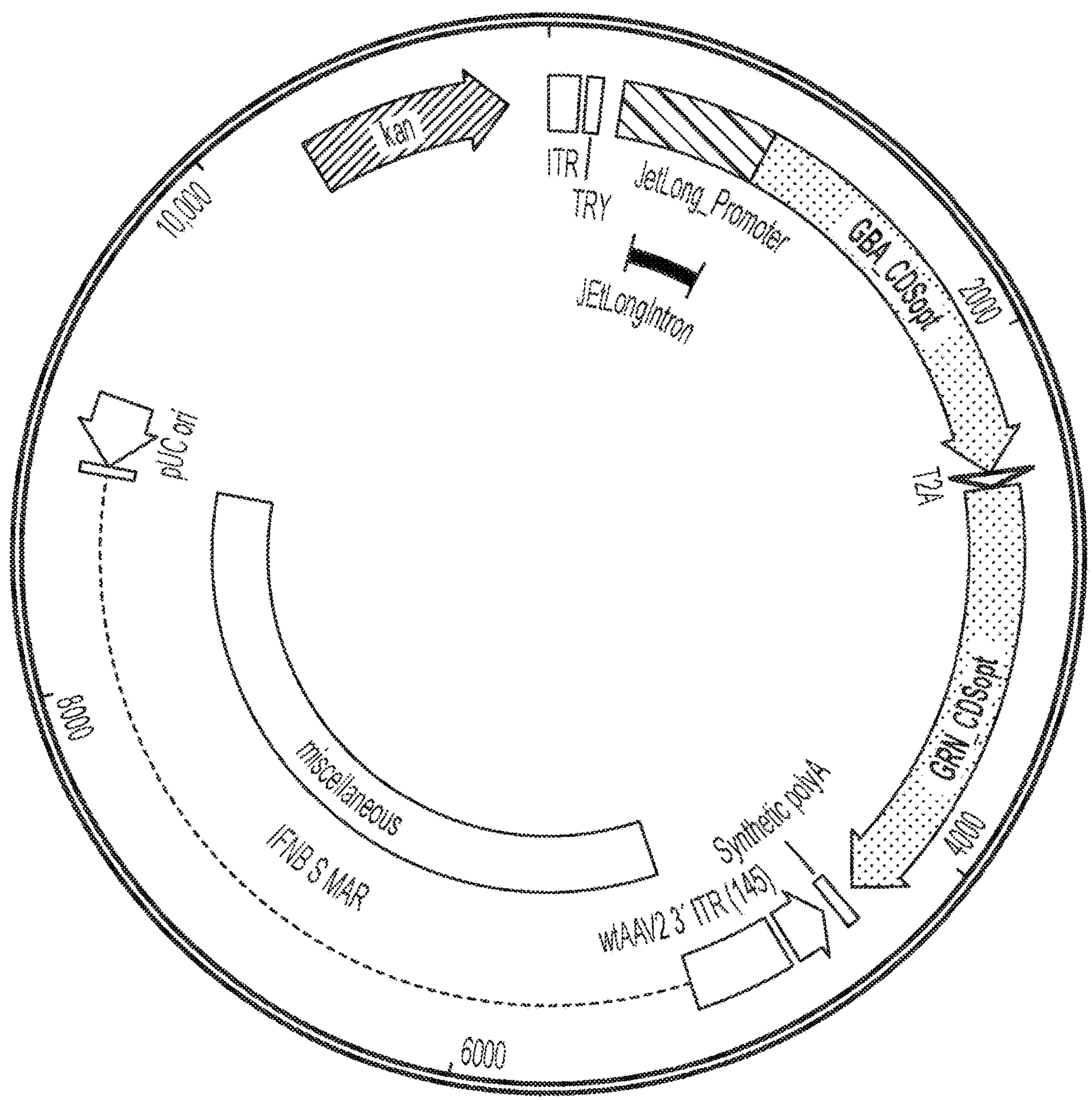
FIG. 13 is a schematic depicting one embodiment of a plasmid comprising an rAAV vector that includes an expression construct encoding Gcase (GBA1) and progranulin (PGRN), and an inhibitory RNA targeting TMEM106B. The inhibitory RNA is positioned within an intron between the promoter sequence and the Gcase encoding sequence.

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

Examples of PD-associated genes

| Name | Gene | Function | NCBI Accession No. |
|---|---|---|---|
| alpha-Synuclein | SNCA | plays a role in maintaining a supply of synaptic vesicles in presynaptic terminals by clustering synaptic vesicles, and may help regulate the release of dopamine | NP_001139527.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |

TABLE 1-continued

| Examples of PD-associated genes | | | |
|---|---|---|---|
| Name | Gene | Function | NCBI Accession No. |
| Transmembrane protein 106B | TMEM106B | plays a role in dendrite morphogenesis and regulation of lysosomal trafficking | NP_060844.2 |
| Progranulin | PGRN | plays a role in development, inflammation, cell proliferation and protein homeostasis | NP_002087.1 |
| Ribosomal protein S25 | RPS25 | ribosomal protein that is a component of the 40S subunit | AB061844.1 |
| Microtubule-associated protein tau | MAPT | Microtubule stabilization | NM_016835.4 |

Isolated Nucleic Acids and Vectors

An isolated nucleic acid may be DNA or RNA. In some aspects, the disclosure provides isolated nucleic acids (e.g., rAAV vectors) encoding one or more inhibitory nucleic acids that target one or more PD-associated gene, for example SCNA, TMEM106B, RPS25, and MAPT. In some embodiments, the isolated nucleic acids further comprise a protein-encoding sequence, for example a nucleic acid sequence encoding a Gcase (e.g., GBA1) or progranulin (e.g., PGRN).

Generally, an isolated nucleic acid as described herein may encode 1, 2, 3, 4, 5, 6, 7, 8, 9, 10, or more inhibitory nucleic acids (e.g., dsRNA, siRNA, shRNA, miRNA, amiRNA, etc.). In some embodiments, an isolated nucleic acid encodes more than 10 inhibitory nucleic acids. In some embodiments, each of the one or more inhibitory nucleic acids targets a different gene or a portion of a gene (e.g., a first miRNA targets a first target sequence of a gene and a second miRNA targets a second target sequence of the gene that is different than the first target sequence). In some embodiments, each of the one or more inhibitory nucleic acids targets the same target sequence of the same gene (e.g., an isolated nucleic acid encodes multiple copies of the same miRNA).

Aspects of the disclosure relate to an isolated nucleic acid comprising an expression construct encoding one or more interfering nucleic acids (e.g., dsRNA, siRNA, miRNA, amiRNA, etc.) that target an α-Synuclein protein (e.g., the gene product of SCNA gene). α-Synuclein protein refers to a protein found in brain tissue, which is plays a role in maintaining a supply of synaptic vesicles in presynaptic terminals by clustering synaptic vesicles and regulating the release of dopamine. In humans, SCNA gene is located on chromosome 4. In some embodiments, the SCNA gene encodes a peptide that is represented by NCBI Reference Sequence NP_001139527.1. In some embodiments, a SCNA gene comprises the sequence set forth in SEQ ID NO: 1.

An inhibitory nucleic acid targeting SCNA may comprise a region of complementarity (e.g., a region of the inhibitory nucleic acid that hybridizes to the target gene, such as SCNA) that is between 6 and 50 nucleotides in length. In some embodiments, an inhibitory nucleic acid comprises a region of complementarity with SCNA that is between about 6 and 30, about 8 and 20, or about 10 and 19 nucleotides in length. In some embodiments, an inhibitory nucleic acid is complementary with at least 3, 4, 5, 6, 7, 8, 9, 10, 11, 12, 13, 14, 15, 16, 17, 18, 19, 20, 21, 22, 23, 24, or 25 contiguous nucleotides of a SCNA sequence.

Aspects of the disclosure relate to an isolated nucleic acid comprising an expression construct encoding one or more interfering nucleic acids (e.g., dsRNA, siRNA, miRNA, amiRNA, etc.) that target an TMEM106B protein (e.g., the gene product of SCNA gene). TMEM106B protein refers to transmembrane protein 106B, which is a protein involved in dendrite morphogenesis and regulation of lysosomal trafficking. In humans, TMEM106B gene is located on chromosome 7. In some embodiments, the TMEM106B gene encodes a peptide that is represented by NCBI Reference Sequence NP_060844.2. In some embodiments, a TMEM106B gene comprises the sequence set forth in SEQ ID NO: 2.

An inhibitory nucleic acid targeting TMEM106B may comprise a region of complementarity (e.g., a region of the inhibitory nucleic acid that hybridizes to the target gene, such as TMEM106B) that is between 6 and 50 nucleotides in length. In some embodiments, an inhibitory nucleic acid comprises a region of complementarity with TMEM106B that is between about 6 and 30, about 8 and 20, or about 10 and 19 nucleotides in length. In some embodiments, an inhibitory nucleic acid is complementary with at least 3, 4, 5, 6, 7, 8, 9, 10, 11, 12, 13, 14, 15, 16, 17, 18, 19, 20, 21, 22, 23, 24, or 25 contiguous nucleotides of a TMEM106B sequence.

Aspects of the disclosure relate to an isolated nucleic acid comprising an expression construct encoding one or more interfering nucleic acids (e.g., dsRNA, siRNA, miRNA, amiRNA, etc.) that target an ribosomal protein s25 (RPS25) (e.g., the gene product of RPS25). RPS25 protein refers to a ribosomal protein which is a subunit of the s40 ribosome, a protein complex involved in protein synthesis. In humans, RPS25 gene is located on chromosome 11. In some embodiments, the RPS25 gene encodes a peptide that is represented by NCBI Reference Sequence NP_001019.1. In some embodiments, a RPS25 gene comprises the sequence set forth in SEQ ID NO: 36.

An inhibitory nucleic acid targeting RPS25 may comprise a region of complementarity (e.g., a region of the inhibitory nucleic acid that hybridizes to the target gene, such as RPS25) that is between 6 and 50 nucleotides in length. In some embodiments, an inhibitory nucleic acid comprises a region of complementarity with RPS25 that is between about 6 and 30, about 8 and 20, or about 10 and 19 nucleotides in length. In some embodiments, an inhibitory nucleic acid is complementary with at least 3, 4, 5, 6, 7, 8, 9, 10, 11, 12, 13, 14, 15, 16, 17, 18, 19, 20, 21, 22, 23, 24, or 25 contiguous nucleotides of a RPS25 sequence.

Aspects of the disclosure relate to an isolated nucleic acid comprising an expression construct encoding one or more interfering nucleic acids (e.g., dsRNA, siRNA, miRNA, amiRNA, etc.) that target an microtubule-associated protein tau, MAPT (e.g., the gene product of MAPT gene). MAPT protein refers to microtubule-associated protein tau, which is a protein involved in microtubule stabilization. In humans, MAPT gene is located on chromosome 17. In some embodiments, the MAPT gene encodes a peptide that is represented by NCBI Reference Sequence NP_005901.2. In some embodiments, a MAPT gene comprises the sequence set forth in SEQ ID NO: 37.

An inhibitory nucleic acid targeting MAPT may comprise a region of complementarity (e.g., a region of the inhibitory nucleic acid that hybridizes to the target gene, such as MAPT) that is between 6 and 50 nucleotides in length. In some embodiments, an inhibitory nucleic acid comprises a region of complementarity with MAPT that is between about 6 and 30, about 8 and 20, or about 10 and 19 nucleotides in length. In some embodiments, an inhibitory nucleic acid is complementary with at least 3, 4, 5, 6, 7, 8, 9, 10, 11, 12, 13, 14, 15, 16, 17, 18, 19, 20, 21, 22, 23, 24, or 25 contiguous nucleotides of a MAPT sequence.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is an inhibitory nucleic acid that targets (e.g., hybridizes to, or comprises a region of complementarity with) a PD-associated gene (e.g., SCNA). A skilled artisan recognizes that the order of expression of a first gene product (e.g., Gcase) and a second gene product (e.g., inhibitory RNA targeting SCNA) can generally be reversed (e.g., the inhibitory RNA is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1. In some embodiments, a gene product (e.g., an inhibitory RNA) hybridizes to portion of a target gene (e.g., is complementary to 5, 6, 7, 8, 9, 10, 11, 12, 13, 14, 15, 16, 17, 18, 19, 20, 21, or more contiguous nucleotides of a target gene, for example SCNA).

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornøe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA).

In some embodiments, an inhibitory nucleic acid is an artificial microRNA (amiRNA). A microRNA (miRNA) typically refers to a small, non-coding RNA found in plants and animals and functions in transcriptional and post-translational regulation of gene expression. MiRNAs are transcribed by RNA polymerase to form a hairpin-loop structure referred to as a pri-miRNAs which are subsequently processed by enzymes (e.g., Drosha. Pasha, spliceosome, etc.) to for a pre-miRNA hairpin structure which is then processed by Dicer to form a miRNA/miRNA* duplex (where * indicates the passenger strand of the miRNA duplex), one strand of which is then incorporated into an RNA-induced silencing complex (RISC). In some embodiments, an inhibitory RNA as described herein is a miRNA targeting SCNA or TMEM106B.

In some embodiments, an inhibitory nucleic acid targeting SCNA comprises a miRNA/miRNA* duplex. In some embodiments, the miRNA strand of a miRNA/miRNA* duplex comprises or consists of the sequence set forth in any one of SEQ ID NOs: 3-8. In some embodiments, the miRNA* strand of a miRNA/miRNA* duplex comprises or consists of the sequence set forth in any one of SEQ ID NOs: 3-8

In some embodiments, an inhibitory nucleic acid targeting TMEM106B comprises a miRNA/miRNA* duplex. In some embodiments, the miRNA strand of a miRNA/miRNA* duplex comprises or consists of the sequence set forth in SEQ ID NO: 9 or 10. In some embodiments, the miRNA* strand of a miRNA/miRNA* duplex comprises or consists of the sequence set forth in SEQ ID NOs: 9 or 10.

An artificial microRNA (amiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an amiRNA. In some embodiments, the pri-miRNA scaffold of the amiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451. In some embodiments, an amiRNA comprises a nucleic acid sequence targeting SCNA or TMEM106B and an eSIBR amiRNA scaffold, for example as described in Fowler et al. Nucleic Acids Res. 2016 Mar. 18; 44(5): e48.

In some embodiments, an amiRNA targeting SCNA comprises or consists of the sequence set forth in any one of SEQ ID NOs: 17-22. In some embodiments, an amiRNA targeting TMEM106B comprises or consists of the sequence set forth in SEQ ID NOs: 11 or 12. In some embodiments, an amiRNA targeting RPS25 comprises or consists of the sequence set forth in SEQ ID NOs: 38 to 45. In some embodiments, an amiRNA targeting MAPT comprises or consists of the sequence set forth in SEQ ID NOs: 46 to 61.

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculovirus vector, etc.). In some embodiments, the vector is a plasmid (e.g., a plasmid comprising an isolated nucleic acid as described herein). In some embodiments, the vector is a recombinant AAV (rAAV) vector. In some embodiments, an rAAV vector is single-stranded (e.g., single-stranded DNA). In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (TTR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a ΔITR, for example as described by McCarty et al. (2003) *Gene Ther.* 10(26):2112-8.

Figure 16:
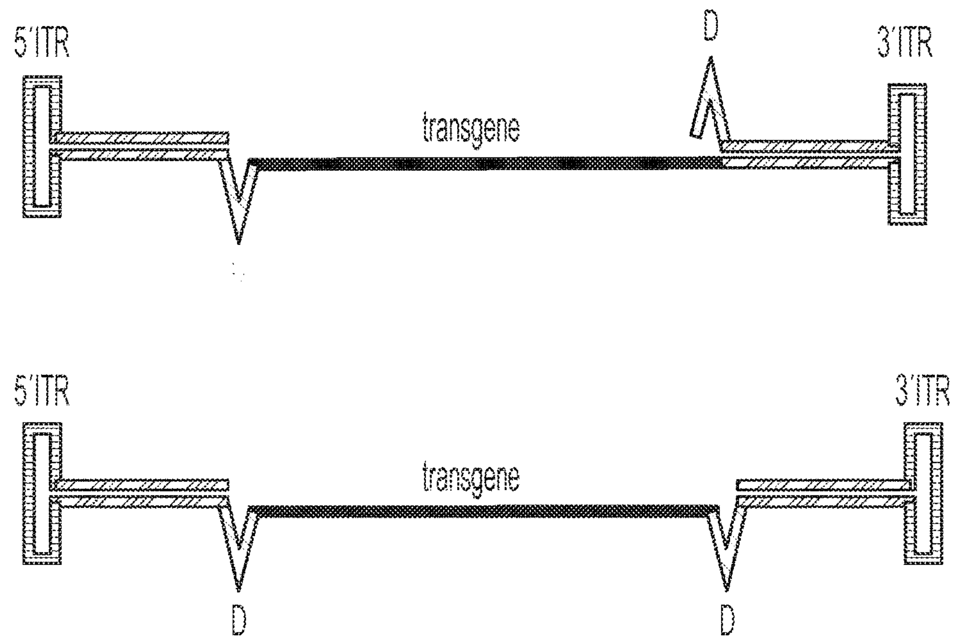
FIG. 16 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 16). The structure of wild-type AAV2 ITR is shown in FIG. 16. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region. (FIG. 16). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 14. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 14). A modified "D" sequence may have at least 1, 2, 3, 4, 5, 6, 7, 8, 9, 10, or more than 10 nucleotide substitutions relative to a wild-type "D" sequence (e.g., SEQ ID NO: 14). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 13). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 14). In some embodiments, a modified "D" sequence comprises the sequence set forth in SEQ ID NO: 13, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 15, as described by Francois, et al. 2005. The Cellular TATA Binding Protein Is Required for Rep-Dependent Replication of a Minimal Adeno-Associated Virus Type 2 p5 Element. J Virol. In some embodiments, a TRY sequence is positioned between an ITR (e.g., a 5' ITR) and an expression construct (e.g., a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) Hum Gene Ther 13(16):1935-43, Smith et al. (2009) Mol Ther 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1: rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and one or more inhibitory nucleic acids (e.g., inhibitory nucleic acids targeting SCNA), for example by expression with 2 separate expression cassettes. The presence of a short intronic sequence that is efficiently spliced, upstream of the expressed gene, can improve expression levels. shRNAs and other regulatory RNAs can potentially be included within these sequences. Examples of expression constructs described by the disclosure are shown in FIGS. 1-13 and 18-24, and in Table 2 below.

TABLE 2

| Name | Promoter 1 | shRNA | CDS1 | PolyA1 | Bicistronic element | Promotor 2 | CDS2 | PolyA2 | Length between ITRs |
|---|---|---|---|---|---|---|---|---|---|
| PrevailVector_0_CMVe_CBAp_mRNA-iaSyn_GBA1_WPRE_bGH_4004nt | CBA | aSyn | GBA1 | WPRE_bGH | — | — | — | — | 4004 |
| PrevailVector_XI_SNCA | CMVe + CBA | — | SNCA | WPRE_bGH | — | — | — | — | — |

Example 2: Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GluCer and GluSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3: In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2\times10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4: Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2\times10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5: Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6: Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7: Treatment of CNS Forms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8: Testing of SCNA and TMEM106B shRNA Constructs

HEK293 Cells

Human embryonic kidney 293 cell line (HEK293) were used in this study (#85120602, Sigma-Aldrich). HEK293 cells were maintained in culture media (D-MEM [#11995065, Thermo Fisher Scientific] supplemented with 10% fetal bovine serum [FBS] [#10082147, Thermo Fisher Scientific]) containing 100 units/ml penicillin and 100 μg/ml streptomycin (#15140122, Thermo Fisher Scientific).

Plasmid Transfection

Plasmid transfection was performed using Lipofectamine 2000 transfection reagent (#11668019, Thermo Fisher Scientific) according to the manufacture's instruction. Briefly, HEK293 cells (#12022001, Sigma-Aldrich) were plated at the density of $3\times10^5$ cells/ml in culture media without antibiotics. On the following day, the plasmid and Lipofectamine 2000 reagent were combined in Opti-MEM solution (#31985062, Thermo Fisher Scientific). After 5 minutes, the mixtures were added into the HEK293 culture. After 72 hours, the cells were harvested for RNA or protein extraction, or subjected to the imaging analyses. For imaging analyses, the plates were pre-coated with 0.01% poly-L-Lysine solution (P8920, Sigma-Aldrich) before the plating of cells.

Gene Expression Analysis by Quantitative Real-Time PCR (qRT-PCR)

Relative gene expression levels were determined by quantitative real-time PCR (qRT-PCR) using Power SYBR Green Cells-to-CT Kit (#4402955, Thermo Fisher Scientific) according to the manufacturer's instruction. The candidate plasmids were transiently transfected into HEK293 cells plated on 48-well plates ($7.5\times10^4$ cells/well) using Lipofectamine 2000 transfection reagent (0.5 μg plasmid and 1.5 μl reagent in 50 μl Opti-MEM solution). After 72 hours, RNA was extracted from the cells and used for reverse transcription to synthesize cDNA according to the manufacturer's instruction. For quantitative PCR analysis, 2-5 μl of cDNA products were amplified in duplicates using gene specific primer pairs (250 nM final concentration) with Power SYBR Green PCR Master Mix (#4367659, Thermo Fisher Scientific). The primer sequences for SNCA, TMEM106B, and GAPDH genes were: 5'-AAG AGG GTG TTC TCT ATG TAG GC-3' (SEQ ID NO: 64), 5'-GCT CCT CCA ACA TTT GTC ACT T-3' (SEQ ID NO: 65) for SNCA, 5'-ACA CAG TAC CTA CCG TTA TAG CA-3' (SEQ ID NO: 66), 5'-TGT TGT CAC AGT AAC TTG CAT CA-3' (SEQ ID NO: 67) for TMEM106B, and 5'-CTG GGC TAC ACT GAG CAC C-3' (SEQ ID NO: 68), 5'-AAG TGG TCG TTG AGG GCA ATG-3' (SEQ ID NO: 69) for GAPDH. Quantitative PCR was performed in a QuantStudio 3 Real-Time PCR system (Thermo Fisher Scientific). Expression levels were normalized by the housekeeping gene GAPDH and calculated using the comparative CT method.

Fluorescence Imaging Analysis

EGFP reporter plasmids, which contain 3'-UTR of human SNCA gene at downstream of EGFP coding region, were used for the validation of SNCA and TMEM106B knockdown plasmids. EGFP reporter plasmids and candidate knockdown plasmids were simultaneously transfected into HEK293 cells plated on poly-L-Lysine coated 96-well plates ($3.0\times10^4$ cells/well) using Lipofectamine 2000 transfection reagent (0.04 μg reporter plasmid, 0.06 μg knockdown plasmid and 0.3 μl reagent in 10 μl Opti-MEM solution). After 72 hours, the fluorescent intensities of EGFP signal were measured at excitation 488 nm/emission 512 nm using Varioskan LUX multimode reader (Thermo Fisher Scientific). Cells were fixed with 4% PFA at RT for 10 minutes, and incubated with D-PBS containing 40 μg/ml 7-aminoactinomycin D (7-AAD) for 30 min at RT. After washing with D-PBS, the fluorescent intensities of 7-AAD signal were measured at excitation 546 nm/emission 647 nm using Varioskan reader to quantify cell number. Normalized EGFP signal per 7-AAD signal levels were compared with the control knockdown samples.

Enzyme-Linked Immunosorbent Assay (ELISA)

α-Synuclein reporter plasmids, which contain 3'-UTR of human SNCA gene or TMEM106B gene downstream of SNCA coding region, were used for the validation of knockdown plasmids at the protein level. Levels of α-synuclein protein were determined by ELISA (#KHB0061, Thermo Fisher Scientific) using the lysates extracted from HEK293 cells. The candidate plasmids were transiently transfected into HEK293 cells plated on 48-well plates ($7.5\times10^4$ cells/well) using Lipofectamine 2000 transfection reagent (0.1 μg reporter plasmid, 0.15 knockdown plasmid and 0.75 μl reagent in 25 μl Opti-MEM solution). After 72 hours, cells were lysed in radioimmunoprecipitation assay (RIPA) buffer (#89900, Thermo Fisher Scientific) supplemented with protease inhibitor cocktail (#P8340, Sigma-Aldrich), and sonicated for a few seconds. After incubation on ice for 30 min, the lysates were centrifuged at 20,000×g at 4° C. for 15 min, and the supernatant was collected. Protein levels were quantified. Plates were read in a Varioskan plate reader at 450 nm, and concentrations were calculated using SoftMax Pro 5 software. Measured protein concentrations were normalized to total protein concentration determined with a bicinchoninic acid assay (#23225, Thermo Fisher Scientific)
.

Figure 14:
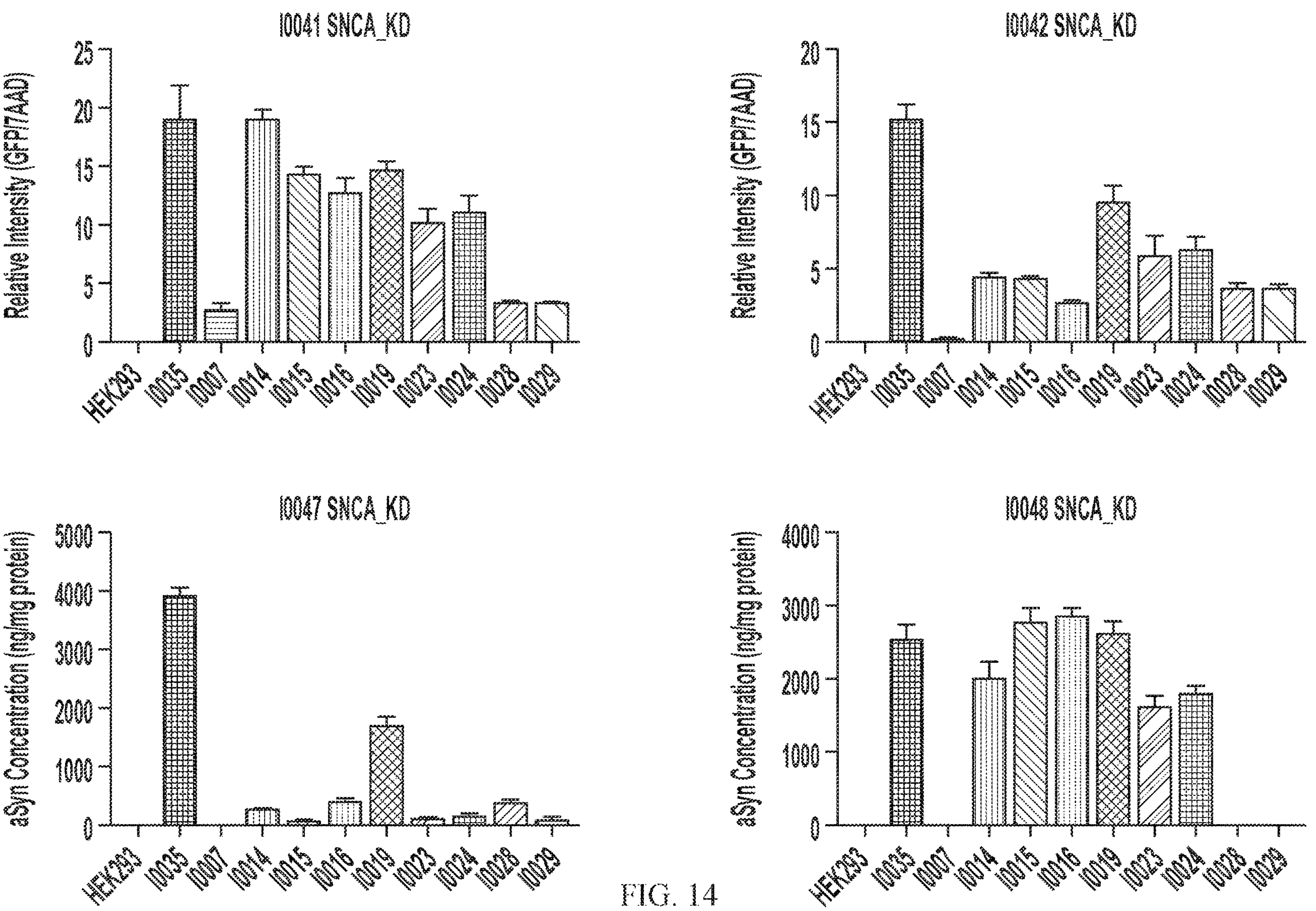
FIG. 14 shows representative data indicating successful silencing of SCNA in vitro by GFP reporter assay (top) and α-Syn assay (bottom).
Figure 15:
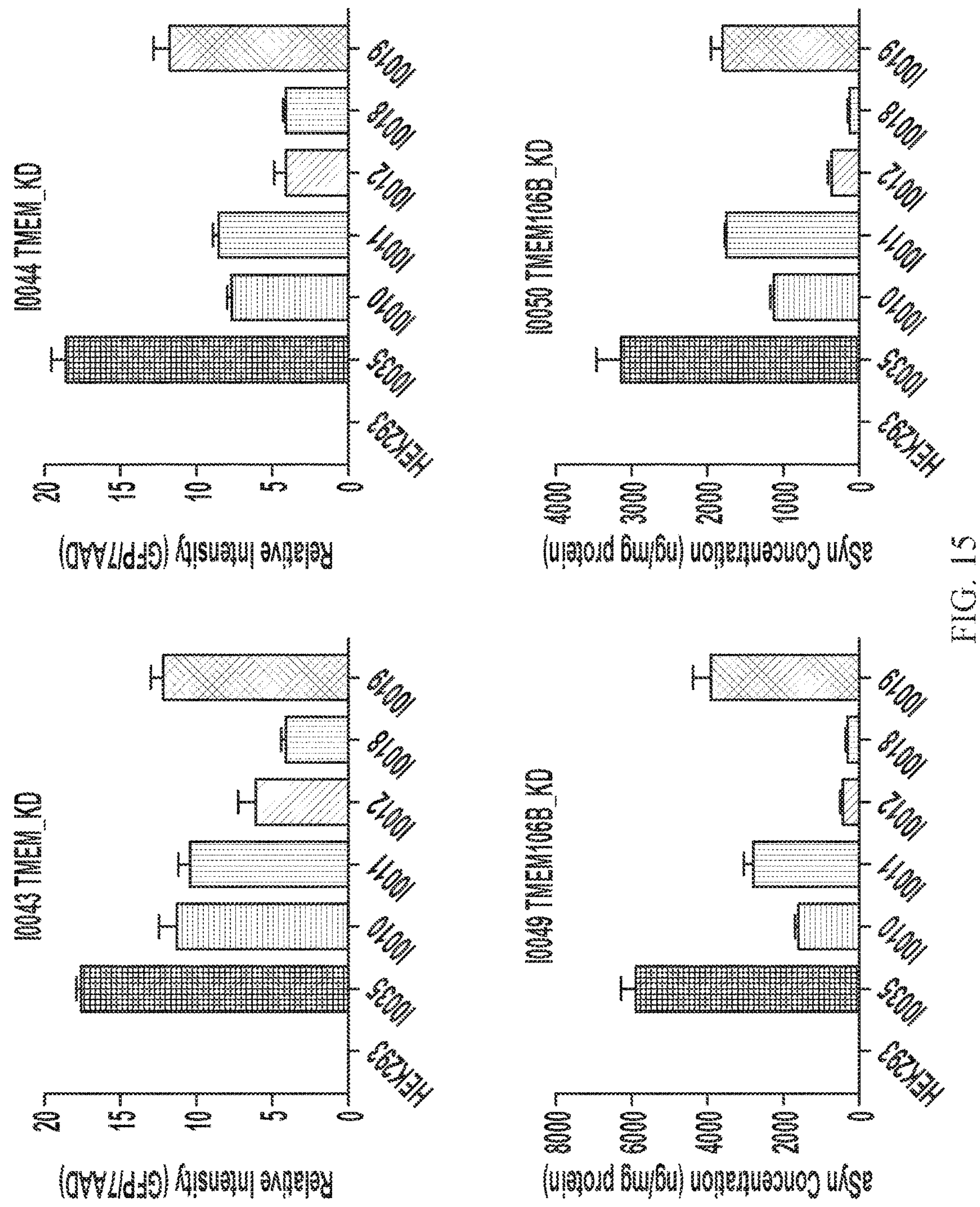
FIG. 15 shows representative data indicating successful silencing of TMEM106B in vitro by GFP reporter assay (top) and α-Syn assay (bottom).

FIG. 14 and Table 3 show representative data indicating successful silencing of SCNA in vitro by GFP reporter assay (top) and α-Syn assay (bottom). FIG. 15 and Table 4 show representative data indicating successful silencing of TMEM106B in vitro by GFP reporter assay (top) and α-Syn assay (bottom).

TABLE 3

| ID | Promoter | Knockdown | Promoter | Overexpress |
|---|---|---|---|---|
| I00007 | CMV_intronic | SNCA_mi | CMV | opt-GBA1 |
| I00008 | H1 | SNCA_sh | CMV | opt-GBA1 |
| I00009 | H1 | SNCA_Pubsh4 | CMV | opt-GBA1 |
| I00014 | JL_intronic | SNCA_mi | JetLong | opt-SCARB2_GBA |
| I00015 | JL_intronic | SNCA_mi | JetLong | opt-PSAP_GBA |
| I00016 | JL_intronic | SNCA_mi | JetLong | opt-CTSB_GBA |
| I00019 | JL_intronic | SNCA_TMEM_mi | JetLong | opt-VPS35 |
| I00023 | JL_intronic | SNCA_mi | JetLong | opt-GBA1_IL34 |
| I00024 | JL_intronic | SNCA_mi | JetLong | opt-GBA2 |
| I00028 | intronic | SNCA_Broadsh | CMV | opt-GBA1 |
| I00029 | intronic | SNCA_Pubsh4 | CMV | opt-GBA1 |

TABLE 4

| ID | Promoter | Knockdown | Promoter | Overexpress |
|---|---|---|---|---|
| I00010 | H1 | TMEM_Pubsh | CMV | opt-GRN |
| I00011 | JL_intronic | TMEM_mi | JetLong | opt-GBA1_GRN |
| I00012 | H1 | TMEM_sh | CMV | opt-GRN |
| I00019 | JL_intronic | SNCA_TMEM_mi | JetLong | opt-VPS35 |

Example 9: ITR "D" Sequence Placement and Cell Transduction

Figure 17:
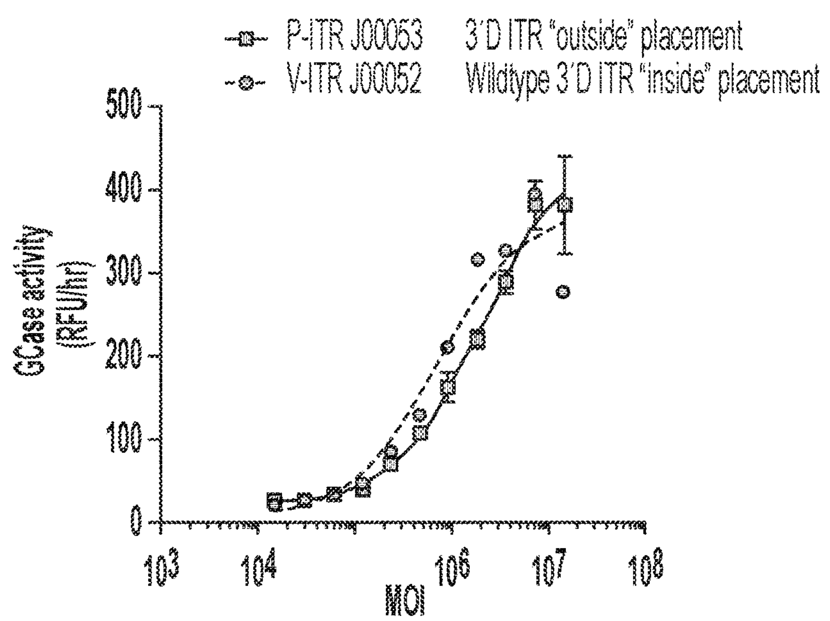
FIG. 17 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type 1TRs.
Figure 18:
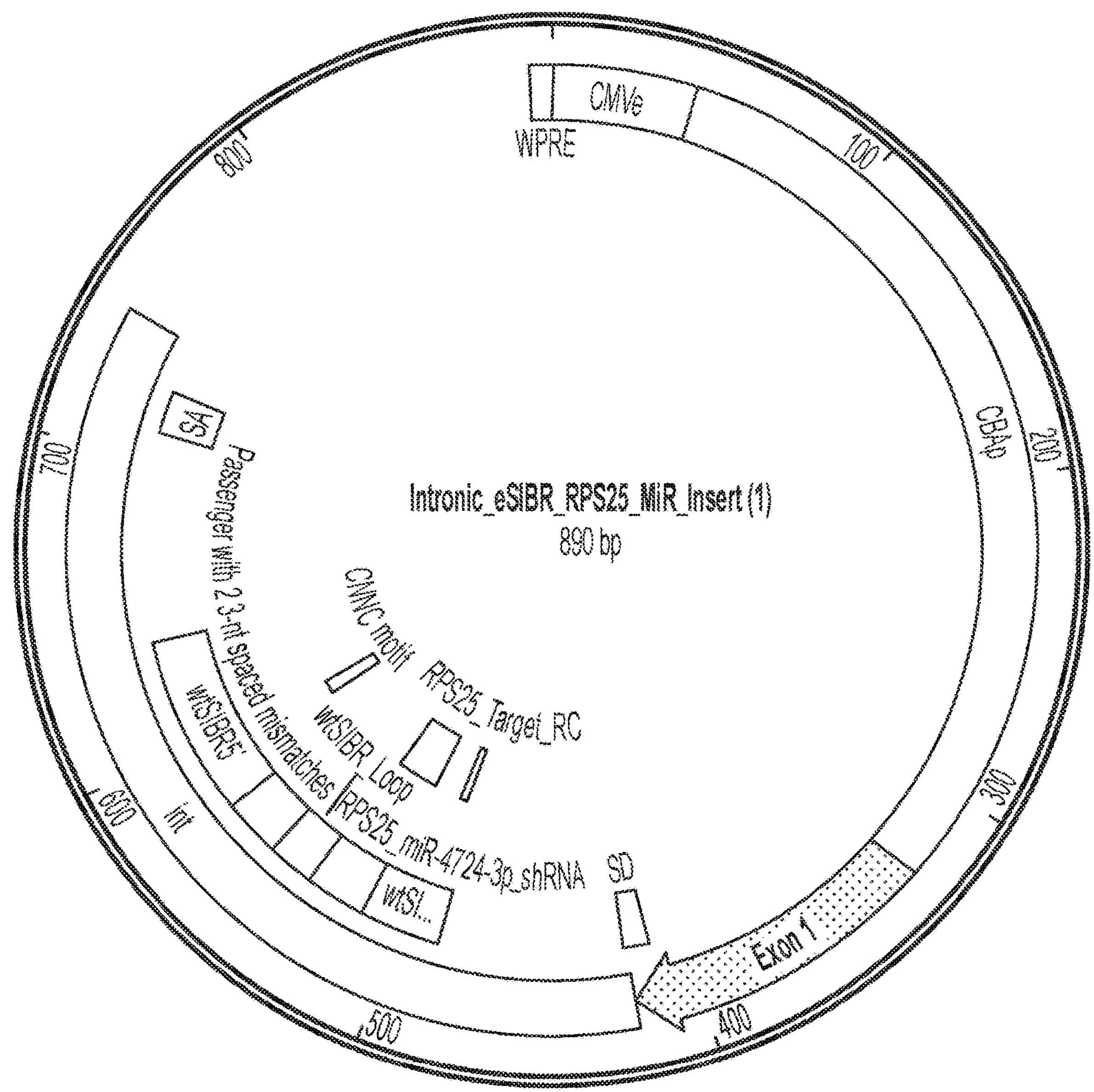
FIG. 18 is a schematic depicting one embodiment of a plasmid comprising an rAAV vector that includes an expression construct encoding an inhibitory RNA targeting RPS25.
Figure 19:
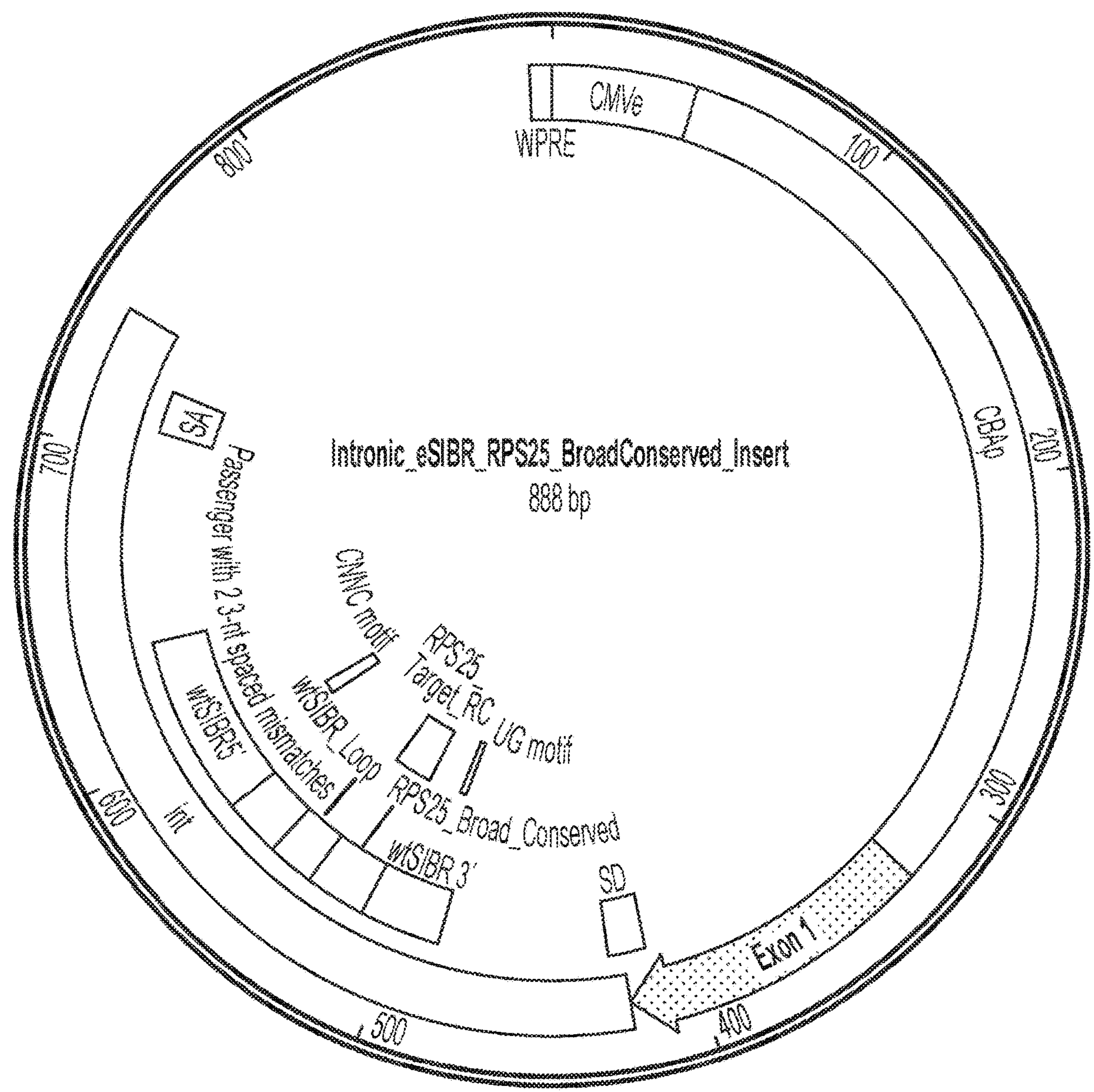
FIG. 19 is a schematic depicting one embodiment of a plasmid comprising an rAAV vector that includes an expression construct encoding an inhibitory RNA targeting RPS25.
Figure 20:
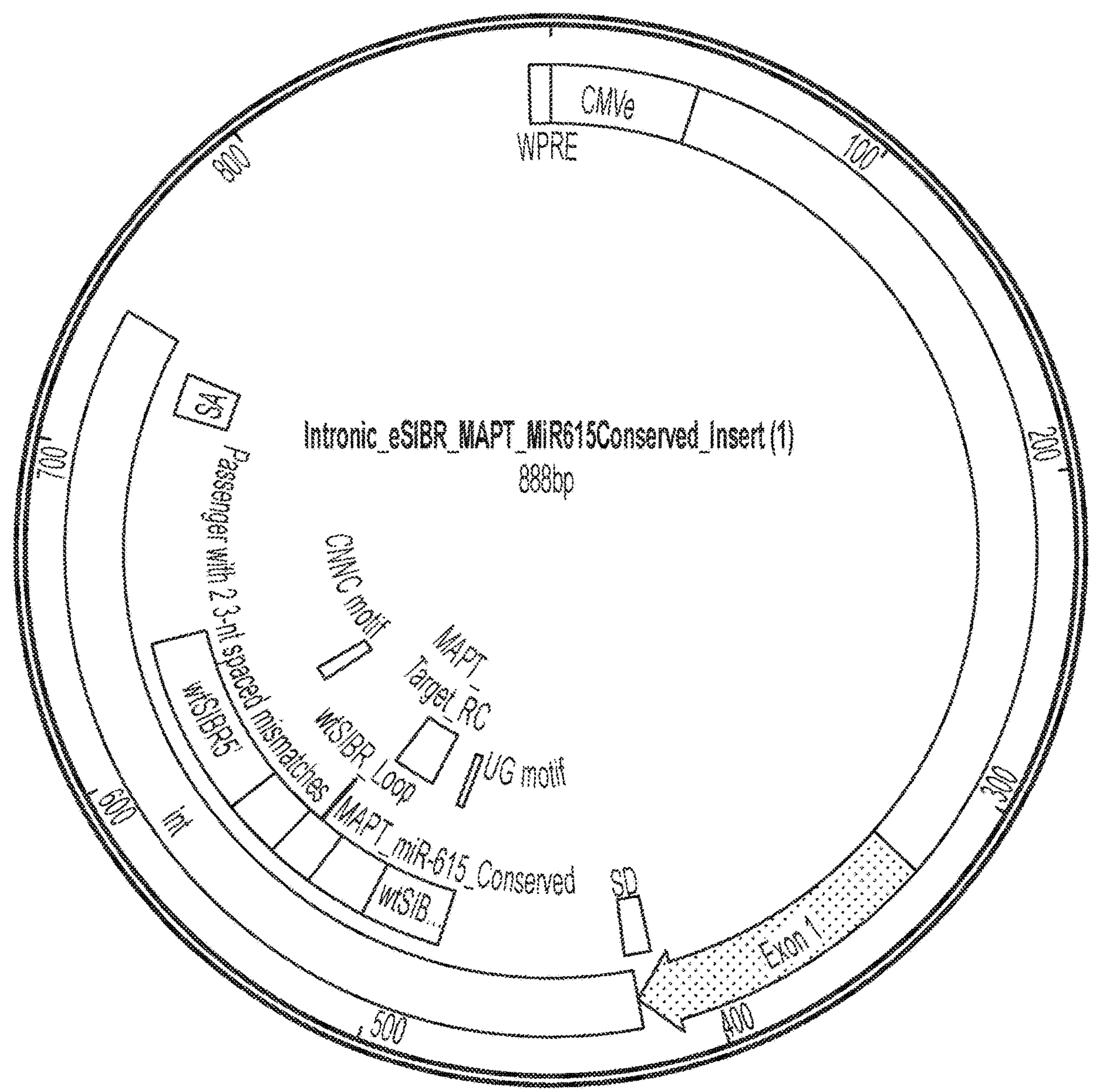
FIG. 20 is a schematic depicting one embodiment of a plasmid comprising an rAAV vector that includes an expression construct encoding an inhibitory RNA targeting MAPT.
Figure 21:
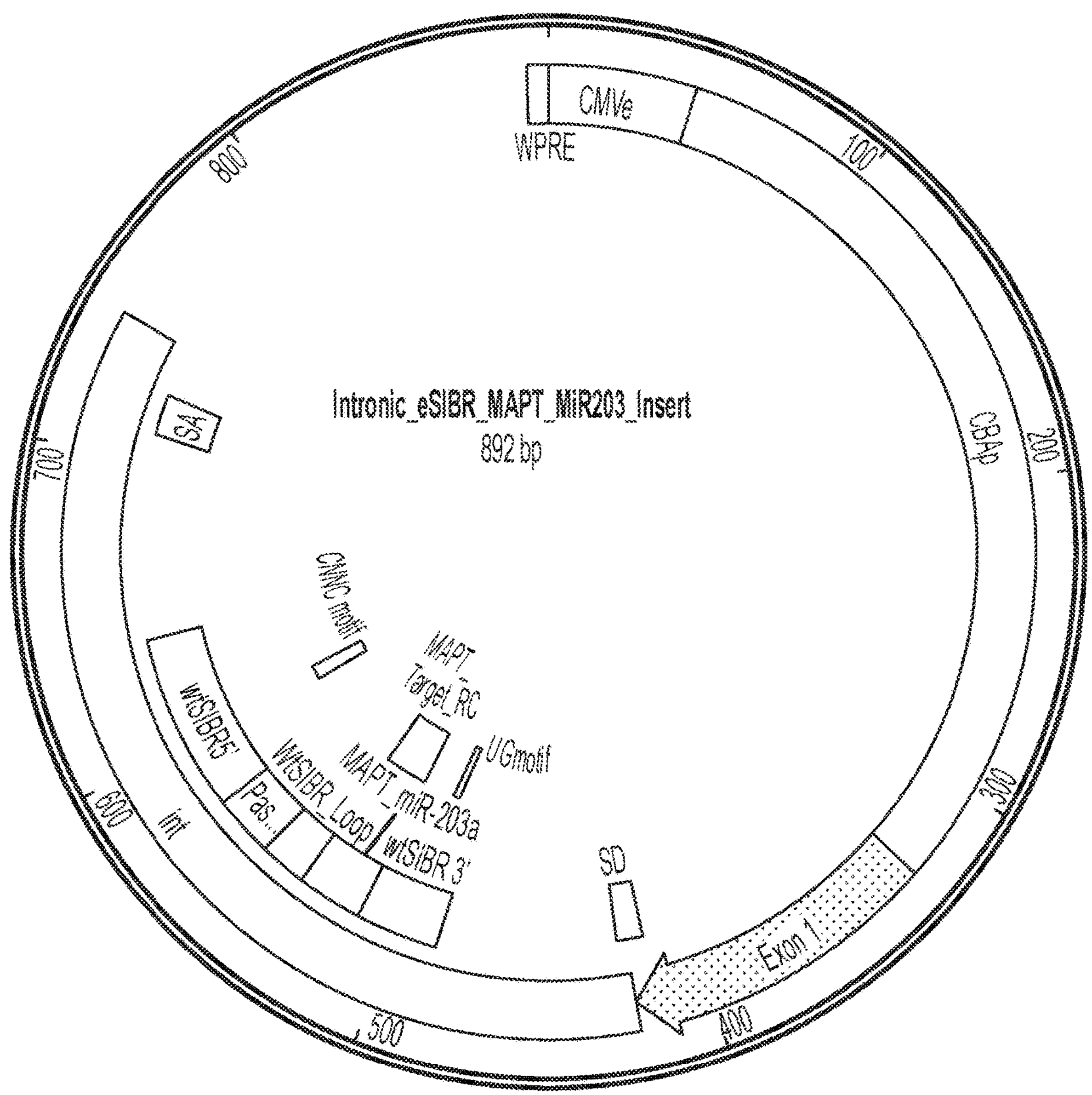
FIG. 21 is a schematic depicting one embodiment of a plasmid comprising an rAAV vector that includes an expression construct encoding an inhibitory RNA targeting MAPT.
Figure 22:
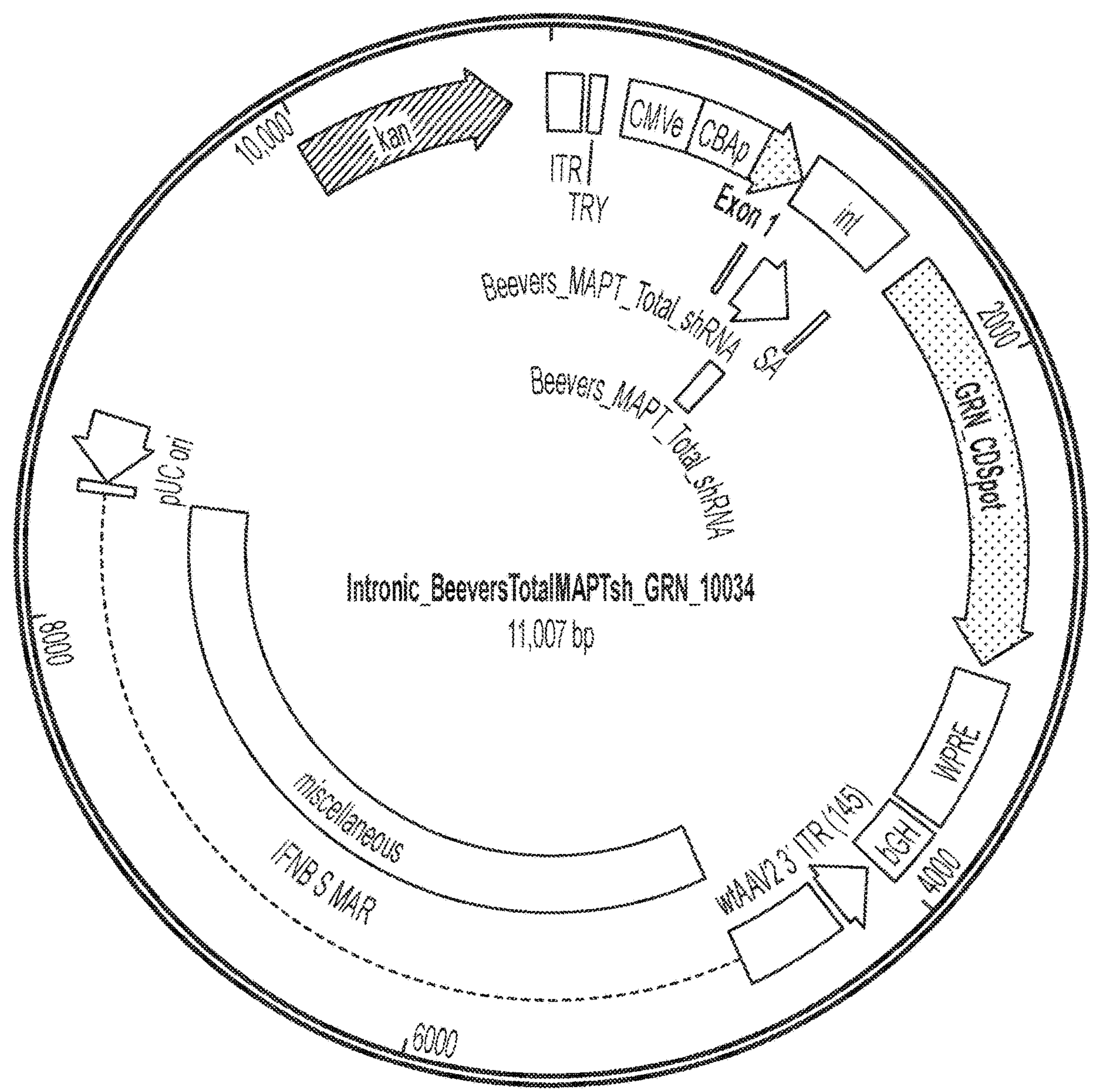
FIG. 22 is a schematic depicting one embodiment of a plasmid comprising an rAAV vector that includes an expression construct encoding progranulin (PGRN) and an inhibitory RNA targeting MAPT. The inhibitory RNA is positioned within an intron between the promoter sequence and the PGRN encoding sequence.
Figure 23:
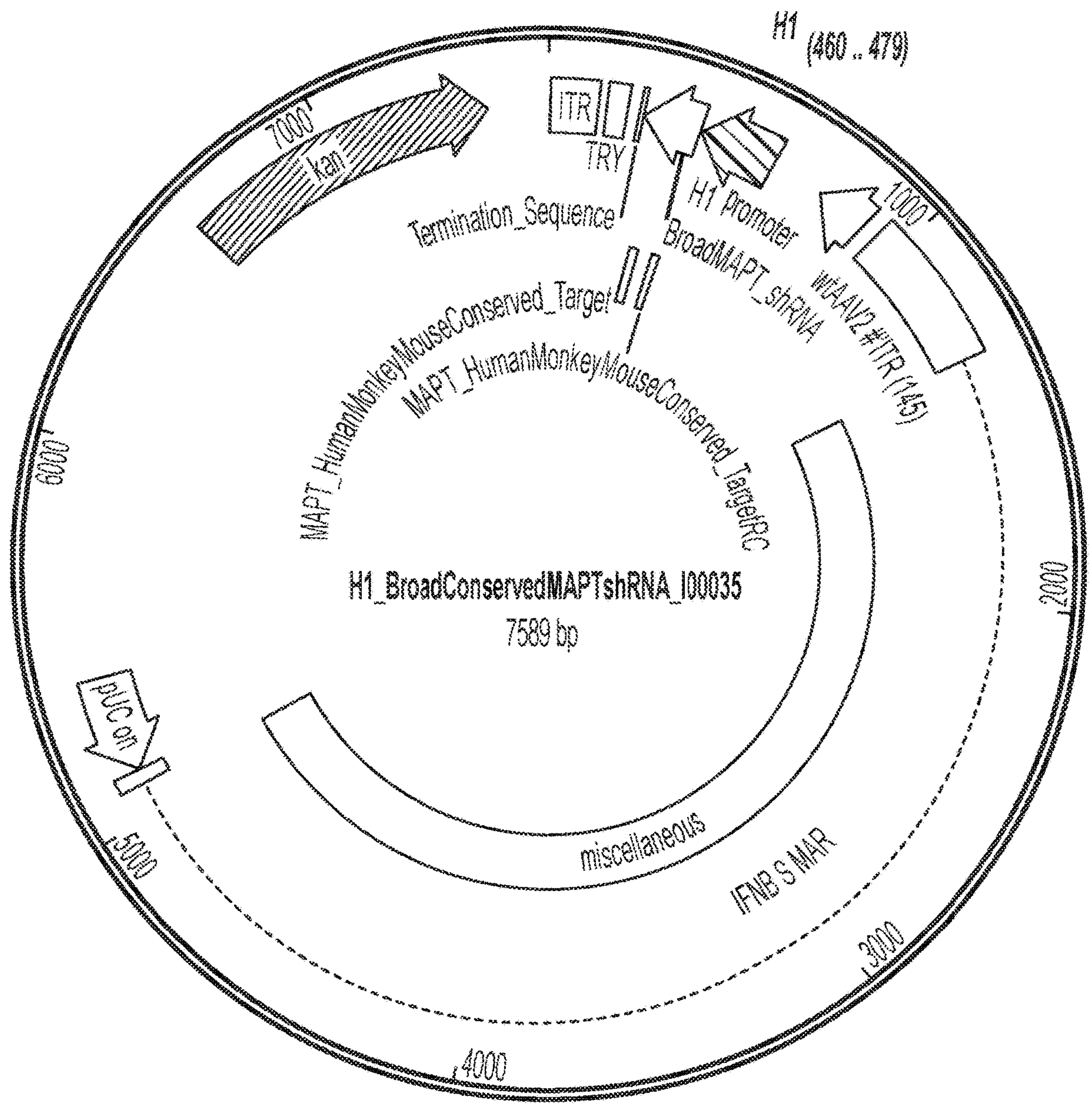
FIG. 23 is a schematic depicting one embodiment of a plasmid comprising an rAAV vector that includes an expression construct encoding an inhibitory RNA targeting MAPT.
Figure 24:
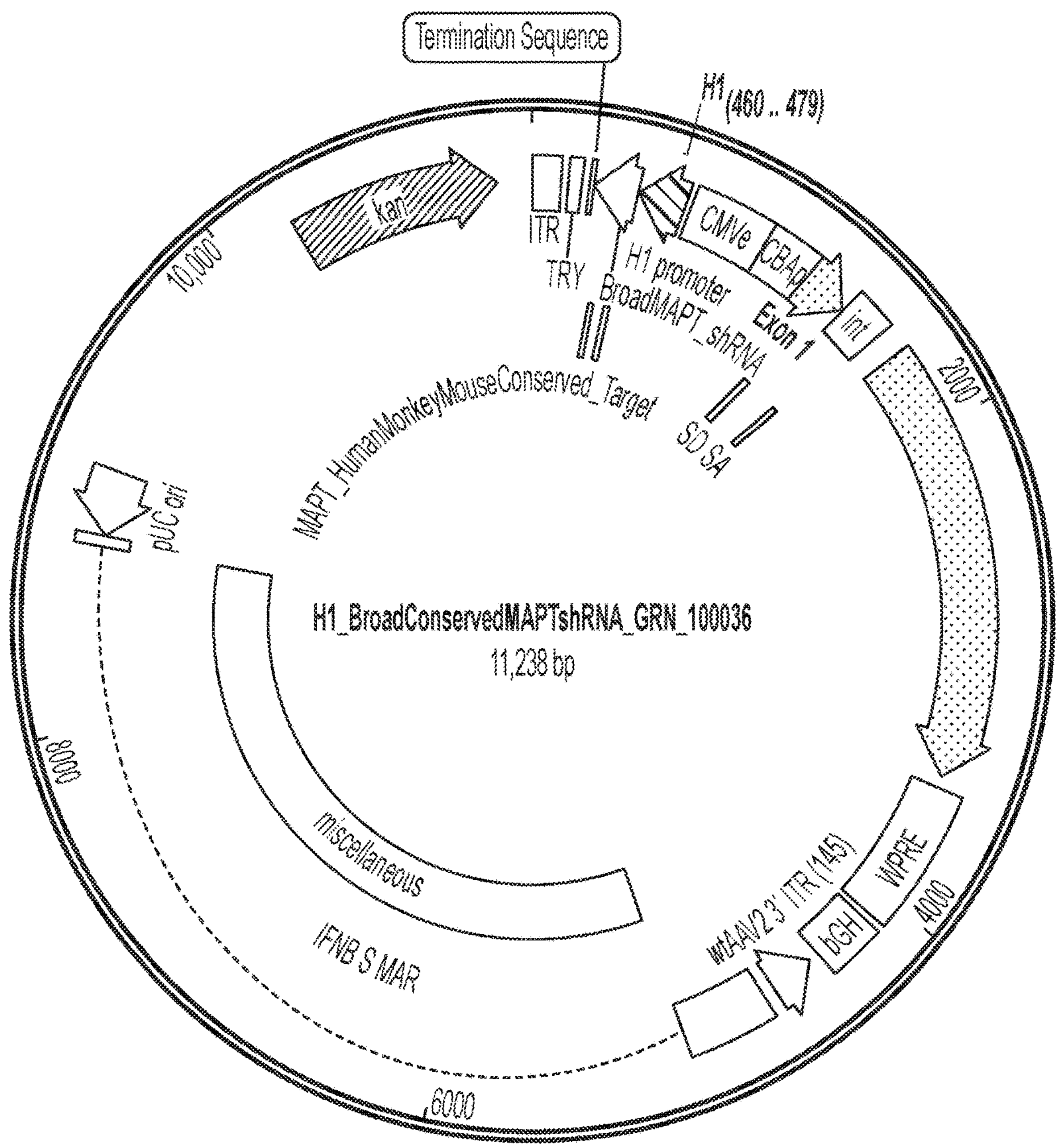
FIG. 24 is a schematic depicting one embodiment of a plasmid comprising an rAAV vector that includes an expression construct encoding progranulin (PGRN) and an inhibitory RNA targeting MAPT. The inhibitory RNA is positioned within an intron between the promoter sequence and the PGRN encoding sequence.

The effect of placement of ITR "D" sequence on cell transduction of rAAV vectors was investigated. HEK293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 20. Surprisingly, data indicate that rAAVs having the "D" sequence located in the "outside" position retain the ability to be packaged and transduce cells efficiently (FIG. 17).

EQUIVALENTS

This application incorporates by reference the contents of the following documents in their entirety: the International PCT Application referred to by International PCT Application referred to by Provisional Application Ser. Nos. 62/567,296, filed Oct. 3, 2017, entitled "GENE THERAPIES FOR LYSOSOMAL DISORDERS"; 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2018, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having." "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

SEQUENCES

In some embodiments, an isolated nucleic acid, rAAV vector, or gene expression cassette encoding one or more gene products (e.g., a first, second and/or third gene product) comprises or consists of (or encodes a polypeptide having) a sequence set forth in any one of SEQ ID NO: 1-69. In some embodiments, a gene product is encoded by a portion (e.g., fragment) of any one of SEQ ID NOs: 1-69.

What is claimed is:

1. An isolated nucleic acid comprising (i) an expression construct comprising a transgene encoding one or more microRNA (miRNA) comprising a region of complementarity to the microtubule-associated protein tau (MAPT) gene, wherein the one or more miRNA is encoded by the sequence set forth in any one of SEQ ID NOs: 46-61, and wherein the region of complementarity of the one or more miRNA is between 6 and 30 nucleotides in length; and (ii) two adeno-associated virus inverted terminal repeats (ITR) sequences flanking the expression construct.

2. The isolated nucleic acid of claim 1, wherein the transgene is operably linked to a promoter.

3. The isolated nucleic acid of claim 2, wherein the promoter is a chicken beta-actin (CBA) promoter.

4. The isolated nucleic acid of claim 1, wherein each ITR sequence is a wild-type AAV2 ITR sequence.

5. A recombinant adeno-associated virus (AAV) vector comprising the isolated nucleic acid of claim 1.

6. The rAAV vector of claim 5, wherein the transgene is operably linked to a promoter.

7. The rAAV vector of claim 6, wherein the promoter is a chicken beta actin (CBA) promoter.

8. A recombinant adeno-associated virus (rAAV) comprising:

(i) an AAV capsid protein; and (ii) the rAAV vector of claim 5.

9. The rAAV of claim 8, wherein the AAV capsid protein is AAV9 capsid protein.

10. A Baculovirus vector comprising the isolated nucleic acid of claim 1.

11. A recombinant adeno-associated virus (rAAV) vector comprising a nucleic acid comprising, in 5' to 3' order:

(a) a 5' AAV inverted terminal repeat (ITR);

(b) a Cytomegalovirus (CMV) enhancer;

(c) a chicken beta actin (CBA) promoter;

(d) a transgene encoding one or more microRNA (miRNA) comprising a region of complementarity of the microtubule-associated protein tau (MAPT) gene, wherein the one or more miRNA is encoded by the sequence set forth in any one of SEQ ID NO: 46-61, and wherein the region of complementarity of the one or more miRNA is between 6 and 30 nucleotides in length;

(e) a Woodchuck Hepatitis Virus Posttranscriptional Regulatory Element (WPRE);

(f) a Bovine Growth Hormone (BGH) polyA signal tail; and (g) a 3' AAV ITR.

12. A recombinant adeno-associated virus (rAAV) comprising:

(i) an AAV capsid protein; and (ii) the rAAV vector of claim 11.

13. The rAAV of claim 12, wherein the AAV capsid protein is AAV9 capsid protein.

14. A plasmid comprising the rAAV vector of claim 11.

15. A cell comprising:

(i) a first vector encoding one or more adeno-associated virus rep protein and/or one or more adeno-associated virus cap protein; and (ii) a second vector comprising the rAAV vector of claim 11.

16. The cell of claim 15, wherein the first vector is a plasmid and the second vector is a plasmid.

17. The cell of claim 16, wherein the first vector is a Baculovirus vector and the second vector is a Baculovirus vector.

18. A method of producing an rAAV, the method comprising:

(i) delivering to a cell a first vector encoding one or more adeno-associated virus rep protein and/or one or more adeno-associated cap protein, and recombinant AAV vector of claim 11;

(ii) culturing the cells under conditions allowing for packaging the rAAV; and (iii) harvesting the cultured host cell or culture medium for collection of the rAAV.

* * * * *

UNITED STATES PATENT AND TRADEMARK OFFICE

CERTIFICATE OF CORRECTION

PATENT NO. : 12,049,626 B2
APPLICATION NO. : 16/838993
DATED : July 30, 2024
INVENTOR(S) : Asa Abeliovich et al.

It is certified that error appears in the above-identified patent and that said Letters Patent is hereby corrected as shown below:

On the Title Page

In item (57) Abstract, please replace:
"This Application is a continuation of international patent application serial number PCT/US2018/054223, filed Oct.3, 2018, which claims the benefit under 35 U.S.C. § 119(e) of U.S. Provisional Application Ser. No. 62/567,303, filed Oct. 3, 2017, entitled "GENE THERAPIES FOR LYSOSOMAL DISORDERS", and 62/567,305, filed Oct.3, 2017, entitled "GENE THERAPIES FOR LYSOSOMAL DISORDERS", the entire contents of each of which are incorporated herein by reference."
With:
--The disclosure relates, in some aspects, to compositions and methods for treatment of diseases associated with aberrant lysosomal function, for example Parkinson's disease and Gaucher disease. In some embodiments, the disclosure provides expression constructs comprising a transgene encoding one or more inhibitory nucleic acids targeting SCNA or a portion thereof, TMEM106B or a portion thereof, or any combination of the foregoing. In some embodiments, the disclosure provides methods of Parkinson's disease by administering such expression constructs to a subject in need thereof.--

In the Specification

At Column 1, please replace paragraph "Related Applications:
"This application claims the benefit under 35 U.S.C. 119(e) of U.S. Provisional Application Ser. No. 62/567,303, filed Oct. 3, 2017, entitled "GENE THERAPIES FOR LYSOSOMAL DISORDERS", and 62/567,305, filed Oct. 3, 2017, entitled "GENE THERAPIES FOR LYSOSOMAL DISORDERS", the entire contents of each of which are incorporated herein by reference."
With:
--This Application is a continuation of International Patent Application Ser. No. PCT/US2018/054223, filed Oct. 3, 2018, which claims the benefit under 35 U.S.C. § 119(e) of U.S. Provisional Application Ser. Nos. 62/567,303, filed Oct. 3, 2017, entitled "GENE THERAPIES FOR Signed and Sealed this
Seventeenth Day of December, 2024

Derrick Brent
*Acting Director of the United States Patent and Trademark Office*

LYSOSOMAL DISORDERS", and 62/567,305, filed Oct. 3, 2017, entitled "GENE THERAPIES FOR LYSOSOMAL DISORDERS", the entire contents of each of which are incorporated herein by reference.--

In the Claims

At Column 190, Line 52, please replace:
"beta actin"
With:
--beta-actin--

At Column 191, Line 3, please replace:
"No:"
With:
--NOs:--